United States Patent [19]

Douglass et al.

[11] Patent Number: 4,854,962
[45] Date of Patent: Aug. 8, 1989

[54] HERBICIDAL SULFONAMIDES

[75] Inventors: David L. Douglass; Marcus P. Moon, both of Wilmington, Del.

[73] Assignee: E. I. Du Pont de Nemours and Company, Wilmington, Del.

[21] Appl. No.: 155,971

[22] Filed: Feb. 16, 1988

Related U.S. Application Data

[60] Division of Ser. No. 39,492, Apr. 16, 1987, Pat. No. 4,746,356, which is a continuation-in-part of Ser. No. 868,239, May 23, 1986, abandoned.

[51] Int. Cl.$^4$ .................. C07D 403/12; C07D 413/12; C07D 417/12; A01N 43/54
[52] U.S. Cl. ............................................ 71/90; 71/91; 71/92; 544/122; 544/123; 544/320; 544/321; 544/323; 544/324; 544/331; 544/332
[58] Field of Search ................ 71/90, 91, 92; 544/122, 544/123, 320, 321, 323, 324, 331, 332

[56] References Cited

U.S. PATENT DOCUMENTS 4,589,911 5/1986 Ehrenfreund et al. ................. 71/91
4,634,465 1/1987 Ehrenfreund et al. ............. 544/209

Primary Examiner—John M. Ford

[57] ABSTRACT

This invention relates to novel sulfonylurea herbicidal compounds, agriculturally suitable compositions thereof and a method-of-use of said compounds and compositions as general preemergence and/or postemergence herbicides or their use as plant growth regulants.

48 Claims, No Drawings

HERBICIDAL SULFONAMIDES

This is a division of application Ser. No. 039,492, filed Apr. 16, 1987, now U.S. Pat. No. 4,746,356, which is a continuation-in-part of U.S. Ser. No. 868,239 filed May 23, 1986, now abandoned.

BACKGROUND OF THE INVENTION

This invention relates to novel sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks and industrial storage areas. There are many products commercially available for these purposes, but the search continues for products which are more effective, less costly and environmentally safe.

The "sulfonylurea" herbicides are an extremely potent class of herbicides discovered within the last few years. A multitude of structural variations exist within this class of herbicides, but they generally consist of a sulfonylurea bridge, —SO$_2$NHCONH—, linking two aromatic or heteroaromatic rings.

U.S. Pat. No. 4,514,211 discloses herbicidal sulfonamides of formula

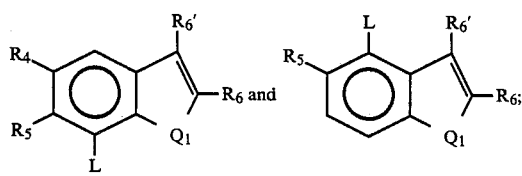

wherein
L is

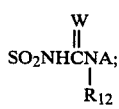

$R_6$ is H, Cl, Br or $C_1$–$C_4$ alkyl;
$R_6'$ is H, CH$_3$, Cl or Br; and
$Q_1$ is O, S or SO$_2$.

EP-A-107,979 discloses herbicidal sulfonamides of formula

wherein J is, in part,

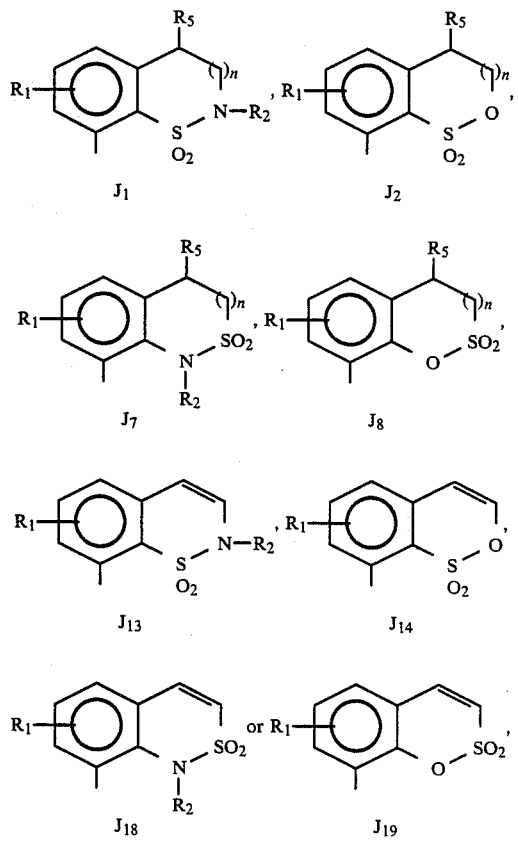

n is 0, 1 or 2;
R is H or CH$_3$;
$R_2$ is H or $C_1$–$C_4$ alkyl; and
$R_5$ is H or CH$_3$.

U.S. Pat. No. 4,391,627 discloses herbicidal sulfonamides of formula

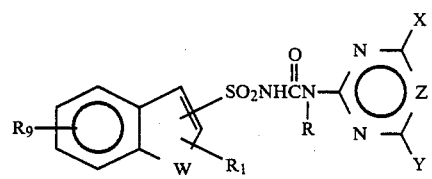

where
W is O or S; and
$R_1$ is H, Cl, Br, NO$_2$, $C_1$–$C_3$ alkyl, $C_1$–$C_3$ alkoxy, CO$_2$R$^2$, C(O)NR$^3$R$^4$, SO$_2$R or SO$_2$NR$^6$R$^7$.

EP-A-70,698 discloses herbicidal sufonamides of formula

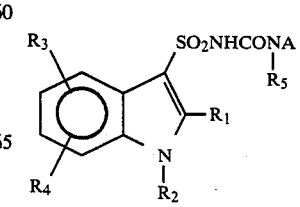

-continued

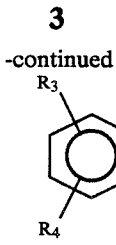

where
- R is H, $C_1$–$C_4$ alkyl, $(CH_2)_mCO_2R_9$, $CH_2OC_2H_5$, $SO_2R_{10}$, CHO, $SO_2NR_{11}R_{12}$, $CH_2N(CH_3)_2$ or $CH_2OCH_3$;
- $R_1$ is H, $C_1$–$C_4$ alkyl, $CO_2R_6$, $C(O)NR_7R_8$, $C(O)R_{10}$, $SO_2R_{10}$, or $SO_2NR_{11}R_{12}$; and
- $R_2$ is H, $C_1$–$C_3$ alkyl or $SO_2C_6H_5$.

EP-A-168,246 discloses herbicidal sulfonamides of formula

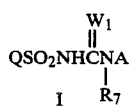

wherein Q is

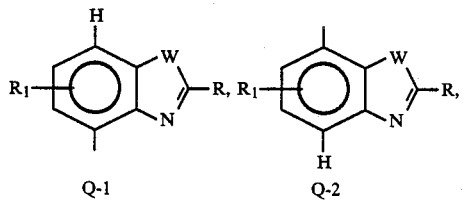

R is H or $C_1$–$C_4$ alkyl optionally substituted with 0–3 halogen atoms selected from 1–3 F, 1–2 Cl or 1 Br, $C_1$–$C_4$ alkylthio, $C_1$–$C_4$ alkoxy, $CH_2OCH_3$, $CH_2CH_2OCH_3$ or $CH_2SCH_3$;
$R_2$ is H or $CH_3$; and
W is O, S, or $NR_3$.

U.S. Pat. No. 4,502,882 discloses, in part, herbicidal sulfonamides of formula

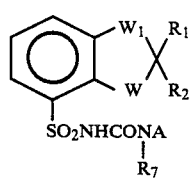

wherein
- W is O, S, SO or $SO_2$;
- $W_1$ is O, S, SO or $SO_2$;
- $R_1$ is H or $CH_3$; and
- $R_2$ is H or $C_1$–$C_4$ alkyl.

U.S. Pat. No. 4,578,108 discloses, in part, herbicidal sulfonamides of formula

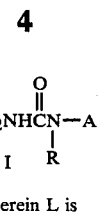

wherein L is

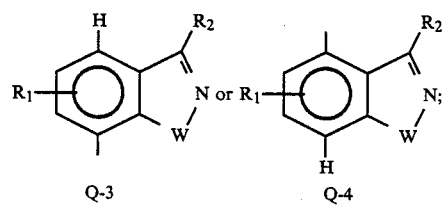

- Q is O, $S(O)_n$ or $NR_3$;
- n is 0, 1 or 2;
- $R_1$ is H, $CH_3$, Cl or F;
- $R_6$ is H, Cl or F;
- $R_7$ is H, Cl or F; and
- $R_8$ is H, Cl or F.

South African patent application No. 83/5165 (Swiss priority 7/16/82, published 1/16/84) discloses herbicidal sulfonamides of formula

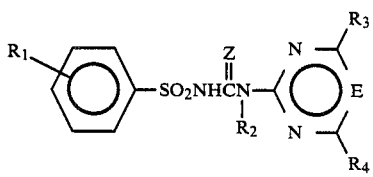

A wherein
- A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group, and $R_2$ is hydrogen, halogen, nitro, $C_1$–$C_4$ alkyl, $C_1$–$C_4$ haloalkyl, $C_1$–$C_4$ alkoxy, $C_1$–$C_2$ haloalkoxy, $C_1$–$C_4$ alkoxycarbonyl, $C_1$–$C_4$ alkylthio, $C_1$–$C_4$ alkylsulfinyl, $C_1$–$C_4$ alkylsulfonyl or $C_2$–$C_5$ alkoxyalkoxy; and
- $R_1$ is H, halogen, $NO_2$, $C_1$–$C_4$ alkyl, $C_1$–$C_4$ haloalkyl, $C_1$–$C_4$ alkoxy, $C_1$–$C_4$ haloalkoxy, $C_1$–$C_4$ alkoxycarbonyl, $C_1$–$C_4$ alkylthio, $C_1$–$C_4$ alkylsulfinyl, $C_1$–$C_4$ alkylsulfonyl or $C_2$–$C_5$ alkoxyalkoxy.

South African patent application No. 84/3522 (Swiss priority 5/11/83, published 11/11/84) discloses herbicidal sulfonamides of formula

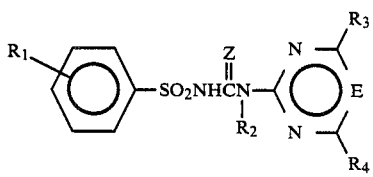

A wherein
R$_1$ is H, halogen, NO$_2$, C$_1$-C$_4$ alkyl, C$_1$-C$_4$ haloalkyl, CN, XR$^5$, COXR$^6$, CONR$^7$R$^8$, SOR$^9$ or SO$_2$R$^{10}$; and A is an unsubstituted or substituted unsaturated bridge of 4 atoms, of the formula —CH=CH—Y—, wherein Y is a bridge member of 2 atoms which is selected from the series consisting of —NH—CO—, —NH—SO$_2$—, —S—CO—, —S—SO$_2$—, —O—CO— or —O—SO$_2$—.

East German Pat. No. 134,184 (VEB Chemiekomb bitterfeld), published 2/14/79, discloses herbicidal sulphamoyl-2,1,3-benzothiadiazole derivatives of the formula

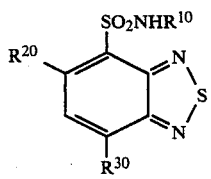

wherein
R$^{20}$ and R$^{30}$ are H or halogen; and R$^{10}$ is carbamoyl N-substituted by a C$_1$-C$_4$ aliphatic or C$_3$-C$_6$ cycloaliphatic group.

SUMMARY OF THE INVENTION

This invention relates to novel compounds of Formula I, agriculturally suitable compositions containing them, and their method-of-use as general preemergence and/or postemergence herbicides or plant growth regulants.

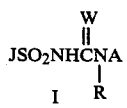

wherein J is

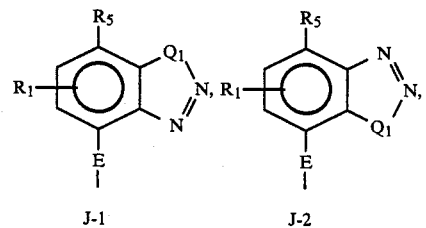

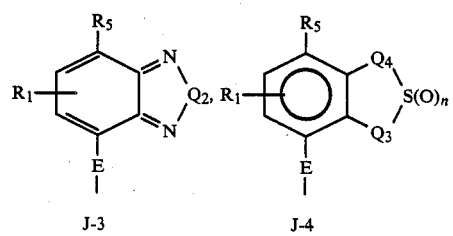

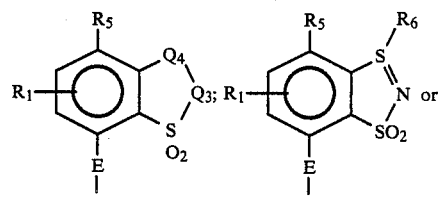

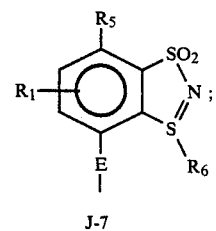

W is O or S;
R is H or CH$_3$;
E is a single bond, CH$_2$ or O;
R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$-C$_3$ alkylsulfinyl, C$_1$-C$_3$ alkylsulfonyl, CH$_2$CN, CN, CO$_2$R$_c$, C$_1$-C$_3$ haloalkoxy, C$_1$-C$_3$ haloalkylthio, C$_2$-C$_4$ alkoxyalkyl, C$_2$-C$_4$ alkylthioalkyl, CH$_2$N$_3$ or NR$_d$R$_e$;
R$_a$ is H, C$_1$-C$_4$ alkyl, C$_2$-C$_3$ cyanoalkyl, methoxy or ethoxy;
R$_b$ is H, C$_1$-C$_4$ alkyl or C$_3$-C$_4$ alkenyl; or
R$_a$ and R$_b$ may be taken together as —(CH$_2$)$_3$—, —(CH$_2$)$_4$—, —(CH$_2$)$_5$— or —CH$_2$CH$_2$OCH$_2$CH$_2$—;
R$_c$ is C$_1$-C$_4$ alkyl, C$_3$-C$_4$ alkenyl, C$_3$-C$_4$ alkynyl, C$_2$-C$_4$ haloalkyl, C$_2$-C$_3$ cyanoalkyl, C$_5$-C$_6$ cycloalkyl, C$_4$-C$_7$ cycloalkylalkyl or C$_2$-C$_4$ alkoxyalkyl;
R$_d$ and R$_e$ are independently H or C$_1$-C$_2$ alkyl;
Q$_1$ is S, SO$_2$ or NR$_2$;
Q$_2$ is O, S or NR$_2$;
Q$_3$ is O, S or NR$_3$;
Q$_4$ is O, S or NR$_4$;
n is 0, 1 or 2;
R$_2$ H, C$_1$-C$_3$ alkyl, phenyl, benzyl, CH$_2$CH=CH$_2$, CH$_2$C≡CH, CN, C$_1$-C$_3$ haloalkyl, OH, OCH$_3$ or OC$_2$H$_5$;
R$_3$ is H or C$_1$-C$_3$ alkyl;
R$_4$ is H or CH$_3$;
R$_5$ is H, halogen, CH$_3$, CH$_2$CH$_3$, OCH$_3$, OCH$_2$CH$_3$, OCF$_2$H or halomethyl;
R$_6$ is C$_1$-C$_4$ alkyl;

A is 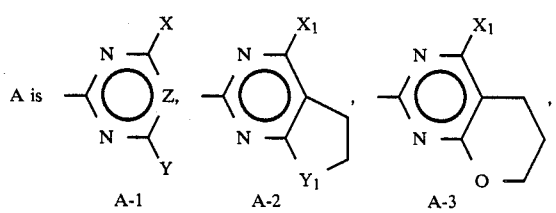

A-4, A-5, A-6, A-7 (structures)

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl, (structures)

$NR_d$ ($C_2$-$C_3$ cyanoalkyl) of $N(OCH_3)CH_3$;
m is 2 or 3;
$L_1$ and $L_2$ are independently O or S;
$R_f$ is H or $C_1$-$C_3$ alkyl;
$R_g$ and $R_h$ are independently $C_1$-$C_3$ alkyl;
Z is CH or N;
$Z_1$ is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that
(a) X is Cl, F, Br or I, then Z is CH and Y is $OCH_3$, $OC_2H_5$, $N(OCH_3)CH_3$, $NHCH_3$, $N(CH_3)_2$ or $OCF_2H$;
(b) when X or Y is $C_1$ haloalkoxy, the Z is CH;
(c) $X_4$ and $Y_4$ are not simultaneously Cl;
(d) when W is S, then E is a single bond, R is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;
(e) when the total number of carbons of X and Y is greater than four, then the number of carbons of $R_1$ must be less than or equal to two;
(f) $Q_3$ and $Q_4$ are not simultaneously S;
(g) when J is J-5, then $Q_3$ is $NR_3$ and $Q_4$ is $NR_4$; and
(h) when n is O, then $Q_3$ is $NR_3$ and $Q_4$ is $NR_4$.
(i) when $R_5$ is other than H, then R is H, $R_1$ is H, W is O, A is A-1 and E is a single bond.
(j) when J is J-6 or J-7, then A is A-1.

In the above definitions, the term "alkyl" used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyl isomers.

Alkynyl denotes straight chain or branch alkynes, e.g. ethynyl, 1-propynyl, 2-propynyl and the different butynyl isomers.

Alkylsulfonyl denotes methylsulfonyl, ethylsulfonyl and the different propylsulfonyl isomers.

Alkylthio, alkylsulfinyl, alkylamino, alkylsulfamoyl, etc. are defined in an analogous manner.

Cycloalkyl denotes, e.g., cyclopropyl, cyclobutyl and cyclopentyl.

The term "halogen", either alone or in compound words such as "haloalky", denotes fluroine, chlorine, bromine and iodine.

The total number of carbon atoms in a substituent group as indicated by the $C_i$-$C_j$ prefix where i and j are numbers from 1 to 5. For example, $C_1$-$C_3$ alkylsulfonyl would designate methylsulfonyl through propylsulfonyl, $C_2$ alkoxyalkoxy would designate $OCH_2OCH_3$.

Compounds preferred for reasons of increased ease of synthesis and/or greater herbicidal efficacy are:
1. Compounds of Formula I where E is a single bond.
2. Compounds of Formula I where E is $CH_2$ and $R_5$ is H.
3. Compounds of Formula I where E is O and $R_5$ is H.
4. Compounds of Preferred 1 where
   W is O;
   $R_1$ is H, F, Cl, Br, $C_1$-$C_2$ alkyl, $C_1$-$C_3$ alkoxy, $C_1$-$C_3$ alkylthio, or $C_1$-$C_2$ alkyl, $C_1$-$C_3$ alkoxy or $C_1$-$C_3$ alkylthio substituted with 1-3 atoms of F, Cl or Br;
   $R_2$ is H or $C_1C_3$ alkyl;
   $R_5$ is H;
   X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$, (structures)

$OCH_2H$, $SCF_2H$, cyclopropyl, $C\equiv CH$, $C\equiv CCH_3$ or $OCF_2Br$.
5. Compounds of Preferred 4 where A is A-1.
6. Compounds of Preferred 5 where J is J-1.
7. Compounds of Preferred 5 where J is J-2.
8. Compounds of Preferred 5 where J is J-3.
9. Compounds of Preferred 5 where J is J-4.
10. Compounds of Preferred 5 where J is J-5.
11. Compounds of Preferred 5 where J is J-6.
12. Compounds of Preferred 5 where J is J-7.
13. Compounds of Preferred 6 where R is H
R₁ is H, Cl, CH₃ or OCH₃;
X is CH₃, OCH₃, Cl, OC₂H₅ or OCF₂H; and
Y is CH₃, OCH₃, C₂H₅, CH₂OCH₃, NHCH₃, CH(OCH₃)₂ or cyclopropyl.

14. Compounds of Preferred 2 where
    R is H;
    J is J-1;
    R₁ is H;
    R₂ is H or CH₃;
    A is A-1;
    X is CH₃, OCH₃, OCH₂CH₃, Cl or OCF₂H; and
    Y is CH₃, OCH₃, C₂H₅, CH₂OCH₃, NHCH₃; CH(OCH₃)₂ or cyclopropyl.

15. Compounds of Preferred 3 where
    R is H;
    J is J-1;
    R₁ is H;
    R₂ is H or CH₃;
    A is A-1;
    X is CH₃, OCH₃, OCH₂CH₃, Cl or OCF₂H; and
    Y is CH₃, OCH₃, C₂H₅, CH₂OCH₃, NHCH₃, CH(OCH₃)₂ or cyclopropyl.

Compounds specifically preferred for reasons of greatest ease of synthesis and/or greatest herbicidal efficacy are:

N[(4,6-Dimethoxypyrimidin-2-yl)aminocarbonyl]-5-methoxy-1,2,3-benzothiadiazole-4-sulfonamide, m.p. 120°–129° C.(d); and N-[(4-methoxy-6-methyl-1,3,5-triazin-2-yl)aminocarbonyl]-5-methoxy-1,2,3-benzothiadiazole-4-sulfonamide, m.p. 176°–178° C.

N-[[4-ethoxy-6-(methylamino)-1,3,5-triazin-2-yl]aminocarbonyl]-1-methyl-1H-benzotriazole-4-sulfonamide, m.p. 203°–209° C.

The compounds of this invention are highly active as preemergent and/or postemergent herbicides or plant growth regulants. Some of the compounds have utility for selective weed control in crops such as oilseed rape, rice, barley, cotton and sugar beets.

DETAILED DESCRIPTION OF THE INVENTION

Synthesis

The following discussion represents a general outline for the preparation of the compounds of this invention. All of the syntheses described below are multistep with one or more methods being taught for each step. This allows for a wide variety of possible synthetic pathways to prepare a particular compound of Formula I. The proper choice of the synthetic pathway and the best ordering of the reaction sequences for each individual compound will be known to one skilled in the art.

The compounds of Formula I can be prepared by one or more of the methods described below in Equations 1 through 5.

As shown in Equation 1, many of the compounds of Formula I can be prepared by reacting a sulfonyl isocyanate (W=O) or, a sulfonyl isothiocyanate (W=S) of Formula II with an appropriate heterocyclic amine of Formula III. R, A and W are as previosuly defined.

EQUATION 1

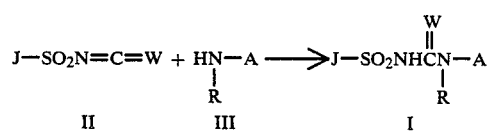

The reaction is carried out at 25° to 100° C. in an inert, aprotic solvent such as methylene chloride or xylene for 0.5 to 24 hours as taught in U.S. Pat. No. 4,127,405.

Many of the compounds of Formula I, where W is S and R is H (Ia), can be prepared by reacting the appropriate sulfonamide of Formula IV with a heterocyclic isothiocyanate of Formula V, as shown in Equation 2.

EQUATION 2

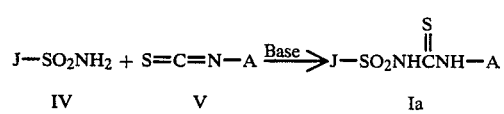

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III which would be known to one skilled in the art as taught in EPO Publication 35,893.

Many of the compounds of Formula I, where W is O (Ib), can be prepared by reacting a sulfonylcarbamate of Formula VI with an appropriate amine of Formula III, as shown in Equation 3.

EQUATION 3

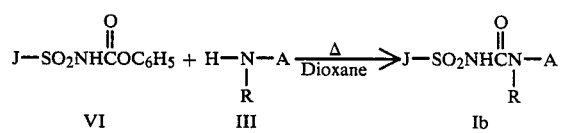

The reaction is carried out at 50° to 100° C. in a solvent such as dioxane for 0.5 to 24 hours. The required carbamates VI are prepared by reacting the corresponding sulfonamides IV with diphenylcarbonate in the presence of a strong base.

Compounds of Formula Ib can also be prepared, as shown in Equation 4, by reacting a heterocyclic carbamate of Formula VII with an appropriate sulfonamide of Formula IV.

EQUATION 4

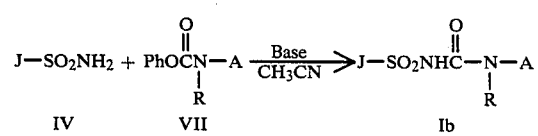

The reaction is carried out at 0° to 50° C. in a solvent such as acetonitrile or dioxane in the presence of a non-nucleophilic base such as DBU for 0.2 to 24 hours. The required phenylcarbamate VII are prepared by reacting the corresponding heterocyclic amines III with diphenylcarbonate or phenylchloroformate in the presence of a strong base.

Many of the compounds of Formula Ib can be prepared by reacting the sulfonamides of Formula IV with an appropriate methylcarbamate of Formula VIII in the presence of an equimolar amount of trimethylaluminum, as shown in Equation 5.

EQUATION 5

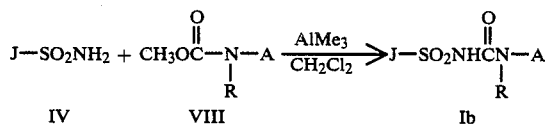

The reaction is carried out at 25° to 40° C. in a solvent such as methylene chloride for 10 to 96 hours under an inert atmosphere. The required carbamates VIII are prepared by reacting the corresponding amines III with dimethylcarbonte or methyl chloroformate in the presence of a strong base.

The intermediate sulfonyl isocyanates (W=O) and sulfonyl isothiocyanates (W=S) of Formula II from Equation 1 can be prepared as shown in Equations 6 through 10.

As shown in Equation 6, many of the sulfonyl isocyanates of Formula IIa can be prepared by the reaction of sulfonamides of Formula IV with phosgene, in the presence of n-butylisocyanate and a tertiary amine catalyst, at reflux in a solvent such as xylene by the method of U.S. Pat. No. 4,238,621.

EQUATION 6

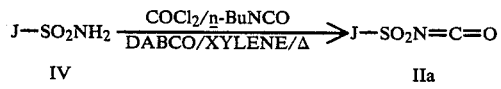

The sulfonyl isocyanates can also be prepared from the sulfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound with phosgene and a tertiary amine catalyst at reflux in xylene solvent. The method is similar to a procedure taught by Ulrich and Sayigh, *Newer Methods of Preparative Organic Chemistry*, Vol. VI, p 223–241, Academic Press, New York and London, W. Foerst Ed.

An alternative two step procedure for preparing sulfonyl isocyanates of Formula IIa is shown in Equation 7.

EQUATION 7

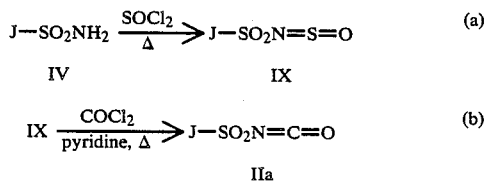

The sulfonamides of Formula IV are heated with excess thionyl chloride forming N-sulfinyl sulfonamides of Formula IX. The intermediate N-sulfinyl sulfonamides are heated in an inert solvent such as toluene with phosgene (e.g. 2–3 equivalents) and pyridine (e.g. 0.1 equivalents) to give sulfonyl isocyanates of Formula IIa. The method is similar to that taught by Ulrich et al. *J. Org. Chem* 34, 3200 (1969).

Alternatively, as shown in Equation 8, many of the sulfonyl isocyanates of Formula IIa can be prepared by reacting the corresponding sulfonyl chlorides X with cyanic acid salts.

EQUATION 8

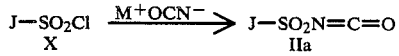

The reaction is carried out at 25° to 100° C. in an inert aprotic solvent such as acetonitrile for 0.5–24 hours in the presence of phosphorus pentoxide and an alkali metal salt such as lithium iodide.

Many of the sulfonyl isocyanates of Formula IIb can be prepared, as shown in Equation 9, by contacting phenols of Formula XI with chlorosulfonyl isocyanate according to the teachings of Lohaus, *Chem. Ber.*, 105, 2791 (1972) or U.S. Pat. No. 4,191,553.

EQUATION 9

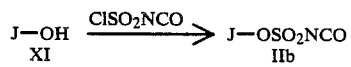

Many of the sulfonyl isothiocyanates of Formula IIc can be prepared, as shown in Equation 10, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

EQUATION 10

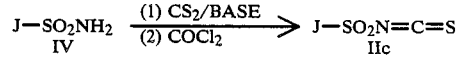

The sulfonamides of Formula IV of Equations 2, 4, 5, 6, 7 and 10 as well as the other sulfonamides required to prepare the compounds of this invention can be prepared from the corresponding sulfonyl chlorides of Formula X by contacting with either anhydrous or aqueous ammonia as shown in Equation 11.

EQUATION 11

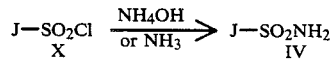

The preparation of sulfonamides from sulfonyl chlorides is widely reported in the literature, for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp., New York, 1948.

Similarly, many sulfonamides of Formula IV can be prepared from the corresponding lithium reagent of Formula XII as shown in Equation 12. M represents the lithium moiety of the metalated reagents.

EQUATION 12

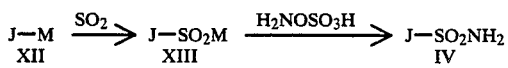

The metalated intermediates XII are contacted with sulfur dioxide to afford the lithium sulfinates of Formula XIII. Intermediates XIII are subsequently contacted with hydroxylamine-O-sulfonic acid to afford the sulfonamides of Formula IV. The procedure for preparing similar sulfonamides by this method is taught in South African patent appln. No. 85-1568.

Alternatively, many sulfonamides IV can be prepared by dealkylation of their corresponding N-t-butyl sulfonamides XIV as shown in Equation 13.

EQUATION 13

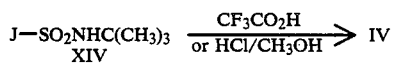

The reaction is carried out by contacting the N-t-butyl sulfonamide XIV with a strong acid such as trifluoroacetic acid or methanolic HCl at 25° to 50° C. for 0.5 to 24 hours. The N-t-butyl sulfonamides XIV are readily prepared by reacting sulfonyl chlorides X with t-butylamine and are useful either as an aid in purification, or to enhance solubility for subsequent reactions, or to protect the sulfonamide function from competing with reactions at other parts of the molecule.

The sulfonyl chlorides of Formula X of Equations 8 and 11 are important intermediates for the preparation of the compounds of this invention. The synthesis of the required sulfonyl chloride intermediates are described in Equations 14 through 20.

As shown in Equation 14, many of the sulfonyl chlorides of Formula X can be prepared by chlorosulfonating the parent ring compounds of Formula XV.

EQUATION 14

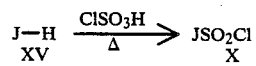

The success of this reaction depends on the nature of compounds XV and their ring substituents which will be known to one skilled in the art. Methods for conducting this reaction are described by E. Gilbert in "Sulfonation and Related Reactions" p. 84–88, Interscience Publishers 1965 and the references cited therein.

As shown in Equation 15, many of the sulfonyl chlorides of Formula X can be prepared from the corresponding amines XVI by a Meerwein reaction.

EQUATION 15

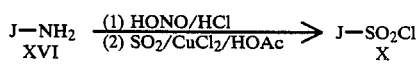

The reaction involves diazotization of the amine XVI with sodium nitrite in aqueous HCl, followed by reaction of the diazonium salt with sulfur dioxide and cupric chloride in acetic acid analogous to the teachings of Yale and Sowinski, *J. Org. Chem.*, 25, 1824 (1960).

Alternatively, sulfonyl chlorides of Formula X can be prepared by a modification of the above procedure as shown in Equation 16.

EQUATION 16

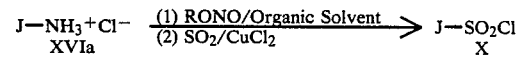

The amine hydrochloride salts XVIa are diazotized with an alkylnitrite in an organic solvent, such as acetonitrile or acetone, and the resulting diazonium salts are reacted with sulfur dioxide and cupric chloride to give sulfonyl chlorides X. M. Doyle, in *J. Org. Chem.* 42, 2426, 2431 (1977), describes conditions for doing similar Meerwein reactions.

Many of the sulfonyl chlorides of Formula X can also be prepared by oxidative chlorination of the corresponding thio compounds of Formula XVII as shown in Equation 17. R' is H, alkyl, benzyl or carbamoyl.

EQUATION 17

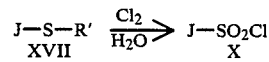

The reaction is carried out by addtion of molecular chlorine or a chlorine equivalent to the thio compound in the presence of water at 0° to 80° C. in an aliphatic carboxylic acid solvent such as acetic acid or an inert organic solvent such as dichloroethane for 1 to 24 hours. Specific reaction conditions are taught by A. Wagenaar in *Recl. Trav. Chim. Pays-Bas*, 101, 91 (1982).

Alternatively, many of the sulfonyl chlorides of Formula X can be prepared by the two-step sequence shown in Equation 18 starting from the thio compounds XVII where R' is H (XVIIa).

EQUATION 18

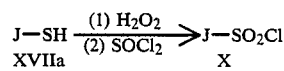

The thiol XVIIa is contacted with excess hydrogen peroxide in the presence of base to give a sulfonic acid salt which in turn is converted to the desired sulfonyl chloride by contacting with a suitable reagent such as thionyl chloride or phosphorous pentachloride as known to one skilled in the art. Thiols XVIIa can also be oxidized to sulfonyl chlorides X with sodium hypochlorite using the methods taught in South African patent appln. No. 84/8844.

Many of the sulfonyl chlorides of Formula X can be prepared from the corresponding lithium or Grignard reagent of Formula XII and sulfuryl chloride as shown in Equation 19. M represents either the lithium or MgX' moiety of the metalated reagent.

EQUATION 19

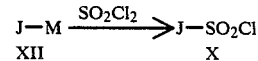

The metalated intermediates XII are contacted with sulfuryl chloride to afford sulfonyl chlorides X. The procedure for preparing similar sulfonyl chlorides by this method is taught by Bhattacharya et al., *J. chem. Soc. (C)*, 1265 (1968).

Sulfonyl chlorides of Formula Xa can be prepared from compounds of Formula XVIII by the sequence of reactions shown in Equation 20. [X] represents a suitable halogenating reagent and X represents a reactive halogen. This method is taught in U.S. Pat. No. 4,420,325.

EQUATION 20

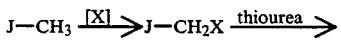

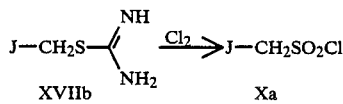

Many of the S-arylthiocarbamates of Formula XVIIc (XVII, R'=CON(CH$_3$)$_2$) can be prepared by the Newman-Kwart rearrangement starting with the corresponding phenols XI as shown in Equation 21.

EQUATION 21

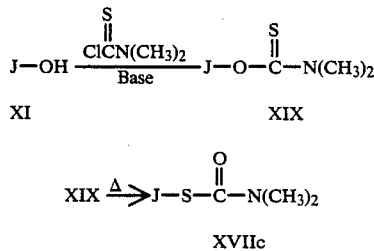

The phenol XI is first reacted with N,N-dimethylthiocarbamoyl chloride in the presence of a base. The resulting O-aryl-N,N-dimethylthiocarbamate XIX is then heated at 150° C. to 300° C. for 2 to 24 hours as taught by Newman and Karnes *J. Org. Chem.*, 31, 3980 (1966) to give the desired S-aryl-N,N-dimethylthiocarbamate XVIIc. The corresponding thiols XVIIa can be obtained by hydrolysis of the thiocarbamates XVIIc.

Many of the sulfides of Formula XVII where R' is alkyl or benzyl can be prepared by reacting a halocompound of Formula XX with an appropriate mercaptan in the presence of a base as shown in Equation 22. R' is alkyl or benzyl and X' is F, Cl or Br.

EQUATION 22

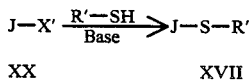

The reaction is carried out in a solvent such as DMF at 25° to 150° C. for 0.5 to 24 hours. The halocompounds XX must not contain functionality which can be attacked by a mercaptide anion as will be known to one skilled in the art.

The amines of Formula XVI in Equation 15 can be prepared by reduction of the corresponding nitro compounds of Formula XXI as shown in Equation 23.

EQUATION 23

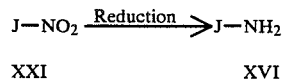

The reduction of nitro compounds to amines can be carried out by any of several known methods as described in *Preparative Organic Chemistry*, 4 Ed., p. 557–563, John Wiley and Sons, New York and London, G. Hilgetag and A. Martini Ed.

The amines of Formula XVI are versatile intermediates for preparing phenols of Formula XI and halocompounds of Formula XX by the diazotization reactions of Equation 24. Compounds XXII represent diazonium salts derived from amines XVI.

EQUATION 24

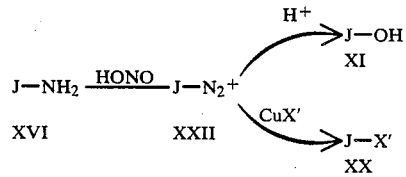

Hodgson and Dodgson, in *J. Soc. Dyers Colour.* 64, 65 (1948), teach methods for conducting the transformation of Equation 24 where J=J-1, J-2 (Q=S). For a general review of methods for diazotizing amines and reactions of diazonium salts see K. Schank, Ch. 14, p. 645 and D. J. Wulfman, Ch. 8, p. 247 in "The Chemistry of Diazonium and Diazo Groups," S. Patai Ed., Wiley, 1978.

Phenols of Formula XI can also be prepared from ethers of Formula XXIII, where A represents a suitable alkyl or arylalkyl protecting group, as shown in Equation 25. T. Green teaches methods for deprotecting ethers to phenols in "Protective Groups in Organic Synthesis," Ch. 2, p. 10, Wiley, 1981.

EQUATION 25

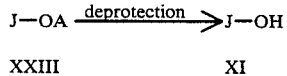

Metalated intermediates of Formula XII in Equations 12 and 19 can be prepared from halocompounds of Formula XX by methods well known in the art.

Many of the nitro compounds of Formula XXI in Equation 23 can be prepared from ring compounds XV by the reaction shown in Equation 26.

EQUATION 26

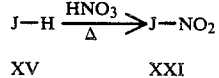

The success of this electrophilic substitution reaction depends on the nature of compounds XV and their ring substituents which will be known to one skilled in the art. Methods for nitrating many of the compounds of Formula XV are taught in "Comprehensive Heterocyclic Chemistry" Vol. 5, Sec. 4.11 and Vol. 6, Sec. 4.22, 4.24, 4.26, K. T. Potts, Ed., Pergamon Press, Oxford 1984 and the reference cited therein. A general review of nitrating procedure is taught by J. G. Hoggett et al. in "Nitration and Aromatic Reactivity", Cambridge University Press, 1971.

Many intermediates of Formula XXIV (J-G) can be prepared by the ring-forming reactions exemplified by Equations 27 to 31. In these equations, G represents the $SO_2NH_2$, $SO_2NHC(Me)_3$, H, SR', $CH_3$, X', $NO_2'$, or OA moiety, as defined above, of Compounds IV, XIV, XV, XVII, XVIII, XX, XXI or XXIII respectively. The suitability of a given reaction to form a particular compound of Formula XXIV will depend on the nature of G and will be known to one skilled in the art.

EQUATION 27

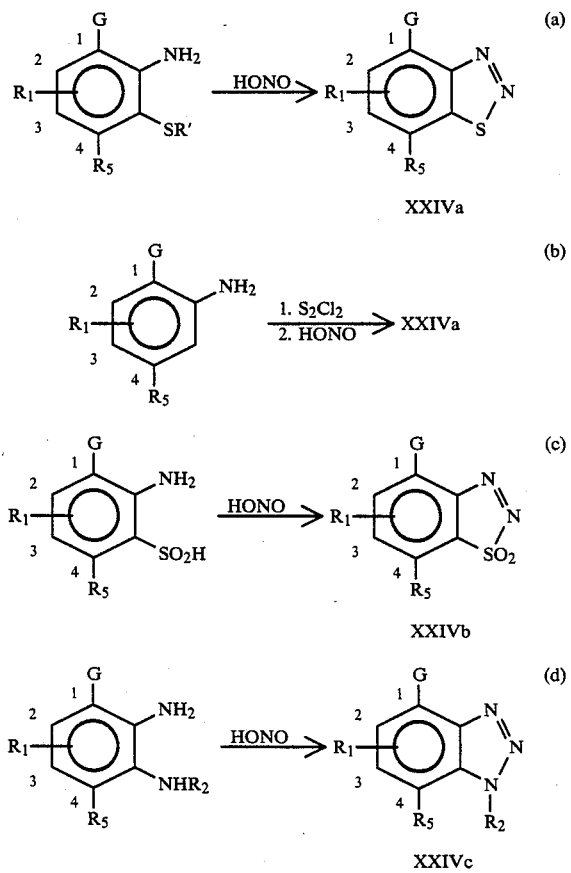

Many of the compounds of Formula XXIV where J=J-1 (XXIVa, XXIVb, XXIVc) can be prepared by the diazotization reactions of Equation 27. Methods for these reactions are described by (a) L. L. Bambas, "The Chemistry of Heterocyclic Compounds", Vol. 4, p. 10, A. Weisberger Ed., Interscience, New York 1952; (b) P. Kirby et al., J. Chem. Soc. (C), 2250 (1970); (c) R. W. Hoffmann et al., Chem. Ber., 98, 3470 (1965); (d) H. Wamhoff, "Comprehensive Heterocyclic Chemistry", Vol. 5, p. 669, K. T. Potts Ed., Pergamon Press, Oxford 1984; and the references cited therein.

Many of the compounds of Formula XXIV where J=J-2 can be prepared by the methods described in Equation 27, but starting with compounds in which the G and $R_5$ substituents are interchanged.

EQUATION 28

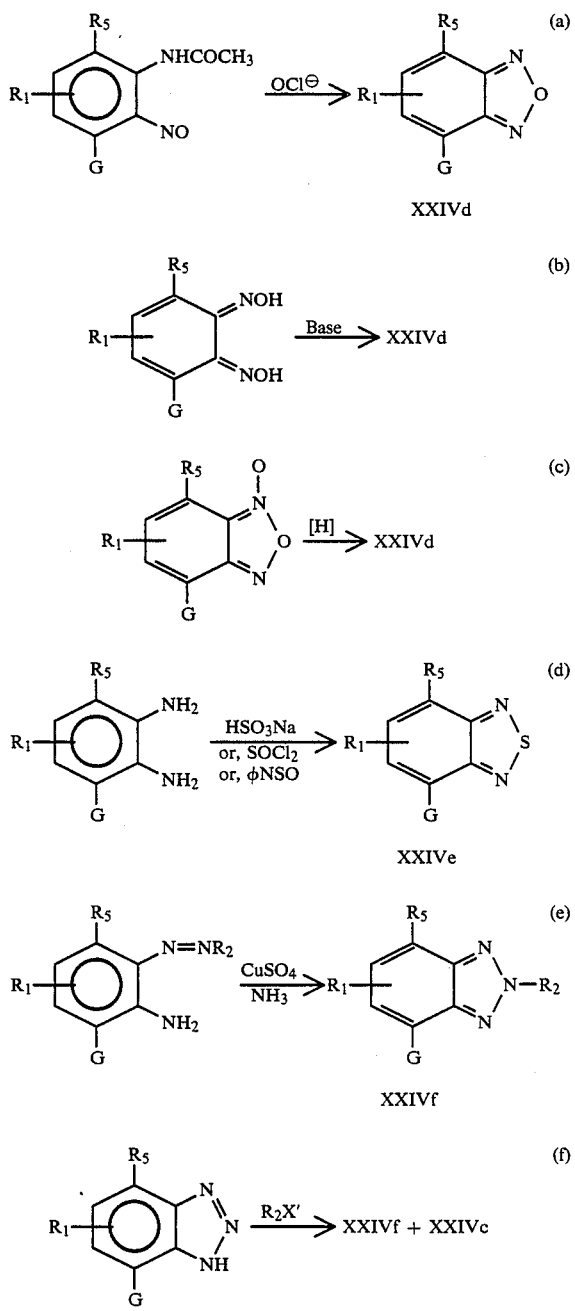

Many of the compounds of Formula XXIV where J=J-3 (XXIVd-f) can be prepared by the reactions of Equation 28. Methods for these reactions are described by (a), (b), (c) M. M. Campbell, "Comprehensive Organic Chemistry", Vol. 4, p. 961, Barton and Ollis Ed., Pergamon Press, Oxford, 1979; (d) W. R. Shipman, "Heterocyclic Compounds", Vol. 7, Ch. 7, R. C. Elderfield Ed., Wiley, N.Y., 1961; (e), (f) H. Wamhoff, "Comprehensive Heterocyclic Chemistry", Vol. 5, p. 669; K. T. Potts Ed., Pergamon Press, Oxford, 1984; and the references cited therein.

EQUATION 29

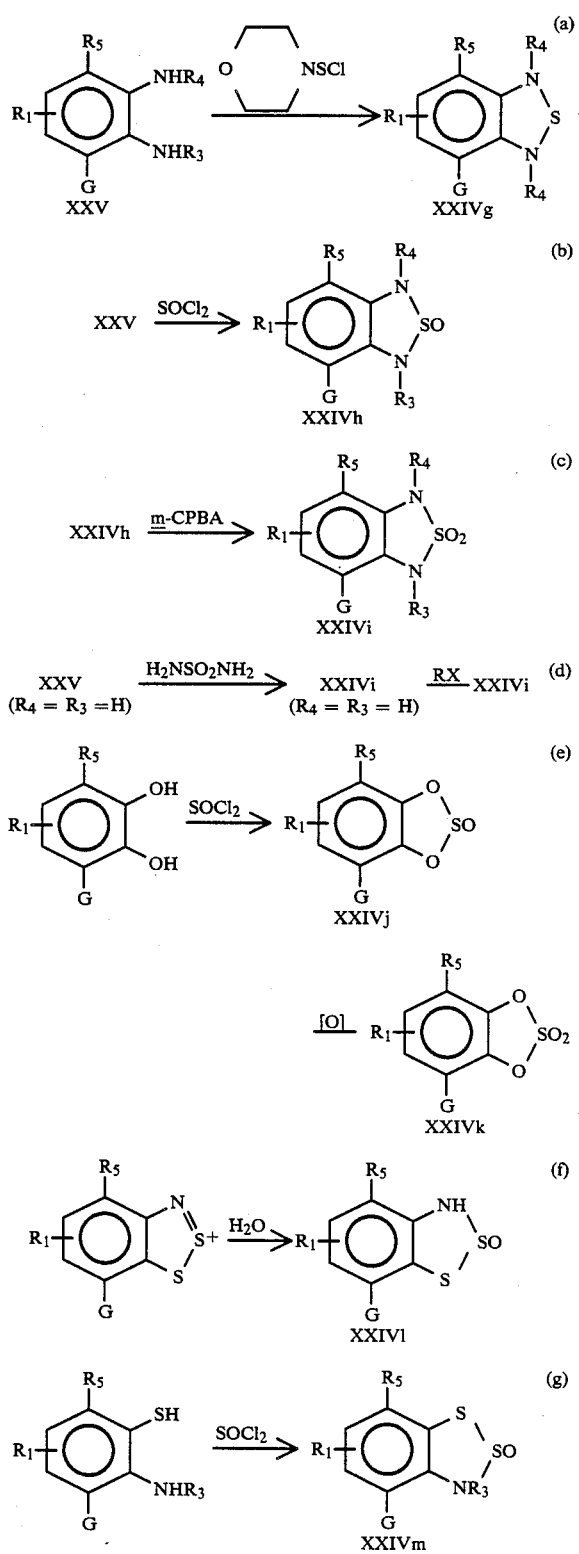

Many compounds of Formula XXIV where J=J-4 (XXIVg-m) can be prepared by the reactions of Equation 29. Methods for these reactions are described by (a) M. Bryce, *J. Chem. Soc. Perk. Trans. I*, 2591 (1984); (b), (c) R. M. Acheson et al., *J. Med. Chem.*, 24, 1300 (1981); (d) J. D. Carson, U.S. Pat. No. 3,177,221; (e), (f), (g) G. W. Fischer and T. Zimmermann, "Comprehensive Heterocyclic Chemistry", Vol. 6, p. 851, K. T. Potts Ed., Pergamon Press, Oxford, 1984; and the references cited therein.

EQUATION 30

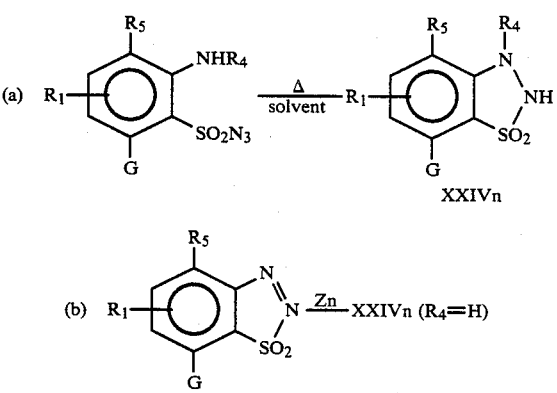

Many of the compounds of Formula XXIV where J=J-5 (XXIVn) can be prepared by the reactions of Equation 30. Methods for these reactions are described by (a) R. A. Abramovitch, *J. Org. Chem.*, 42, 2920 (1977); (b) R. W. Hoffmann et al., *Chem. Ber.*, 98, 3470 (1965); and the references cited therein.

EQUATION 31

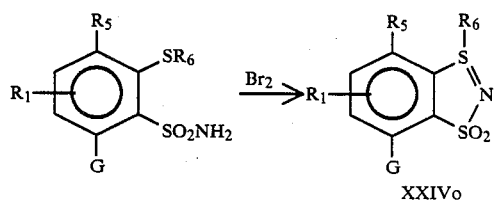

Many of the compounds of Formula XXIV where J=J-6 (XXIVo) can be prepared as shown in Equation 31. A. W. Wagner and R. Banholzer teach methods for such reactions in *Chem Ber.*, 96, 1177(1963). Similarly, many compounds of Formula XXIV where J=J-7 can be prepared as described in Equation 31, but starting with compounds in which the G and $R_5$ substituents are interchanged.

The heterocyclic amines of Formula III in Equations 1 and 3 can be prepared by methods known in the literature, or simple modifications thereof, by one skilled in the art.

For a review of the synthesis and reactions of 2-amino- and 2-methylaminopyrimidines III (A=A-1, Z=CH) see *The Chemistry of Heterocyclic Compounds*, Vol. 16, Wiley-Interscience, New York (1962). For a review of the synthesis and reactions of 2-amino- and 2-methylamino-s-triazines III (A=A-1, Z=N) see *The Chemistry of Heterocyclic Compounds*, Vol. 13, Wiley-Interscience, New York (1959), F. C. Schaefer, U.S. Pat. No. 3,154,547 and F. C. Schaefer and K. R. Huffman, *J. Org. Chem.*, 28, 1812 (1963). EP-A No. 84,224 and W. Braker et al., *J. Chem. Soc.*, 69, 3072 (1947) describes methods for preparing aminopyrimidines and triazines substituted by acetal groups such as dialkoxymethyl or 1,3-dioxolan-2-yl. South African Patent Application No. 83/7434 describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cyclopenta[d]pyrimidines-2-amines (III, A is A-2) and the 6,7-dihydro-5H-pyrano[2.3-d]pyrimidin-2-amines (III, A is A-3) can be prepared as taught in EP-A No. 15,683. The furo[2.3-d]pyrimidin-2-amines (III, A is A-4) are described in EP-A No. 46,677.

Compounds of Formula III, where A is A-5, are described in EP-A-73,562. Compounds of Formula III, where A is A-6, are described in EP-A-94,260.

The amines of Formula III where A is A-7 can be prepared by methods taught in European Publication No. 125,864 (published 11/21/84) or by suitable modifications that would be obvious to one skilled in the art.

The preparation of the compounds of this invention is further illustrated by the following examples.

EXAMPLE 1

5-Methoxy-1,2,3-benzothiadiazole-4-sulfonyl chloride

To a stirred solution of 50 mL of chlorosulfonic acid at 0° C. was added 4.15 g of 5-methoxy-1,2,3-benzothiadiazole under an inert atmosphere. The resulting mixture was heated at reflux for 30 minutes. After cooling to room temperature, the reaction mixture was added to 600 mL ice-water mixture. The precipitate was collected, washed with water and ether, and air dried to give 5.6 g of the title compound as a white solid, m.p. 131°–134° C.

90 MHz NMR (CDCl$_3$)δ: 4.27 (s, 3H, CH$_3$); 7.71 (d, 1H, arom.); and 8.51 (d, 1H, arom.).

IR (nujol) 1375, 1180, 832 cm$^{-1}$.

EXAMPLE 2

2,1,3-Benzothiadiazole-4-sulfonyl chloride

To a stirred solution of 100 mL of chlorosulfonic acid at 0° C. was added 10.0 g of 2,1,3-benzothiadiazole under an inert atmosphere. The resulting mixture was heated at reflux for 30 minutes and cooled to room temperature. The reaction mixture was added dropwise to 1000 mL ice. The precipitate was collected, washed with water, and air dried to give the title compound as a beige solid, m.p. 146°–148° C.

90 MHz NMR (CDCl$_3$)δ: 7.83 (m, 1H, arom.); and 8.42 (m, 2H, arom.).

IR (nujol) 1370, 1165, 835, 815, 750, 730 cm$^{-1}$.

EXAMPLE 3

2,1,3-Benzoxadiazole-4-sulfonamide

To a stirred solution of 3.0 g of 2,1,3-benzoxadiazole-4-sulfonyl chloride and 200 mL of tetrahydrofuran at −30° C. was added 10 mL of ammonia under an inert atmosphere. The resulting suspension was stirred at ambient temperature for 3 hours. Concentrated ammonium hydroxide (20 mL) and water (20 mL) were added. The reaction was extracted with ethyl acetate and the organic extracts were combined, dried over magnesium sulfate, filtered, and stripped to give a crude solid. Recrystallization from chlorobutaneethanol afforded 1.82 g of the title compound as an orange-tan solid, m.p. 157°–159° C.

90 MHz NMR (CDCl$_3$-DMSO-d$_6$)δ: 7.6 (m, 3H, arom. and NH$_2$); and 8.09 (m, 2H, arom.).

IR (nujol) 3300, 3200, 1330, 1160 cm$^{-1}$.

EXAMPLE 4

1-Methyl-1H-benzotriazole-7-sulfonamide

To a stirred solution of 1.5 g of 1-methyl-1H-benzotriazole-7-sulfonyl chloride and 75 mL of tetrahydrofuran at 0° C. was added 5 mL of ammonia under an inert atmosphere. The resulting suspension was stirred at ambient temperature for 15 hours. Concentrated ammonium hydroxide (10 mL) and brine (10 mL) were added. The aqueous layer was adjusted to pH 7 with concentrated hydrochloric acid and was extracted with ethyl acetate. The combined organic extracts were dried over magnesium sulfate, filtered, and stripped to afford 1.38 g of the title compound as a white solid, m.p. 198°–200° C.

90 MHz NMR (CDCl$_3$-DMSO-d$_6$)δ: 4.63 (s, 3H, CH$_3$); 7.43 (m, 1H, arom.); 7.80 (s, 2H, NH$_2$); and 8.13 (m, 2H, arom.).

IR (nujol) 3250, 1315, 1150 cm$^{-1}$.

EXAMPLE 5

N-[(4,6-Dimethoxypyrimidin-2-yl)aminocarbonyl]-5-methoxy-1,2,3-benzothiadiazole-4-sulfonamide A solution of 5-methoxy-1,2,3-benzothiadiazole-4-sulfonamide (0.20 g) and of O-phenyl-N-(4,6-dimethoxypyrimidin-2-yl)carbamate (0.24 g) in 7 mL of acetonitrile was treated with 0.12 mL of 1,8-diazabicyclo[5.4.0]undec-7-ene. The solution was stirred for 2 hours. After diluting the reaction with water (10 mL) and acidifying it with 1N hydrochloric acid, the resulting precipitate was filtered, washed with water and ether, and air dried to give 0.24 g of the title compound as a beige solid, m.p. 120°–129° C. with decomposition.

200 MHz NMR (DMSO-d$_6$)δ:3.94 (s, 6H, OCH$_3$); 3.99 (s, 3H, NCH$_3$); 6.04 (s, 1H, CH); 7.92 (d, 1H, arom.); 8.74 (d, 1H, arom.); 10.57 (s, 1H, NH); and 13.09 (s, 1H, NH).

IR (nujol 1700 cm$^{-1}$.

EXAMPLE 6

N-[(4-Methoxy-6-methyl-1,3,5-triazin-2-yl)aminocarbonyl]-1-methyl-1H-benzotriazole-4-sulfonamide A solution of 1-methyl-1H-benzotriazole-4-sulfonamide (0.32 g) and of O-phenyl-N-(4-methoxy-6-methyltriazin-2-yl)carbamate (0.42 g) in 10 mL of acetonitrile was treated with 0.24 mL of 1,8-diazabicyclo[5.4.0]undec-7-ene. The mixture was stirred for 2 hours. After diluting the reaction with water (15 mL) and acidifying it with 1N hydrochloric acid, the resulting precipitate was filtered, washed with water and ether, and air dried to give 0.40 g of the title compound as a white solid, m.p. 134°–136° C. with decomposition.

200 MHz NMR (DMSO-d$_6$)δ: 2.46 (s, 3H, CH$_3$); 4.02 (s, 3H, OCH$_3$); 4.35 (s, 3H, NCH$_3$); 7.76 (m, 1H, arom.); 8.05 (d, 1H, arom.); 8.27 (d, 1H, arom.); 10.87 (s, 1H, NH); and 12.85 (s, 1H, NH).

IR (nujol) 1730 cm$^{-1}$.

EXAMPLE 7

N-[(4-Ethoxy-6-(methylamino)-1,3,5-triazin-2-yl)aminocarbonyl]-1-methyl-1H-benzotriazole-4-sulfonamide A solution of 1-methyl-1H-benzotriazole-4-sulfonamide (0.32 g) and of O-phenyl-N-(4-ethoxy-6-(methylamino)triazin-2-yl)carbamate (0.46 g) in 10 mL of acetonitrile was treated with 0.24 mL of 1,8-diazabicyclo[5.4.0]undec-7-ene. The mixture was stirred for 2 hours. After diluting the reaction with water (15 mL) and acidifying it with 1N hydrochloric acid, the resulting precipitate was filtered, washed with water and ether, and air dried to give 0.31 g of the title compound as a white solid, m.p. 203°–209° C.

200 MHz NMR (DMSO-d$_6$)δ: 1.30 (m, 3H, CH$_3$); 2.81 and 2.96 (m, 3H, NHCH$_3$); 4.35 (bs, 5H, OCH$_2$ and NCH$_3$); 7.6–8.4 (m, 4H, NH and arom); 10.28 and 10.46 (s, 1H, NH); 13.11 and 13.76 (s, 1H, NH).

IR (nujol) 1730, 1720 cm$^{-1}$.

EXAMPLE 8

N-[(Butylamino)carbonyl]-1-methyl-1H-benzotriazole-4-sulfonamide

To a stirred mixture of 1-methyl-1H-benzotriazole-4-sulfonamide (7.5 g), potassium carbonate (5.1 g), and 2-butanone (250 mL) was added butylisocyanate (3.9 mL) under an inert atmosphere. The reaction was heated at reflux for 15 hours. The cooled reaction mixture was poured into ice (500 mL), acidified with concentrated hydrochloric acid, and extracted with ethyl acetate-tetrahydrofuran. The extracts were dried over magnesium sulfate, filtered, and evaporated. The crude solid was washed with chlorobutane-hexanes and air dried to give 8.65 g of the title compound as a white solid, m.p. 170°–173° C.

90 MHz NMR (CDCl$_3$-DMSO-d$_6$)δ: 0.80 (m, 3H, CH$_3$); 1.27 (m, 4H, CH$_2$); 2.97 (q, 2H, CH$_2$); 4.41 (s, 3H, NCH$_3$); 6.40 (t, 1H, NH); 7.67 (m, 1H, arom); 8.07 (m, 2H, arom); 10.73 (s, 1H, NH).

IR (nujol) 1650 cm$^{-1}$.

EXAMPLE 9

1-Methyl-1H-benzotriazole-4-sulfonylisocyanate

To a stirred mixture of N-[(butylamino)carbonyl]-1-methyl-1H-benzotriazole-4-sulfonamide (8.25 g), 1,4-diazabicyclo[2,2,2]octane (catalytic amount), and xylenes (175 mL), heated at reflux under a nitrogen atmosphere, was added phosgene (2 mL) in small portions over 1 hour. The resulting suspension was heated an additional 0.5 hours and was cooled prior to filtering off the insoluble material. The filtrate was evaporated to give 3.05 g of the title compound as a pale yellow solid. IR (nujol) 2260 cm$^{-1}$. The compound was immediately diluted to 100 mL with dry acetonitrile and stored under nitrogen to give a 0.125M solution of the title compound for further use.

EXAMPLE 10

N-[(5,6-Dihydro-4-methylfuro(2,3-d)pyrimidin-2-yl)aminocarbonyl]-1-methyl-1H-benzotriazole-4-sulfonamide To a stirred solution of 5,6-dihydro-4-methylfuro(2,3-d)pyrimidin-2-amine (0.08 g) and 1,4-diazabicyclo[2,2,2]octane (catalytic amount) in acetonitrile (5 mL) was added 0.125M 1-methyl-1H-benzotriazole-4-sulfonylisocyanate in acetonitrile (4.0 mL) under a nitrogen atmosphere. After stirring for 4 hours, the reaction was diluted with water (20 mL) and the precipitate was filtered, washed with water and ether, and dried to give 0.09 g of the title compound as a white solid. m.p. 234°–240° C. with decomposition.

200 MHz NMR (DMSO-d$_6$)δ: 2.40 (s, 3H, CH$_3$); 3.18 (t, 2H, CH$_2$); 4.34 (s, 3H, NCH$_3$); 4.70 (t, 2H, OCH$_2$); 7.74 (t, 1H, arom); 7.98 (d, 1H, arom); 8.23 (d, 1H, arom); 10.38 (s, 1H, NH); 13.92 (s, 1H, NH).

IR (nujol) 1720, 1700 cm$^{-1}$.

EXAMPLE 11

1-Methyl-1H-1,3,2-benzodithiazole-4-sulfonamide, 3,3-dioxide

To a stirred suspension of 3-methylthio-1,2-benzenedisulfonamide (1.55 g) and methanol (50 mL) was added bromine (2 mL). The reaction was stirred under a nitrogen atmosphere for 6 days. It was stirred for an hour after adding 6N sodium hydroxide (2 mL) and water (6 mL). The resulting precipitate was filtered, washed with chlorobutane and ethanol, and dried to give 1.36 g of the title compound as an off-white solid; m.p. 249°–254° C.

90 MHz NMR (DMSO-d$_6$) δ: 3.12 (S, 3H, CH$_3$); 7.42 (S, 2H, NH$_2$); 8.0–8.4(m, 2H, arom.); 8.53 (d, 1H, arom.).

IR (nujol) 3400, 3250 cm$^{-1}$.

GENERAL STRUCTURES FOR TABLES I THROUGH VI

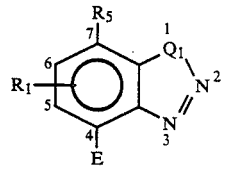

J-1

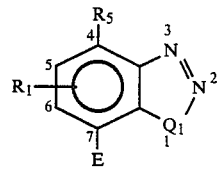

J-2

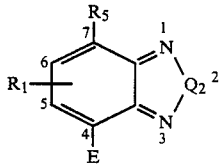

J-3

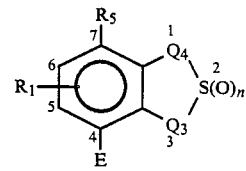

J-4

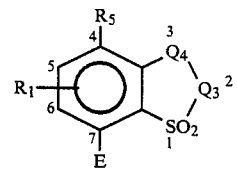

J-5

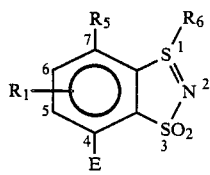

J-6

-continued TABLE I $$\text{structure with } R_5, R_1, R_6, SO_2, N_2, S_1 \text{ (positions 3,4,5,6,7)}$$

JSO₂NHCNA (A = A-1) with J-W, R substituents

| J | W | E | R | R₁ | R₅ | Q₁ | X | Y | Z | m.p. (°C.) |
|---|---|---|---|---|---|---|---|---|---|---|
| J-1 | O | — | H | H | H | S | CH₃ | CH₃ | CH | 207–209 |
| J-1 | O | — | H | H | H | S | CH₂CH₂CH₃ | CH₃ | CH | |
| J-1 | O | — | H | H | H | S | OCH₃ | CH₃ | CH | 206–208 |
| J-1 | O | — | H | H | H | S | OCF₃ | CH₃ | CH | |
| J-1 | O | — | H | H | H | S | OCH₂CH₂OCH₃ | CH₃ | CH | |
| J-1 | O | — | H | H | H | S | SCH₃ | CH₃ | CH | |
| J-1 | O | — | H | H | H | S | Br | CH₃ | CH | |
| J-1 | O | — | H | H | H | S | N(CH₃)₂ | CH₃ | CH | |
| J-1 | O | — | H | H | H | S | OCH₃ | OCH₃ | CH | 222–224 |
| J-1 | O | — | H | H | H | S | N(CH₃)₂ | OCH₂CH₃ | CH | |
| J-1 | O | — | H | H | H | S | Cl | OCH₃ | CH | 211–213 |
| J-1 | O | — | H | H | H | S | Br | OCH₃ | CH | |
| J-1 | O | — | H | H | H | S | OCH₃ | NHCH₃ | N | 263–271 (d) |
| J-1 | O | — | H | H | H | S | CH₃ | CF₃ | CH | |
| J-1 | O | — | H | H | H | S | CH₃ | CH₃ | N | |
| J-1 | O | — | H | H | H | S | CH₃ | OCH₃ | N | 179–181 |
| J-1 | O | — | H | H | H | S | CH₃ | OCH₂CH₂CH₂CH₃ | N | |
| J-1 | O | — | H | H | H | S | OCH₃ | OCH₃ | N | 183–184 |
| J-1 | O | — | H | H | H | S | NHCH₃ | OCH₂CH₃ | N | 233–234 |
| J-1 | O | — | H | H | H | S | OCH₃ | CN | N | |
| J-1 | O | — | H | H | OCF₂H | S | OCH₂ | OCH₂ | CH | |
| J-1 | O | — | H | 5-CH₃ | H | S | OCH₃ | OCH₃ | N | |
| J-1 | O | — | H | 5-CH₃ | H | S | OCH₃ | CH₃ | CH | |
| J-1 | O | — | H | 5-CH₃ | H | S | OCH₃ | OCH₃ | CH | |
| J-1 | O | — | H | 5-CH(CH₃)₂ | H | S | OCH₃ | OCH₃ | CH | |
| J-1 | O | — | H | 5-CF₃ | H | S | OCH₃ | OCH₃ | CH | |
| J-1 | O | — | H | 5-F | H | S | OCH₃ | OCH₃ | CH | |
| J-1 | O | — | H | 5-F | H | S | OCH₃ | OCH₃ | N | |
| J-1 | O | — | H | 5-Cl | H | S | OCH₃ | OCH₃ | N | |
| J-1 | O | — | H | 5-Cl | H | S | OCH₃ | OCH₃ | CH | |
| J-1 | O | — | H | 5-Cl | H | S | OCH₃ | CH₃ | CH | |
| J-1 | O | — | H | 5-Cl | H | S | Cl | OCH₃ | CH | |
| J-1 | O | — | H | 5-Cl | H | S | CH₃ | OCH₃ | N | |
| J-1 | O | — | H | 5-Br | H | S | CH₃ | OCH₃ | N | |
| J-1 | O | — | H | 5-Br | H | S | CH₃ | OCH₃ | CH | |
| J-1 | O | — | H | 5-NO₂ | H | S | CH₃ | OCH₃ | CH | |
| J-1 | O | — | H | 5-NO₂ | H | S | CH₃ | OCH₃ | N | |
| J-1 | O | — | H | 5-OCH₃ | H | S | H | H | CH | |
| J-1 | O | — | H | 5-OCH₃ | H | S | H | CH₃ | CH | |
| J-1 | O | — | H | 5-OCH₃ | H | S | CH₃ | CH₃ | CH | 195–198 |
| J-1 | O | — | H | 5-OCH₃ | H | S | OCH₃ | CH₃ | CH | 192–194 |
| J-1 | O | — | H | 5-OCH₃ | H | S | OCH₂CF₃ | CH₃ | CH | |
| J-1 | O | — | H | 5-OCH₃ | H | S | SCH₃ | CH₃ | CH | |
| J-1 | O | — | H | 5-OCH₃ | H | S | OCH₃ | OCH₃ | CH | 120–129 (d) |
| J-1 | O | — | H | 5-OCH₃ | H | S | Cl | OCH₃ | CH | 130–137 (d) |
| J-1 | O | — | H | 5-OCH₃ | H | S | OCH₃ | OCH₃ | N | 180–181 |
| J-1 | O | — | H | 5-OCH₃ | H | S | CH₃ | OCH₃ | N | 176–178 |
| J-1 | O | — | H | 5-OCH₃ | H | S | CH₃ | CH₃ | N | 190–191 |
| J-1 | O | — | H | 5-OCH₃ | H | S | OCH₂CH₃ | NHCH₃ | N | |
| J-1 | O | — | H | 5-OCH₃ | H | S | OCH₃ | C≡CH | N | |
| J-1 | O | — | H | 5-OCH₃ | H | S | OCH₃ | OCH₂CHCH₂ | N | |
| J-1 | O | — | H | 5-OCH₃ | H | S | OCH₃ | CH₂SO₂CH₃ | N | |
| J-1 | O | — | H | 5-OCH₃ | H | S | OCH₃ | CH₂COCH₂CH₃ | N | |
| J-1 | O | — | H | 5-SO₂N(CH₃)₂ | H | S | OCH₃ | CH₃ | N | |
| J-1 | O | — | H | 5-SO₂N(CH₃)₂ | H | S | OCH₃ | CH₃ | CH | |
| J-1 | O | — | H | 5-SO₂NHCH₂CN | H | S | OCH₃ | CH₃ | CH | |
| J-1 | O | — | H | 5-SO₂N | H | S | OCH₃ | CH₃ | CH | |
| J-1 | O | — | H | 5-SCH₃ | H | S | OCH₃ | CH₃ | CH | |
| J-1 | O | — | H | 5-SOCH₂CH₃ | H | S | OCH₃ | CH₃ | CH | |
| J-1 | O | — | H | 5-SO₂CH₂CH₃ | H | S | OCH₃ | CH₃ | CH | |
| J-1 | O | — | H | 5-CH₂CN | H | S | OCH₃ | CH₃ | CH | |
| J-1 | O | — | H | 5-CO₂CH₂CF₃ | H | S | OCH₃ | CH₃ | CH | |
| J-1 | O | — | H | 5-OCF₂H | H | S | OCH₃ | CH₃ | CH | |
| J-1 | O | — | H | 5-CH₂OCH₃ | H | S | OCH₃ | CH₃ | CH | |
| J-1 | O | — | H | 5-N(CH₃)₂ | H | S | OCH₃ | CH₃ | CH | |
| J-1 | O | — | H | 6-Cl | H | S | OCH₃ | CH₃ | CH | |
| J-1 | O | — | H | 6-Cl | H | S | OCH₃ | CH₃ | N | |
| J-1 | O | — | H | 6-Cl | H | S | OCH₃ | OCH₃ | N | |
| J-1 | O | — | H | 6-OCH₃ | H | S | OCH₃ | OCH₃ | CH | 220–222 |

TABLE I-continued $$\text{JSO}_2\text{NHCNA} \quad (A = A\text{-}1)$$
with W (=O double bond) on C and R on N.

| J | W | E | R | R₁ | R₅ | Q₁ | X | Y | Z | m.p. (°C.) |
|---|---|---|---|---|---|---|---|---|---|---|
| J-1 | O | — | H | 6-OCH₃ | H | S | CH₃ | OCH₃ | CH | 219–220 |
| J-1 | O | — | H | 6-OCH₃ | H | S | CH₃ | CH₃ | CH | 206–209 |
| J-1 | O | — | H | 6-OCH₃ | H | S | OCH₃ | Cl | CH | 202–205 |
| J-1 | O | — | H | 6-OCH₃ | H | S | OCH₃ | N(CH₃)₂ | N | 215–217 |
| J-1 | O | — | H | 6-OCH₃ | H | S | OCH₃ | CH₃ | N | 176–179 |
| J-1 | O | — | H | 6-OCH(CH₃)₂ | H | S | OCH₃ | OCH₃ | CH | |
| J-1 | O | — | H | 6-OCH(CH₃)₂ | H | S | NHCH₃ | OCH₃ | CH | |
| J-1 | O | — | H | 6-OCH(CH₃)₂ | H | S | NHCH₃ | NHCH₃ | CH | |
| J-1 | O | — | H | 6-SCH₂CH₃ | H | S | CH₃ | OCH₃ | N | |
| J-1 | O | — | H | 6-SCH₂CH₃ | H | S | CH₃ | N(CH₃)₂ | N | |
| J-1 | O | — | H | 6-SCH₂CH₃ | H | S | CH₃ | N₃ | N | |
| J-1 | O | — | H | 6-SCH₂CH₃ | H | S | CH₃ | CN | CH | |
| J-1 | O | — | H | 6-SO₂CH₃ | H | S | CH₃ | OCH₃ | CH | |
| J-1 | O | — | H | 6-SO₂CH₃ | H | S | CH₃ | OCH₃ | N | |
| J-1 | O | — | H | 6-N(CH₃)₂ | H | S | CH₃ | OCH₃ | N | |
| J-1 | O | — | H | 6-N(CH₃)₂ | H | S | CH₃ | OCH₃ | CH | |
| J-1 | O | — | H | 6-N(CH₃)₂ | H | S | OCH₃ | OCH₃ | CH | |
| J-1 | O | — | H | 6-N(CH₃)₂ | H | S | OCH₃ | OCH₃ | N | |
| J-1 | O | — | H | 6-N(CH₃)₂ | H | S | OCH₃ | CH₃ | N | |
| J-1 | O | — | H | H | H | SO₂ | OCH₃ | CH₃ | N | |
| J-1 | O | — | H | H | H | SO₂ | OCH₃ | OCH₃ | N | |
| J-1 | O | — | H | H | CH₃ | SO₂ | OCH₃ | OCH₃ | CH | |
| J-1 | O | — | H | H | H | SO₂ | CH₃ | OCH₃ | CH | |
| J-1 | O | — | H | H | H | SO₂ | Cl | OCH₃ | CH | |
| J-1 | O | — | H | H | H | SO₂ | Cl | N(CH₃)₂ | CH | |
| J-1 | O | — | H | 5-CH₂CF₃ | H | SO₂ | CH₃ | OCH₃ | N | |
| J-1 | O | — | H | 5-Br | H | SO₂ | CH₃ | OCH₃ | N | |
| J-1 | O | — | H | 5-OCH₂CH₃ | H | SO₂ | CH₃ | OCH₃ | N | |
| J-1 | O | — | H | 5-OCF₃ | H | SO₂ | CH₃ | OCH₃ | CH | |
| J-1 | O | — | H | 5-OCF₂H | H | SO₂ | CH₃ | OCH₃ | CH | |
| J-1 | O | — | H | 5-N(CH₃)₂ | H | SO₂ | CH₃ | OCH₃ | CH | |
| J-1 | O | — | H | 5-N(CH₃)₂ | H | SO₂ | OCH₃ | OCH₃ | CH | |
| J-1 | O | — | H | 5-N(CH₃)₂ | H | SO₂ | OCH₃ | OCH₃ | N | |
| J-1 | O | — | H | 5-N(CH₃)₂ | H | SO₂ | OCH₃ | CH₃ | N | |
| J-1 | O | — | H | 6-Cl | H | SO₂ | OCH₃ | CH₃ | N | |
| J-1 | O | — | H | 6-Cl | H | SO₂ | OCH₃ | CH₃ | CH | |
| J-1 | O | — | H | 6-OCH₃ | H | SO₂ | OCH₃ | CH₃ | CH | |
| J-1 | O | — | H | 6-OCH₃ | H | SO₂ | OCH₃ | CH₃ | N | |
| J-1 | O | — | H | 6-CN | H | SO₂ | OCH₃ | CH₃ | N | |
| J-1 | O | — | H | 6-CH₃ | H | SO₂ | OCH₃ | CH₃ | N | |
| J-1 | O | — | H | 6-SCH₂CH₃ | H | SO₂ | OCH₃ | CH₃ | N | |
| J-1 | O | — | H | 6-SCH₃ | H | SO₂ | OCH₃ | CH₃ | N | |
| J-1 | O | — | H | 6-SCH₃ | H | SO₂ | OCH₃ | CH₃ | CH | |
| J-1 | O | — | H | H | H | NH | CH₃ | H | CH | |
| J-1 | O | — | H | H | H | NH | CH₃ | CH₃ | CH | |
| J-1 | O | — | H | H | Cl | NH | OCH₃ | CH₃ | CH | |
| J-1 | O | — | H | H | H | NH | OCH₃ | CH₃ | N | |
| J-1 | O | — | H | H | H | NH | OCH₃ | N(CH₃)₂ | N | |
| J-1 | O | — | H | 5-Cl | H | NH | OCH₃ | CH₃ | N | |
| J-1 | O | — | H | 5-Cl | H | NH | OCH₃ | CH₃ | CH | |
| J-1 | O | — | H | 5-Cl | H | NH | OCH₃ | OCH₃ | CH | |
| J-1 | O | — | H | 6-OCH₃ | H | NH | OCH₃ | OCH₃ | CH | |
| J-1 | O | — | H | 6-OCH₃ | H | NH | CH₃ | OCH₃ | CH | |
| J-1 | O | — | H | H | H | NCH₃ | CH₃ | OCH₃ | CH | 210–216 |
| J-1 | O | — | H | H | H | NCH₃ | CH₃ | CH₃ | CH | 216–218 |
| J-1 | O | — | H | H | H | NCH₃ | SCH₃ | CH₃ | CH | |
| J-1 | O | — | H | H | H | NCH₃ | OCH₃ | OCH₃ | CH | 195–200 |
| J-1 | O | — | H | H | H | NCH₃ | OCH₃ | OCH₃ | N | 194–197 |
| J-1 | O | — | H | H | H | NCH₃ | OCH₃ | CH₃ | N | 134–136 (d) |
| J-1 | O | — | H | H | H | NCH₃ | CH₃ | CH₃ | N | 221–226 |
| J-1 | O | — | H | H | H | NCH₃ | N(CH₃)₂ | CH₃ | N | |
| J-1 | O | — | H | H | H | NCH₃ | NHCH₃ | OCH₂CH₃ | N | 203–209 |
| J-1 | O | — | H | H | H | NCH₃ | NHCH₃ | OCH₃ | N | 265–270 (d) |
| J-1 | O | — | H | H | H | NCH₃ | Cl | OCH₃ | CH | 123–126 (d) |
| J-1 | O | — | H | H | H | NCH₃ | OCH₂OCH₃ | OCH₃ | CH | |
| J-1 | O | — | H | H | H | NCH₃ | OC₂H₅ | OC₂H₅ | N | 154–159 |
| J-1 | O | — | H | H | H | NCH₃ | CH₃ | OC(=O)CH₃ | CH | |
| J-1 | O | — | H | H | H | NCH₃ | CH₃ | CH(OCH₃)₂ | CH | |
| J-1 | O | — | H | H | H | NCH₃ | N(CH₃)₂ | OCH₃ | N | 197–200 |
| J-1 | O | — | H | H | H | NCH₃ | N(CH₃)₂ | OC₂H₅ | N | 193–196 |
| J-1 | O | — | H | H | H | NCH₃ | OCH₂CF₃ | N(CH₃)₂ | N | 185–188 |

TABLE I-continued $$\text{JSO}_2\text{NHCNA} \quad (A = A\text{-}1)$$
$$\overset{\overset{W}{\|}}{\underset{R}{|}}$$

| J | W | E | R | R₁ | R₅ | Q₁ | X | Y | Z | m.p. (°C.) |
|---|---|---|---|---|---|---|---|---|---|---|
| J-1 | O | — | H | H | H | NCH₃ | SC₂H₅ | NHCH₃ | N | 232–234 |
| J-1 | O | — | H | H | H | NCH₃ | NHCH₃ | OCH(CH₃)₂ | N | 217–221 (d) |
| J-1 | O | — | H | H | H | NCH₃ | OCH₃ | N(CH₃)CH₂CN | N | 192–193 (d) |
| J-1 | O | — | H | H | H | NCH₃ | OCH₃ | NHCH₂CN | N | 190–195 (d) |
| J-1 | O | — | H | H | H | NCH₃ | CH₃ | OCH₂C≡CH | N | 120–124 (d) |
| J-1 | O | — | H | H | H | NCH₃ | OCH₂CF₃ | NHCH₃ | N | 229–235 (d) |
| J-1 | O | — | H | H | H | NCH₃ | NHCH₃ | OC₂H₅ | CH | 218–221 |
| J-1 | O | — | H | H | H | NCH₃ | CH₃ | CH₂OCH₃ | CH | 193–195 |
| J-1 | O | — | H | 5-CH₃ | H | NCH₃ | CH₃ | OCH₃ | CH | 212–214 |
| J-1 | O | — | H | 5-CH₃ | H | NCH₃ | CH₃ | OCH₃ | N | 177–183 |
| J-1 | O | — | H | H | Br | NCH₃ | CH₃ | OCH₃ | CH | |
| J-1 | O | — | H | 5-CH₃ | H | NCH₃ | CH₃ | CH₃ | CH | 226–228 |
| J-1 | O | — | H | 5-CH₃ | H | NCH₃ | OCH₃ | OCH₃ | CH | 194–197 |
| J-1 | O | — | H | 5-CH₃ | H | NCH₃ | OCH₃ | Cl | CH | 203–205 |
| J-1 | O | — | H | 5-OCH₃ | H | NCH₃ | CH₃ | OCH₃ | N | |
| J-1 | O | — | H | 5-OCH₃ | H | NCH₃ | OCH₃ | OCH₃ | N | |
| J-1 | O | — | H | 5-OCH₃ | H | NCH₃ | OC₂H₅ | NHCH₃ | N | |
| J-1 | O | — | H | 5-OCH₃ | H | NCH₃ | CH₃ | CH₃ | CH | |
| J-1 | O | — | H | 5-OCH₃ | H | NCH₃ | CH₃ | OCH₃ | CH | |
| J-1 | O | — | H | 5-OCH₃ | H | NCH₃ | OCH₃ | OCH₃ | CH | |
| J-1 | O | — | H | 5-OCH₃ | H | NCH₃ | Cl | OCH₃ | CH | |
| J-1 | O | — | H | 5-OCF₂H | H | NCH₃ | Cl | OCH₃ | CH | |
| J-1 | O | — | H | 5-Cl | H | NCH₃ | Cl | OCH₃ | CH | |
| J-1 | O | — | H | 5-Cl | H | NCH₃ | OCH₃ | CH₃ | CH | |
| J-1 | O | — | H | 5-NO₂ | H | NCH₃ | OCH₃ | CH₃ | N | |
| J-1 | O | — | H | 5-NO₂ | H | NCH₃ | OCH₃ | NHCH₂CH₃ | N | |
| J-1 | O | — | H | 5-CN | H | NCH₃ | OCH₃ | CH₃ | N | |
| J-1 | O | — | H | 5-CN | H | NCH₃ | OCH₃ | CH₃ | CH | |
| J-1 | O | — | H | 6-Br | H | NCH₃ | CH₃ | CH₃ | N | |
| J-1 | O | — | H | 6-Br | H | NCH₃ | CH₃ | OCH₃ | N | |
| J-1 | O | — | H | 6-CH₃ | H | NCH₃ | CH₃ | CH₃ | CH | 215–217 |
| J-1 | O | — | H | 6-CH₃ | H | NCH₃ | CH₃ | OCH₃ | CH | 204–208 |
| J-1 | O | — | H | 6-CH₃ | H | NCH₃ | OCH₃ | OCH₃ | CH | 209–212 |
| J-1 | O | — | H | 6-CH₃ | H | NCH₃ | CL | OCH₃ | CH | 208–212 |
| J-1 | O | — | H | 6-CH₃ | H | NCH₃ | CH₃ | CH₃ | N | 141–143 (d) |
| J-1 | O | — | H | 6-CH₃ | H | NCH₃ | CH₃ | OCH₃ | N | 198–205 (d) |
| J-1 | O | — | H | 6-CH₃ | H | NCH₃ | OCH₃ | OCH₃ | N | 186–195 |
| J-1 | O | — | H | 6-CH₃ | H | NCH₃ | OC₂H₅ | NHCH₃ | N | 234–237 |
| J-1 | O | — | H | 6-SCH₃ | H | NCH₃ | CH₃ | OCH₃ | N | |
| J-1 | O | — | H | 6-SCH₃ | H | NCH₃ | CH₃ | OCH₃ | CH | |
| J-1 | O | — | H | 6-N(CH₃)₂ | H | NCH₃ | CH₃ | OCH₃ | CH | |
| J-1 | O | — | H | 6-N(CH₃)₂ | H | NCH₃ | CH₃ | OCH₃ | N | |
| J-1 | O | — | H | 5-Cl | H | NC₆H₅ | CH₃ | OCH₃ | N | |
| J-1 | O | — | H | 5-OCH₃ | H | NCH₂C₆H₅ | CH₃ | OCH₃ | N | |
| J-1 | O | — | H | 6-OCH₃ | H | NCH₂CHCH₂ | CH₃ | OCH₃ | N | |
| J-1 | O | — | H | 6-NHCH₃ | H | NCN | CH₃ | OCH₃ | N | |
| J-1 | O | — | H | 6-CO₂CH₃ | H | NCH₂CH₂Cl | CH₃ | OCH₃ | N | |
| J-1 | O | — | CH₃ | H | H | NOCH₃ | CH₃ | OCH₃ | N | |
| J-1 | O | — | CH₃ | 5-OCH₃ | H | NCH | CH₃ | OCH₃ | N | |
| J-1 | O | — | CH₃ | 5-Cl | H | S | CH | OCH₃ | CH | |
| J-1 | O | — | CH₃ | 6-OCH₃ | H | NH | CH₃ | OCH₃ | CH | |
| J-1 | O | — | CH₃ | 6-N(CH₃)₂ | H | S | CH₃ | OCH₃ | CH | |
| J-1 | O | CH₂ | H | H | H | S | OCH₃ | OCH₃ | CH | |
| J-1 | O | CH₂ | H | H | H | S | OCH₃ | OCH₃ | N | |
| J-1 | O | CH₂ | H | H | H | NCH₃ | OCH₃ | OCH₃ | CH | |
| J-1 | O | CH₂ | H | 5-Cl | H | NCH₃ | OCH₃ | OCH₃ | CH | |
| J-1 | O | CH₂ | H | 5-OCH₃ | H | S | OCH₃ | OCH₃ | CH | |
| J-1 | O | O | H | H | H | S | OCH₃ | OCH₃ | CH | |
| J-1 | O | O | H | 5-OCH₃ | H | S | OCH₃ | OCH₃ | CH | |
| J-1 | O | O | H | 5-OCH₃ | H | S | OCH₃ | OCH₃ | N | |
| J-1 | O | O | H | H | H | NCH₃ | OCH₃ | OCH₃ | N | |
| J-1 | O | O | H | H | H | NCH₃ | OCH₃ | OCH₃ | CH | |
| J-1 | S | — | H | H | H | S | OCH₃ | OCH₃ | CH | |
| J-1 | S | — | H | 5-N(CH₃)₂ | H | S | OCH₃ | OCH₃ | CH | |
| J-1 | S | — | H | 5-OCF₃ | H | S | OCH₃ | OCH₃ | CH | |
| J-1 | S | — | H | 6-OCH₃ | H | S | OCH₃ | OCH₃ | CH | |
| J-1 | S | — | H | H | H | NCH₂C₆H₅ | OCH₃ | OCH₃ | CH | |
| J-1 | S | — | H | 5-Cl | H | NCH₃ | OCH₃ | OCH₃ | CH | |
| J-1 | S | — | H | 6-SCH₃ | H | NCH₃ | OCH₃ | OCH₃ | CH | |
| J-1 | S | CH₂ | H | H | H | NCH₃ | OCH₃ | OCH₃ | CH | |
| J-2 | O | — | H | H | H | S | CH₃ | CH₃ | CH | 207–208 (d) |
| J-2 | O | — | H | H | H | S | CH₂CH₂CH₃ | CH₃ | CH | |

TABLE I-continued $$\text{JSO}_2\text{NHCNA} \quad (A = A\text{-}1)$$
$$\overset{W}{\underset{R}{\|}}$$

| J | W | E | R | $R_1$ | $R_5$ | $Q_1$ | X | Y | Z | m.p. (°C.) |
|---|---|---|---|---|---|---|---|---|---|---|
| J-2 | O | — | H | H | H | S | $OCH_3$ | $CH_3$ | CH | 195–197 |
| J-2 | O | — | H | H | H | S | $OCF_3$ | $CH_3$ | CH | |
| J-2 | O | — | H | H | H | S | $OCH_2CH_2OCH_3$ | $CH_3$ | CH | |
| J-2 | O | — | H | H | H | S | $OCH_3$ | $OCH_3$ | CH | 220–223 (d) |
| J-2 | O | — | H | H | H | S | Br | $CH_3$ | CH | |
| J-2 | O | — | H | H | H | S | $N(CH_3)_2$ | $CH_3$ | CH | |
| J-2 | O | — | H | H | H | S | $N(CH_3)_2$ | $OCH_3$ | CH | |
| J-2 | O | — | H | H | H | S | $N(CH_3)_2$ | $OCH_2CH_3$ | CH | |
| J-2 | O | — | H | H | $OCH_3$ | S | Cl | $OCH_3$ | CH | |
| J-2 | O | — | H | H | H | S | Br | $OCH_3$ | CH | |
| J-2 | O | — | H | H | H | S | $CH_3$ | $NHCH_3$ | CH | |
| J-2 | O | — | H | H | H | S | $CH_3$ | $CF_3$ | CH | |
| J-2 | O | — | H | H | H | S | $CH_3$ | $CH_3$ | N | |
| J-2 | O | — | H | H | H | S | $CH_3$ | $OCH_3$ | N | 187–196 (d) |
| J-2 | O | — | H | H | H | S | $CH_3$ | $OCH_2CH_2CH_2CH_3$ | N | |
| J-2 | O | — | H | H | H | S | $OCH_3$ | $OCH_3$ | N | 198–200 (d) |
| J-2 | O | — | H | H | H | S | $NHCH_3$ | $OCH_2CH_3$ | N | |
| J-2 | O | — | H | H | H | S | $OCH_3$ | CN | N | |
| J-2 | O | — | H | 6-$CH_3$ | H | S | $OCH_3$ | $OCH_3$ | N | |
| J-2 | O | — | H | 6-$CH_3$ | H | S | $OCH_3$ | $CH_3$ | N | |
| J-2 | O | — | H | 6-$CH_3$ | H | S | $OCH_3$ | $CH_3$ | CH | |
| J-2 | O | — | H | 6-$CH_3$ | H | S | $OCH_3$ | $OCH_3$ | CH | |
| J-2 | O | — | H | 6-$CH(CH_3)_2$ | H | S | $OCH_3$ | $OCH_3$ | CH | |
| J-2 | O | — | H | 6-$CF_3$ | H | S | $OCH_3$ | $OCH_3$ | CH | |
| J-2 | O | — | H | 6-F | H | S | $OCH_3$ | $OCH_3$ | CH | |
| J-2 | O | — | H | 6-F | H | S | $OCH_3$ | $OCH_3$ | N | |
| J-2 | O | — | H | 6-Cl | H | S | $OCH_3$ | $OCH_3$ | N | |
| J-2 | O | — | H | 6-Cl | H | S | $OCH_3$ | $OCH_3$ | CH | |
| J-2 | O | — | H | 6-Cl | H | S | $OCH_3$ | $CH_3$ | CH | |
| J-2 | O | — | H | 6-Cl | H | S | Cl | $OCH_3$ | CH | |
| J-2 | O | — | H | 6-Cl | H | S | $CH_3$ | $OCH_3$ | N | |
| J-2 | O | — | H | 6-Br | H | S | $CH_3$ | $OCH_3$ | N | |
| J-2 | O | — | H | 6-Br | H | S | $CH_3$ | $OCH_3$ | CH | |
| J-2 | O | — | H | 6-$NO_2$ | H | S | $CH_3$ | $OCH_3$ | CH | |
| J-2 | O | — | H | 6-$NO_2$ | H | S | $CH_3$ | $OCH_3$ | N | |
| J-2 | O | — | H | 6-$OCH_3$ | H | S | H | H | CH | |
| J-2 | O | — | H | 6-$OCH_3$ | H | S | H | $CH_3$ | CH | |
| J-2 | O | — | H | 6-$OCH_3$ | H | S | $CH_3$ | $CH_3$ | CH | |
| J-2 | O | — | H | 6-$OCH_3$ | H | S | $OCH_3$ | $CH_3$ | CH | |
| J-2 | O | — | H | 6-$OCH_3$ | H | S | $OCH_2CF_3$ | $CH_3$ | CH | |
| J-2 | O | — | H | 6-$OCH_3$ | H | S | $SCH_3$ | $CH_3$ | CH | |
| J-2 | O | — | H | 6-$OCH_3$ | H | S | $OCH_3$ | $OCH_3$ | CH | |
| J-2 | O | — | H | 6-$OCH_3$ | H | S | Cl | $OCH_3$ | CH | |
| J-2 | O | — | H | 6-$OCH_3$ | H | S | $OCH_3$ | $OCH_3$ | N | |
| J-2 | O | — | H | 6-$OCH_3$ | H | S | $CH_3$ | $OCH_3$ | N | |
| J-2 | O | — | H | 6-$OCH_3$ | H | S | $CH_3$ | $CH_3$ | N | |
| J-2 | O | — | H | 6-$OCH_3$ | H | S | $OCH_2CH_3$ | $NHCH_3$ | N | |
| J-2 | O | — | H | 6-$OCH_3$ | H | S | $OCH_3$ | C≡CH | N | |
| J-2 | O | — | H | 6-$OCH_3$ | H | S | $OCH_3$ | $OCH_2CHCH_2$ | N | |
| J-2 | O | — | H | 6-$OCH_3$ | H | S | $OCH_3$ | $CH_2SO_2CH_3$ | N | |
| J-2 | O | — | H | 6-$OCH_3$ | H | S | $OCH_3$ | $CH_2COCH_2CH_3$ | N | |
| J-2 | O | — | H | 6-$SO_2N(CH_3)_2$ | H | S | $OCH_3$ | $CH_3$ | N | |
| J-2 | O | — | H | 6-$SO_2N(CH_3)_2$ | H | S | $OCH_3$ | $CH_3$ | CH | |
| J-2 | O | — | H | 6-$SO_2NHCH_2CN$ | H | S | $OCH_3$ | $CH_3$ | CH | |
| J-2 | O | — | H | 6-$SO_2N$ | H | S | $OCH_3$ | $CH_3$ | CH | |
| J-2 | O | — | H | 6-$SCH_3$ | H | S | $OCH_3$ | $CH_3$ | CH | |
| J-2 | O | — | H | 6-$SOCH_2CH_3$ | H | S | $OCH_3$ | $CH_3$ | CH | |
| J-2 | O | — | H | 6-$SO_2CH_2CH_3$ | H | S | $OCH_3$ | $CH_3$ | CH | |
| J-2 | O | — | H | 6-$CH_2CN$ | H | S | $OCH_3$ | $CH_3$ | CH | |
| J-2 | O | — | H | 6-$CO_2CH_2CF_3$ | H | S | $OCH_3$ | $CH_3$ | CH | |
| J-2 | O | — | H | 6-$OCF_2H$ | H | S | $OCH_3$ | $CH_3$ | CH | |
| J-2 | O | — | H | 6-$CH_2OCH_3$ | H | S | $OCH_3$ | $CH_3$ | CH | |
| J-2 | O | — | H | 6-$N(CH_3)_2$ | H | S | $OCH_3$ | $CH_3$ | CH | |
| J-2 | O | — | H | 5-Cl | H | S | $OCH_3$ | $CH_3$ | CH | |
| J-2 | O | — | H | 5-Cl | H | S | $OCH_3$ | $CH_3$ | N | |
| J-2 | O | — | H | 5-Cl | H | S | $OCH_3$ | $OCH_3$ | N | |
| J-2 | O | — | H | 5-$OCH_3$ | H | S | $OCH_3$ | $OCH_3$ | CH | |
| J-2 | O | — | H | 5-$OCH_3$ | H | S | $CH_3$ | $OCH_3$ | CH | |
| J-2 | O | — | H | 5-$OCH_3$ | H | S | $OCH_3$ | $OCH_3$ | N | |
| J-2 | O | — | H | 5-$OCH(CH_3)_2$ | H | S | $OCH_3$ | $OCH_3$ | CH | |
| J-2 | O | — | H | 5-$OCH(CH_3)_2$ | H | S | $NHCH_3$ | $OCH_3$ | CH | |
| J-2 | O | — | H | 5-$OCH(CH_3)_2$ | H | S | $NHCH_3$ | $NHCH_3$ | CH | |
| J-2 | O | — | H | 5-$SCH_2CH_3$ | H | S | $CH_3$ | $OCH_3$ | N | |
| J-2 | O | — | H | 5-$SCH_2CH_3$ | H | S | $CH_3$ | $N(CH_3)_2$ | N | |
| J-2 | O | — | H | 5-$SCH_2CH_3$ | H | S | $CH_3$ | $N_3$ | N | |

TABLE I-continued $$\text{JSO}_2\text{NHCNA} \quad (A = A\text{-}1)$$
$$\overset{\overset{W}{\|}}{\underset{R}{|}}$$

| J | W | E | R | $R_1$ | $R_5$ | $Q_1$ | X | Y | Z | m.p. (°C.) |
|---|---|---|---|---|---|---|---|---|---|---|
| J-2 | O | — | H | 5-SCH$_2$CH$_3$ | H | S | CH$_3$ | CN | CH | |
| J-2 | O | — | H | 5-SO$_2$CH$_3$ | H | S | CH$_3$ | OCH$_3$ | CH | |
| J-2 | O | — | H | 5-SO$_2$CH$_3$ | H | S | CH$_3$ | OCH$_3$ | N | |
| J-2 | O | — | H | 5-N(CH$_3$)$_2$ | H | S | CH$_3$ | OCH$_3$ | N | |
| J-2 | O | — | H | 5-N(CH$_3$)$_2$ | H | S | CH$_3$ | OCH$_3$ | CH | |
| J-2 | O | — | H | 5-N(CH$_3$)$_2$ | H | S | OCH$_3$ | OCH$_3$ | CH | |
| J-2 | O | — | H | 5-N(CH$_3$)$_2$ | H | S | OCH$_3$ | OCH$_3$ | N | |
| J-2 | O | — | H | 5-N(CH$_3$)$_2$ | H | S | OCH$_3$ | CH$_3$ | N | |
| J-2 | O | — | H | H | H | SO$_2$ | OCH$_3$ | CH$_3$ | N | |
| J-2 | O | — | H | H | H | SO$_2$ | OCH$_3$ | OCH$_3$ | N | |
| J-2 | O | — | H | H | H | SO$_2$ | OCH$_3$ | OCH$_3$ | CH | |
| J-2 | O | — | H | H | H | SO$_2$ | CH$_3$ | OCH$_3$ | CH | |
| J-2 | O | — | H | H | H | SO$_2$ | Cl | OCH$_3$ | CH | |
| J-2 | O | — | H | H | H | SO$_2$ | Cl | N(CH$_3$)$_2$ | CH | |
| J-2 | O | — | H | 6-CH$_2$CF$_3$ | H | SO$_2$ | CH$_3$ | OCH$_3$ | N | |
| J-2 | O | — | H | 6-Br | H | SO$_2$ | CH$_3$ | OCH$_3$ | N | |
| J-2 | O | — | H | 6-OCH$_2$CH$_3$ | H | SO$_2$ | CH$_3$ | OCH$_3$ | N | |
| J-2 | O | — | H | 6-OCF$_3$ | H | SO$_2$ | CH$_3$ | OCH$_3$ | CH | |
| J-2 | O | — | H | 6-OCF$_2$H | H | SO$_2$ | CH$_3$ | OCH$_3$ | CH | |
| J-2 | O | — | H | 6-N(CH$_3$)$_2$ | H | SO$_2$ | CH$_3$ | OCH$_3$ | CH | |
| J-2 | O | — | H | 6-N(CH$_3$)$_2$ | H | SO$_2$ | OCH$_3$ | OCH$_3$ | CH | |
| J-2 | O | — | H | 6-N(CH$_3$)$_2$ | H | SO$_2$ | OCH$_3$ | OCH$_3$ | N | |
| J-2 | O | — | H | 6-N(CH$_3$)$_2$ | H | SO$_2$ | OCH$_3$ | CH$_3$ | N | |
| J-2 | O | — | H | 5-Cl | H | SO$_2$ | OCH$_3$ | CH$_3$ | N | |
| J-2 | O | — | H | 5-Cl | H | SO$_2$ | OCH$_3$ | CH$_3$ | CH | |
| J-2 | O | — | H | 5-OCH$_3$ | H | SO$_2$ | OCH$_3$ | CH$_3$ | CH | |
| J-2 | O | — | H | 5-OCH$_3$ | H | SO$_2$ | OCH$_3$ | CH$_3$ | N | |
| J-2 | O | — | H | 5-CN | H | SO$_2$ | OCH$_3$ | CH$_3$ | N | |
| J-2 | O | — | H | 5-CH$_3$ | H | SO$_2$ | OCH$_3$ | CH$_3$ | N | |
| J-2 | O | — | H | 5-SCH$_2$CH$_3$ | H | SO$_2$ | OCH$_3$ | CH$_3$ | N | |
| J-2 | O | — | H | 5-SCH$_3$ | H | SO$_2$ | OCH$_3$ | CH$_3$ | N | |
| J-2 | O | — | H | 5-SCH$_3$ | H | SO$_2$ | OCH$_3$ | CH$_3$ | CH | |
| J-2 | O | — | H | H | OC$_2$H$_5$ | NH | CH$_3$ | H | CH | |
| J-2 | O | — | H | H | H | NH | CH$_3$ | CH$_3$ | CH | |
| J-2 | O | — | H | H | H | NH | OCH$_3$ | CH$_3$ | N | |
| J-2 | O | — | H | H | H | NH | OCH$_3$ | N(CH$_3$)$_2$ | N | |
| J-2 | O | — | H | 6-Cl | H | NH | OCH$_3$ | CH$_3$ | N | |
| J-2 | O | — | H | 6-Cl | H | NH | OCH$_3$ | CH$_3$ | CH | |
| J-2 | O | — | H | 5-Cl | H | NH | OCH$_3$ | OCH$_3$ | CH | |
| J-2 | O | — | H | 5-Cl | H | NH | CH$_3$ | OCH$_3$ | CH | 184–187 (d) |
| J-2 | O | — | H | 5-Cl | H | NH | Cl | OCH$_3$ | CH | 165–175 (d) |
| J-2 | O | — | H | 5-Cl | H | NH | CH$_3$ | CH$_3$ | CH | 189–192 (d) |
| J-2 | O | — | H | 5-Cl | H | NH | OCH$_3$ | CH$_3$ | N | 107–110 (d) |
| J-2 | O | — | H | 5-Cl | H | NH | OCH$_3$ | OCH$_3$ | N | 174–176 (d) |
| J-2 | O | — | H | 5-Cl | H | NH | NHCH$_3$ | OCH$_2$CH$_3$ | N | 156–162 (d) |
| J-2 | O | — | H | 5-OCH$_3$ | H | NH | OCH$_3$ | OCH$_3$ | CH | |
| J-2 | O | — | H | 5-OCH$_3$ | H | NH | CH$_3$ | OCH$_3$ | CH | |
| J-2 | O | — | H | H | H | NCH$_3$ | CH$_3$ | OCH$_3$ | CH | 192–194 |
| J-2 | O | — | H | H | H | NCH$_3$ | CH$_3$ | CH$_3$ | CH | 198–200 |
| J-2 | O | — | H | H | H | NCH$_3$ | SCH$_3$ | CH$_3$ | CH | |
| J-2 | O | — | H | H | H | NCH$_3$ | OCH$_3$ | OCH$_3$ | CH | 199–200 |
| J-2 | O | — | H | H | H | NCH$_3$ | OCH$_3$ | OCH$_3$ | N | 203–207 |
| J-2 | O | — | H | H | H | NCH$_3$ | OCH$_3$ | CH$_3$ | N | 190–198 (d) |
| J-2 | O | — | H | H | H | NCH$_3$ | CH$_3$ | CH$_3$ | N | 191–194 |
| J-2 | O | — | H | H | H | NCH$_3$ | N(CH$_3$)$_2$ | CH$_3$ | N | |
| J-2 | O | — | H | H | H | NCH$_3$ | NHCH$_3$ | OCH$_2$CH$_3$ | N | |
| J-2 | O | — | H | H | H | NCH$_3$ | NHCH$_3$ | C≡CH | N | |
| J-2 | O | — | H | H | H | NCH$_3$ | Cl | OCH$_3$ | CH | 170–175 |
| J-2 | O | — | H | H | H | NCH$_3$ | OCH$_2$OCH$_3$ | OCH$_3$ | CH | |
| J-2 | O | — | H | H | H | NCH$_3$ | CH$_3$ | $\overset{\overset{O}{\|}}{\underset{}{\text{CCH}_3}}$ | CH | |
| J-2 | O | — | H | H | H | NCH$_3$ | CH$_3$ | CH(OCH$_3$)$_2$ | CH | |
| J-2 | O | — | H | 6-CH$_3$ | H | NCH$_3$ | OCH$_3$ | OCH$_3$ | CH | 206–210 |
| J-2 | O | — | H | 6-CH$_3$ | H | NCH$_3$ | CH$_3$ | OCH$_3$ | N | |
| J-2 | O | — | H | 6-OCH$_3$ | H | NCH$_3$ | OCH$_3$ | OCH$_3$ | N | 185–188 |
| J-2 | O | — | H | 6-OCH$_3$ | H | NCH$_3$ | CH$_3$ | OCH$_3$ | N | 113–118 (d) |
| J-2 | O | — | H | 6-OCH$_3$ | H | NCH$_3$ | OC$_2$H$_5$ | NHCH$_3$ | N | 221–225 (d) |
| J-2 | O | — | H | 6-OCH$_3$ | H | NCH$_3$ | CH$_3$ | OCH$_3$ | CH | 168–170 |
| J-2 | O | — | H | 6-OCH$_3$ | H | NCH$_3$ | OCH$_3$ | OCH$_3$ | CH | 157–161 |
| J-2 | O | — | H | 6-OCH$_3$ | H | NCH$_3$ | CH$_3$ | CH$_3$ | CH | 180–182 |
| J-2 | O | — | H | 6-OCH$_3$ | H | NCH$_3$ | Cl | OCH$_3$ | CH | 122–129 (d) |
| J-2 | O | — | H | 6-OCF$_2$H | H | NCH$_3$ | Cl | OCH$_3$ | CH | |

TABLE I-continued $$\text{JSO}_2\text{NHCNA} \quad (A = A\text{-}1)$$
with W (=O) double bond on C, and R on N.

| J | W | E | R | $R_1$ | $R_5$ | $Q_1$ | X | Y | Z | m.p. (°C.) |
|---|---|---|---|---|---|---|---|---|---|---|
| J-2 | O | — | H | 6-Cl | H | $NCH_3$ | Cl | $OCH_3$ | CH | |
| J-2 | O | — | H | 6-Cl | H | $NCH_3$ | $OCH_3$ | $CH_3$ | CH | |
| J-2 | O | — | H | 6-$NO_2$ | H | $NCH_3$ | $OCH_3$ | $CH_3$ | N | |
| J-2 | O | — | H | 6-$NO_2$ | H | $NCH_3$ | $OCH_3$ | $NHCH_2CH_3$ | N | |
| J-2 | O | — | H | 6-CN | H | $NCH_3$ | $OCH_3$ | $CH_3$ | N | |
| J-2 | O | — | H | 6-CN | H | $NCH_3$ | $OCH_3$ | $CH_3$ | CH | |
| J-2 | O | — | H | 5-Br | H | $NCH_3$ | $CH_3$ | $CH_3$ | N | |
| J-2 | O | — | H | 5-Br | H | $NCH_3$ | $CH_3$ | $OCH_3$ | N | |
| J-2 | O | — | H | 5-$SCH_3$ | H | $NCH_3$ | $CH_3$ | $OCH_3$ | N | |
| J-2 | O | — | H | 5-$SCH_3$ | H | $NCH_3$ | $CH_3$ | $OCH_3$ | CH | |
| J-2 | O | — | H | 5-$N(CH_3)_2$ | H | $NCH_3$ | $CH_3$ | $OCH_3$ | CH | |
| J-2 | O | — | H | 5-$N(CH_3)_2$ | H | $NCH_3$ | $CH_3$ | $OCH_3$ | N | |
| J-2 | O | — | H | H | H | $NC_6H_5$ | $CH_3$ | $OCH_3$ | N | |
| J-2 | O | — | H | 6-Cl | H | $NCH_2C_6H_5$ | $CH_3$ | $OCH_3$ | N | |
| J-2 | O | — | H | 6-$OCH_3$ | H | $NCH_2CH_2CH_3$ | $CH_3$ | $OCH_3$ | N | |
| J-2 | O | — | H | 5-$OCH_3$ | H | NCN | $CH_3$ | $OCH_3$ | N | |
| J-2 | O | — | H | 5-$NHCH_3$ | H | $NCH_2CH_2Cl$ | $CH_3$ | $OCH_3$ | N | |
| J-2 | O | — | H | 5-$CO_2CH_3$ | H | $NOCH_3$ | $CH_3$ | $OCH_3$ | N | |
| J-2 | O | — | $CH_3$ | H | H | $NCH_3$ | $CH_3$ | $OCH_3$ | N | |
| J-2 | O | — | $CH_3$ | 6-$OCH_3$ | H | S | $CH_3$ | $OCH_3$ | CH | |
| J-2 | O | — | $CH_3$ | 6-Cl | H | NH | $CH_3$ | $OCH_3$ | CH | |
| J-2 | O | — | $CH_3$ | 5-OCH | H | S | $CH_3$ | $OCH_3$ | CH | |
| J-2 | O | — | $CH_3$ | 5-$N(CH_3)_2$ | H | S | $OCH_3$ | $OCH_3$ | CH | |
| J-2 | O | $CH_2$ | H | H | H | S | $OCH_3$ | $OCH_3$ | N | |
| J-2 | O | $CH_2$ | H | H | H | S | $OCH_3$ | $OCH_3$ | CH | |
| J-2 | O | $CH_2$ | H | 6-Cl | H | $NCH_3$ | $OCH_3$ | $OCH_3$ | CH | |
| J-2 | O | $CH_2$ | H | 6-$OCH_3$ | H | S | $OCH_3$ | $OCH_3$ | CH | |
| J-2 | O | O | H | H | H | S | $OCH_3$ | $OCH_3$ | CH | |
| J-2 | O | O | H | 6-$OCH_3$ | H | S | $OCH_3$ | $OCH_3$ | CH | |
| J-2 | O | O | H | 6-$OCH_3$ | H | S | $OCH_3$ | $OCH_3$ | N | |
| J-2 | O | O | H | H | H | $NCH_3$ | $OCH_3$ | $OCH_3$ | N | |
| J-2 | O | O | H | H | H | $NCH_3$ | $OCH_3$ | $OCH_3$ | CH | |
| J-2 | S | — | H | H | H | S | $OCH_3$ | $OCH_3$ | CH | |
| J-2 | S | — | H | 6-$N(CH_3)_2$ | H | S | $OCH_3$ | $OCH_3$ | CH | |
| J-2 | S | — | H | 6-$OCF_3$ | H | S | $OCH_3$ | $OCH_3$ | CH | |
| J-2 | S | — | H | 5-$OCH_3$ | H | S | $OCH_3$ | $OCH_3$ | CH | |
| J-2 | S | — | H | H | H | $NCH_3$ | $OCH_3$ | $OCH_3$ | CH | |
| J-2 | S | — | H | H | H | $NCH_2C_6H_5$ | $OCH_3$ | $OCH_3$ | CH | |
| J-2 | S | — | H | 6-Cl | H | $NCH_3$ | $OCH_3$ | $OCH_3$ | CH | |
| J-2 | S | — | H | 5-$SCH_3$ | H | $NCH_3$ | $OCH_3$ | $OCH_3$ | CH | |
| J-2 | S | $CH_2$ | H | H | H | $NCH_3$ | $OCH_3$ | $OCH_3$ | CH | |

TABLE II $$\text{JSO}_2\text{NHCNA} \quad \begin{array}{l} J = J\text{-}3 \\ A = A\text{-}1 \end{array}$$

| W | E | R | $R_1$ | $R_5$ | $Q_2$ | X | Y | Z | m.p.(°C.) |
|---|---|---|---|---|---|---|---|---|---|
| O | — | H | H | $OCF_2H$ | O | $CH_3$ | H | N | |
| O | — | H | H | H | O | $CH_3$ | $CH_3$ | N | 189–191 |
| O | — | H | H | H | O | $CH_3$ | $OCH_3$ | N | 181–183 |
| O | — | H | H | H | O | $CH_3$ | $NHCH_3$ | N | |
| O | — | H | H | H | O | $OCH_2CH_3$ | $NHCH_3$ | N | 237–239 |
| O | — | H | H | H | O | $OCH_3$ | $OCH_3$ | N | 191–194 |
| O | — | H | H | H | O | $OCH_3$ | $OCH_3$ | CH | 232–233 |
| O | — | H | H | H | O | $CH_3$ | $OCH_3$ | CH | 188–189 |
| O | — | H | H | H | O | Cl | $OCH_3$ | CH | 214–215 |
| O | — | H | H | H | O | $OCF_3$ | $CH_3$ | CH | |
| O | — | H | H | H | O | $CH_3$ | $CH_3$ | CH | 179–181 |
| O | — | H | H | H | O | $CH_3$ | $H_3$ | CH | |
| O | — | H | H | H | O | $CH_3$ | $SCH_2CH_3$ | CH | |
| O | — | H | H | H | O | $CH_3$ | $CH_2OCH_3$ | CH | |
| O | — | H | H | $CH_2OCH_3$ | O | $CH_3$ | C≡CH | N | |
| O | — | H | 5-Cl | H | O | $CH_3$ | $OCH_3$ | N | |
| O | — | H | 5-Cl | H | O | $CH_3$ | $OCH_3$ | CH | |
| O | — | H | 5-Cl | H | O | Cl | $OCH_3$ | CH | |
| O | — | H | 5-Br | H | O | $OCH_3$ | $OCH_3$ | CH | |
| O | — | H | 5-F | H | O | $OCH_3$ | $CH_3$ | N | |
| O | — | H | 5-$CH_3$ | H | O | $OCH_3$ | $CH_3$ | N | |
| O | — | H | 5-$CH_3$ | H | O | $OCH_3$ | $CH_3$ | CH | |

TABLE II-continued $$JSO_2NHCNA \quad \begin{array}{l} J = J\text{-}3 \\ A = A\text{-}1 \end{array}$$
with W double-bonded to C, and R attached to N

| W | E | R | R₁ | R₅ | Q₂ | X | Y | Z | m.p.(°C.) |
|---|---|---|---|---|---|---|---|---|---|
| O | — | H | 5-CF₂H | H | O | OCH₃ | CH₃ | CH | |
| O | — | H | 5-OCH₃ | H | O | OCH₃ | CH₃ | CH | |
| O | — | H | 5-OCH₃ | H | O | OCH₃ | CH₃ | N | |
| O | — | H | 5-OCH₃ | H | O | NHCH₃ | CH₃ | N | |
| O | — | H | 5-OCH₂CH₂CH₃ | H | O | NHCH₃ | OCH₃ | N | |
| O | — | H | 5-SCH₂CH₃ | H | O | CH₃ | OCH₂CF₃ | CH | |
| O | — | H | 5-SOCH₃ | H | O | CH₃ | OCH₃ | CH | |
| O | — | H | 5-CN | H | O | CH₃ | OCH₃ | CH | |
| O | — | H | 5-NO₂ | H | O | CH₃ | OCH₃ | CH | |
| O | — | H | 5-CO₂CH₂CHCH₃ | H | O | CH₃ | OCH₃ | CH | |
| O | — | H | 5-CO₂CH₃ | H | O | CH₃ | OCH₃ | CH | |
| O | — | H | 5-NHCH₃ | H | O | CH₃ | OCH₃ | CH | |
| O | — | H | 5-NHCH₃ | H | O | CH₃ | OCH₃ | N | |
| O | — | H | 5-NHCH₃ | H | O | SCH₃ | OCH₃ | N | |
| O | — | H | 5-N(CH₂CH₃)₂ | H | O | CH₃ | OCH₃ | N | |
| O | — | H | 6-OCH₃ | H | O | CH₃ | CH₃ | CH | |
| O | — | H | 6-OCH₃ | H | O | CH₃ | OCH₃ | CH | |
| O | — | H | 6-Br | H | O | CH₃ | OCH₃ | N | |
| O | — | H | 6-Br | H | O | CH₃ | SCH₃ | N | |
| O | — | H | 6-SCH₂CH₃ | H | O | OCH₃ | CH₃ | CH | |
| O | — | H | 6-SCH₂CH₃ | H | O | Cl | CH₃ | CH | |
| O | — | H | 6-SOCH₃ | H | O | Cl | OCF₂H | CH | |
| O | — | H | 6-CH | H | O | OCH₃ | OCH₃ | CH | |
| O | — | H | 6-OCH₂CF₃ | H | O | OCH₃ | OCH₃ | CH | |
| O | — | H | 6-NH₂ | H | O | OCH₃ | OCH₃ | CH | |
| O | — | H | 6-N(CH₃)₂ | H | O | CH₃ | OCH₃ | N | |
| O | — | H | 6-N(CH₃)₂ | H | O | OCH₃ | C≡CH | N | |
| O | — | H | 6-N(CH₃)₂ | H | O | OCH₃ | COCH₃ | CH | |
| O | — | H | 6-N(CH₂CH₃)₂ | N | O | OCH₃ | CH₃ | CH | |
| O | — | CH₃ | H | H | O | OCH₃ | CH₃ | CH | |
| O | — | CH₃ | H | H | O | OCH₃ | CH₃ | N | |
| O | — | CH₃ | 5-Br | H | O | OCH₃ | CH₃ | N | |
| O | — | CH₃ | 6-OCH₃ | H | O | OCH₃ | CH₃ | N | |
| O | CH₂ | H | H | H | O | OCH₃ | CH₃ | N | |
| O | CH₂ | H | H | H | O | OCH₃ | CH₃ | CH | |
| O | CH₂ | H | 5-F | H | O | OCH₃ | OCH₃ | CH | |
| O | CH₂ | H | 6-NHCH₂CH₃ | H | O | OCH₃ | OCH₃ | CH | |
| O | O | H | H | H | O | OCH₃ | OCH₃ | CH | |
| O | O | H | 5-NO₂ | H | O | OCH₃ | OCH₃ | CH | |
| O | O | H | 5-OCH₃ | H | O | OCH₂CH₃ | OCH₃ | CH | |
| O | O | H | 6-Br | H | O | OCH₂CH₃ | NHCH₃ | N | |
| S | — | H | H | H | O | OCH₂CH₃ | CH₃ | N | |
| S | — | H | H | H | O | OCH₃ | CH₃ | N | |
| S | — | H | 6-OCH₃ | H | O | OCH₃ | CH₃ | N | |
| S | O | H | H | H | O | OCH | CH₃ | N₃ | |
| O | — | H | H | H | S | CH₃ | H | N | |
| O | — | H | H | H | S | CH₃ | CH₃ | N | 199–201 |
| O | — | H | H | H | S | CH₃ | OCH₃ | N | 195–199 |
| O | — | H | H | H | S | CH₃ | NHCH₃ | N | |
| 0 | — | H | H | H | S | OCH₂CH₃ | NHCH₃ | N | 183–185 |
| O | — | H | H | H | S | OCH₃ | OCH₃ | N | 216–217 |
| O | — | H | H | H | S | OCH₃ | OCH₃ | CH | 216–219 |
| O | — | H | H | H | S | CH₃ | OCH₃ | CH | 220–221 |
| O | — | H | H | H | S | Cl | OCH₃ | CH | 227–228 |
| O | — | H | H | H | S | OCF₃ | CH₃ | CH | |
| O | — | H | H | H | S | CH₃ | CH₃ | CH | 204–206 |
| O | — | H | H | H | S | CH₃ | N₃ | CH | |
| O | — | H | H | H | S | CH₃ | SCH₂CH₃ | CH | |
| O | — | H | H | H | S | CH₃ | CH₂OCH₃ | CH | |
| O | — | H | H | H | S | CH₃ | C≡CH | N | |
| O | — | H | H | CH₂Br | S | CH₃ | N(CH₃)₂ | N | |
| O | — | H | 5-Cl | H | S | CH₃ | OCH₃ | N | |
| O | — | H | 5-Cl | H | S | CH₃ | OCH₃ | CH | |
| O | — | H | 5-Cl | H | S | Cl | OCH₃ | CH | |
| O | — | H | 5-Br | H | S | OCH₃ | OCH₃ | CH | |
| O | — | H | 5-F | H | S | OCH₃ | CH₃ | N | |
| O | — | H | 5-CH₃ | H | S | OCH₃ | CH₃ | N | |
| O | — | H | 5-CH₃ | H | S | OCH₃ | CH₃ | CH | |
| O | — | N | 5-CF₂H | H | S | OCH₃ | CH₃ | CH | |
| O | — | H | 5-OCH₃ | H | S | OCH₃ | CH₃ | CH | |
| O | — | H | 5-OCH₃ | H | S | OCH₃ | CH₃ | N | |
| O | — | H | 5-OCH₃ | H | S | NHCH₃ | CH₃ | N | |
| O | — | H | 5-OCH₂CH₂CH₃ | H | S | NHCH₃ | OCH₃ | N | |
| O | — | H | 5-SCH₂CH₃ | H | S | CH₃ | OCH₂CF₃ | CH | |
| O | — | H | 5-SOCH₃ | H | S | CH₃ | OCH₃ | CH | |

TABLE II-continued $$JSO_2NHCNA \quad \overset{W}{\underset{R}{\|}} \quad \begin{array}{l} J = J\text{-}3 \\ A = A\text{-}1 \end{array}$$

| W | E | R | R$_1$ | R$_5$ | Q$_2$ | X | Y | Z | m.p.(°C.) |
|---|---|---|---|---|---|---|---|---|---|
| O | — | H | 5-CH | H | S | CH$_3$ | OCH$_3$ | OH | |
| O | — | H | 5-NO$_2$ | H | S | CH$_3$ | OCH$_3$ | CH | |
| O | — | H | 5-CO$_2$CH$_2$CH$_3$ | H | S | CH$_3$ | OCH$_3$ | CH | |
| O | — | H | 5-CO$_2$CH$_3$ | H | S | CH$_3$ | OCH$_3$ | CH | |
| O | — | H | 5-NHCH$_3$ | H | S | CH$_3$ | OCH$_3$ | CH | |
| O | — | H | 5-NHCH$_3$ | H | S | CH$_3$ | OCH$_3$ | N | |
| O | — | H | 5-NHCH$_3$ | H | S | SCH$_3$ | OCH$_3$ | N | |
| O | — | H | 5-N(CH$_2$CH$_3$)$_2$ | H | S | CH$_3$ | OCH$_3$ | N | |
| O | — | H | 6-OCH$_3$ | H | S | CH$_3$ | CH$_3$ | CH | |
| O | — | H | 6-OCH$_3$ | H | S | CH$_3$ | OCH$_3$ | CH | |
| O | — | H | 6-Br | H | S | CH$_3$ | OCH$_3$ | N | |
| O | — | H | 6-Br | H | S | CH$_3$ | SCH$_3$ | N | |
| O | — | H | 6-SCH$_2$CH$_3$ | H | S | OCH$_3$ | CH$_3$ | CH | |
| O | — | H | 6-SCH$_2$CH$_3$ | H | S | Cl | CH$_3$ | CH | |
| O | — | H | 6-SOCH$_3$ | H | S | Cl | OCF$_2$H | CH | |
| O | — | H | 6-CN | H | S | OCH$_3$ | OCH$_3$ | CH | |
| O | — | H | 6-OCH$_2$CF$_3$ | H | S | OCH$_3$ | OCH$_3$ | CH | |
| O | — | H | 6-NH$_2$ | H | S | OCH$_3$ | OCH$_3$ | CH | |
| O | — | H | 6-N(CH$_3$)$_2$ | H | S | CH$_3$ | OCH$_3$ | N | |
| O | — | H | 6-N(CH$_3$)$_2$ | H | S | OCH$_3$ | C≡CH | N | |
| O | — | H | 6-N(CH$_3$)$_2$ | H | S | OCH$_3$ | COCH$_3$ | CH | |
| O | — | H | 6-N(CH$_2$CH$_3$)$_2$ | H | S | OCH$_3$ | CH$_3$ | CH | |
| O | — | CH$_3$ | H | H | S | OCH$_3$ | CH$_3$ | CH | |
| O | — | CH$_3$ | H | H | S | OCH$_3$ | CH$_3$ | N | |
| O | — | CH$_3$ | 5-Br | H | S | OCH$_3$ | CH$_3$ | N | |
| O | — | CH$_3$ | 6-OCH$_3$ | N | S | OCH$_3$ | CH$_3$ | N | |
| O | CH$_2$ | H | H | H | S | OCH$_3$ | CH$_3$ | N | |
| O | CH$_2$ | H | H | H | S | OCH$_3$ | CH$_3$ | CH | |
| O | CH$_2$ | H | 5-F | H | S | OCH$_3$ | OCH$_3$ | CH | |
| O | CH$_2$ | H | 6-NHCH$_2$CH$_3$ | H | S | OCH$_3$ | OCH$_3$ | CH | |
| O | O | H | H | H | S | OCH$_3$ | OCH$_3$ | CH | |
| O | O | H | 5-NO$_2$ | H | S | OCH$_3$ | OCH$_3$ | CH | |
| O | O | H | 5-OCH$_3$ | H | S | OCH$_2$CH$_3$ | OCH$_3$ | CH | |
| O | O | H | 6-Br | H | S | OCH$_2$CH$_3$ | NHCH$_3$ | N | |
| S | — | H | H | H | S | OCH$_2$CH$_3$ | CH$_3$ | N | |
| S | — | H | H | H | S | OCH$_3$ | CH$_3$ | N | |
| S | — | N | 6-OCH$_3$ | H | S | OCH$_3$ | CH$_3$ | N | |
| S | O | H | H | H | S | OCH$_3$ | CH$_3$ | N | |
| O | — | H | H | H | NH | CH$_3$ | N | N | |
| O | — | H | H | H | NH | CH$_3$ | CH$_3$ | N | |
| O | — | H | H | H | NH | CH$_3$ | OCH$_3$ | N | |
| O | — | H | H | H | NCH$_3$ | CH$_3$ | OCH$_3$ | N | 188–192 |
| O | — | H | H | H | NCH$_3$ | OCH$_2$CH$_3$ | NHCH$_3$ | N | 225–230 |
| O | — | H | H | H | NCH$_3$ | OCH$_3$ | N(CH$_3$)$_2$ | N | 203–205 |
| O | — | H | H | H | NCH$_3$ | OCH$_3$ | OCH$_3$ | N | 214–216 |
| O | — | H | H | H | NCH$_3$ | OCH$_3$ | Cl | CH | 217–218 |
| O | — | H | H | H | NCH$_3$ | OCH$_3$ | OCH$_3$ | CH | 218–219 |
| O | — | H | H | H | NCH$_3$ | CH$_3$ | OCH$_3$ | CH | 209–211 |
| O | — | H | H | H | NCH$_3$ | CH$_3$ | CH$_3$ | CH | 210–211 |
| O | — | H | H | H | NCH$_2$CH$_3$ | Cl | OCH$_3$ | CH | |
| O | — | H | H | H | NC$_6$H$_5$ | CF$_3$ | CH$_3$ | CH | |
| O | — | H | H | H | NCH$_2$C$_6$H$_5$ | CH$_3$ | CH$_3$ | CH | |
| O | — | H | H | H | NCH$_3$ | CH$_3$ | N$_3$ | CH | |
| O | — | H | H | H | NH | CH$_3$ | SCH$_2$CH$_3$ | CH | |
| O | — | H | H | H | NH | CH$_3$ | CH$_2$OCH$_3$ | CH | |
| O | — | H | H | H | NH | CH$_3$ | C≡CH | N | |
| O | — | H | 5-Cl | H | NH | CH$_3$ | OCH$_3$ | N | |
| O | — | H | 5-Cl | H | NCN | CH$_3$ | OCH$_3$ | CH | |
| O | — | H | 5-Cl | N | NCH$_3$ | Cl | OCH$_3$ | CH | 208–210 |
| O | — | H | 5-Cl | H | NCH$_3$ | OCH$_3$ | OCH$_3$ | CH | 181–185 |
| O | — | H | 5-Cl | N | NCH$_3$ | OCH$_3$ | OCH$_3$ | CH | 169–172 |
| O | — | H | 5-Cl | H | NCH$_3$ | CH$_3$ | CH$_3$ | CH | 206–207 |
| O | — | H | 5-Cl | H | NCH$_3$ | CH$_3$ | CH$_3$ | N | 191–194 |
| O | — | H | 5-Cl | H | NCH$_3$ | OCH$_3$ | CH$_3$ | N | 189–190 |
| O | — | H | 5-Cl | H | NCH$_3$ | OCH$_3$ | OCH$_3$ | N | 198–199 |
| O | — | H | 5-Cl | H | NCH$_3$ | OC$_2$H$_5$ | NHCH$_3$ | N | 168–173 |
| O | — | N | 5-Br | N | NCH$_2$C$_6$N$_5$ | OCH$_3$ | CH$_3$ | N | |
| O | — | N | 5-CH$_3$ | H | NCH$_3$ | CH$_3$ | CH$_3$ | CH | 212–213 |
| O | — | H | 5-CH$_3$ | H | NCH$_3$ | CH$_3$ | OCH$_3$ | CH | 207–208 |
| O | — | H | 5-CH$_3$ | H | NCH$_3$ | OCH$_3$ | OCH$_3$ | CH | 193–194 |
| O | — | H | 5-CH$_3$ | H | NCH$_3$ | Cl | OCH$_3$ | CH | 192–194 |
| O | — | H | 5-CH$_3$ | H | NCH$_3$ | CH$_3$ | CH$_3$ | N | 213–216 |
| O | — | H | 5-CH$_3$ | H | NCH$_3$ | OCH$_3$ | CH$_3$ | N | 203–206 |
| O | — | N | 5-CH$_3$ | H | NCH$_3$ | OCH$_3$ | OCH$_3$ | N | 199–201 |
| O | — | H | 5-CH$_3$ | H | NCH$_3$ | NHCH$_3$ | OC$_2$H$_5$ | N | 232–233 |

TABLE II-continued $$JSO_2NHCNA \quad J = J-3$$
$$\overset{\|}{R} \quad A = A-1$$

Where W is above C, and R is below N.

| W | E | R | R₁ | R₅ | Q₂ | X | Y | Z | m.p.(°C.) |
|---|---|---|----|----|----|----|---|---|-----------|
| O | — | H | 5-CH₃ | H | NCH₂C₆H₅ | OCH₃ | CH₃ | N | |
| O | — | H | 5-CH₃ | H | NCH₂C₆H₅ | OCH₃ | CH₃ | CH | |
| O | — | H | 5-CF₂H | H | NCH₃ | OCH₃ | CH₃ | CH | |
| O | — | H | 5-OCH₃ | H | NCH₃ | OCH₃ | Cl | CH | 192–194 |
| O | — | H | 5-OCH₃ | H | NCH₃ | OCH₃ | CH₃ | CH | 197–200 |
| O | — | H | 5-OCH₃ | H | NCH₃ | OCH₃ | OCH₃ | CH | 223–225 |
| O | — | H | 5-OCH₃ | H | NCH₃ | OCH₃ | CH₃ | N | 189–193 |
| O | — | H | 5-OCH₃ | H | NCH₃ | NHCH₃ | OC₂H₅ | N | 232–237 |
| O | — | H | 5-OCH(CH₃)₂ | H | NH | NHCH₃ | OCH₃ | N | |
| O | — | H | 5-SCH₃ | N | NH | CH₃ | OCH₂CF₃ | CH | |
| O | — | H | 5-SO₂CH₃ | H | NH | CH₃ | OCH₃ | CH | |
| O | — | H | 5-CN | H | NH | CH₃ | OCH₃ | CH | |
| O | — | H | 5-NO₂ | H | NCH₃ | CH₃ | OCH₃ | CH | |
| O | — | H | 5-CO₂CH_CN | H | NCH₃ | CH₃ | OCH₃ | CN | |
| O | — | H | 5-CO₂CH₂CH₃ | H | NCH₃ | CH₃ | OCH₃ | CH | |
| O | — | H | 5-N(CH₃)₂ | H | NCH₃ | CH₃ | OCH₃ | CH | |
| O | — | H | 5-N(CH₃)₂ | H | NCH₃ | CH₃ | OCH₃ | N | |
| O | — | H | 5-N(CH₃)₂ | H | NH | SCH₃ | OCH₃ | N | |
| O | — | H | 5-NHCH₂CH₃ | H | NH | CH₃ | OCH₃ | N | |
| O | — | H | 6-OCH₃ | H | NH | CH₃ | CH₃ | CH | |
| O | — | H | 6-OCH₃ | H | NCH₃ | CH₃ | OCH₃ | CH | |
| O | — | H | 6-Br | H | NCH₃ | CH₃ | OCH₃ | N | |
| O | — | H | 6-Br | H | NCH₂CH₃ | CH₃ | SCH₃ | N | |
| O | — | H | 6-OCH₂CH₃ | H | NCH₂CH₃ | OCH₃ | CH₃ | CH | |
| O | — | H | 6-OCH₂CH₃ | H | NCH₂C₆H₅ | Cl | CH₃ | CH | |
| O | — | H | 6-SCH₃ | H | NCH₃ | Cl | OCF₂H | CH | |
| O | — | H | 6-CN | H | NCH₃ | OCH₃ | OCH₃ | CH | |
| O | — | H | 6-SOCH₂CH₃ | H | NCH₃ | OCH₃ | OCH₃ | CH | |
| O | — | H | 6-NH₂ | H | NH | OCH₃ | OCH₃ | CH | |
| O | — | H | 6-NHCH₃ | H | NCH₃ | CH₃ | OCH₃ | N | |
| O | — | H | 6-NHCH₃ | H | NCH₃ | OCH₃ | C≡CH | N | |
| O | — | H | 6-NHCH | H | NC₆H₅ | OCH₃ | COCH₃ | CH | |
| O | — | H | 6-N(CH₃)₂ | H | NH | OCH₃ | CH₃ | CH | |
| O | — | CH₃ | H | H | NCH₃ | OCH₃ | CH₃ | CH | |
| O | — | CH₃ | H | H | NOCH₃ | OCH₃ | CH₃ | N | |
| O | — | CH₃ | 5-Cl | H | NH | OCH₃ | CH₃ | N | |
| O | — | CH₃ | 6-Br | H | NH | OCH₃ | CH₃ | N | |
| O | CH₂ | H | H | H | NCH₃ | OCH₃ | CH₃ | N | |
| O | CH₂ | H | H | H | S | OCH₃ | CH₃ | CH | |
| O | CH₂ | H | H | H | O | OCH₃ | OCH₃ | OH | |
| O | CH₂ | H | 5-OCH₃ | H | S | OCH₃ | OCH₃ | CH | |
| O | O | H | H | H | S | OCH₃ | OCH₃ | CH | |
| O | O | H | 6-N(CH₃)₂ | H | S | OCH₃ | OCH₃ | CH | |
| O | O | H | 6-Cl | H | NCH₃ | OCH₂CH₃ | OCH₃ | CH | |
| O | O | H | 5-OCH₃ | H | O | OCH₂CH₃ | NHCH₃ | N | |
| S | — | H | H | H | O | OCH₂CH₃ | CH₃ | N | |
| S | — | H | H | H | S | OCH₃ | CH₃ | N | |
| S | — | H | 5-N(CH₃)₂ | H | NCH₃ | OCH₃ | CH₃ | N | |
| S | CH₂ | H | H | H | S | OCH₃ | CH₃ | N | |

TABLE III $$JSO_2NHCNA \quad J = J-4$$
$$\overset{\|}{R} \quad A = A-1$$

| W | E | R | R₁ | R₅ | n | Q₃ | Q₄ | X | Y | Z | m.p. (°C.) |
|---|---|---|----|----|---|----|----|----|---|---|-----------|
| O | — | H | H | H | 0 | NH | NH | CH₃ | OCH₃ | N | |
| O | — | H | H | H | 0 | NCH₃ | NH | CH₃ | OCH₃ | CH | 212–215 |
| O | — | H | H | H | 0 | NCH₃ | NH | CH₃ | OCH₃ | N | 202–205 |
| O | — | H | H | H | 0 | NCH₃ | NH | OCH₃ | OCH₃ | CH | 222–225 |
| O | — | H | H | H | 0 | NCH₃ | NCH₃ | CH₃ | OCH₃ | N | |
| O | — | H | H | H | 0 | NCH₃ | NCH₃ | CH₃ | OCH₃ | CH | |
| O | — | H | H | C₂H₅ | 0 | NCH₃ | NCH₃ | Cl | OCH₃ | CH | |
| O | — | H | 5-Cl | H | 0 | NCH₃ | NCH₃ | OCH₃ | OCH₃ | CH | |
| O | — | H | 5-OCH₃ | H | 0 | NCH₃ | NCH₃ | OCH₃ | OCH₃ | CH | |
| O | — | H | 6-N(CH₃)₂ | H | 0 | NCH₃ | NCH₃ | OCH₃ | NHCH₃ | CH | |
| O | — | H | H | H | 0 | NCH₂CH₃ | NCH₃ | OCH₃ | CH₃ | CH | |
| O | — | H | H | H | 0 | NCH(CH₃)₂ | NCH₃ | OCH₃ | CH₃ | N | |
| O | — | H | H | H | 1 | O | O | CH₃ | CH₃ | CH | |
| O | — | H | H | H | 1 | O | O | CH₃ | OCH₃ | CH | |
| O | — | H | H | H | 1 | O | O | Cl | OCH₃ | CH | |

TABLE III-continued $$JSO_2NHCNA \quad \begin{array}{l} J = J\text{-}4 \\ A = A\text{-}1 \end{array}$$

with W=O (double bond on C), R on N

| W | E | R | R₁ | R₅ | n | Q₃ | Q₄ | X | Y | Z | m.p. (°C.) |
|---|---|---|---|---|---|---|---|---|---|---|---|
| O | — | H | H | H | 1 | O | O | N(CH₃)₂ | OCH₃ | CH | |
| O | — | H | H | H | 1 | O | O | N(CH₃)₂ | C≡CH | N | |
| O | — | H | 5-Br | H | 1 | O | O | OCH₃ | CH₃ | N | |
| O | — | H | 5-NO₂ | H | 1 | O | O | OCH₃ | CH₃ | N | |
| O | — | H | 5-OCH₃ | H | 1 | O | O | OCH₃ | CH₃ | N | |
| O | — | H | 5-OCH₃ | H | 1 | O | O | OCH₃ | CH₃ | CH | |
| O | — | H | 5-SO₂N(CH₂CH₃)₂ | H | 1 | O | O | OCH₂CH₃ | OCH₂CH₃ | CH | |
| O | — | H | 6-SCH₃ | H | 1 | O | O | CH₃ | CH₂OCH₃ | CH | |
| O | — | H | 6-CN | H | 1 | O | O | CH₃ | CH₃ | CH | |
| O | — | H | 6-OCF₃ | H | 1 | O | O | CH₃ | OCH₃ | N | |
| O | — | H | 6-N(CH₃)₂ | H | 1 | O | O | CH₃ | SCH₃ | N | |
| O | — | H | H | H | 1 | O | S | CH₃ | OCH₃ | N | |
| O | — | H | H | H | 1 | O | S | CH₃ | OCH₃ | CH | |
| O | — | H | H | H | 1 | O | S | OCH₃ | OCH₃ | N | |
| O | — | H | H | H | 1 | O | S | Cl | OCH₃ | CH | |
| O | — | H | 5-Cl | H | 1 | O | S | OCH₃ | OCH₃ | CH | |
| O | — | H | 5-Cl | H | 1 | S | O | OCH₃ | OCH₃ | N | |
| O | — | H | 5-CH₃ | H | 1 | S | O | OCH₃ | CH₃ | N | |
| O | — | H | 5-CF₃ | H | 1 | S | O | OCH₃ | CH₃ | N | |
| O | — | H | 5-CF₃ | H | 1 | O | S | OCH₃ | CH₃ | N | |
| O | — | H | 5-CN | H | 1 | O | S | OCF₂H | CH₃ | CH | |
| O | — | H | 5-NHCH₃ | H | 1 | O | S | OCF₂H | CH₃ | CH | |
| O | — | H | 6-Br | H | 1 | S | O | CH₃ | OCH₃ | CH | |
| O | — | H | 6-NCH₃(CH₂CH₃) | H | 1 | S | O | CH₃ | OCH₃ | CH | |
| O | — | H | H | H | 1 | O | NH | CF₂H | OCH₃ | CH | |
| O | — | H | H | H | 1 | O | NH | NHCH₃ | OCH₃ | N | |
| O | — | H | H | H | 1 | O | NH | NHCH₃ | OCH₂CH₃ | CH | |
| O | — | H | H | H | 1 | NH | O | NHCH₃ | OCH₂CH₃ | N | |
| O | — | H | H | H | 1 | NCH₃ | O | N(CH₃)₂ | CH₃ | CH | |
| O | — | H | 5-CH₂CH₃ | H | 1 | NCH₃ | O | CH₃ | CH₃ | CH | |
| O | — | H | 5-CF₂H | H | 1 | NCH₃ | O | CH₃ | OCH₃ | CH | |
| O | — | H | 5-OCH₃ | H | 1 | NCH₂CH₃ | O | CH₃ | OCH₃ | CH | |
| O | — | H | 5-SCH₃ | H | 1 | O | NCH₃ | OCH₃ | OCH₃ | CH | |
| O | — | H | 5-SOCH₂CH₃ | H | 1 | NCH₂CH₃ | O | OCH₃ | OCH₃ | N | |
| O | — | H | 6-F | H | 1 | O | NCH₃ | OCH₃ | OCH₃ | N | |
| O | — | H | 6-OCH₃ | H | 1 | O | NCH₃ | OCH₃ | CH₃ | N | |
| O | — | H | 6-SO₂CH(CH₃)₂ | H | 1 | NCH₃ | O | OCH₃ | CH₃ | N | |
| O | — | H | 6-NCH₃(CH₂CH₃) | H | 1 | O | NCH₃ | OCH₃ | CH₃ | CH | |
| O | — | H | H | H | 1 | S | NH | OCH₃ | CH₃ | CH | |
| O | — | H | H | H | 1 | S | NCH₃ | CH₂—cyclopropyl | CH₃ | CH | |
| O | — | H | H | H | 1 | NH | S | CH₃ | CH₃ | CH | |
| O | — | H | H | H | 1 | NCH₃ | S | CH₃ | OCH₃ | CH | |
| O | — | H | H | H | 1 | NCH₂CH₃ | S | CH₃ | OCH₃ | N | |
| O | — | H | 5-Br | H | 1 | S | NCH₃ | CH₃ | OCH₃ | N | |
| O | — | H | 5-CH | H | 1 | S | NCH₃ | CH₃ | OCH₃ | CH | |
| O | — | H | 5-CH₃ | H | 1 | NH | S | OCH₃ | OCH₃ | CH | |
| O | — | H | 5-OCH₃ | H | 1 | S | NH | OCH₃ | OCH₃ | CH | |
| O | — | H | 5-CH₂OCH₃ | H | 1 | S | NCH₃ | CH₃ | OCH₃ | CH | |
| O | — | H | 6-CH₃ | H | 1 | NCH₃ | S | OCH₃ | OCH₃ | CH | |
| O | — | H | 6-Cl | H | 1 | S | NCH₃ | OCH₃ | OCH₃ | N | |
| O | — | H | 6-NO₂ | H | 1 | S | NCH₃ | OCH₃ | CH₃ | N | |
| O | — | H | H | H | 1 | N | NH | OCH₃ | CH₃ | N | |
| O | — | H | H | H | 1 | N | NH | CH₃ | CH₃ | N | |
| O | — | H | H | H | 1 | NCH₃ | NH | CH₃ | CH₃ | CH | |
| O | — | H | H | H | 1 | NCH₃ | NCH₃ | OCH₂CH₃ | CH₃ | CH | |
| O | — | H | H | H | 1 | NCH₃ | NCH₃ | OCH₂CH₃ | CH₃ | N | |
| O | — | H | H | H | 1 | NCH₃ | NCH₃ | CF₂H | CF₂H | CH | |
| O | — | H | 5-Cl | H | 1 | NH | NCH₃ | OCF₃ | CH₃ | CH | |
| O | — | H | 5-CF₂H | H | 1 | NCH₂CH₃ | NCH₃ | OCH₃ | CH₃ | CH | |
| O | — | H | 5-OCF₃ | H | 1 | NC₃H₇ | NCH₃ | OCH₃ | CH₃ | CH | |
| O | — | H | 5-N(CH₃)₂ | H | 1 | NCH₃ | NCH₃ | OCH₃ | CH₃ | CH | |
| O | — | H | 6-Br | H | 1 | NH | NH | OCH₃ | CH₃ | N | |
| O | — | H | 6-SCH₃ | H | 1 | NCH₃ | NCH₃ | OCH₃ | CH₃ | CH | |
| O | — | H | 6-CH₃ | H | 1 | NCH₃ | NCH₃ | OCH₃ | CH₃ | N | |
| O | — | H | 6-OCH₃ | H | 1 | NCH₃ | NCH₃ | OCH₃ | CH₃ | N | |
| O | — | H | H | H | 2 | O | O | CH₃ | CH₃ | CH | |
| O | — | H | H | H | 2 | O | O | Cl | OCH₃ | CH | |
| O | — | H | H | H | 2 | O | O | N(CH₃)₂ | OCH₃ | CH | |
| O | — | H | H | H | 2 | O | O | N(CH₃)₂ | C≡CH | N | |
| O | — | H | H | F | 2 | O | O | CH₃ | CH₃ | CH | |
| O | — | H | 5-Br | H | 2 | O | O | OCH₃ | CH₃ | N | |
| O | — | H | 5-NO₂ | H | 2 | O | O | OCH₃ | CH₃ | N | |

TABLE III-continued $$\text{JSO}_2\text{NHCNA} \quad \overset{\overset{W}{\|}}{\underset{R}{|}} \quad \begin{array}{l} J = J\text{-}4 \\ A = A\text{-}1 \end{array}$$

| W | E | R | R₁ | R₅ | n | Q₃ | Q₄ | X | Y | Z | m.p. (°C.) |
|---|---|---|----|----|---|----|----|---|---|---|---|
| O | — | H | 5-OCH₃ | H | 2 | O | O | OCH₃ | CH₃ | N | |
| O | — | H | 5-OCH₃ | H | 2 | O | O | OCH₃ | CH₃ | CH | |
| O | — | H | 5-SO₂N(CH₂CH₃)₂ | H | 2 | O | O | OCH₂CH₃ | OCH₂CH₃ | CH | |
| O | — | H | 6-SCH₃ | H | 2 | O | O | CH₃ | CH₂OCH₃ | CH | |
| O | — | H | 6-CH | H | 2 | O | O | CH₃ | CH₃ | CH | |
| O | — | H | 6-OCF₃ | H | 2 | O | O | CH₃ | OCH₃ | N | |
| O | — | H | 6-N(CH₃)₂ | H | 2 | O | O | CH₃ | SCH₃ | N | |
| O | — | H | H | H | 2 | O | S | CH₃ | OCH₃ | N | |
| O | — | H | H | H | 2 | O | S | CH₃ | OCH₃ | CH | |
| O | — | H | H | H | 2 | O | S | OCH₃ | OCH₃ | N | |
| O | — | H | H | H | 2 | O | S | Cl | OCH₃ | CH | |
| O | — | H | 5-Cl | H | 2 | O | S | OCH₃ | OCH₃ | CH | |
| O | — | H | 5-Cl | H | 2 | S | O | OCH₃ | OCH₃ | N | |
| O | — | H | 5-CH₃ | H | 2 | S | O | OCH₃ | CH₃ | N | |
| O | — | H | 5-CF₃ | H | 2 | S | O | OCH₃ | CH₃ | N | |
| O | — | H | 5-CF₃ | H | 2 | O | S | OCH₃ | CH₃ | N | |
| O | — | H | 5-CN | H | 2 | O | S | OCF₂H | CH₃ | CH | |
| O | — | H | 5-NHCH₃ | H | 2 | O | S | OCF₂H | CH₃ | CH | |
| O | — | H | 6-Br | H | 2 | S | O | CH₃ | OCH₃ | CH | |
| O | — | H | 6-NCH₃(CH₂CH₃) | H | 2 | S | O | CH₃ | OCH₃ | CH | |
| O | — | H | H | H | 2 | O | NH | CF₂H | OCH₃ | CH | |
| O | — | H | H | H | 2 | O | NH | NHCH₃ | OCH₃ | N | |
| O | — | H | H | H | 2 | O | NH | NHCH₃ | OCH₂CH₃ | CH | |
| O | — | H | H | H | 2 | NH | O | NHCH₃ | OCH₂CH₃ | N | |
| O | — | H | H | H | 2 | NCH₃ | O | N(CH₃)₂ | CH₃ | CH | |
| O | — | H | 5-CH₂CH₃ | H | 2 | NCH₃ | O | CH₃ | CH₃ | CH | |
| O | — | H | 5-CF₂H | H | 2 | NCH₃ | O | CH₃ | OCH₃ | CH | |
| O | — | H | 5-OCH₃ | H | 2 | NCH₂CH₃ | O | CH₃ | OCH₃ | CH | |
| O | — | H | 5-SCH₃ | H | 2 | O | NCH₃ | OCH₃ | OCH₃ | CH | |
| O | — | H | 5-SOCH₂CH₃ | H | 2 | NCH₂CH₃ | O | OCH₃ | OCH₃ | N | |
| O | — | H | 6-F | H | 2 | O | NCH₃ | OCH₃ | OCH₃ | N | |
| O | — | H | 6-OCH₃ | H | 2 | O | NCH₃ | OCH₃ | CH₃ | N | |
| O | — | H | 6-SO₂CH(CH₃)₂ | H | 2 | NCH₃ | O | OCH₃ | CH₃ | N | |
| O | — | H | 6-NCH₃(CH₂CH₃) | H | 2 | O | NCH₃ | OCH₃ | CH₃ | CH | |
| O | — | H | H | H | 2 | S | NH | OCH₃ | CH₃ | CH | |
| O | — | H | H | H | 2 | S | NCH₃ | CH₂—cyclopropyl | CH₃ | CH | |
| O | — | H | H | H | 2 | NH | S | CH₃ | CH₃ | CH | |
| O | — | H | H | H | 2 | NCH₃ | S | CH₃ | OCH₃ | CH | |
| O | — | H | H | H | 2 | NCH₂CH₃ | S | CH₃ | OCH₃ | N | |
| O | — | H | 5-Br | H | 2 | S | NCH₃ | CH₃ | OCH₃ | N | |
| O | — | H | 5-CN | H | 2 | S | NCH₃ | CH₃ | CH₃ | CH | |
| O | — | H | 5-CH₃ | H | 2 | NH | S | OCH₃ | OCH₃ | CH | |
| O | — | H | 5-OCH₃ | H | 2 | S | NH | OCH₃ | OCH₃ | CH | |
| O | — | H | 5-CH₂OCH₃ | H | 2 | S | NCH₃ | OCH₃ | OCH₃ | CH | |
| O | — | H | 6-CH₃ | H | 2 | NCH₃ | S | OCH₃ | OCH₃ | CH | |
| O | — | H | 6-Cl | H | 2 | S | NCH₃ | OCH₃ | OCH₃ | N | |
| O | — | H | 6-NO₂ | H | 2 | S | NCH₃ | OCH₃ | CH₃ | N | |
| O | — | H | H | H | 2 | N | NH | OCH₃ | CH₃ | N | |
| O | — | H | H | H | 2 | N | NH | CH₃ | CH₃ | N | |
| O | — | H | H | H | 2 | NCH₃ | NH | CH₃ | CH₃ | CH | |
| O | — | H | H | H | 2 | NCH₃ | NCH₃ | OCH₂CH₃ | CH₃ | N | |
| O | — | H | H | CH₃ | 2 | NCH₃ | NCH₃ | CF₂H | CF₂H | CH | |
| O | — | H | 5-Cl | H | 2 | NH | NCH₃ | OCF₃ | CH₃ | CH | |
| O | — | H | 5-CF₂H | H | 2 | NCH₂CH₃ | NCH₃ | OCH₃ | CH₃ | CH | |
| O | — | H | 5-OCF₃ | H | 2 | NC₃H₇ | NCH₃ | OCH₃ | CH₃ | CH | |
| O | — | H | 5-N(CH₃)₂ | H | 2 | NCH₃ | NCH₃ | OCH₃ | CH₃ | CH | |
| O | — | H | 6-Br | H | 2 | NH | NH | OCH₃ | CH₃ | N | |
| O | — | H | 6-SCH₃ | H | 2 | NCH₃ | NCH₃ | OCH₃ | CH₃ | N | |
| O | — | H | 6-CH₃ | H | 2 | NCH₃ | NCH₃ | OCH₃ | CH₃ | N | |
| O | — | H | 6-OCH₃ | H | 2 | NCH₃ | NCH₃ | OCH₃ | CH₃ | N | |
| O | — | CH₃ | H | H | 0 | NCH₃ | NCH₃ | CH₃ | CH₃ | N | |
| O | — | CH₃ | H | H | 1 | O | O | OCH₃ | CH₃ | N | |
| O | — | CH₃ | H | H | 2 | O | O | OCH₃ | CH₃ | N | |
| O | — | CH₃ | 5-Cl | H | 1 | O | O | OCH₃ | CH₃ | CH | |
| O | CH₂ | H | H | H | 1 | O | O | OCH₃ | OCH₃ | CH | |
| O | CH₂ | H | H | H | 1 | O | O | OCH₃ | OCH₃ | CH | |
| O | CH₂ | H | H | H | 1 | O | NCH₃ | OCH₃ | OCH₃ | CH | |
| O | CH₂ | H | 6-OCH₃ | H | 1 | S | O | OCH₃ | OCH₃ | CH | |
| O | O | H | H | H | 2 | O | S | CH₃ | OCH₃ | N | |
| O | O | H | H | H | 1 | O | S | CH₃ | NHCH₃ | N | |
| O | O | H | H | H | 1 | NCH₃ | NCH₃ | CH₃ | CH₃ | CH | |

TABLE III-continued $$\text{JSO}_2\text{NHCNA} \quad \begin{array}{l} J = J\text{-}4 \\ A = A\text{-}1 \end{array}$$

with W double-bonded above C, and R attached below N.

| W | E | R | R₁ | R₅ | n | Q₃ | Q₄ | X | Y | Z | m.p. (°C.) |
|---|---|---|---|---|---|---|---|---|---|---|---|
| S | — | H | 5-CH₃ | H | 1 | S | NCH₃ | OCH₃ | CH₃ | CH | |
| S | — | H | H | H | 2 | S | O | OCF₂H | CH₃ | CH | |
| S | — | H | H | H | 2 | O | O | OCH₃ | OCH₃ | CH | |
| S | — | H | H | H | 0 | NCH₃ | NCH₃ | OCH₃ | OCH₃ | N | |
| S | CH₂ | H | 6-Br | H | 1 | O | O | OCH₃ | OCH₃ | CH | |

TABLE IV $$\text{JSO}_2\text{NHCNA} \quad \begin{array}{l} J = J\text{-}5 \\ A = A\text{-}1 \end{array}$$

| W | E | R | R₁ | R₅ | Q₃ | Q₄ | X | Y | Z | m.p.(° C.) |
|---|---|---|---|---|---|---|---|---|---|---|
| O | — | H | H | H | NH | NH | H | H | N | |
| O | — | H | H | H | NH | NH | CH₃ | H | N | |
| O | — | H | H | H | NH | NH | CH₃ | CH₃ | N | |
| O | — | H | H | H | NH | NH | CH₃ | OCH₃ | N | |
| O | — | H | H | H | NH | NH | OCH₃ | OCH₃ | N | |
| O | — | H | H | H | NH | NH | OCH₃ | NHCH₃ | N | |
| O | — | H | H | H | NH | NH | NHCH₃ | NHCH₃ | CH | |
| O | — | H | H | H | NH | NH | NHCH₃ | OCH₃ | CH | |
| O | — | H | H | H | NH | NH | OCH₃ | OCH₃ | CH | |
| O | — | H | H | H | NH | NH | CH₃ | OCH₃ | CH | |
| O | — | H | H | H | NH | NH | CH₃ | CH₃ | CH | |
| O | — | H | H | H | NH | NH | Cl | CH₃ | CH | |
| O | — | H | H | H | NH | NH | Br | OCH₃ | CH | |
| O | — | H | H | H | NH | NH | OCH₂CH₃ | OCH₃ | N | |
| O | — | H | H | Cl | NH | NH | SCH₃ | OCH₃ | N | |
| O | — | H | 5-CH₂CH₂CH₃ | H | NH | NH | CH₃ | OCH₃ | N | |
| O | — | H | 5-CH₂CH₂CH₃ | H | NH | NH | CH₃ | OCH₃ | CH | |
| O | — | H | 5-CH₂CH₂Cl | H | NH | NH | OCH₃ | OCH₃ | CH | |
| O | — | H | 5-Cl | H | NH | NH | OCH₃ | OCH₃ | CH | |
| O | — | H | 5-Cl | H | NH | NH | OCH₃ | CH₃ | CH | |
| O | — | H | 5-OCH(CH₃)₂ | H | NH | NH | OCH₃ | CH₃ | CH | |
| O | — | H | 5-OCH₃ | H | NH | NH | OCH₃ | CH₃ | CH | |
| O | — | H | 5-SCH₃ | H | NH | NH | OCH₃ | CH₃ | N | |
| O | — | H | 5-SO₂CH₂CH₃ | H | NH | NH | OCH₃ | CH₃ | N | |
| O | — | H | 5-CN | H | NH | NH | OCH₃ | CH₃ | N | |
| O | — | H | 5-N(CH₃)₂ | H | NH | NH | OCH₃ | CH₃ | N | |
| O | — | H | 6-Br | H | NH | NH | OCH₃ | CH₃ | N | |
| O | — | H | 6-Br | H | NH | NH | OCH₃ | CH₃ | CH | |
| O | — | H | 6-SCH₂CH₃ | H | NH | NH | OCH₃ | OCH₃ | CH | |
| O | — | H | 6-SOCH₃ | H | NH | NH | Br | OCH₃ | OH | |
| O | — | H | 6-CF₃ | H | NH | NH | OCF₃ | OCH₃ | CH | |
| O | — | H | 6-OCH₃ | H | NH | NH | OCH₃ | OCH₃ | CH | |
| O | — | H | 6-OCH₃ | H | NH | NH | OCH₃ | OCH₃ | CN | |
| O | — | H | 6-OCH₂CF₃ | H | NH | NH | OCH₃ | OCH₃ | N | |
| O | — | H | 6-N(CH₃)₂ | N | NH | NH | OCH₃ | CH₃ | N | |
| O | — | H | 6-N(CH₃)₂ | H | NH | NH | OCH₃ | OCH₃ | N | |
| O | — | H | H | H | NCH₃ | NH | CH₃ | OCH₃ | N | |
| O | — | H | H | H | NCH₃ | NH | CH₃ | OCH₃ | CH | |
| O | — | H | 5-Br | H | NCH₃ | NH | CH₃ | OCH₃ | CH | |
| O | — | H | 6-OCH₃ | H | NHCH₃ | NH | CH₃ | OCH₃ | CH | |
| O | — | H | H | H | NH | NCH₃ | CH₃ | OCH₃ | CH | |
| O | — | H | H | H | NH | NCH₃ | OCH₃ | OCH₃ | CH | |
| O | — | H | 5-N(CH₃)₂ | H | NH | NCH₃ | OCH₃ | OCH₃ | CH | |
| O | — | H | 6-Cl | H | NH | NCH₃ | OCH₃ | OCH₃ | CH | |
| O | — | H | 6-OCH₃ | H | NH | HCH₃ | OCH₃ | NHCH₃ | CH | |
| O | — | H | H | H | NCH₂CH₃ | NH | Cl | OCH₃ | CH | |
| O | — | H | H | H | NCH₂CH₂CH₃ | NH | Cl | CH₃ | CH | |
| O | — | H | 5-CF₂H | H | NCH₃ | NCH₃ | CH₃ | CH₃ | CH | |
| O | — | H | 6-SCH₃ | H | NCH₃ | NCH₃ | OCH₃ | CH₃ | CH | |
| O | — | H | H | H | NCH₂CH₃ | NCH₃ | OCH₃ | CH₃ | N | |
| O | — | CH₃ | H | H | NH | NH | OCH₃ | CH₃ | N | |
| O | — | CH₃ | H | H | NH | NH | OCH₃ | CH₃ | CH | |
| O | — | CH₃ | H | H | NH | NH | Cl | CH₃ | CH | |
| O | CH₂ | H | H | H | NH | NH | Cl | OCH₃ | CH | |
| O | CH₂ | H | N | H | NH | NH | CH₃ | OCH₃ | CH | |
| O | O | H | H | H | NH | NH | CH₃ | OCH₃ | CH | |
| O | O | H | H | H | NH | NH | CH₃ | OCH₃ | N | |

TABLE IV-continued $$\underset{\underset{R}{|}}{JSO_2NHC}\overset{\overset{W}{\|}}{N}A \qquad \begin{array}{l} J = J\text{-}5 \\ A = A\text{-}1 \end{array}$$

| W | E | R | R₁ | R₅ | Q₃ | Q₄ | X | Y | Z | m.p.(° C.) |
|---|---|---|----|----|-----|-----|---|---|---|------------|
| S | — | H | H | H | NH | NH | CH₃ | OCH₃ | N | |
| S | — | H | H | H | NH | NH | OCH₃ | OCH₃ | CH | |

TABLE V $$\underset{\underset{R}{|}}{JSO_2NHC}\overset{\overset{W}{\|}}{N}A \qquad (A = A\text{-}1)$$

| J | W | E | R | R₁ | R₅ | R₆ | X | Y | Z | m.p. (°C.) |
|---|---|---|---|----|----|-----|---|---|---|------------|
| J-6 | O | — | H | H | H | CH₃ | CH₃ | H | CH | |
| J-6 | O | — | H | H | H | CH₃ | CH₃ | CH₃ | CH | 226–230 (d) |
| J-6 | O | — | H | H | H | CH₃ | OCH₃ | OCH₃ | CH | 232–235 (d) |
| J-6 | O | — | H | H | H | CH₃ | OCH₃ | OC₂H₅ | CH | 237–240 (d) |
| J-6 | O | — | H | H | H | CH₃ | Cl | OCH₃ | CH | 195–198 |
| J-6 | O | — | H | H | H | CH₃ | NHCH₃ | OCH₃ | CH | |
| J-6 | O | — | H | H | H | CH₃ | NHCH₃ | OC₂H₅ | N | 216–220 (d) |
| J-6 | O | — | H | H | H | CH₃ | OCH₃ | OC₂H₅ | N | |
| J-6 | O | — | H | H | H | CH₃ | OCH₃ | CH₃ | N | 222–226 (d) |
| J-6 | O | — | H | H | H | CH₃ | CH₃ | CH₃ | N | |
| J-6 | O | — | H | H | H | CH₃ | CH₃ | Cl | N | |
| J-6 | O | — | H | H | Cl | CH₃ | OCH₃ | OCH₃ | CH | |
| J-6 | O | — | H | H | H | C₂H₅ | OCH₃ | OCH₃ | CH | |
| J-6 | O | — | H | H | H | C₂H₅ | OCH₃ | CH₃ | CH | |
| J-6 | O | — | H | H | H | C₂H₅ | OCH₃ | CH₃ | N | |
| J-6 | O | — | H | H | H | CH₂CH(CH₃)₂ | OCH₃ | CH₃ | N | |
| J-6 | O | — | H | 5-Cl | H | CH₃ | OCH₃ | CH₃ | N | |
| J-6 | O | — | H | 5-Cl | H | CH₃ | OCH₃ | CH₃ | CH | |
| J-6 | O | — | H | 5-Cl | H | CH₃ | OCH₃ | OCH₃ | CH | |
| J-6 | O | — | H | 5-OCH₃ | H | CH₃ | OCH₃ | OCH₃ | CH | |
| J-6 | O | — | H | 5-OCH₃ | H | CH₂CH₂CH₃ | OCH₃ | OCH₃ | CH | |
| J-6 | O | — | H | 5-OCH₃ | H | CH₂CH₂CH₃ | CH₃ | OCH₃ | CH | |
| J-6 | O | — | H | 5-CN | H | CH₂CH₂CH₃ | CH₃ | OCH₃ | N | |
| J-6 | O | — | H | 5-N(CH₃)₂ | H | CH₂CH₃ | CH₃ | OCH₃ | N | |
| J-6 | O | — | H | 5-CF₃ | H | CH₃ | CH₃ | OCH₃ | CH | |
| J-6 | O | — | H | 6-Br | H | CH₃ | CH₃ | OCH₃ | CH | |
| J-6 | O | — | H | 6-Br | H | CH₃ | OCH₃ | OCH₃ | CH | |
| J-6 | O | — | H | 6-OCH₃ | H | CH₃ | OCH₃ | OCH₃ | CH | |
| J-6 | O | — | H | 6-OC₂H₅ | H | CH₃ | OCH₃ | OCH₃ | CH | |
| J-6 | O | — | H | 6-SCH₃ | H | CH₃ | OCH₃ | OCH₃ | CH | |
| J-6 | O | — | H | 6-NO₂ | H | CH₃ | OCH₃ | OCH₃ | CH | |
| J-6 | O | — | CH₃ | H | H | CH₃ | OCH₃ | OCH₃ | CH | |
| J-6 | O | CH₂ | H | H | H | CH₃ | OCH₃ | OCH₃ | CH | |
| J-6 | O | O | H | H | H | CH₃ | OCH₃ | OCH₃ | CH | |
| J-6 | S | — | H | H | H | CH₃ | OCH₃ | OCH₃ | CH | |
| J-7 | O | — | H | H | H | CH₃ | H | CH₃ | N | |
| J-7 | O | — | H | H | H | CH₃ | CH₃ | CH₃ | N | |
| J-7 | O | — | H | H | H | CH₃ | OCH₃ | CH₃ | N | |
| J-7 | O | — | H | H | H | CH₃ | OCH₃ | CH₃ | CH | |
| J-7 | O | — | H | H | H | CH₃ | OCH₃ | OCH₃ | CH | |
| J-7 | O | — | H | H | H | CH₃ | Cl | OCH₃ | CH | |
| J-7 | O | — | H | H | H | CH₃ | OCH₂F | OCH₃ | CH | |
| J-7 | O | — | H | H | H | CH₃ | N(CH₃)₂ | OC₂H₅ | N | |
| J-7 | O | — | H | H | OCH₃ | CH₃ | OCH₃ | OCH₃ | CH | |
| J-7 | O | — | H | H | H | C₂H₅ | OCH₃ | OCH₃ | CH | |
| J-7 | O | — | H | H | H | C₂H₅ | OCH₃ | CH₃ | N | |
| J-7 | O | — | H | H | H | CH(CH₃)₂ | CH₃ | CH₃ | N | |
| J-7 | O | — | H | H | H | CH(CH₃)₂ | CH₃ | CH₃ | CH | |
| J-7 | O | — | H | H | H | CH₂CH₂CH₃ | Cl | CH₃ | CH | |
| J-7 | O | — | H | H | H | CH₂CH₂CH₃ | Cl | NHCH₃ | N | |
| J-7 | O | — | H | H | H | CH₂CH₂CH₂CH₃ | OCH₃ | NHCH₃ | N | |
| J-7 | O | — | H | H | H | CH₂CH₂CH₂CH₃ | OCH₃ | OCH₃ | CH | |
| J-7 | O | — | H | H | H | CH₂CH(CH₃)₂ | OCH₃ | CH₃ | CH | |
| J-7 | O | — | H | H | H | CH₂CH(CH₃)₂ | OCH₃ | CH₃ | N | |
| J-7 | O | — | H | 6-Br | H | CH₃ | OCH₃ | CH₃ | CH | |
| J-7 | O | — | H | 6-Br | H | CH₃ | Cl | OCH₃ | CH | |
| J-7 | O | — | H | 6-SCH₃ | H | CH₃ | CH₃ | OCH₃ | CH | |
| J-7 | O | — | H | 6-SCH₃ | H | CH₃ | OCH₃ | OCH₃ | N | |
| J-7 | O | — | H | 6-OCH₃ | H | CH₂CH₂CH₃ | CH₃ | OCH₃ | N | |
| J-7 | O | — | H | 6-OCH₃ | H | CH₃ | CH₃ | CH₃ | CH | |
| J-7 | O | — | H | 6-NHCH₃ | H | CH₃ | OCH₃ | OCH₃ | CH | |
| J-7 | O | — | H | 5-F | H | C₂H₅ | OCH₃ | CH₃ | CH | |

TABLE V-continued $$\text{JSO}_2\text{NHCNA} \quad (A = A\text{-}1)$$

with W (double bond) above C, and R below N.

| J | W | E | R | R₁ | R₅ | R₆ | X | Y | Z | m.p. (°C.) |
|---|---|---|---|---|---|---|---|---|---|---|
| J-7 | O | — | H | 5-NO₂ | H | CH₃ | OCH₃ | CH₃ | CH | |
| J-7 | O | — | H | 5-OCH₂ | H | CH₃ | OCH₃ | CH₃ | CH | |
| J-7 | O | — | CH₃ | H | H | CH₃ | OCH₃ | CH₃ | CH | |
| J-7 | O | CH₂ | H | H | H | CH₃ | OCH₃ | CH₃ | CH | |
| J-7 | O | O | H | H | H | CH₃ | OCH₃ | CH₃ | CH | |
| J-7 | S | — | H | H | H | CH₃ | OCH₃ | CH₃ | CH | |

TABLE VI $$\text{JSO}_2\text{NHCCNA}$$

i = 1–3 depending on J
j = 1–4 depending on A

| J | W | E | R | R₁ | n | Qᵢ | Q₄ | A | Xⱼ | Yⱼ | Z₁ | m.p. (°C.) |
|---|---|---|---|---|---|---|---|---|---|---|---|---|
| J-1 | O | — | H | H | — | S | — | A-2 | CH₃ | O | — | |
| J-1 | O | — | H | 5-Cl | — | S | — | A-2 | OCH₃ | O | — | |
| J-1 | O | — | H | 5-OCH₃ | — | S | — | A-2 | OCH₂CH₃ | O | — | |
| J-1 | O | — | H | 6-Br | — | S | — | A-2 | OCH₂CH₃ | CH₂ | — | |
| J-1 | O | — | H | 6-OCH₃ | — | SO₂ | — | A-2 | CH₃ | CH₂ | — | |
| J-1 | O | — | H | H | — | SO₂ | — | A-2 | OCH₃ | CH₂ | — | |
| J-1 | O | — | H | H | — | SO₂ | — | A-2 | OCH₃ | CH₂ | — | |
| J-1 | O | — | H | 5-CH₃ | — | NH | — | A-2 | OCH₃ | O | — | |
| J-1 | O | — | H | H | — | NCH₃ | — | A-2 | OCF₂H | O | — | |
| J-1 | O | — | H | H | — | NCH₃ | — | A-2 | CH₃ | O | — | 234–240 (d) |
| J-1 | O | — | H | 5-CF₃ | — | NCH₃ | — | A-2 | OCH₃ | CH₂ | — | |
| J-1 | O | — | H | 6-Cl | — | NCH₃ | — | A-2 | OCH₃ | CH₂ | — | |
| J-1 | O | — | H | H | — | NC₆H₅ | — | A-2 | OCF₂H | CH₂ | — | |
| J-1 | O | — | H | H | — | NCH₂C₆H₅ | — | A-2 | OCH₃ | CH₂ | — | |
| J-1 | O | O | H | H | — | S | — | A-2 | OCH₃ | CH₂ | — | |
| J-1 | O | — | CH₃ | H | — | NCH₃ | — | A-2 | CH₃ | O | — | |
| J-2 | O | — | H | H | — | S | — | A-2 | OCF₂H | O | — | |
| J-2 | O | — | H | 5-SCH₃ | — | S | — | A-2 | OCH₃ | O | — | |
| J-2 | O | — | H | 5-CN | — | S | — | A-2 | OCH₃ | CH₂ | — | |
| J-2 | O | — | H | 6-N(CH₃)₂ | — | S | — | A-2 | OCH₃ | CH₂ | — | |
| J-2 | O | — | H | H | — | SO₂ | — | A-2 | OCH₂CH₃ | CH₂ | — | |
| J-2 | O | — | H | H | — | SO₂ | — | A-2 | OCH₃ | O | — | |
| J-2 | O | — | H | 6-CH₃ | — | SO₂ | — | A-2 | OCH₃ | CH₂ | — | |
| J-2 | O | — | H | H | — | NH | — | A-2 | CH₃ | CH₂ | — | |
| J-2 | O | — | H | H | — | NCH₃ | — | A-2 | CH₃ | O | — | |
| J-2 | O | — | H | 5-OCH₃ | — | NCH₃ | — | A-2 | CH₃ | O | — | |
| J-2 | O | — | H | 6-SCH₃ | — | NCH₂CH₃ | — | A-2 | CH₃ | O | — | |
| J-2 | O | — | H | H | — | NC₆H₅ | — | A-2 | OCH₃ | O | — | |
| J-2 | O | — | H | H | — | NCH₂CHCH₂ | — | A-2 | OCH₃ | CH₂ | — | |
| J-2 | O | CH₂ | H | H | — | S | — | A-2 | OCH₃ | CH₂ | — | |
| J-2 | S | — | H | H | — | NCH₃ | — | A-2 | OCH₃ | CH₂ | — | |
| J-3 | O | — | H | H | — | O | — | A-2 | OCH₃ | O | — | |
| J-3 | O | — | H | H | — | O | — | A-2 | OCH₃ | CH₂ | — | |
| J-3 | O | — | H | H | — | O | — | A-2 | CH₃ | CH₂ | — | |
| J-3 | O | — | H | 5-CH₂CH₃ | — | O | — | A-2 | OCH₃ | CH₂ | — | |
| J-3 | O | — | H | 5-F | — | O | — | A-2 | OCH₃ | O | — | |
| J-3 | O | — | H | 6-NHCH₃ | — | O | — | A-2 | OCH₃ | O | — | |
| J-3 | O | — | H | 6-CN | — | O | — | A-2 | CH₃ | O | — | |
| J-3 | O | — | H | H | — | S | — | A-2 | CH₃ | CH₂ | — | |
| J-3 | O | — | H | H | — | S | — | A-2 | OCH₃ | CH₂ | — | |
| J-3 | O | — | H | 5-F | — | S | — | A-2 | OCH₃ | CH₂ | — | |
| J-3 | O | — | H | 6-OCH₃ | — | S | — | A-2 | OCF₂H | CH₂ | — | |
| J-3 | O | — | H | H | — | NCH₃ | — | A-2 | OCF₂H | O | — | |
| J-3 | O | — | H | 5-Cl | — | NCH₃ | — | A-2 | OCH₂ | O | — | |
| J-3 | O | — | H | 6-N(CH₃)₂ | — | NCH₃ | — | A-2 | OCH₃ | O | — | |
| J-3 | O | — | H | H | — | NCH₂CH₃ | — | A-2 | OCH₂CH₃ | O | — | |
| J-3 | S | — | H | H | — | O | — | A-2 | CH₃ | CH₂ | — | |
| J-3 | O | — | CH₃ | H | — | S | — | A-2 | CH₃ | CH₂ | — | |
| J-4 | O | — | H | H | 0 | NCH₃ | NCH₃ | A-2 | CH₃ | O | — | |
| J-4 | O | — | H | H | 1 | O | O | A-2 | OCF₂H | O | — | |
| J-4 | O | — | H | H | 1 | O | NCH₃ | A-2 | OCH₂CH₃ | O | — | |
| J-4 | O | — | H | H | 1 | S | O | A-2 | OCH₃ | CH₂ | — | |
| J-4 | O | — | H | H | 1 | S | NCH₃ | A-2 | CH₃ | CH₂ | — | |
| J-4 | O | — | H | H | 1 | NCH₃ | NCH₃ | A-2 | CH₃ | CH₂ | — | |
| J-4 | O | — | H | H | 2 | O | O | A-2 | OCH₃ | CH₂ | — | |
| J-4 | O | — | H | 5-Cl | 2 | O | O | A-2 | OCH₃ | CH₂ | — | |
| J-4 | O | — | H | H | 2 | S | O | A-2 | CH₃ | CH₂ | — | |

TABLE VI-continued $$JSO_2NHCCNA \text{ with } W= \text{ double bond to C, R on C}$$

i = 1-3 depending on J
j = 1-4 depending on A

| J | W | E | R | R₁ | n | Qᵢ | Q₄ | A | Xⱼ | Yⱼ | Z₁ | m.p. (°C.) |
|---|---|---|---|---|---|---|---|---|---|---|---|---|
| J-4 | O | — | H | H | 2 | NCH₃ | O | A-2 | CH₃ | O | — | |
| J-4 | O | CH₂ | H | H | 1 | O | O | A-2 | OCH₃ | O | — | |
| J-4 | O | — | H | H | 2 | O | O | A-2 | OCF₂H | O | — | |
| J-5 | O | — | H | H | — | NH | NH | A-2 | OCH₃ | O | — | |
| J-5 | O | — | H | H | — | NH | NH | A-2 | OCH₃ | CH₂ | — | |
| J-5 | O | — | H | H | — | NCH₃ | NH | A-2 | CH₃ | CH₂ | — | |
| J-5 | O | — | H | H | — | NCH₃ | NCH₃ | A-2 | CH₃ | CH₂ | — | |
| J-5 | O | — | H | 5-OCH₃ | — | NCH₂CH₃ | NCH₃ | A-2 | CH₃ | CH₂ | — | |
| J-5 | O | — | H | 6-Cl | — | NCH₃ | NH | A-2 | CH₃ | CH₂ | — | |
| J-5 | O | — | CH₃ | H | — | NH | NH | A-2 | OCH₃ | CH₂ | — | |
| J-1 | O | — | H | H | — | S | — | A-3 | CH₃ | — | — | |
| J-1 | O | — | H | 5-Cl | — | S | — | A-3 | OCH₃ | — | — | |
| J-1 | O | — | H | 5-OCH₃ | — | S | — | A-3 | OC₂H₅ | — | — | |
| J-1 | O | — | H | 6-Br | — | S | — | A-3 | OCH₃ | — | — | |
| J-1 | O | — | H | 6-OCH₃ | — | SO₂ | — | A-3 | OCH₃ | — | — | |
| J-1 | O | — | H | H | — | SO₂ | — | A-3 | OCH₃ | — | — | |
| J-1 | O | — | H | H | — | SO₂ | — | A-3 | CH₃ | — | — | |
| J-1 | O | — | H | 5-CH₃ | — | NH | — | A-3 | OCH₃ | — | — | |
| J-1 | O | — | H | H | — | NCH₃ | — | A-3 | CH₃ | — | — | |
| J-1 | O | — | H | 5-CF₃ | — | NCH₃ | — | A-3 | CH₃ | — | — | |
| J-1 | O | — | H | 6-Cl | — | NCH₃ | — | A-3 | CH₃ | — | — | |
| J-1 | O | — | H | H | — | NC₆H₅ | — | A-3 | CH₃ | — | — | |
| J-1 | O | — | H | H | — | NCH₂C₆H₅ | — | A-3 | OCH₃ | — | — | |
| J-1 | O | O | H | H | — | S | — | A-3 | OCH₃ | — | — | |
| J-1 | O | — | CH₃ | H | — | NCH₃ | — | A-3 | CH₃ | — | — | |
| J-2 | O | — | H | H | — | S | — | A-3 | CH₃ | — | — | |
| J-2 | O | — | H | 5-SCH₃ | — | S | — | A-3 | OCH₃ | — | — | |
| J-2 | O | — | H | 5-CN | — | S | — | A-3 | OCH₃ | — | — | |
| J-2 | O | — | H | 6-N(CH₃)₂ | — | S | — | A-3 | OCH₃ | — | — | |
| J-2 | O | — | H | H | — | SO₂ | — | A-3 | OCH₃ | — | — | |
| J-2 | O | — | H | H | — | SO₂ | — | A-3 | CH₃ | — | — | |
| J-2 | O | — | H | 6-CH₃ | — | SO₂ | — | A-3 | CH₃ | — | — | |
| J-2 | O | — | H | H | — | NH | — | A-3 | CH₃ | — | — | |
| J-2 | O | — | H | H | — | NCH₃ | — | A-3 | OCF₂H | — | — | |
| J-2 | O | — | H | 5-OCH₃ | — | NCH₃ | — | A-3 | OCH₃ | — | — | |
| J-2 | O | — | H | 6-SCH₃ | — | NCH₂CH₃ | — | A-3 | OCH₃ | — | — | |
| J-2 | O | — | H | H | — | NC₆H₅ | — | A-3 | OCH₃ | — | — | |
| J-2 | O | — | H | H | — | NCH₂CHCH₂ | — | A-3 | OCH₃ | — | — | |
| J-2 | O | CH₂ | H | H | — | S | — | A-3 | CH₃ | — | — | |
| J-2 | S | — | H | H | — | NCH₃ | — | A-3 | CH₃ | — | — | |
| J-3 | O | — | H | H | — | O | — | A-3 | CH₃ | — | — | |
| J-3 | O | — | H | H | — | O | — | A-3 | OCH₃ | — | — | |
| J-3 | O | — | H | H | — | O | — | A-3 | OC₂H₅ | — | — | |
| J-3 | O | — | H | 5-CH₂CH₃ | — | O | — | A-3 | OCH₃ | — | — | |
| J-3 | O | — | H | 5-F | — | O | — | A-3 | OCH₃ | — | — | |
| J-3 | O | — | H | 6-NHCH₃ | — | O | — | A-3 | OCH₃ | — | — | |
| J-3 | O | — | H | 6-CN | — | O | — | A-3 | CH₃ | — | — | |
| J-3 | O | — | H | H | — | S | — | A-3 | CH₃ | — | — | |
| J-3 | O | — | H | H | — | S | — | A-3 | OCH₃ | — | — | |
| J-3 | O | — | H | 5-F | — | S | — | A-3 | OCH₃ | — | — | |
| J-3 | O | — | H | 6-OCH₃ | — | S | — | A-3 | OCH₃ | — | — | |
| J-3 | O | — | H | H | — | NCH₃ | — | A-3 | CH₃ | — | — | |
| J-3 | O | — | H | 5-Cl | — | NCH₃ | — | A-3 | OCF₂H | — | — | |
| J-3 | O | — | H | 6-N(CH₃)₂ | — | NCH₃ | — | A-3 | OCH₃ | — | — | |
| J-3 | O | — | H | H | — | NCH₂CH₃ | — | A-3 | OCH₃ | — | — | |
| J-3 | S | — | H | H | — | O | — | A-3 | OCH₃ | — | — | |
| J-3 | O | — | CH₃ | H | — | S | — | A-3 | OCH₃ | — | — | |
| J-4 | O | — | H | H | 0 | NCH₃ | NCH₃ | A-3 | CH₃ | — | — | |
| J-4 | O | — | H | H | 1 | O | O | A-3 | OCH₃ | — | — | |
| J-4 | O | — | H | H | 1 | O | NCH₃ | A-3 | OCH₃ | — | — | |
| J-4 | O | — | H | H | 1 | S | O | A-3 | CH₃ | — | — | |
| J-4 | O | — | H | H | 1 | S | NCH₃ | A-3 | OCH₃ | — | — | |
| J-4 | O | — | H | H | 1 | NCH₃ | NCH₃ | A-3 | OCH₃ | — | — | |
| J-4 | O | — | H | H | 2 | O | O | A-3 | OCH₃ | — | — | |
| J-4 | O | — | H | 5-Cl | 2 | O | O | A-3 | CH₃ | — | — | |
| J-4 | O | — | H | H | 2 | S | O | A-3 | OCF₂H | — | — | |
| J-4 | O | — | H | H | 2 | NCH₃ | O | A-3 | CH₃ | — | — | |
| J-4 | O | CH₂ | H | H | 1 | O | O | A-3 | CH₃ | — | — | |
| J-4 | S | — | H | H | 2 | O | O | A-3 | CH₃ | — | — | |
| J-5 | O | — | H | H | — | NH | NH | A-3 | CH₃ | — | — | |
| J-5 | O | — | H | H | — | NH | NH | A-3 | OCH₃ | — | — | |
| J-5 | O | — | H | H | — | NCH₃ | NH | A-3 | OCH₂CH₃ | — | — | |
| J-5 | O | — | H | H | — | NCH₃ | NCH₃ | A-3 | OCH₃ | — | — | |
| J-5 | O | — | H | 5-OCH₃ | — | NCH₂CH₃ | NCH₃ | A-3 | CH₃ | — | — | |

TABLE VI-continued $$\text{JSO}_2\text{NHCCNA}\overset{\overset{W}{\|}}{\underset{R}{|}}$$

i = 1-3 depending on J
j = 1-4 depending on A

| J | W | E | R | R₁ | n | Qᵢ | Q₄ | A | Xⱼ | Yⱼ | Z₁ | m.p. (°C.) |
|---|---|---|---|---|---|---|---|---|---|---|---|---|
| J-5 | O | — | H | 6-Cl | — | NCH₃ | NH | A-3 | OCH₃ | — | — | |
| J-5 | O | — | CH₃ | H | — | NH | NH | A-3 | OCH₃ | — | — | |
| J-1 | O | — | H | H | — | S | — | A-4 | CH₃ | H | — | |
| J-1 | O | — | H | 5-Cl | — | S | — | A-4 | OCH₃ | H | — | |
| J-1 | O | — | H | 5-OCH₃ | — | S | — | A-4 | OCH₃ | H | — | |
| J-1 | O | — | H | 6-Br | — | S | — | A-4 | OCH₃ | H | — | |
| J-1 | O | — | H | 6-OCH₃ | — | SO₂ | — | A-4 | OCH₃ | H | — | |
| J-1 | O | — | H | H | — | SO₂ | — | A-4 | CH₃ | CH₃ | — | |
| J-1 | O | — | H | H | — | SO₂ | — | A-4 | OCH₃ | CH₃ | — | |
| J-1 | O | — | H | 5-CH₃ | — | NH | — | A-4 | OCH₃ | CH₃ | — | |
| J-1 | O | — | H | H | — | NCH₃ | — | A-4 | OCH₂CH₃ | CH₃ | — | |
| J-1 | O | — | H | 5-CF₃ | — | NCH₃ | — | A-4 | CH₃ | CH₃ | — | |
| J-1 | O | — | H | 6-Cl | — | NCH₃ | — | A-4 | CH₃ | CH₃ | — | |
| J-1 | O | — | H | H | — | NC₆H₅ | — | A-4 | CH₃ | CH₃ | — | |
| J-1 | O | — | H | H | — | NCH₂C₆H₅ | — | A-4 | CH₃ | H | — | |
| J-1 | O | O | H | H | — | S | — | A-4 | OCH₃ | H | — | |
| J-1 | O | — | CH₃ | H | — | NCH₃ | — | A-4 | OCH₃ | H | — | |
| J-2 | O | — | H | H | — | S | — | A-4 | OCH₃ | H | — | |
| J-2 | O | — | H | 5-SCH₃ | — | S | — | A-4 | CH₃ | H | — | |
| J-2 | O | — | H | 5-CN | — | S | — | A-4 | CH₃ | CH₃ | — | |
| J-2 | O | — | H | 6-N(CH₃)₂ | — | S | — | A-4 | CH₃ | CH₃ | — | |
| J-2 | O | — | H | H | — | SO₂ | — | A-4 | OCH₃ | CH₃ | — | |
| J-2 | O | — | H | H | — | SO₂ | — | A-4 | OCH₃ | H | — | |
| J-2 | O | — | H | 6-CH₃ | — | SO₂ | — | A-4 | OCH₃ | H | — | |
| J-2 | O | — | H | H | — | NH | — | A-4 | OCH₃ | H | — | |
| J-2 | O | — | H | H | — | NCH₃ | — | A-4 | OCF₂H | H | — | |
| J-2 | O | — | H | 5-OCH₃ | — | NCH₃ | — | A-4 | OCF₂H | H | — | |
| J-2 | O | — | H | 6-SCH₃ | — | NCH₂CH₃ | — | A-4 | CH₃ | CH₃ | — | |
| J-2 | O | — | H | H | — | NC₆H₅ | — | A-4 | CH₃ | CH₃ | — | |
| J-2 | O | — | H | H | — | NCH₂CHCH₂ | — | A-4 | CH₃ | CH₃ | — | |
| J-2 | O | CH₂ | H | H | — | S | — | A-4 | OCH₃ | CH₃ | — | |
| J-2 | S | — | H | H | — | NCH₃ | — | A-4 | OCH₃ | CH₃ | — | |
| J-3 | O | — | H | H | — | O | — | A-4 | OCH₃ | CH₃ | — | |
| J-3 | O | — | H | H | — | O | — | A-4 | CH₃ | CH₃ | — | |
| J-3 | O | — | H | H | — | O | — | A-4 | CH₃ | H | — | |
| J-3 | O | — | H | 5-CH₂CH₃ | — | O | — | A-4 | CH₃ | H | — | |
| J-3 | O | — | H | 5-F | — | O | — | A-4 | OCH₃ | H | — | |
| J-3 | O | — | H | 6-NHCH₃ | — | O | — | A-4 | OCH₃ | H | — | |
| J-3 | O | — | H | 6-CN | — | O | — | A-4 | OCH₃ | H | — | |
| J-3 | O | — | H | H | — | S | — | A-4 | OCF₂H | H | — | |
| J-3 | O | — | H | H | — | S | — | A-4 | OCH₃ | H | — | |
| J-3 | O | — | H | 5-F | — | S | — | A-4 | CH₃ | H | — | |
| J-3 | O | — | H | 6-OCH₃ | — | S | — | A-4 | CH₃ | H | — | |
| J-3 | O | — | H | H | — | NCH₃ | — | A-4 | CH₃ | H | — | |
| J-3 | O | — | H | 5-Cl | — | NCH₃ | — | A-4 | CH₃ | H | — | |
| J-3 | O | — | H | 6-N(CH₃)₂ | — | NCH₃ | — | A-4 | OCH₃ | H | — | |
| J-3 | O | — | H | H | — | NCH₂CH₃ | — | A-4 | OCH₃ | CH₃ | — | |
| J-3 | S | — | H | H | — | O | — | A-4 | OCH₃ | CH₃ | — | |
| J-3 | O | — | CH₃ | H | — | S | — | A-4 | CH₃ | CH₃ | — | |
| J-4 | O | — | H | H | 0 | NCH₃ | NCH₃ | A-4 | CH₃ | CH₃ | — | |
| J-4 | O | — | H | H | 1 | O | O | A-4 | CH₃ | CH₃ | — | |
| J-4 | O | — | H | H | 1 | O | NCH₃ | A-4 | OCH₃ | CH₃ | — | |
| J-4 | O | — | H | H | 1 | S | O | A-4 | CH₃ | CH₃ | — | |
| J-4 | O | — | H | H | 1 | S | NCH₃ | A-4 | OCF₂H | CH₃ | — | |
| J-4 | O | — | H | H | 1 | NCH₃ | NCH₃ | A-4 | CH₃ | CH₃ | — | |
| J-4 | O | — | H | H | 2 | O | O | A-4 | CH₃ | H | — | |
| J-4 | O | — | H | 5-Cl | 2 | O | O | A-4 | OCH₃ | H | — | |
| J-4 | O | — | H | H | 2 | S | O | A-4 | OCH₂CH₃ | H | — | |
| J-4 | O | — | H | H | 2 | NCH₃ | O | A-4 | OCH₂CH₃ | H | — | |
| J-4 | O | CH₂ | H | H | 1 | O | O | A-4 | OCH₂CH₃ | CH₃ | — | |
| J-4 | S | — | H | H | 2 | O | O | A-4 | CH₃ | CH₃ | — | |
| J-5 | O | — | H | H | — | NH | NH | A-4 | CH₃ | CH₃ | — | |
| J-5 | O | — | H | H | — | NH | NH | A-4 | OCH₃ | CH₃ | — | |
| J-5 | O | — | H | H | — | NCH₃ | NH | A-4 | OCH₃ | H | — | |
| J-5 | O | — | H | H | — | NCH₃ | NCH₃ | A-4 | CH₃ | H | — | |
| J-5 | O | — | H | 5-OCH₃ | — | NCH₂CH₃ | NCH₃ | A-4 | CH₃ | H | — | |
| J-5 | O | — | H | 6-Cl | — | NCH₃ | NH | A-4 | OCH₃ | H | — | |
| J-5 | O | — | CH₃ | H | — | NH | NH | A-4 | CH₃ | H | — | |
| J-1 | O | — | H | H | — | S | — | A-5 | CH₃ | OCH₃ | — | |
| J-1 | O | — | H | 5-Cl | — | S | — | A-5 | CH₃ | CH₃ | — | |
| J-1 | O | — | H | 5-OCH₃ | — | S | — | A-5 | CH₃ | OCH₃ | — | |
| J-1 | O | — | H | 6-Br | — | S | — | A-5 | CH₃ | CH₃ | — | |
| J-1 | O | — | H | 6-OCH₃ | — | SO₂ | — | A-5 | CH₃ | CH₃ | — | |
| J-1 | O | — | H | H | — | SO₂ | — | A-5 | CH₃ | CH₃ | — | |

TABLE VI-continued $$JSO_2NHC(=W)CNA | R$$

i = 1–3 depending on J
j = 1–4 depending on A

| J | W | E | R | R₁ | n | Qᵢ | Q₄ | A | Xⱼ | Yⱼ | Z₁ | m.p. (°C.) |
|---|---|---|---|---|---|---|---|---|---|---|---|---|
| J-1 | O | — | H | H | — | SO₂ | — | A-5 | CH₃ | OCH₃ | — | |
| J-1 | O | — | H | 5-CH₃ | — | NH | — | A-5 | CH₂CH₃ | OCH₃ | — | |
| J-1 | O | — | H | H | — | NCH₃ | — | A-5 | CH₂CH₃ | CH₃ | — | |
| J-1 | O | — | H | 5-CF₃ | — | NCH₃ | — | A-5 | CH₃ | CH₃ | — | |
| J-1 | O | — | H | 6-Cl | — | NCH₃ | — | A-5 | CH₃ | OCH₃ | — | |
| J-1 | O | — | H | H | — | NC₆H₅ | — | A-5 | CH₃ | OCH₂CH₃ | — | |
| J-1 | O | — | H | H | — | NCH₂C₆H₅ | — | A-5 | CH₃ | SCH₃ | — | |
| J-1 | O | O | H | H | — | S | — | A-5 | CH₃ | CH₃ | — | |
| J-1 | O | — | CH₃ | H | — | NCH₃ | — | A-5 | CH₃ | CH₃ | — | |
| J-2 | O | — | H | H | — | S | — | A-5 | CH₂CF₃ | CH₃ | — | |
| J-2 | O | — | H | 5-SCH₃ | — | S | — | A-5 | CH₂CF₃ | OCH₂ | — | |
| J-2 | O | — | H | 5-CN | — | S | — | A-5 | CH₃ | OCH₃ | — | |
| J-2 | O | — | H | 6-N(CH₃)₂ | — | S | — | A-5 | CH₃ | SCH₃ | — | |
| J-2 | O | — | H | H | — | S | — | A-5 | CH₃ | OCH₂CH₃ | — | |
| J-2 | O | — | H | H | — | SO₂ | — | A-5 | CH₃ | CH₂CH₃ | — | |
| J-2 | O | — | H | 6-CH₃ | — | SO₂ | — | A-5 | CH₂CF₃ | CH₃ | — | |
| J-2 | O | — | H | H | — | NH | — | A-5 | CH₃ | OCH₃ | — | |
| J-2 | O | — | H | H | — | NCH₃ | — | A-5 | CH₃ | OCH₂CH₃ | — | |
| J-2 | O | — | H | 5-OCH₃ | — | NCH₃ | — | A-5 | CH₃ | OCH₃ | — | |
| J-2 | O | — | H | 6-SCH₃ | — | NCH₂CH₃ | — | A-5 | CH₃ | OCH₃ | — | |
| J-2 | O | — | H | H | — | NC₆H₅ | — | A-5 | CH₃ | OCH₃ | — | |
| J-2 | O | — | H | H | — | NCH₂CHCH₂ | — | A-5 | CH₃ | CH₃ | — | |
| J-2 | O | CH₂ | H | H | — | S | — | A-5 | CH₃ | CH₃ | — | |
| J-2 | S | — | H | H | — | NCH₃ | — | A-5 | CH₃ | CH₃ | — | |
| J-3 | O | — | H | H | — | O | — | A-5 | CH₂CH₃ | CH₃ | — | |
| J-3 | O | — | H | H | — | O | — | A-5 | CH₃ | OCH₃ | — | |
| J-3 | O | — | H | H | — | O | — | A-5 | CH₃ | SCH₃ | — | |
| J-3 | O | — | H | 5-CH₂CH₃ | — | O | — | A-5 | CH₃ | CH₃ | — | |
| J-3 | O | — | H | 5-F | — | O | — | A-5 | CH₃ | CH₃ | — | |
| J-3 | O | — | H | 6-NHCH₃ | — | O | — | A-5 | CH₃ | OCH₃ | — | |
| J-3 | O | — | H | 6-CN | — | O | — | A-5 | CH₃ | OCH₃ | — | |
| J-3 | O | — | H | H | — | S | — | A-5 | CH₃ | OCH₃ | — | |
| J-3 | O | — | H | H | — | S | — | A-5 | CH₃ | OCH₂CH₃ | — | |
| J-3 | O | — | H | 5-F | — | S | — | A-5 | CH₃ | SCH₃ | — | |
| J-3 | O | — | H | 6-OCH₃ | — | S | — | A-5 | CH₃ | CH₃ | — | |
| J-3 | O | — | H | H | — | NCH₃ | — | A-5 | CH₂CF₃ | CH₃ | — | |
| J-3 | O | — | H | 5-Cl | — | NCH₃ | — | A-5 | CH₃ | CH₃ | — | |
| J-3 | O | — | H | 6-N(CH₃)₂ | — | NCH₃ | — | A-5 | CH₂CH₃ | CH₃ | — | |
| J-3 | O | — | H | H | — | NCH₂CH₃ | — | A-5 | CH₂CH₃ | SCH₃ | — | |
| J-3 | S | — | H | H | — | O | — | A-5 | CH₃ | SCH₃ | — | |
| J-3 | O | — | CH₃ | H | — | S | — | A-5 | CH₃ | CH₃ | — | |
| J-4 | O | — | H | H | 0 | NCH₃ | NCH₃ | A-5 | CH₃ | OCH₃ | — | |
| J-4 | O | — | H | H | 1 | O | O | A-5 | CH₃ | CH₂CH₃ | — | |
| J-4 | O | — | H | H | 1 | O | NCH₃ | A-5 | CH₂CH₃ | CH₃ | — | |
| J-4 | O | — | H | H | 1 | S | O | A-5 | CH₂CH₃ | OCH₃ | — | |
| J-4 | O | — | H | H | 1 | S | NCH₃ | A-5 | CH₂CF₃ | OCH₃ | — | |
| J-4 | O | — | H | H | 1 | NCH₃ | NCH₃ | A-5 | CH₂CF₃ | CH₃ | — | |
| J-4 | O | — | H | H | 2 | O | O | A-5 | CH₃ | SCH₃ | — | |
| J-4 | O | — | H | 5-Cl | 2 | O | O | A-5 | CH₃ | OCH₃ | — | |
| J-4 | O | — | H | H | 2 | S | O | A-5 | CH₃ | CH₃ | — | |
| J-4 | O | — | H | H | 2 | NCH₃ | O | A-5 | CH₃ | OCH₃ | — | |
| J-4 | O | CH₂ | H | H | 1 | O | O | A-5 | CH₂CH₃ | OCH₃ | — | |
| J-4 | S | — | H | H | 2 | O | O | A-5 | CH₃ | OCH₃ | — | |
| J-5 | O | — | H | H | — | NH | NH | A-5 | CH₃ | CH₃ | — | |
| J-5 | O | — | H | H | — | NH | NH | A-5 | CH₃ | SCH₂CH₃ | — | |
| J-5 | O | — | H | H | — | NCH₃ | NH | A-5 | CH₃ | OCH₃ | — | |
| J-5 | O | — | H | H | — | NCH₃ | NCH₃ | A-5 | CH₃ | CH₃ | — | |
| J-5 | O | — | H | 5-OCH₃ | — | NCH₂CH₃ | NCH₃ | A-5 | CH₃ | OCH₃ | — | |
| J-5 | O | — | H | 6-Cl | — | NCH₃ | NH | A-5 | CH₃ | CH₃ | — | |
| J-5 | O | — | CH₃ | H | — | NH | NH | A-5 | CH₃ | CH₃ | — | |
| J-1 | O | — | H | H | — | S | — | A-6 | CH₃ | — | — | |
| J-1 | O | — | H | 5-Cl | — | S | — | A-6 | CH₃ | — | — | |
| J-1 | O | — | H | 5-OCH₃ | — | S | — | A-6 | CH₃ | — | — | |
| J-1 | O | — | H | 6-Br | — | S | — | A-6 | CH₃ | — | — | |
| J-1 | O | — | H | 6-OCH₃ | — | SO₂ | — | A-6 | CH₃ | — | — | |
| J-1 | O | — | H | H | — | SO₂ | — | A-6 | CH₃ | — | — | |
| J-1 | O | — | H | H | — | SO₂ | — | A-6 | OCH₃ | — | — | |
| J-1 | O | — | H | 5-CH₃ | — | NH | — | A-6 | OCH₃ | — | — | |
| J-1 | O | — | H | H | — | NCH₃ | — | A-6 | OCH₃ | — | — | |
| J-1 | O | — | 5-CF₃ | — | NCH₃ | — | A-6 | OCH₃ | — | — | | |
| J-1 | O | — | H | 6-Cl | — | NCH₃ | — | A-6 | CH₃ | — | — | |
| J-1 | O | — | H | H | — | NC₆H₅ | — | A-6 | CH₃ | — | — | |
| J-1 | O | — | H | H | — | NCH₂C₆H₅ | — | A-6 | CH₃ | — | — | |
| J-1 | O | O | H | H | — | S | — | A-6 | OCH₃ | — | — | |

TABLE VI-continued $$\underset{R}{\overset{W}{\underset{\|}{JSO_2NHCCNA}}}$$

i = 1-3 depending on J
j = 1-4 depending on A

| J | W | E | R | $R_1$ | n | $Q_i$ | $Q_4$ | A | $X_j$ | $Y_j$ | $Z_1$ | m.p. (°C.) |
|---|---|---|---|---|---|---|---|---|---|---|---|---|
| J-1 | O | — | $CH_3$ | H | — | $NCH_3$ | — | A-6 | $CH_3$ | — | — | |
| J-2 | O | — | H | H | — | S | — | A-6 | $OCH_3$ | — | — | |
| J-2 | O | — | H | 5-$SCH_3$ | — | S | — | A-6 | $CH_3$ | — | — | |
| J-2 | O | — | H | 5-CN | — | S | — | A-6 | $OCH_3$ | — | — | |
| J-2 | O | — | H | 6-$N(CH_3)_2$ | — | S | — | A-6 | $CH_3$ | — | — | |
| J-2 | O | — | H | H | — | $SO_2$ | — | A-6 | $OCH_3$ | — | — | |
| J-2 | O | — | H | H | — | $SO_2$ | — | A-6 | $CH_3$ | — | — | |
| J-2 | O | — | H | 6-$CH_3$ | — | $SO_2$ | — | A-6 | $OCH_3$ | — | — | |
| J-2 | O | — | H | H | — | NH | — | A-6 | $OCH_3$ | — | — | |
| J-2 | O | — | H | H | — | $NCH_3$ | — | A-6 | $OCH_3$ | — | — | |
| J-2 | O | — | H | 5-$OCH_3$ | — | $NCH_3$ | — | A-6 | $OCH_3$ | — | — | |
| J-2 | O | — | H | 6-$SCH_3$ | — | $NCH_2CH_3$ | — | A-6 | $OCH_3$ | — | — | |
| J-2 | O | — | H | H | — | $NC_6H_5$ | — | A-6 | $CH_3$ | — | — | |
| J-2 | O | — | H | H | — | $NCH_2CHCH_2$ | — | A-6 | $CH_3$ | — | — | |
| J-2 | O | $CH_2$ | H | H | — | S | — | A-6 | $CH_3$ | — | — | |
| J-2 | S | — | H | H | — | $NCH_3$ | — | A-6 | $OCH_3$ | — | — | |
| J-3 | O | — | H | H | — | O | — | A-6 | $CH_3$ | — | — | |
| J-3 | O | — | H | H | — | O | — | A-6 | $OCH_3$ | — | — | |
| J-3 | O | — | H | 5-$CH_2CH_3$ | — | O | — | A-6 | $CH_3$ | — | — | |
| J-3 | O | — | H | 5-F | — | O | — | A-6 | $OCH_3$ | — | — | |
| J-3 | O | — | H | 6-$NHCH_3$ | — | O | — | A-6 | $OCH_3$ | — | — | |
| J-3 | O | — | H | 6-CN | — | O | — | A-6 | $OCH_3$ | — | — | |
| J-3 | O | — | H | H | — | S | — | A-6 | $CH_3$ | — | — | |
| J-3 | O | — | H | H | — | S | — | A-6 | $OCH_3$ | — | — | |
| J-3 | O | — | H | 5-F | — | S | — | A-6 | $OCH_3$ | — | — | |
| J-3 | O | — | H | 6-$OCH_3$ | — | S | — | A-6 | $OCH_3$ | — | — | |
| J-3 | O | — | H | H | — | $NCH_3$ | — | A-6 | $CH_3$ | — | — | |
| J-3 | O | — | H | 5-Cl | — | $NCH_3$ | — | A-6 | $OCH_3$ | — | — | |
| J-3 | O | — | H | 6-$N(CH_3)_3$ | — | $NCH_3$ | — | A-6 | $CH_3$ | — | — | |
| J-3 | O | — | H | H | — | $NCH_2CH_2$ | — | A-6 | $CH_3$ | — | — | |
| J-3 | S | — | H | H | — | O | — | A-6 | $CH_3$ | — | — | |
| J-3 | O | — | $CH_3$ | H | — | S | — | A-6 | $CH_3$ | — | — | |
| J-4 | O | — | H | H | 0 | $NCH_3$ | $NCH_3$ | A-6 | $OCH_3$ | — | — | |
| J-4 | O | — | H | H | 1 | O | O | A-6 | $OCH_3$ | — | — | |
| J-4 | O | — | H | H | 1 | O | $NCH_3$ | A-6 | $CH_3$ | — | — | |
| J-4 | O | — | H | H | 1 | S | O | A-6 | $CH_3$ | — | — | |
| J-4 | O | — | H | H | 1 | S | $NCH_3$ | A-6 | $OCH_3$ | — | — | |
| J-4 | O | — | H | H | 1 | $NCH_3$ | $NCH_3$ | A-6 | $OCH_3$ | — | — | |
| J-4 | O | — | H | H | 2 | O | O | A-6 | $OCH_3$ | — | — | |
| J-4 | O | — | H | 5-Cl | 2 | O | O | A-6 | $OCH_3$ | — | — | |
| J-4 | O | — | H | H | 2 | S | O | A-6 | $OCH_3$ | — | — | |
| J-4 | O | — | H | H | 2 | $NCH_3$ | O | A-6 | $OCH_3$ | — | — | |
| J-4 | O | $CH_2$ | H | H | 1 | O | O | A-6 | $CH_3$ | — | — | |
| J-4 | S | — | H | H | 2 | O | O | A-6 | $CH_3$ | — | — | |
| J-5 | O | — | H | H | — | NH | NH | A-6 | $CH_3$ | — | — | |
| J-5 | O | — | H | H | — | $NCH_3$ | NH | A-6 | $OCH_3$ | — | — | |
| J-5 | O | — | H | H | — | $NCH_3$ | $NCH_3$ | A-6 | $CH_3$ | — | — | |
| J-5 | O | — | H | 5-$OCH_3$ | — | N-$CH_2CH_3$ | $NCH_3$ | A-6 | $OCH_3$ | — | — | |
| J-5 | O | — | H | 6-Cl | — | $NCH_3$ | NH | A-6 | $OCH_3$ | — | — | |
| J-5 | O | — | $CH_3$ | H | — | NH | NH | A-6 | $CH_3$ | — | — | |
| J-1 | O | — | H | H | — | S | — | A-7 | $CH_3$ | $CH_3$ | CH | |
| J-1 | O | — | H | 5-Cl | — | S | — | A-7 | Cl | $CH_3$ | CH | |
| J-1 | O | — | H | 5-$OCH_3$ | — | S | — | A-7 | $OCH_3$ | $CH_3$ | CH | |
| J-1 | O | — | H | 5-$OCH_3$ | — | S | — | A-7 | $OCH_3$ | $CH_3$ | CH | |
| J-1 | O | — | H | 6-Br | — | S | — | A-7 | $OCH_3$ | $OCH_3$ | CH | |
| J-1 | O | — | H | 6-$OCH_3$ | — | $SO_2$ | — | A-7 | $CH_3$ | Cl | CH | |
| J-1 | O | — | H | H | — | $SO_2$ | — | A-7 | $CH_2OCH_3$ | $CH_3$ | CH | |
| J-1 | O | — | H | H | — | $SO_2$ | — | A-7 | $CH_3$ | $CH_3$ | N | |
| J-1 | O | — | H | 5-$CH_3$ | — | NH | — | A-7 | $OCH_3$ | $CH_3$ | N | |
| J-1 | O | — | H | H | — | $NCH_3$ | — | A-7 | $OCH_2CH_3$ | $CH_3$ | N | |
| J-1 | O | — | H | 5-$CF_3$ | — | $NCH_3$ | — | A-7 | $OCH_3$ | $CH_3$ | CH | |
| J-1 | O | — | H | 6-Cl | — | $NCH_3$ | — | A-7 | $OCH_3$ | $OCH_3$ | CH | |
| J-1 | O | — | H | H | — | $NC_6H_5$ | — | A-7 | Cl | $OCH_3$ | CH | |
| J-1 | O | — | H | H | — | $NCH_2C_6H_5$ | — | A-7 | $CH_3$ | $OCH_3$ | CH | |
| J-1 | O | O | H | H | — | S | — | A-7 | $CH_3$ | $OCH_3$ | CH | |
| J-1 | O | — | $CH_3$ | H | — | $NCH_3$ | — | A-7 | $OCH_3$ | $OCH_3$ | CH | |
| J-2 | O | — | H | H | — | S | — | A-7 | $CH_3$ | $OCH_3$ | CH | |
| J-2 | O | — | H | 5-$SCH_3$ | — | S | — | A-7 | $CH_3$ | $OCH_2CH_3$ | CH | |
| J-2 | O | — | H | 5-CN | — | S | — | A-7 | $CH_3$ | $CH_3$ | N | |
| J-2 | O | — | H | 6-$N(CH_3)_2$ | — | S | — | A-7 | $OCH_3$ | $CH_3$ | N | |
| J-2 | O | — | H | H | — | $SO_2$ | — | A-7 | $OCH_3$ | $CH_3$ | N | |

TABLE VI-continued $$JSO_2NHCCNA \quad \overset{W}{\underset{R}{\|}}$$

i = 1-3 depending on J
j = 1-4 depending on A

| J | W | E | R | $R_1$ | n | $Q_i$ | $Q_4$ | A | $X_j$ | $Y_j$ | $Z_1$ | m.p. (°C.) |
|---|---|---|---|---|---|---|---|---|---|---|---|---|
| J-2 | O | — | H | H | — | $SO_2$ | — | A-7 | $CH_3$ | $CH_3$ | N | |
| J-2 | O | — | H | 6-$CH_3$ | — | $SO_2$ | — | A-7 | $CH_3$ | $CH_3$ | CH | |
| J-2 | O | — | H | H | — | NH | — | A-7 | $CH_3$ | $OCH_3$ | CH | |
| J-2 | O | — | H | H | — | $NCH_3$ | — | A-7 | $CH_3$ | $OCH_3$ | CH | |
| J-2 | O | — | H | 5-$OCH_3$ | — | $NCH_3$ | — | A-7 | $CH_3$ | $OCH_3$ | CH | |
| J-2 | O | — | H | 6-$SCH_3$ | — | $NCH_2CH_3$ | — | A-7 | $CH_3$ | $OCH_3$ | CH | |
| J-2 | O | — | H | H | — | $NC_6H_5$ | — | A-7 | $CH_3$ | $OCH_3$ | CH | |
| J-2 | O | — | H | H | — | $NCH_2CHCH_2$ | — | A-7 | $OCH_3$ | $OCH_3$ | CH | |
| J-2 | O | $CH_2$ | H | H | — | S | — | A-7 | $OCH_3$ | $OCH_3$ | N | |
| J-2 | S | — | H | H | — | $NCH_3$ | — | A-7 | $OCH_3$ | $CH_3$ | N | |
| J-3 | O | — | H | H | — | O | — | A-7 | $OCH_3$ | $CH_3$ | N | |
| J-3 | O | — | H | H | — | O | — | A-7 | $OCH_3$ | $CH_3$ | CH | |
| J-3 | O | — | H | H | — | O | — | A-7 | $OCH_3$ | $OCH_3$ | CH | |
| J-3 | O | — | H | 5-$CH_2CH_3$ | — | O | — | A-7 | Cl | $OCH_3$ | CH | |
| J-3 | O | — | H | 5-F | — | O | — | A-7 | $CH_3$ | $OCH_3$ | CH | |
| J-3 | O | — | H | 6-$NHCH_3$ | — | O | — | A-7 | $CH_3$ | $OCH_3$ | CH | |
| J-3 | O | — | H | 6-CN | — | O | — | A-7 | $CH_3$ | $OCH_3$ | CH | |
| J-3 | O | — | H | H | — | S | — | A-7 | $CH_3$ | $CH_3$ | N | |
| J-3 | O | — | H | H | — | S | — | A-7 | $OCH_3$ | $CH_3$ | N | |
| J-3 | O | — | H | 5-F | — | S | — | A-7 | $OCH_3$ | $CH_3$ | N | |
| J-3 | O | — | H | 6-$OCH_3$ | — | S | — | A-7 | $OCH_3$ | $CH_3$ | N | |
| J-3 | O | — | H | H | — | $NCH_3$ | — | A-7 | $OCH_3$ | $CH_3$ | N | |
| J-3 | O | — | H | 5-Cl | — | $NCH_3$ | — | A-7 | $OCH_3$ | $CH_3$ | CH | |
| J-3 | O | — | H | 6-$N(CH_3)_2$ | — | $NCH_3$ | — | A-7 | $OCH_3$ | $CH_3$ | CH | |
| J-3 | O | — | H | H | — | $NCH_2CH_3$ | — | A-7 | $OCH_3$ | $CH_3$ | CH | |
| J-3 | S | — | H | H | — | O | — | A-7 | $OCH_3$ | $CH_3$ | CH | |
| J-3 | O | — | $CH_3$ | H | — | S | — | A-7 | $OCH_3$ | $CH_3$ | CH | |
| J-4 | O | — | H | H | 0 | $NCH_3$ | $NCH_3$ | A-7 | $OCH_3$ | $OCH_3$ | CH | |
| J-4 | O | — | H | H | 1 | O | O | A-7 | $CH_3$ | $OCH_3$ | N | |
| J-4 | O | — | H | H | 1 | O | $NCH_3$ | A-7 | $CH_3$ | $OCH_3$ | CH | |
| J-4 | O | — | H | H | 1 | S | O | A-7 | $CH_2OCH_3$ | $OCH_3$ | CH | |
| J-4 | O | — | H | H | 1 | S | $NCH_3$ | A-7 | $OCH_3$ | $OCH_3$ | CH | |
| J-4 | O | — | H | H | 1 | $NCH_3$ | $NCH_3$ | A-7 | $OCH_3$ | Cl | CH | |
| J-4 | O | — | H | H | 2 | O | O | A-7 | $OCH_3$ | $CH_3$ | N | |
| J-4 | O | — | H | 5-Cl | 2 | O | O | A-7 | $OCH_3$ | $CH_3$ | N | |
| J-4 | O | — | H | H | 2 | S | O | A-7 | $OCH_3$ | $CH_3$ | N | |
| J-4 | O | — | H | H | 2 | $NCH_3$ | O | A-7 | $OCH_3$ | $CH_3$ | N | |
| J-4 | O | $CH_2$ | H | H | 1 | O | O | A-7 | $OCH_3$ | $CH_3$ | CH | |
| J-4 | S | — | H | H | 2 | O | O | A-7 | $OCH_3$ | $OCH_3$ | CH | |
| J-5 | O | — | H | H | — | NH | NH | A-7 | $CH_3$ | $OCH_3$ | CH | |
| J-5 | O | — | H | H | — | NH | NH | A-7 | $CH_3$ | $CH_3$ | CH | |
| J-5 | O | — | H | H | — | $NCH_3$ | NH | A-7 | $CH_3$ | $OCH_2CH_3$ | CH | |
| J-5 | O | — | H | H | — | $NCH_3$ | $NCH_3$ | A-7 | $OCH_2CH_3$ | $CH_3$ | CH | |
| J-5 | O | — | H | 5-$OCH_3$ | — | $NCH_2CH_3$ | $NCH_3$ | A-7 | $OCH_3$ | $CH_3$ | N | |
| J-5 | O | — | H | 6-Cl | — | $NCH_3$ | NH | A-7 | $OCH_3$ | $CH_3$ | N | |
| J-5 | O | — | $CH_3$ | H | — | NH | NH | A-7 | $OCH_3$ | $CH_3$ | CH | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE VII

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:
H. M. Loux, U.S. Pat. No. 3,235,361, Feb. 15, 1966, Col. 6, line 16 through Col. 7, line 19 and Examples 10 through 41;
R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 1662–164, 166, 167 and 169–182;
H. Gysin and E. Knusli, U.S. Pat. No. 2,891,855, June 23, 1959, Col. 3, line 66 through Col. 5, line 17 and Examples 1–4;
G. C. Klingman, "Weed Control as a Science", John Wiley and Sons, Inc., New York, 1961, pp. 81–96; and
J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 12

Wettable Powder

N-[(4,6-Dimethoxypyrimidin-2-yl)aminocarbonyl]-5-methoxy-1,2,3-benzothiadiazole-4-sulfonamide: 80%
  sodium alkylnaphthalenesulfonate: 2%
  sodium ligninsulfonate: 2%
  synthetic amorphous silica: 3%
  kaolinite: 13%

The ingredients are blended, hammer-milled until all the solids are essentially under 50 microns, reblended, and packaged.

EXAMPLE 13

Wettable Powder

N-[(4,6-Dimethoxypyrimidin-2-yl)aminocarbonyl]-5-methoxy-1,2,3-benzothiadiazole-4-sulfonamide: 50%
  sodium alkylnaphthalenesulfonate: 2%
  low viscosity methyl cellulose: 2%
  diatomaceous earth: 46%

The ingredients are blended, corasely hammer-milled and then air-milled to produce particles essentially all below 10 microns in diameter. The product is reblended before packaging.

EXAMPLE 14

Granule

Wettable Powder of Example 13: 5%
attapulgite granules: 95%
(U.S.S. 20–40 mesh; 0.84–0.42 mm)

A slurry of wettable powder containing 25% solids is sprayed on the surface of attapulgite granules in a double-cone blender. The granules are dried and packaged.

EXAMPLE 15

Extruded Pellet

N-[(4,6-Dimethoxypyrimidin-2-yl)aminocarbonyl]-5-methoxy-1,2,3-benzothiadiazole-4-sulfonamide: 25%
  anhydrous sodium sulfate: 10%
  crude calcium ligninsulfonate: 5%
  sodium alkylnaphthalenesulfonate: 1%
  calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

Oil Suspension

N-[(4,6-Dimethoxypyrimidin-2-yl)aminocarbonyl]-5-methoxy-1,2,3-benzothiadiazole-4-sulfonamide: 25%
  polyoxyethylene sorbitol hexaoleate: 5%
  highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 17

Wettable Powder

N-[(4,6-Dimethoxypyrimidin-2-yl)aminocarbonyl]-5-methoxy-1,2,3-benzothiadiazole-4-sulfonamide: 20%
  sodium alkylnaphthalenesulfonate: 4%
  sodium ligninsulfonate: 4%
  low viscosity methyl cellulose: 3%
  attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 18

Low Strength Granule

N-[(4,6-Dimethoxypyrimidin-2-yl)aminocarbonyl]-5-methoxy-1,2,3-benzothiadiazole-4-sulfonamide: 1%
  N,N-dimethylformamide: 9% attapulgite granules: 90%
(U.S.S. 20–40 sieve)

The active ingredient is dissolved in the solvent and the solution is sprayed upon dedusted granules in a double cone blender. After spraying of the solution has been completed, the blender is allowed to run for a short period and then the granules are packaged.

EXAMPLE 19

Aqueous Suspension

N-[(4,6-Dimethoxypyrimidin-2-yl)aminocarbonyl]-5-methoxy-1,2,3-benzothiadiazole-4-sulfonamide: 40%
  polyacrylic acid thickener: 0.3%
  dodecylphenol polyethylene glycol ether: 0.5%
  disodium phosphate: 1%
  monosodium phosphate: 0.5%
  polyvinyl alcohol: 1.0%
  water: 56.7%

The ingredients are blended and ground together in a sand mill to produce particles essentially all under 5 microns in size.

EXAMPLE 20

Solution

N-[(4,6-Dimethoxypyrimidin-2-yl)aminocarbonyl]-5-methoxy-1,2,3-benzothiadiazole-4-sulfonamide, ammonium salt: 5%
  water: 95%

The salt is added directly to the water with stirring to produce the solution, which may then be packaged for use.

EXAMPLE 21

Low Strength Granule

N-[(4,6-Dimethoxypyrimidin-2-yl)aminocarbonyl]-5-methoxy-1,2,3-benzothiadiazole-4-sulfonamide: 0.1%
  attapulgite granules: 99.9%
  (U.S.S. 20–40 mesh)

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 22

Granule

N-[(4,6-Dimethoxypyrimidin-2-yl)aminocarbonyl]-5-methoxy-1,2,3-benzothiadiazole-4-sulfonamide: 80%
  wetting agent: 1%
  crude ligninsulfonate salt (containing 5–20% of the natural sugars): 10%
  attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 23

High Strength Concentrate

N-[(4,6-Dimethoxypyrimidin-2-yl)aminocarbonyl]-5-methoxy-1,2,3-benzothiadiazole-4-sulfonamide: 99%
  silica aerogel: 0.5%
  synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 24

Wettable Powder

N-[(4,6-Dimethoxypyrimidin-2-yl)aminocarbonyl]-5-methoxy-1,2,3-benzothiadiazole-4-sulfonamide: 90%
  dioctyl sodium sulfosuccinate: 0.1%
  synthetic fine silica: 9.9%

The ingredients are blended and ground in a hammer-mill to produce particles essentially all below 100 microns. The material is sifted through a U.S.S. No. 50 screen and then packaged.

EXAMPLE 25

Wettable Powder

N-[(4,6-Dimethoxypyrimidin-2-yl)aminocarbonyl]-5-methoxy-1,2,3-benzothiadiazole-4-sulfonamide: 40%
  sodium ligninsulfonate: 20%
  montmorillonite clay: 40%

The ingredients are thoroughly blended, coarsely hammer-milled and then air-milled to produce particles essentially all below 10 microns in size. The material is reblended and then packaged.

EXAMPLE 26

Oil Suspension

N-[(4,6-Dimethoxypyrimidin-2-yl)aminocarbonyl]-5-methoxy-1,2,3-benzothiadiazole-4-sulfonamide: 35%
  blend of polyalcohol carboxylic esters and oil soluble petroleum sulfonates: 6%
  xylene: 59%

The ingredients are combined and ground together in a sand mill to produce particles essentially all below 5 microns. The product can be used directly, extended with oils, or emulsified in water.

EXAMPLE 27

Dust

N-[(4,6-Dimethoxypyrimidin-2-yl)aminocarbonyl]-5-methoxy-1,2,3-benzothiadiazole-4-sulfonamide: 10%
  attapulgite: 10%
  Pyrophyllite: 80%

The active ingredient is blended with attapulgite and then passed through a hammer-mill to produce particles substantially all below 200 microns. The ground concentrate is then blended with powdered pyrophyllite until homogeneous.

EXAMPLE 28

Emulsifiable Concentrate

N-[(4,6-Dimethoxypyrimidin-2-yl)aminocarbonyl]-5-methoxy-1,2,3-benzothiadiazole-4-sulfonamide: 10%
  chlorobenzene: 84%
  sorbitan monostearate and polyoxyethylene condensates thereof: 6%

The ingredients are combined and stirred to produce a solution which can be emulsified in water for application.

Utility

Test results indicate that the compounds of the present invention are highly active preemergent or postemergent herbicides or plant growth regulants. Many of them have utility for broad-spectrum pre- and/or post-emergence weed control in areas where complete control of all vegetation is desired, such as around industrial storage areas, parking lots, drive-in theaters, around billboards, highway and railroad structures. Some of the compounds have utility for selective weed control in crops, such as rice, barley, cotton, oilseed rape and sugarbeets. Some of the compounds were found to be especially selective to sugarbeets and oilseed rape. Alternatively, the subject compounds are useful to modify plant growth.

The rates of application for the compounds of the invention are determined by a number of factors, including their use as plant growth regulators or as herbicides, the crop species involved, the types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types. Some of them are particularly useful when combined with the herbicides below:

DESMEDIPHAM (Betanex ®)
  Ethyl m-hydroxycarbanilate carbonilate (ester)
PHENMEDIPHAM (Bentanal ®)
  Methyl m-hydroxycarbanilate
  m-methylcarbanilate
ETHOFUMESATE (Nortron ®)
  (±)-2-ethoxy-2,3-dihydro-3,3-dimethyl-5-benzo=-furanyl methanesulfonate
DIETHATYL ETHYL (Antor ®)
  N-chloroacetyl-N-(2,6-diethylphenyl)-glycine ethyl ester
ENDOTHALL
  7-oxabicyclo[2,2,1]heptane-2,3-dicarboxylic acid
TCA
  Trichloroacetic acid
DALAPON (Dowpon ®)
  2,2-dichloroproprionic acid
FENURON
  1,1-dimethyl-3-phenylurea
CHLORPROPHAM
  Isopropyl m-chlorocarbanilate
PROPHAM
  Isopropyl carbanilate
PYRAZON (Pyramin ®)
  5-amino-4-chloro-2-phenyl-3(2H)-pyridazinone
METAMITRON (Goltix ®)
  4-amino-3-methyl-6-phenyl-1,2,4-triazia-5(4H)-one
LENACIL (Venzar ®)
  3-cyclohexyl-6,7-dihydro-1H-cyclopentapyrimidine-2,4(3H, 5H)-dione
SETHOXYDIM (Poast ®)
  (±)2-[1-(ethoxyimino)butyl]-5-[2-(ethylthio)propyl]-3-hydroxy-2-cyclohexene-1-one
FLUAZIFOP-BUTYL (Fusilade ®)
  (35 )-butyl-2-[4-[(5-trifluoromethyl)-2-pyridinyl)oxy]-phenoxy]propanoate
DIALLATE (Avadex ®)
  S-(2,3-dichloroallyl)diisopropylthio carbamate
BARBAN (Carbyne ®)
  4-chloro-2-butynyl m-chlorocarbanilate
DICLOFOP-METHYL (Hoelon ®)
  Methyl 2-[4-(2,4-dichlorophenoxy)phenoxy]propanoate
QUIZALOFOP
  (RS)-2-[4-(6-chloroquinoxalin-2-yloxy)phenoxy]-proprionic acid The herbicidal properties of the subject compounds were discovered in a number of greenhouse tests. The test procedures and results follow.

It is believed that the compounds which show weak activity at low rates will show herbicidal activity at higher rates.

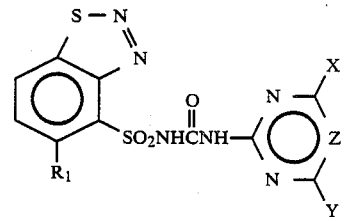

| Compounds | $R_1$ | $R_1'$ | X | Y | Z |
|---|---|---|---|---|---|
| 1 | OCH$_3$ | | CH$_3$ | CH$_3$ | CH |
| 2 | OCH$_3$ | | CH$_3$O | CH$_3$ | CH |
| 3 | OCH$_3$ | | CH$_3$O | CH$_3$O | CH |
| 4 | OCH$_3$ | | Cl | CH$_3$O | CH |
| 5 | OCH$_3$ | | CH$_3$ | CH$_3$ | N |
| 6 | OCH$_3$ | | CH$_3$O | CH$_3$ | N |
| 7 | OCH$_3$ | | CH$_3$O | CH$_3$O | N |
| 8 | H | | CH$_3$ | CH$_3$ | CH |
| 9 | H | | OCH$_3$ | CH$_3$ | CH |
| 10 | H | | OCH$_3$ | OCH$_3$ | CH |
| 11 | H | | Cl | OCH$_3$ | CH |
| 12 | H | | CH$_3$ | OCH$_3$ | N |
| 13 | H | | OCH$_3$ | OCH$_3$ | N |
| 14 | H | | OCH$_2$CH$_3$ | NHCH$_3$ | N |
| 15 | | | CH$_3$ | CH$_3$ | CH |
| 16 | | | CH$_3$ | OCH$_3$ | CH |
| 17 | | | OCH$_3$ | OCH$_3$ | N |
| 18 | | | OCH$_3$ | CH$_3$ | N |
| 19 | | | OCH$_2$CH$_3$ | NHCH$_3$ | N |
| 20 | | | Cl | OCH$_3$ | CH |

-continued

Compounds

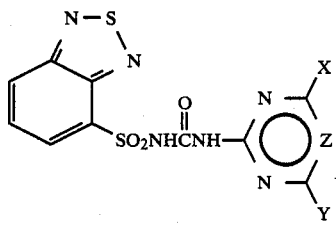

| Compounds | R₁ | R₁' | X | Y | Z |
|---|---|---|---|---|---|
| 21 | | | CH₃ | CH₃ | CH |
| 22 | | | OCH₃ | CH₃ | CH |
| 23 | | | OCH₃ | OCH₃ | CH |
| 24 | | | Cl | OCH₃ | CH |
| 25 | | | CH₃ | CH₃ | N |
| 26 | | | CH₃ | OCH₃ | N |
| 27 | | | OCH₃ | OCH₃ | N |
| 28 | | | OCH₂CH₃ | NHCH₃ | N |

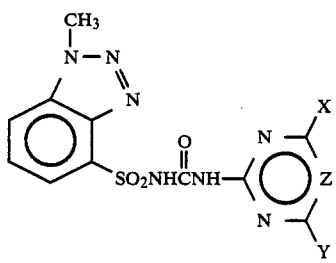

| Compounds | R₁ | R₁' | X | Y | Z |
|---|---|---|---|---|---|
| 29 | | | CH₃ | CH₃ | CH |
| 30 | | | CH₃ | OCH₃ | CH |
| 31 | | | OCH₃ | OCH₃ | CH |
| 32 | | | Cl | OCH₃ | CH |
| 33 | | | CH₃ | CH₃ | N |
| 34 | | | OCH₃ | CH₃ | N |
| 35 | | | OCH₃ | OCH₃ | N |
| 36 | | | OCH₂CH₃ | NHCH₃ | N |

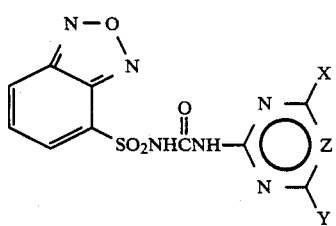

| Compounds | R₁ | R₁' | X | Y | Z |
|---|---|---|---|---|---|
| 37 | | | CH₃ | CH₃ | CH |
| 38 | | | OCH₃ | CH₃ | CH |
| 39 | | | OCH₃ | OCH₃ | CH |
| 40 | | | Cl | OCH₃ | CH |
| 41 | | | CH₃ | CH₃ | N |
| 42 | | | CH₃ | OCH₃ | N |
| 43 | | | OCH₃ | OCH₃ | N |
| 44 | | | OCH₂CH₃ | NHCH₃ | N |

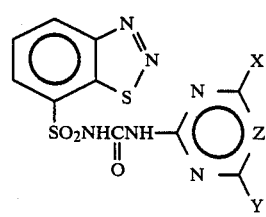

| Compounds | R₁ | R₁' | X | Y | Z |
|---|---|---|---|---|---|
| 45 | | | CH₃ | CH₃ | CH |
| 46 | | | OCH₃ | CH₃ | CH |
| 47 | | | OCH₃ | OCH₃ | CH |
| 48 | | | OCH₃ | CH₃ | N |
| 49 | | | OCH₃ | OCH₃ | N |

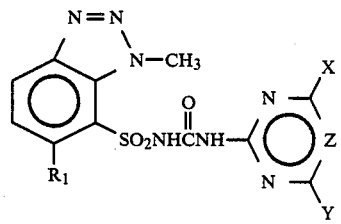

| Compounds | R₁ | R₁' | X | Y | Z |
|---|---|---|---|---|---|
| 50 | H | | CH₃ | CH₃ | CH |
| 51 | H | | CH₃ | OCH₃ | CH |
| 52 | H | | OCH₃ | OCH₃ | CH |
| 53 | H | | Cl | OCH₃ | CH |
| 54 | H | | CH₃ | CH₃ | N |
| 55 | H | | OCH₃ | CH₃ | N |
| 56 | H | | OCH₃ | OCH₃ | N |
| 57 | CH₃ | | OCH₃ | OCH₃ | CH |

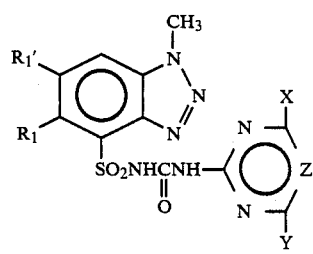

| Compounds | R₁ | R₁' | X | Y | Z |
|---|---|---|---|---|---|
| 58 | H | CH₃ | CH₃ | CH₃ | CH |
| 59 | H | CH₃ | CH₃ | OCH₃ | CH |
| 60 | H | CH₃ | OCH₃ | OCH₃ | CH |
| 61 | H | CH₃ | Cl | OCH₃ | CH |
| 62 | H | CH₃ | CH₃ | CH₃ | N |
| 63 | H | CH₃ | CH₃ | OCH₃ | N |
| 64 | H | CH₃ | OCH₃ | OCH₃ | N |
| 65 | H | CH₃ | OCH₂CH₃ | NHCH₃ | N |
| 66 | CH₃ | H | CH₃ | CH₃ | CH |
| 67 | CH₃ | H | CH₃ | OCH₃ | CH |
| 68 | CH₃ | H | OCH₃ | OCH₃ | CH |
| 69 | CH₃ | H | Cl | OCH₃ | CH |
| 70 | CH₃ | H | CH₃ | OCH₃ | N |
| 71 | CH₃ | H | CH₃ | CH₃ | N |

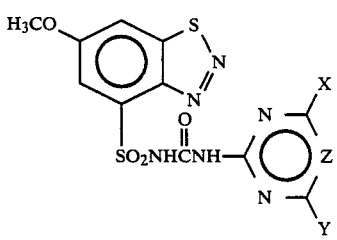

| Compounds | R₁ | R₁' | X | Y | Z |
|---|---|---|---|---|---|
| 72 | | | OCH₃ | CH₃ | CH |
| 73 | | | OCH₃ | OCH₃ | CH |
| 74 | | | Cl | OCH₃ | CH |
| 75 | | | OCH₃ | CH₃ | N |
| 76 | | | OCH₃ | N(CH₃)₂ | N |

-continued

| Compounds | | | | | |
|---|---|---|---|---|---|
| Compounds | $R_1$ | $R_1'$ | X | Y | Z |

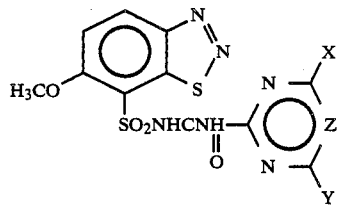

| | | | | | |
|---|---|---|---|---|---|
| 77 | | | CH$_3$ | CH$_3$ | CH |
| 78 | | | OCH$_3$ | CH$_3$ | CH |
| 79 | | | OCH$_3$ | OCH$_3$ | CH |
| 80 | | | Cl | OCH$_3$ | CH |
| 81 | | | OCH$_3$ | CH$_3$ | N |
| 82 | | | OCH$_3$ | N(CH$_3$)$_2$ | N |

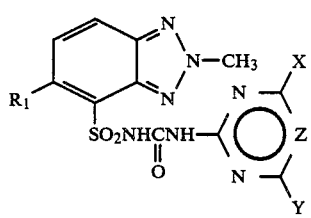

| | | | | | |
|---|---|---|---|---|---|
| 83 | CH$_3$ | CH$_3$ | CH$_3$ | CH$_3$ | CH |
| 84 | CH$_3$ | CH$_3$ | CH$_3$ | OCH$_3$ | CH |
| 85 | CH$_3$ | CH$_3$ | OCH$_3$ | OCH$_3$ | CH |
| 86 | CH$_3$ | CH$_3$ | OCH$_3$ | Cl | CH |
| 87 | CH$_3$ | CH$_3$ | CH$_3$ | CH$_3$ | N |
| 88 | CH$_3$ | CH$_3$ | OCH$_3$ | CH$_3$ | N |
| 89 | CH$_3$ | CH$_3$ | OCH$_3$ | OCH$_3$ | N |
| 90 | CH$_3$ | CH$_3$ | OCH$_2$CH$_3$ | NHCH$_3$ | N |
| 91 | H | | CH$_3$ | CH$_3$ | CH |
| 92 | H | | CH$_3$ | OCH$_3$ | CH |
| 93 | H | | OCH$_3$ | OCH$_3$ | CH |
| 94 | H | | Cl | OCH$_3$ | CH |
| 95 | H | | OCH$_3$ | CH$_3$ | N |
| 96 | H | | OCH$_3$ | OCH$_3$ | N |
| 97 | H | | OCH$_2$CH$_3$ | NHCH$_3$ | N |
| 98 | H | | OCH$_3$ | N(CH$_3$)$_2$ | N |
| 99 | Cl | | CH$_3$ | CH$_3$ | CH |
| 100 | Cl | | OCH$_3$ | CH$_3$ | CH |
| 101 | Cl | | OCH$_3$ | OCH$_3$ | CH |
| 102 | Cl | | Cl | OCH$_3$ | CH |
| 103 | Cl | | CH$_3$ | CH$_3$ | N |
| 104 | Cl | | OCH$_3$ | CH$_3$ | N |
| 105 | Cl | | OCH$_3$ | OCH$_3$ | N |
| 106 | Cl | | OCH$_2$CH$_3$ | NHCH$_3$ | N |

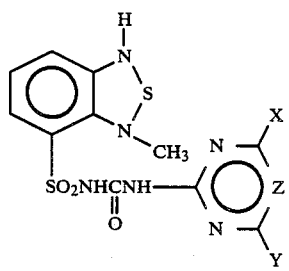

| | | | | | |
|---|---|---|---|---|---|
| 107 | | | OCH$_3$ | CH$_3$ | CH |
| 108 | | | OCH$_3$ | OCH$_3$ | CH |
| 109 | | | OCH$_3$ | CH$_3$ | N |

-continued

| Compounds | | | | | |
|---|---|---|---|---|---|
| Compounds | $R_1$ | $R_1'$ | X | Y | Z |

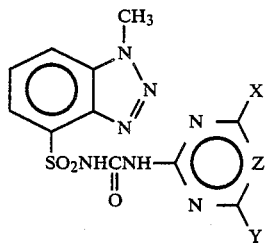

| | | | | | |
|---|---|---|---|---|---|
| 110 | | | N(CH$_3$)$_2$ | OCH$_3$ | N |
| 111 | | | N(CH$_3$)$_2$ | OC$_2$H$_5$ | N |
| 112 | | | OCH$_2$CF$_3$ | N(CH$_3$)$_2$ | N |
| 113 | | | SC$_2$H$_5$ | NHCH$_3$ | N |
| 114 | | | NHCH$_3$ | OCH(CH$_3$)$_2$ | N |
| 115 | | | OCH$_3$ | N(CH$_3$)CH$_2$CN | N |
| 116 | | | OCH$_3$ | NHCH$_2$CN | N |
| 117 | | | NHCH$_3$ | OC$_2$H$_5$ | CH |
| 118 | | | CH$_3$ | CH$_2$OCH$_3$ | CH |
| 119 | | | CH$_3$ | OCH$_2$C≡CH | N |
| 120 | | | OCH$_2$CF$_3$ | NHCH$_3$ | N |

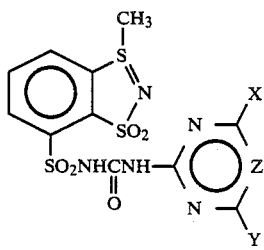

| | | | | | |
|---|---|---|---|---|---|
| 121 | | | CH$_3$ | CH$_3$ | CH |
| 122 | | | OCH$_3$ | CH$_3$ | CH |
| 123 | | | OCH$_3$ | OCH$_3$ | CH |
| 124 | | | Cl | OCH$_3$ | CH |
| 125 | | | OCH$_3$ | CH$_3$ | N |
| 126 | | | OCH$_2$CH$_3$ | NHCH$_3$ | N |

Test A

Seeds of crabgrass (Digitaria spp.), barnyard-grass (Echinochloa crusgalli), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;

H=formative effect;
U=unusual pigmentation;
X=axillary stimulation;
S=albinism; and
6Y=abscised buds or flowers.

TABLE A

|  | CMPD 1 | | CMPD 2 | |
|---|---|---|---|---|
| RATE = K/HA | 0.05 | 0.01 | 0.05 | 0.01 |
| POSTEMERGENCE | | | | |
| MORNINGGLORY | 2C,7G | 2G | 3C,9G | 7G |
| COCKLEBUR | 7G | 5H | 10C | 8G |
| VELVETLEAF | 5C,9G | 6G | 9C | 5G |
| NUTSEDGE | 9G | 0 | 3C,9G | 0 |
| CRABGRASS | 9G | 5G | 5C,9G | 5G |
| BARNYARDGRASS | 9C | 3C,9H | 10C | 8H |
| CHEATGRASS | 9G | 9G | 9C | 6G |
| WILD OATS | 9C | 3C,9G | 9C | 9C |
| WHEAT | 9C | 9G | 9C | 9G |
| CORN | 9C | 9G | 9C | 5U,9H |
| SOYBEAN | 9C | 9C | 10C | 9C |
| RICE | 6C,8G | — | 9C | 2C,8G |
| SORGHUM | 4C,9G | 9G | 9C | 3C,9H |
| SUGAR BEET | 5C,9G | 3C,5G | 9C | 2G |
| COTTON | 10C | 2C,9G | 10C | 9C |
| PREEMERGENCE | | | | |
| MORNINGGLORY | 3G | 0 | 6G | 0 |
| COCKLEBUR | — | — | 5G | 1H |
| VELVETLEAF | 5H | 0 | 7G | 5H |
| NUTSEDGE | 10E | 0 | 10E | 5G |
| CRABGRASS | 6G | 0 | 4C,9G | 4G |
| BARNYARDGRASS | 7G | 0 | 9H | 5G |
| CHEATGRASS | 9G | 5G | 9H | 8G |
| WILD OATS | 2C,8G | 0 | 3C,8G | 0 |
| WHEAT | 9H | 0 | 3C,9H | 8G |
| CORN | 9H | 2C | 2C,9H | 9G |
| SOYBEAN | 5G | 0 | 2C,7H | 0 |
| RICE | 9H | 7G | 9H | 9G |
| SORGHUM | 4C,9H | 5G | 9H | 5G |
| SUGAR BEETS | 4G | 4H | 7G | 2H |
| COTTON | 7G | 0 | 9G | 2G |

|  | CMPD 3 | | CMPD 4 | |
|---|---|---|---|---|
| RATE = K/HA | 0.05 | 0.01 | 0.05 | 0.01 |
| POSTEMERGENCE | | | | |
| MORNINGGLORY | 10C | 4C,9G | 3C,7G | 3H |
| COCKLEBUR | 10C | 9C | 10C | 10C |
| VELVETLEAF | 9C | 4C,9G | 9C | 7G |
| NUTSEDGE | 9C | 3C,7G | 3C,9G | 5G |
| CRABGRASS | 2C,9G | 2C,9G | 3C,9G | 3C,9G |
| BARNYARDGRASS | 9C | 9C | 9C | 9C |
| CHEATGRASS | 5C,9G | 4C,9G | 4C,9G | 7G |
| WILD OATS | 9C | 9C | 4C,8G | 6G |
| WHEAT | 9C | 2C,9G | 9G | 7G |
| CORN | 10C | 7U,9C | 9C | 9C |
| SOYBEAN | 9C | 9C | 9C | 9C |
| RICE | 5C,9G | 5C,9G | 5C,9G | 8G |
| SORGHUM | 9C | 5C,9G | 9C | 5C,9G |
| SUGAR BEETS | 6C,9G | 4C,9G | 9C | 2H |
| COTTON | 10C | — | 5C,9G | 6G |
| PREEMERGENCE | | | | |
| MORNINGGLORY | 9G | 5G | 9G | 6H |
| COCKLEBUR | 5H | 0 | 4H | 0 |
| VELVETLEAF | 8G | 0 | 3C,8G | 0 |
| NUTSEDGE | 9G | 8G | 4G | 0 |
| CRABGRASS | 8G | 2G | 5G | 0 |
| BARNYARDGRASS | 9H | 0 | 8H | 2G |
| CHEATGRASS | 9H | 5G | 9G | 7G |
| WILD OATS | 8G | 0 | 0 | 0 |
| WHEAT | 9G | 7G | 4G | 0 |
| CORN | 9H | 2C,5G | 3C,9H | 3G |
| SOYBEAN | 3C,7H | 0 | 2C,5G | 2G |
| RICE | 9H | 9H | 9H | 9H |
| SORGHUM | 9H | 8G | 10H | 9H |
| SUGAR BEETS | 6G | 0 | 5G | 2H |
| COTTON | 9G | 5G | 8G | 5G |

|  | CMPD 5 | | CMPD 6 | |
|---|---|---|---|---|
| RATE = K/HA | 0.05 | 0.01 | 0.05 | 0.01 |
| POSTEMERGENCE | | | | |
| MORNINGGLORY | 0 | 0 | 3C,7G | 0 |
| COCKLEBUR | 0 | 0 | — | 8H |
| VELVETLEAF | 0 | 0 | 6G | 2H |
| NUTSEDGE | 0 | 0 | 0 | 0 |
| CRABGRASS | 0 | 0 | 3C,9G | 0 |
| BARNYARDGRASS | 5C,9H | 3H | 9C | 9C |
| CHEATGRASS | 8G | 3G | 5C,9G | 9G |
| WILD OATS | 9G | 4G | 9C | 9C |
| WHEAT | 9G | 6G | 5C,9G | 9C |
| CORN | 5C,9G | 2C,8H | 9C | 9C |
| SOYBEAN | 5H | 1H | 9C | 2C,9G |
| RICE | 8G | 5G | 9C | 5C,9G |
| SORGHUM | 9G | 6G | 9C | 9C |
| SUGAR BEETS | 0 | 0 | 3C,8G | 3G |
| COTTON | 2G | 0 | 6G | 0 |
| PREEMERGENCE | | | | |
| MORNINGGLORY | 0 | 0 | 9G | 4G |
| COCKLEBUR | 0 | 0 | 8G | 0 |
| VELVETLEAF | 0 | 0 | 7G | 0 |
| NUTSEDGE | 0 | 0 | 8G | 0 |
| CRABGRASS | 0 | 0 | 2C,8G | 7G |
| BARNYARDGRASS | 0 | 0 | 9H | 5G |
| CHEATGRASS | 0 | 0 | 9H | 6G |
| WILD OATS | 0 | 0 | 2C,8G | 0 |
| WHEAT | 7G | 0 | 3C,9H | 9H |
| CORN | 2C,3G | 0 | 3C,9G | 2C,7H |
| SOYBEAN | 0 | 0 | 3C,7G | 0 |
| RICE | 9G | 0 | 10H | 10H |
| SORGHUM | 9G | 0 | 9H | 9H |
| SUGAR BEETS | 0 | 0 | 8G | 0 |
| COTTON | 2G | 0 | 9G | 0 |

|  | CMPD 7 | |
|---|---|---|
| RATE = K/HA | 0.05 | 0.01 |
| POSTEMERGENCE | | |
| MORNINGGLORY | 2C,5G | 0 |
| COCKLEBUR | 9C | 4C,9G |
| VELVETLEAF | 5G | 1H |
| NUTSEDGE | 2C,8G | 0 |
| CRABGRASS | 3C,9G | 3C,8G |
| BARNYARDGRASS | 9C | 3C,9H |
| CHEATGRASS | 9G | 2C,9G |
| WILD OATS | 9C | 9C |
| WHEAT | 3C,9G | 9G |
| CORN | 9C | 3C,9G |
| SOYBEAN | 9C | 3C,8H |
| RICE | 9C | 4C,9G |
| SORGHUM | 9C | 3C,9G |
| SUGAR BEETS | 10C | 6G |
| COTTON | 5C,9G | 1H |
| PREEMERGENCE | | |
| MORNINGGLORY | 8G | 0 |
| COCKLEBUR | 1H | 0 |
| VELVETLEAF | 0 | 0 |
| NUTSEDGE | 10E | 0 |
| CRABGRASS | 3C,8G | 5G |
| BARNYARDGRASS | 4G | 0 |
| CHEATGRASS | 8G | 0 |
| WILD OATS | 3C,9G | 0 |
| WHEAT | 3C,9H | 3G |
| CORN | 3C,9H | 3C,8H |
| SOYBEAN | 2G | 0 |
| RICE | 10H | 8G |
| SORGHUM | 10H | 3C,9H |
| SUGAR BEETS | 3C,9G | 3H |
| COTTON | 7G | 9H |

|  | CMPD 8 | | CMPD 9 | |
|---|---|---|---|---|
| RATE = KG/HA | 0.05 | 0.01 | 0.05 | 0.01 |
| POSTEMERGENCE | | | | |
| MORNINGGLORY | 10C | 6G | 10C | 10C |
| COCKLEBUR | 10C | 10C | 10C | 9C |
| VELVETLEAF | 10C | 10C | 10C | 10C |
| NUTSEDGE | 10C | 5C,9G | 10C | 9C |
| CRABGRASS | 9C | 4C,9G | 10C | 5C,9G |
| GIANT FOXTAIL | 10C | 4C,9G | 10C | 9C |
| BARNYARDGRASS | 9C | 9C | 10C | 9C |
| CHEATGRASS | 9C | 7G | 10C | 9C |
| WILD OATS | 2G | 0 | 5C,9G | 7G |
| WHEAT | 10C | 9C | 9C | 9C |
| CORN | 10C | 10C | 10C | 10C |

TABLE A-continued

| | CMPD 8 | | CMPD 9 | |
|---|---|---|---|---|
| BARLEY | 5C,9G | 2G | 9G | 7G |
| SOYBEAN | 9C | 9C | 9C | 5C,9G |
| RICE | 9C | 9C | 9C | 9C |
| SORGHUM | 9C | 10C | 9C | 5C,9G |
| SUGAR BEETS | 10C | 10C | 10C | 10C |
| COTTON | 10C | 10C | 10C | 10C |
| PREEMERGENCE | | | | |
| MORNINGGLORY | 9G | 7G | 9G | 9G |
| COCKLEBUR | 7H | 0 | 9H | 0 |
| VELVETLEAF | 9G | 9G | 9G | 7H |
| NUTSEDGE | 10E | 2G | 5G | 3G |
| CRABGRASS | 8G | 0 | 8G | 7G |
| GIANT FOXTAIL | 9H | 0 | 9H | 8G |
| BARNYARDGRASS | 9H | 0 | 9H | 5H |
| CHEATGRASS | 9G | 3G | 9H | 9G |
| WILD OATS | 2C,4G | 2G | 3C,7G | 3G |
| WHEAT | 9H | 7G | 4C,9H | 9H |
| CORN | 9H | 8H | 3C,9H | 8H |
| BARLEY | 2G | 0 | 9G | 7G |
| SOYBEAN | 9H | 2C,7H | 9H | 2C,8H |
| RICE | 10H | 9H | 10H | 9H |
| SORGHUM | 10H | 10H | 9H | 9H |
| SUGAR BEETS | 9C | 4G | 9C | 4G |
| COTTON | 9G | 5G | 9G | 8G |

| | CMPD 10 | | CMPD 11 | |
|---|---|---|---|---|
| RATE = KG/HA | 0.05 | 0.01 | 0.05 | 0.01 |
| POSTEMERGENCE | | | | |
| MORNINGGLORY | 10C | 9C | 10C | 10C |
| COCKLEBUR | 10C | 9C | 9C | 9C |
| VELVETLEAF | 10C | 10C | 10C | 10C |
| NUTSEDGE | 10C | 3C,7G | 9C | 3C,5G |
| CRABGRASS | 9C | 3C,8G | 9C | 4C,8G |
| GIANT FOXTAIL | 10C | 10C | 10C | 9C |
| BARNYARDGRASS | 9C | 9C | 10C | 9C |
| CHEATGRASS | 10C | 9C | 9C | 6G |
| WILD OATS | 6C,9G | 3C,9G | 5G | 0 |
| WHEAT | 9C | 5C,9G | 4C,9G | 6G |
| CORN | 10C | 10C | 10C | 9C |
| BARLEY | 5C,9G | 4C,9G | 4G | 0 |
| SOYBEAN | 9C | 9C | 9C | 2C,6H |
| RICE | 9C | 9C | 9C | 9C |
| SORGHUM | 10C | 9C | 9C | 10C |
| SUGAR BEETS | 10C | 9C | 10C | 10C |
| COTTON | 10C | 10C | 10C | 10C |
| PREEMERGENCE | | | | |
| MORNINGGLORY | 9H | 3G | 9G | 7G |
| COCKLEBUR | 8H | 5G | — | — |
| VELVETLEAF | 4C,9G | 8G | 8G | 7H |
| NUTSEDGE | 4C,9G | 2C,6G | 3C,6G | 0 |
| CRABGRASS | 3C,9G | 2C,5G | 7G | 4G |
| GIANT FOXTAIL | 9H | 9H | 8G | 3C,6G |
| BARNYARDGRASS | 9H | 3H | 9H | 3H |
| CHEATGRASS | 4C,9G | 7G | 7G | 0 |
| WILD OATS | 6G | 8G | 3G | 2C |
| WHEAT | 4C,9H | 9H | 8G | 2G |
| CORN | 4C,9H | 3C,9H | 9H | 9H |
| BARLEY | 8G | 4G | 7G | 0 |
| SOYBEAN | 9H | 7G | 3C,8H | 2G |
| RICE | 9H | 9G | 9H | 9H |
| SORGHUM | 4C,9H | 8H | 9H | 9H |
| SUGAR BEETS | 9C | 9C | 9C | 7G |
| COTTON | 9G | 7G | 8G | 2G |

| | CMPD 12 | | CMPD 13 | |
|---|---|---|---|---|
| RATE = KG/HA | 0.05 | 0.01 | 0.05 | 0.01 |
| POSTEMERGENCE | | | | |
| MORNINGGLORY | 10C | 10C | 10C | 10C |
| COCKLEBUR | 9C | 10C | 10C | 10C |
| VELVETLEAF | 10C | 10C | 10C | 10C |
| NUTSEDGE | 2C,5G | 2G | 5C,9G | 2C,8G |
| CRABGRASS | 10C | 9C | 9C | 9C |
| GIANT FOXTAIL | 10C | 10C | 10C | 10C |
| BARNYARDGRASS | 9C | 10C | 9C | 9C |
| CHEATGRASS | 9C | 4C,8G | 6G | 6G |
| WILD OATS | 0 | 0 | 2C | 0 |
| WHEAT | 9C | 5C,9G | 9C | 9G |
| CORN | 10C | 10C | 10C | 6C,9G |
| BARLEY | 9G | 8G | 9G | 4G |
| SOYBEAN | 9C | 9C | 9C | 9C |
| RICE | 9C | 9C | 9C | 9C |
| SORGHUM | 9C | 10C | 9C | 9C |
| SUGAR BEETS | 10C | 10C | 10C | 7G |
| COTTON | 10C | 9C | 10C | 10C |
| PREEMERGENCE | | | | |
| MORNINGGLORY | 9G | 9G | 9G | 9G |
| COCKLEBUR | 9H | 9G | 7H | 0 |
| VELVETLEAF | 4C,9G | 3C,7G | 4C,9G | 0 |
| NUTSEDGE | 9G | 0 | 10E | 0 |
| CRABGRASS | 5C,9G | 4C,8G | 4C,9G | 6G |
| GIANT FOXTAIL | 9H | 4C,9H | 4C,9H | 5G |
| BARNYARDGRASS | 9H | 3C,9H | 9H | 5H |
| CHEATGRASS | 9H | 7G | 8H | 0 |
| WILD OATS | 2C,4G | 0 | 2G | 0 |
| WHEAT | 9H | 9H | 9H | 8G |
| CORN | 9C | 3C,9H | 9G | 2C,7H |
| BARLEY | 9G | 7G | 9G | 3G |
| SOYBEAN | 9H | 8G | 4C,8H | 6G |
| RICE | 10E | 5C,9H | 5C,9H | 9H |
| SORGHUM | 10H | 4C,9H | 10H | 9G |
| SUGAR BEETS | 9C | 4C,9G | 7G | 3G |
| COTTON | 4C,9G | 7G | 2C,9G | 4G |

| | CMPD 14 | | CMPD 15 | |
|---|---|---|---|---|
| RATE = KG/HA | 0.05 | 0.01 | 0.05 | 0.01 |
| POSTEMERGENCE | | | | |
| MORNINGGLORY | 4C,9G | 2C,2H | 0 | — |
| COCKLEBUR | 10C | 3G | 0 | — |
| VELVETLEAF | 10C | 8G | 0 | — |
| NUTSEDGE | 4G | 0 | 0 | — |
| CRABGRASS | 9C | 8G | 0 | — |
| GIANT FOXTAIL | 9C | 4C,9H | 0 | — |
| BARNYARDGRASS | 4C,9G | 6H | 0 | — |
| CHEATGRASS | 5C,9G | 7G | 0 | — |
| WILD OATS | 3C,8G | 5G | 0 | — |
| WHEAT | 5C,9G | 2C,7G | 0 | — |
| CORN | 5U,9G | 5C,9G | 0 | — |
| BARLEY | 7G | 4G | 0 | — |
| SOYBEAN | 4C,9G | 5C,9G | 0 | — |
| RICE | 9C | 5C,9G | 0 | — |
| SORGHUM | 4C,9G | 9G | 0 | — |
| SUGAR BEETS | 6G | 2G | 0 | — |
| COTTON | 10C | 7G | 0 | — |
| PREEMERGENCE | | | | |
| MORNINGGLORY | 9G | 2G | 0 | — |
| COCKLEBUR | — | 0 | 0 | — |
| VELVETLEAF | 8H | 0 | 0 | — |
| NUTSEDGE | 7G | 0 | 0 | — |
| CRABGRASS | 7G | 2G | 0 | — |
| GIANT FOXTAIL | 8G | 2G | 0 | — |
| BARNYARDGRASS | 8H | 0 | 0 | — |
| CHEATGRASS | 9G | 0 | 0 | — |
| WILD OATS | 3G | 0 | 0 | — |
| WHEAT | 3G | 0 | 0 | — |
| CORN | 2C,9H | 5G | 0 | — |
| BARLEY | 0 | 0 | 0 | — |
| SOYBEAN | 7H | 2G | 0 | — |
| RICE | 10E | 7G | 0 | — |
| SORGHUM | 9H | 9G | 0 | — |
| SUGAR BEETS | 0 | 0 | 0 | — |
| COTTON | 7G | 0 | 0 | — |

| | CMPD 16 | | CMPD 17 | |
|---|---|---|---|---|
| RATE = KG/HA | 0.05 | 0.01 | 0.05 | 0.01 |
| POSTEMERGENCE | | | | |
| MORNINGGLORY | 0 | — | 0 | — |
| COCKLEBUR | 3C,7H | — | 0 | — |
| VELVETLEAF | 0 | — | 0 | — |
| NUTSEDGE | 0 | — | 0 | — |
| CRABGRASS | 0 | — | 0 | — |
| GIANT FOXTAIL | 0 | — | 0 | — |
| BARNYARDGRASS | 0 | — | 0 | — |
| CHEATGRASS | 0 | — | 0 | — |
| WILD OATS | 0 | — | 0 | — |
| WHEAT | 0 | — | 0 | — |
| CORN | 0 | — | 0 | — |
| BARLEY | 0 | — | 0 | — |
| SOYBEAN | 7G | — | 0 | — |
| RICE | 0 | — | 0 | — |
| SORGHUM | 0 | — | 0 | — |
| SUGAR BEETS | 3C,5G | — | 0 | — |
| COTTON | 0 | — | 0 | — |

TABLE A-continued

| PREEMERGENCE | | | | |
|---|---|---|---|---|
| MORNINGGLORY | 0 | — | 0 | — |
| COCKLEBUR | 0 | — | 0 | — |
| VELVETLEAF | 0 | — | 0 | — |
| NUTSEDGE | 0 | — | 0 | — |
| CRABGRASS | 0 | — | 0 | — |
| GIANT FOXTAIL | 0 | — | 0 | — |
| BARNYARDGRASS | 0 | — | 0 | — |
| CHEATGRASS | 0 | — | 0 | — |
| WILD OATS | 0 | — | 0 | — |
| WHEAT | 0 | — | 0 | — |
| CORN | 0 | — | 0 | — |
| BARLEY | 0 | — | 0 | — |
| SOYBEAN | 0 | — | 0 | — |
| RICE | 0 | — | 0 | — |
| SORGHUM | 0 | — | 0 | — |
| SUGAR BEETS | 5G | — | 0 | — |
| COTTON | 2G | — | 0 | — |

|  | CMPD 18 | | CMPD 19 | |
|---|---|---|---|---|
| RATE = KG/HA | 0.05 | 0.01 | 0.05 | 0.01 |
| POSTEMERGENCE | | | | |
| MORNINGGLORY | 0 | — | 0 | — |
| COCKLEBUR | 2G | — | 0 | — |
| VELVETLEAF | 0 | — | 0 | — |
| NUTSEDGE | 0 | — | 0 | — |
| CRABGRASS | 0 | — | 0 | — |
| GIANT FOXTAIL | 0 | — | 0 | — |
| BARNYARDGRASS | 0 | — | 0 | — |
| CHEATGRASS | 0 | — | 0 | — |
| WILD OATS | 0 | — | 0 | — |
| WHEAT | 0 | — | 0 | — |
| CORN | 2C,5H | — | 0 | — |
| BARLEY | 0 | — | 0 | — |
| SOYBEAN | 0 | — | 0 | — |
| RICE | 2G | — | 0 | — |
| SORGHUM | 2C,5G | — | 2C,5G | — |
| SUGAR BEETS | 0 | — | 2H | — |
| COTTON | 2H | — | 0 | — |
| PREEMERGENCE | | | | |
| MORNINGGLORY | 0 | — | 0 | — |
| COCKLEBUR | 0 | — | 0 | — |
| VELVETLEAF | 0 | — | 0 | — |
| NUTSEDGE | 0 | — | 0 | — |
| CRABGRASS | 0 | — | 0 | — |
| GIANT FOXTAIL | 0 | — | 0 | — |
| BARNYARDGRASS | 0 | — | 0 | — |
| CHEATGRASS | 0 | — | 0 | — |
| WILD OATS | 0 | — | 0 | — |
| WHEAT | 0 | — | 0 | — |
| CORN | 0 | — | 0 | — |
| BARLEY | 0 | — | 0 | — |
| SOYBEAN | 0 | — | 0 | — |
| RICE | 0 | — | 0 | — |
| SORGHUM | 0 | — | 0 | — |
| SUGAR BEETS | 0 | — | 0 | — |
| COTTON | 0 | — | 0 | — |

|  | CMPD 20 | | CMPD 21 | |
|---|---|---|---|---|
| RATE = KG/HA | 0.05 | 0.01 | 0.05 | 0.01 |
| POSTEMERGENCE | | | | |
| MORNINGGLORY | 0 | — | 1C | 0 |
| COCKLEBUR | 0 | — | 1C | 0 |
| VELVETLEAF | 0 | — | 0 | 0 |
| NUTSEDGE | 0 | — | 0 | 0 |
| CRABGRASS | 0 | — | 0 | 0 |
| GIANT FOXTAIL | 0 | — | 0 | 0 |
| BARNYARDGRASS | 0 | — | 0 | 0 |
| CHEATGRASS | 0 | — | 0 | 0 |
| WILD OATS | 0 | — | 0 | 0 |
| WHEAT | 0 | — | 0 | 0 |
| CORN | 0 | — | 0 | 0 |
| BARLEY | 0 | — | 0 | 0 |
| SOYBEAN | 0 | — | 1C | 0 |
| RICE | 0 | — | 0 | 0 |
| SORGHUM | 0 | — | 2C | 0 |
| SUGAR BEETS | 0 | — | 2C | 0 |
| COTTON | 0 | — | 2C | 0 |
| PREEMERGENCE | | | | |
| MORNINGGLORY | 0 | — | 0 | 0 |
| COCKLEBUR | 0 | — | 0 | 0 |
| VELVETLEAF | 0 | — | 0 | 0 |
| NUTSEDGE | 0 | — | 0 | 0 |
| CRABGRASS | 0 | — | 0 | 0 |
| GIANT FOXTAIL | 0 | — | 0 | 0 |
| BARNYARDGRASS | 0 | — | 0 | 0 |
| CHEATGRASS | 0 | — | 0 | 0 |
| WILD OATS | 0 | — | 0 | 0 |
| WHEAT | 0 | — | 0 | 0 |
| CORN | 0 | — | 0 | 0 |
| BARLEY | 0 | — | 0 | 0 |
| SOYBEAN | 0 | — | 0 | 0 |
| RICE | 0 | — | 0 | 0 |
| SORGHUM | 0 | — | 0 | 0 |
| SUGAR BEETS | 4G | — | 0 | 0 |
| COTTON | 0 | — | 0 | 0 |

|  | CMPD 22 | | CMPD 23 | |
|---|---|---|---|---|
| RATE = KG/HA | 0.05 | 0.01 | 0.05 | 0.01 |
| POSTEMERGENCE | | | | |
| MORNINGGLORY | 2C,3G | 0 | 0 | 0 |
| COCKLEBUR | 2C,3H | 0 | 3H | 0 |
| VELVETLEAF | 4C,9H | 2C,6G | 5C,9G | 4C,9G |
| NUTSEDGE | 2G | 0 | 5C,9G | 5G |
| CRABGRASS | 2G | 0 | 0 | 0 |
| GIANT FOXTAIL | 2C,5G | 0 | 0 | 0 |
| BARNYARDGRASS | 2C,7G | 2G | 0 | 0 |
| CHEATGRASS | 2C,6G | 0 | 0 | 0 |
| WILD OATS | 2C | 0 | 0 | 0 |
| WHEAT | 0 | 0 | 0 | 0 |
| CORN | 3C,6H | 0 | 0 | 0 |
| BARLEY | 0 | 0 | 0 | 0 |
| SOYBEAN | 4C,9G | 3C,6G | 5C,9G | 3C,7G |
| RICE | 4C,8G | 2G | 2G | 0 |
| SORGHUM | 3C,6G | 2G | 0 | 0 |
| SUGAR BEETS | 9C | 3C,7G | 4C,9G | 9C |
| COTTON | 4C,9G | 2C,5G | 4C,9G | 7G |
| PREEMERGENCE | | | | |
| MORNINGGLORY | 2C | 0 | 0 | 0 |
| COCKLEBUR | 2C | 0 | 0 | 0 |
| VELVETLEAF | 2C,6H | 0 | 1H | 0 |
| NUTSEDGE | 0 | 0 | 3G | 0 |
| CRABGRASS | 4G | 0 | 2G | 0 |
| GIANT FOXTAIL | 3C,3H | 0 | 0 | 0 |
| BARNYARDGRASS | 3C,3H | 0 | 0 | 0 |
| CHEATGRASS | 5G | 0 | 8G | 0 |
| WILD OATS | 0 | 0 | 0 | 0 |
| WHEAT | 0 | 0 | 0 | 0 |
| CORN | 3C,4G | 2C | 2C | 0 |
| BARLEY | 3C,3G | 0 | 0 | 0 |
| SOYBEAN | 3C,4G | 2C | 2C,2H | 0 |
| RICE | 6G | 0 | 3G | 0 |
| SORGHUM | 3C,4G | 0 | 2C | 0 |
| SUGAR BEETS | 4C,9H | 7G | 7H | 0 |
| COTTON | 2C | 0 | 0 | 0 |

|  | CMPD 24 | | CMPD 25 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | 0 |
| COCKLEBUR | 2C,3H | 0 | 0 | 0 |
| VELVETLEAF | 0 | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 2H | 0 | 2G | 0 |
| COTTON | 0 | 0 | 0 | 0 |
| PREEMERGENCE | | | | |
| MORNINGGLORY | 0 | 0 | 0 | 0 |
| COCKLEBUR | 0 | 0 | 0 | 0 |
| VELVETLEAF | 0 | 0 | 0 | 0 |
| NUTSEDGE | 0 | 0 | 0 | 0 |

TABLE A-continued

| | | | | |
|---|---|---|---|---|
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 0 | 0 | 0 | 0 |
| COTTON | 0 | 0 | 0 | 0 |

| | CMPD 26 | | CMPD 27 | |
|---|---|---|---|---|
| RATE = KG/HA | 0.05 | 0.01 | 0.05 | 0.01 |
| POSTEMERGENCE | | | | |
| MORNINGGLORY | 2H | 0 | 2G | 0 |
| COCKLEBUR | 3H | 1H | 0 | 0 |
| VELVETLEAF | 3C,7G | 1C | 2C,6G | 1C |
| NUTSEDGE | 5G | 0 | 0 | 0 |
| CRABGRASS | 6G | 0 | 0 | 0 |
| GIANT FOXTAIL | 3C,6G | 0 | 0 | 0 |
| BARNYARDGRASS | 4C,8H | 2G | 2H | 0 |
| CHEATGRASS | 3G | 0 | 0 | 0 |
| WILD OATS | 1C | 0 | 0 | 0 |
| WHEAT | 0 | 0 | 0 | 0 |
| CORN | 3C,8H | 5H | 0 | 0 |
| BARLEY | 0 | 0 | 0 | 0 |
| SOYBEAN | 3C,7H | 3G | 3C,5H | 0 |
| RICE | 8G | 3G | 3G | 0 |
| SORGHUM | 4C,9G | 3G | 2C,5G | 0 |
| SUGAR BEETS | 4C,9G | 2C,4G | 5C,9G | 0 |
| COTTON | 4C,8H | 2C,2G | 5C,9H | 0 |
| PREEMERGENCE | | | | |
| MORNINGGLORY | 0 | 0 | 0 | 0 |
| COCKLEBUR | 0 | 0 | 2H | 0 |
| VELVETLEAF | 0 | 0 | 0 | 0 |
| NUTSEDGE | 0 | 0 | 2G | 0 |
| CRABGRASS | 2G | 0 | 0 | 0 |
| GIANT FOXTAIL | 5G | 0 | 0 | 0 |
| BARNYARDGRASS | 2C | 0 | 0 | 0 |
| CHEATGRASS | 3G | 0 | 0 | 0 |
| WILD OATS | 0 | 0 | 0 | 0 |
| WHEAT | 2G | 0 | 0 | 0 |
| CORN | 3C,5G | 0 | 0 | 0 |
| BARLEY | 7G | 0 | 0 | 0 |
| SOYBEAN | 0 | 0 | 0 | 0 |
| RICE | 7G | 0 | 0 | 0 |
| SORGHUM | 8H | 2C | 0 | 0 |
| SUGAR BEETS | 4H | 1H | 0 | 0 |
| COTTON | 0 | 0 | 0 | 0 |

| | CMPD 28 | | CMPD 29 | |
|---|---|---|---|---|
| RATE = KG/HA | 0.05 | 0.01 | 0.05 | 0.01 |
| POSTEMERGENCE | | | | |
| MORNINGGLORY | 0 | 0 | 4C,8H | 2C,4G |
| COCKLEBUR | 0 | 0 | 9C | 3C,6G |
| VELVETLEAF | 0 | 0 | 5C,9H | 3C,7H |
| NUTSEDGE | 0 | 0 | 3C,7G | 0 |
| CRABGRASS | 0 | 0 | 3C,3G | 0 |
| GIANT FOXTAIL | 0 | 0 | 4G | 0 |
| BARNYARDGRASS | 0 | 0 | 3C,7G | 3G |
| CHEATGRASS | 0 | 0 | 5C,9G | 2C,5G |
| WILD OATS | 0 | 0 | 2C,7G | 3G |
| WHEAT | 0 | 0 | 8G | 3G |
| CORN | 0 | 0 | 4C,9H | 2C,8G |
| BARLEY | 0 | 0 | 2G | 0 |
| SOYBEAN | 0 | 0 | 4C,8G | 2G |
| RICE | 0 | 0 | 9C | 3C,8G |
| SORGHUM | 0 | 0 | 5C,9G | 5G |
| SUGAR BEETS | 2G | 0 | 9C | 3C,8H |
| COTTON | 2G | 0 | 4C,9H | 7G |
| PREEMERGENCE | | | | |
| MORNINGGLORY | 1C | 0 | 0 | 0 |
| COCKLEBUR | 0 | 0 | — | 0 |
| VELVETLEAF | 0 | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 2G | 0 |
| WILD OATS | 0 | 0 | 3G | 0 |
| WHEAT | 0 | 0 | 3G | 0 |
| CORN | 0 | 0 | 1C | 0 |
| BARLEY | 0 | 0 | 0 | 0 |
| SOYBEAN | 0 | 0 | 0 | 0 |
| RICE | 0 | 0 | 3C,4G | 0 |
| SORGHUM | 0 | 0 | 0 | 0 |
| SUGAR BEETS | 0 | 0 | 5G | 3G |
| COTTON | 0 | 0 | 0 | 0 |

| | CMPD 30 | | CMPD 31 | |
|---|---|---|---|---|
| RATE = KG/HA | 0.05 | 0.01 | 0.05 | 0.01 |
| POSTEMERGENCE | | | | |
| MORNINGGLORY | 9C | 9C | 10C | 9C |
| COCKLEBUR | 10C | 10C | 10C | 10C |
| VELVETLEAF | 10C | 9C | 10C | 10C |
| NUTSEDGE | 4C,8G | 2C,8G | 10C | 9C |
| CRABGRASS | 4C,9G | 7G | 4C,9G | 2C,8G |
| GIANT FOXTAIL | 9C | 8G | 10C | 9C |
| BARNYARDGRASS | 9C | 8H | 9C | 5C,9H |
| CHEATGRASS | 9C | 9C | 10C | 9C |
| WILD OATS | 9C | 9G | 4C,9C | 3C,9G |
| WHEAT | 2C,9G | 9G | 3C,9G | 2C,9G |
| CORN | 9C | 3C,9G | 9C | 4U,9C |
| BARLEY | 3C,9G | 5G | 4C,9G | 8G |
| SOYBEAN | 9C | 9C | 9C | 9C |
| RICE | 9C | 9C | 9C | 9C |
| SORGHUM | 9C | 5C,9G | 9C | 9C |
| SUGAR BEETS | 9C | 9C | 10C | 9C |
| COTTON | 10C | 5C,9G | 10C | 9C |
| PREEMERGENCE | | | | |
| MORNINGGLORY | 9G | 0 | 9H | 8H |
| COCKLEBUR | 3C,7H | 0 | 8H | 2C,3H |
| VELVETLEAF | 3C,8G | 0 | 4C,9G | 7G |
| NUTSEDGE | 9G | 0 | 10E | 9G |
| CRABGRASS | 3C,7G | 0 | 6G | 2G |
| GIANT FOXTAIL | 2G | 0 | 8H | 2G |
| BARNYARDGRASS | 7G | 0 | 3C,9H | 1H |
| CHEATGRASS | 4C,9G | 0 | 4C,9G | 8G |
| WILD OATS | 2C,5G | 0 | 3C,7G | 2C,5G |
| WHEAT | 9H | 0 | 9H | 8G |
| CORN | 3C,9H | 2C | 9H | 9H |
| BARLEY | 8G | 0 | 7G | 8G |
| SOYBEAN | 9H | 1H | 3C,9H | 3C,8H |
| RICE | 4C,9H | 4G | 4C,9H | 9H |
| SORGHUM | 2C,9H | 3C,3G | 5C,9H | 9H |
| SUGAR BEETS | 3C,8G | 0 | 4C,9G | 8G |
| COTTON | 8G | 0 | 9G | 8G |

| | CMPD 32 | | CMPD 33 | |
|---|---|---|---|---|
| RATE = KG/HA | 0.05 | 0.01 | 0.05 | 0.01 |
| POSTEMERGENCE | | | | |
| MORNINGGLORY | 5C,9G | 3C,8G | 0 | 0 |
| COCKLEBUR | 10C | 10C | 1C | 0 |
| VELVETLEAF | 10C | 9C | 1C | 0 |
| NUTSEDGE | 4C,9G | 6G | 0 | 0 |
| CRABGRASS | 2C,5G | 0 | 0 | 0 |
| GIANT FOXTAIL | 6G | 1H | 0 | 0 |
| BARNYARDGRASS | 3C,9H | 3C,7H | 1H | 0 |
| CHEATGRASS | 7G | 6G | 0 | 0 |
| WILD OATS | 2G | 0 | 0 | 0 |
| WHEAT | 2G | 0 | 0 | 0 |
| CORN | 4C,9G | 9G | 0 | 0 |
| BARLEY | 2G | 0 | 0 | 0 |
| SOYBEAN | 2C,6H | 3H | 0 | 0 |
| RICE | 9C | 9C | 2G | 0 |
| SORGHUM | 4C,9G | 4C,9G | 2G | 0 |
| SUGAR BEETS | 9C | 9C | 0 | 0 |
| COTTON | 10C | 9C | 0 | 0 |
| PREEMERGENCE | | | | |
| MORNINGGLORY | 9G | 5G | 0 | 0 |
| COCKLEBUR | 9H | 0 | 0 | — |
| VELVETLEAF | 4C,9H | 2C | 0 | 0 |
| NUTSEDGE | 2C,5G | 0 | 0 | 0 |
| CRABGRASS | 3C,5G | 0 | 0 | 0 |
| GIANT FOXTAIL | 2G | 0 | 0 | 0 |
| BARNYARDGRASS | 3C,8H | 0 | 0 | 0 |
| CHEATGRASS | 6G | 2G | 0 | 0 |
| WILD OATS | 2G | 0 | 0 | 0 |
| WHEAT | 0 | 0 | 0 | 0 |

TABLE A-continued

| | | | | |
|---|---|---|---|---|
| CORN | 3C,9H | 2C | 0 | 0 |
| BARLEY | 5G | 0 | 0 | 0 |
| SOYBEAN | 2C,5G | 4G | 0 | 0 |
| RICE | 10E | 8G | 0 | 0 |
| SORGHUM | 3C,9H | 2C,5G | 0 | 0 |
| SUGAR BEETS | 4C,9G | 4G | 0 | 0 |
| COTTON | 9G | 4G | 0 | 0 |

| | CMPD 34 | | CMPD 35 | |
|---|---|---|---|---|
| RATE = KG/HA | 0.05 | 0.01 | 0.05 | 0.01 |
| POSTEMERGENCE | | | | |
| MORNINGGLORY | 3C,8G | 1H | 4C,8H | 3G |
| COCKLEBUR | 4C,9G | 3C,3H | 4C,9H | 2G |
| VELVETLEAF | 8H | 2C,5G | 3C,8H | 2C,5G |
| NUTSEDGE | 3C,8G | 0 | 8G | 0 |
| CRABGRASS | 3C,8G | 2C,4G | 2C,8G | 3G |
| GIANT FOXTAIL | 2C,8G | 2H | 9C | 3C,8G |
| BARNYARDGRASS | 9C | 3C,9H | 9C | 3C,7G |
| CHEATGRASS | 9C | 4C,9G | 9C | 5C,9G |
| WILD OATS | 9G | 3G | 3C,9G | 8G |
| WHEAT | 4C,9G | 9G | 3C,9G | 9G |
| CORN | 3C,9G | 2C,9G | 2C,9G | 2C,9G |
| BARLEY | 9G | 2G | 2C,9G | 6G |
| SOYBEAN | 4C,9G | 3C,7G | 3C,9G | 2C,6G |
| RICE | 9C | 9C | 9C | 9C |
| SORGHUM | 4C,9G | 3C,9G | 3C,9G | 2C,9G |
| SUGAR BEETS | 5C,9G | 3C,6G | 3C,8G | 5G |
| COTTON | 3C,8H | 5G | 2C,7G | 2G |
| PREEMERGENCE | | | | |
| MORNINGGLORY | 2G | 1H | 3G | 0 |
| COCKLEBUR | 4G | 0 | 0 | 0 |
| VELVETLEAF | 0 | 0 | 0 | 0 |
| NUTSEDGE | 0 | 0 | 8G | 0 |
| CRABGRASS | 0 | 0 | 0 | 0 |
| GIANT FOXTAIL | 0 | 0 | 2G | 0 |
| BARNYARDGRASS | 2C,5G | 0 | 2C,5G | 0 |
| CHEATGRASS | 4G | 0 | 8G | 0 |
| WILD OATS | 2C,2G | 2G | 3C,3G | 0 |
| WHEAT | 9G | 4G | 2C,9H | 5G |
| CORN | 3C,9G | 3C,5G | 3C,8H | 2C |
| BARLEY | 9G | 0 | 8G | 1C |
| SOYBEAN | 2C,4H | 0 | 3G | 0 |
| RICE | 8G | 3G | 9H | 3G |
| SORGHUM | 3C,9H | 3C | 9H | 2C |
| SUGAR BEETS | 3H | 2C | 3H | 0 |
| COTTON | 4G | 2G | 8G | 0 |

| | CMPD 36 | | CMPD 37 | |
|---|---|---|---|---|
| RATE = KG/HA | 0.05 | 0.01 | 0.05 | 0.01 |
| POSTEMERGENCE | | | | |
| MORNINGGLORY | 3C,7H | 2C,3G | 0 | 0 |
| COCKLEBUR | 7H | 2C,2H | 2C,6H | 0 |
| VELVETLEAF | 4C,8G | 3C,8G | 3C,9H | 2G |
| NUTSEDGE | 3G | 0 | 0 | 0 |
| CRABGRASS | 6G | 4G | 2G | 0 |
| GIANT FOXTAIL | 4C,9G | 4C,9H | 0 | 0 |
| BARNYARDGRASS | 3G | 2C | 0 | 0 |
| CHEATGRASS | 4C,9G | 4C,9G | 0 | 0 |
| WILD OATS | 3C,9G | 2C,9G | 0 | 0 |
| WHEAT | 9G | 7G | 0 | 0 |
| CORN | 9G | 3C,9G | 2C,6H | 1C |
| BARLEY | 8G | 3C,7G | 3G | 0 |
| SOYBEAN | 4C,9G | 3C,7H | 5H | 0 |
| RICE | 9C | 9C | 1C,8H | 5G |
| SORGHUM | 3C,9G | 3C,9G | 1C,5G | 5G |
| SUGAR BEETS | 0 | 0 | 10C | 4C,9G |
| COTTON | 7G | 2C,4G | 2C,6H | 3G |
| PREEMERGENCE | | | | |
| MORNINGGLORY | 2G | 0 | 2G | 0 |
| COCKLEBUR | — | 0 | — | 0 |
| VELVETLEAF | 0 | 0 | 1C,3H | 0 |
| NUTSEDGE | 0 | 0 | 0 | 0 |
| CRABGRASS | 0 | 0 | 3G | 0 |
| GIANT FOXTAIL | 0 | 0 | 0 | 0 |
| BARNYARDGRASS | 0 | 0 | 0 | 0 |
| CHEATGRASS | 8G | 0 | 0 | 0 |
| WILD OATS | 3G | 0 | 0 | 0 |
| WHEAT | 0 | 0 | 0 | 0 |
| CORN | 3C,4G | 0 | 2C,4G | 0 |
| BARLEY | 0 | 0 | 0 | 0 |
| SOYBEAN | 2H | 0 | 1C | 0 |

| | | | | |
|---|---|---|---|---|
| RICE | 2C,5G | 0 | 7H | 0 |
| SORGHUM | 2C,5G | 0 | 3C,6H | 0 |
| SUGAR BEETS | 0 | 0 | 2C,4H | 2H |
| COTTON | 0 | 0 | 1H | 0 |

| | CMPD 38 | | CMPD 39 | |
|---|---|---|---|---|
| RATE = KG/HA | 0.05 | 0.01 | 0.05 | 0.01 |
| POSTEMERGENCE | | | | |
| MORNINGGLORY | 7G | 4G | 6G | 3G |
| COCKLEBUR | 4C,8H | 4H | 5G | 0 |
| VELVETLEAF | 10C | 10C | 10C | 10C |
| NUTSEDGE | 2C,9G | 1C,8G | 9G | 2C,8G |
| CRABGRASS | 4G | 0 | 4G | 0 |
| GIANT FOXTAIL | 6G | 0 | 4G | 0 |
| BARNYARDGRASS | 2C,7G | 0 | 5G | 0 |
| CHEATGRASS | 8G | 0 | 2C,8G | 0 |
| WILD OATS | 3G | 0 | 4G | 0 |
| WHEAT | 5G | 0 | 4G | 0 |
| CORN | 9G | 2C,7G | 2C,8G | 2C,5H |
| BARLEY | 7G | 0 | 6G | 0 |
| SOYBEAN | 3C,8H | 2C,7H | 4C,9G | 2C,8G |
| RICE | 3C,9G | 8G | 2C,9G | 6G |
| SORGHUM | 2C,9G | 1C,6H | 7H | 0 |
| SUGAR BEETS | 10C | 5C,9G | 10C | 10C |
| COTTON | 10C | 2C,8H | 9C | 1C,8G |
| PREEMERGENCE | | | | |
| MORNINGGLORY | 6G | 4G | 6G | 1H |
| COCKLEBUR | 2H | 1H | 2G | 0 |
| VELVETLEAF | 2C,7G | 1H | 2C,9G | 8H |
| NUTSEDGE | 2C,8G | 0 | 10E | 2C,8G |
| CRABGRASS | 3G | 0 | 5G | 0 |
| GIANT FOXTAIL | 4G | 0 | 4G | 0 |
| BARNYARDGRASS | 5H | 0 | 6H | 0 |
| CHEATGRASS | 8G | 3G | 9G | 0 |
| WILD OATS | 0 | 0 | 6G | 0 |
| WHEAT | 2G | 0 | 5G | 0 |
| CORN | 9G | 3C,5G | 2C,7H | 0 |
| BARLEY | 0 | 0 | 0 | 0 |
| SOYBEAN | 3C,9H | 2C,4G | 2C,8H | 1C,4G |
| RICE | 2C,7H | 2G | 6G | 0 |
| SORGHUM | 3C,9H | 2C,6G | 2C,8H | 2C,4G |
| SUGAR BEETS | 3C,9G | 2C,9G | 9C | 2C,8G |
| COTTON | 2C,8G | 0 | 2C,7G | 0 |

| | CMPD 40 | | CMPD 41 | |
|---|---|---|---|---|
| RATE = KG/HA | 0.05 | 0.01 | 0.05 | 0.01 |
| POSTEMERGENCE | | | | |
| MORNINGGLORY | 2G | 0 | 0 | 0 |
| COCKLEBUR | 4G | 0 | 0 | 0 |
| VELVETLEAF | 3G | 0 | 0 | 0 |
| NUTSEDGE | 4G | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 2H | 1C | 0 | 0 |
| RICE | 0 | 0 | 0 | 0 |
| SORGHUM | 0 | 0 | 0 | 0 |
| SUGAR BEETS | 3C,8G | 2C,6G | 0 | 0 |
| COTTON | 2C,9G | 3G | 0 | 0 |
| PREEMERGENCE | | | | |
| MORNINGGLORY | 1H | 0 | 0 | 0 |
| COCKLEBUR | 0 | 0 | 2G | 3H |
| VELVETLEAF | 0 | 0 | 0 | 0 |
| NUTSEDGE | 4G | 0 | 0 | 0 |
| CRABGRASS | 0 | 5G | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 1H | 0 | 0 |
| RICE | 2G | 0 | 0 | 0 |
| SORGHUM | 2G | 0 | 0 | 0 |
| SUGAR BEETS | 3C,8G | 2H | 0 | 0 |

TABLE A-continued

| | | | | |
|---|---|---|---|---|
| COTTON | 2G | 0 | 0 | 0 |

| | CMPD 42 | | CMPD 43 | |
|---|---|---|---|---|
| RATE = KG/HA | 0.05 | 0.01 | 0.05 | 0.01 |
| POSTEMERGENCE | | | | |
| MORNINGGLORY | 1C | 0 | 7H | 0 |
| COCKLEBUR | 1C,7H | 4H | 0 | 0 |
| VELVETLEAF | 1C,6H | 3G | 7H | 0 |
| NUTSEDGE | 0 | 0 | 0 | 0 |
| CRABGRASS | 2G | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 2C,8H | 2C,7H | 1C,2H | 0 |
| BARLEY | 0 | 0 | 0 | 0 |
| SOYBEAN | 2C,7H | 1H | 2C,4H | 0 |
| RICE | 2G | 0 | 4G | 0 |
| SORGHUM | 1H,6G | 0 | 0 | 0 |
| SUGAR BEETS | 5C,9G | 3C,8G | 2C,8G | 2C,8G |
| COTTON | 1C,5H | 2C | 5G | 0 |
| PREEMERGENCE | | | | |
| MORNINGGLORY | 0 | 0 | 0 | 0 |
| COCKLEBUR | 0 | 0 | 0 | 0 |
| VELVETLEAF | 0 | 0 | 0 | 0 |
| NUTSEDGE | 0 | 0 | 0 | 0 |
| CRABGRASS | 0 | 0 | 4G | 0 |
| GIANT FOXTAIL | 2G | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 8G | 2C,7H | 0 | 0 |
| BARLEY | 0 | 0 | 0 | 0 |
| SOYBEAN | 2H | 0 | 0 | 0 |
| RICE | 2C,7G | 2G | 0 | 0 |
| SORGHUM | 2C,8H | 2C,4G | 0 | 0 |
| SUGAR BEETS | 3C,7H | 4H | 1H | 0 |
| COTTON | 0 | 0 | 0 | 0 |

| | CMPD 44 | | CMPD 45 | |
|---|---|---|---|---|
| RATE = KG/HA | 0.05 | 0.01 | 0.05 | 0.01 |
| POSTEMERGENCE | | | | |
| MORNINGGLORY | 2G | 0 | 0 | 0 |
| COCKLEBUR | 0 | 0 | 2C,5H | 0 |
| VELVETLEAF | 2C,8H | 0 | 5G | 0 |
| NUTSEDGE | 1C,7G | 0 | 2G | 0 |
| CRABGRASS | 3G | 0 | 0 | 0 |
| GIANT FOXTAIL | 2G | 0 | 0 | 0 |
| BARNYARDGRASS | 0 | 0 | 2H | 0 |
| CHEATGRASS | 0 | 0 | 0 | 0 |
| WILD OATS | 0 | 0 | 0 | 0 |
| WHEAT | 0 | 0 | 0 | 0 |
| CORN | 2C,7H | 2C,7H | 3G | 0 |
| BARLEY | 0 | 0 | 0 | 0 |
| SOYBEAN | 3C,8G | 0 | 0 | 0 |
| RICE | 2G | 0 | 2G | 0 |
| SORGHUM | 3G | 0 | 0 | 0 |
| SUGAR BEETS | 3C,9G | 0 | 4C,8G | 2C,5G |
| COTTON | 5G | 0 | 8H | 0 |
| PREEMERGENCE | | | | |
| MORNINGGLORY | 0 | 0 | 0 | 0 |
| COCKLEBUR | 0 | 0 | 3G | 0 |
| VELVETLEAF | 1C | 1C | 0 | 0 |
| NUTSEDGE | 0 | 0 | 0 | 0 |
| CRABGRASS | 0 | 0 | 0 | 0 |
| GIANT FOXTAIL | 3G | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 1C,2G | 0 | 0 | 0 |
| BARLEY | 0 | 0 | 0 | 0 |
| SOYBEAN | 2C | 0 | 0 | 0 |
| RICE | 0 | 0 | 0 | 0 |
| SORGHUM | 1C,6G | 0 | 0 | 0 |
| SUGAR BEETS | 5G | 2H | 3G | 0 |
| COTTON | 0 | 0 | 0 | 0 |

| | CMPD 46 | | CMPD 47 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | 0 |
| COCKLEBUR | 4C,9G | 5H | 0 | 0 |
| VELVETLEAF | 10C | 4C,8G | 2C,8H | 7G |
| NUTSEDGE | 2C,8G | 3G | 2C,7G | 2C,7G |
| CRABGRASS | 0 | 0 | 0 | 0 |
| GIANT FOXTAIL | 0 | 0 | 0 | 0 |
| BARNYARDGRASS | 0 | 0 | 2G | 0 |
| CHEATGRASS | 2G | 0 | 0 | 0 |
| WILD OATS | 0 | 0 | 0 | 0 |
| WHEAT | 0 | 0 | 0 | 0 |
| CORN | 0 | 0 | 3G | 2H |
| BARLEY | 0 | 0 | 0 | 0 |
| SOYBEAN | 2H | 0 | 2C,7H | 2C,7H |
| RICE | 0 | 0 | 4G | 0 |
| SORGHUM | 3C,8G | 2C,5G | 0 | 0 |
| SUGAR BEETS | 10C | 10C | 10C | 4C,8G |
| COTTON | 10C | 4C,8G | 2C,8H | 7H |
| PREEMERGENCE | | | | |
| MORNINGGLORY | 0 | 0 | 0 | 0 |
| COCKLEBUR | 2H | 0 | — | 0 |
| VELVETLEAF | 3H | 0 | 1H | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 2C,5G | 0 | 0 | 0 |
| SUGAR BEETS | 8G | 4H | 0 | 0 |
| COTTON | 5G | 0 | 0 | 0 |

| | CMPD 48 | | CMPD 49 | |
|---|---|---|---|---|
| RATE = KG/HA | 0.05 | 0.01 | 0.05 | 0.01 |
| POSTEMERGENCE | | | | |
| MORNINGGLORY | 2C | 2C | 0 | 1H |
| COCKLEBUR | — | 0 | 0 | 0 |
| VELVETLEAF | 2C,4G | 7G | 4G | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 2G | 0 | 3G | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 2G | 0 |
| BARLEY | 0 | 0 | 0 | 0 |
| SOYBEAN | 2C,7H | 4H | 2C,7H | 3G |
| RICE | 0 | 0 | 5G | 0 |
| SORGHUM | 0 | 0 | 5G | 0 |
| SUGAR BEETS | 4C,8G | 3C,3G | 3C,6G | 0 |
| COTTON | 2C,8H | 4G | 7H | 0 |
| PREEMERGENCE | | | | |
| MORNINGGLORY | 0 | 0 | 0 | 0 |
| COCKLEBUR | 0 | 0 | 0 | 0 |
| VELVETLEAF | 0 | 0 | 1H | 1H |
| NUTSEDGE | 9G | 0 | 0 | 0 |
| CRABGRASS | 0 | — | 2G | — |
| GIANT FOXTAIL | 0 | 0 | 0 | — |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 0 | 4H | 0 | 0 |
| COTTON | 0 | 0 | 0 | 0 |

| | CMPD 50 | | CMPD 51 | |
|---|---|---|---|---|
| = KG/HA | 0.05 | 0.01 | 0.05 | 0.01 |
| POSTEMERGENCE | | | | |

TABLE A-continued

| | | | | |
|---|---|---|---|---|
| MORNINGGLORY | 0 | 0 | 5H | 0 |
| COCKLEBUR | 0 | 0 | 5G | 0 |
| VELVETLEAF | 0 | 0 | 3C,6G | 2G |
| NUTSEDGE | 0 | 0 | 0 | 0 |
| CRABGRASS | 0 | 0 | 5G | 0 |
| GIANT FOXTAIL | 0 | 0 | 0 | 0 |
| BARNYARDGRASS | 0 | 0 | 2H | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 1H | 0 |
| RICE | 0 | 0 | 2G | 0 |
| SORGHUM | 0 | 0 | 0 | 0 |
| SUGAR BEETS | 0 | 0 | 5C,9H | 3G |
| COTTON | 0 | 0 | 4C,9H | 0 |
| PREEMERGENCE | | | | |
| MORNINGGLORY | 0 | 0 | 0 | 0 |
| COCKLEBUR | 0 | 0 | 0 | — |
| VELVETLEAF | 0 | 0 | 0 | 0 |
| NUTSEDGE | 0 | 0 | 0 | 0 |
| CRABGRASS | 0 | 0 | — | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 4H | 0 | — | 0 |
| COTTON | 0 | 0 | 0 | 0 |

| | CMPD 52 | | CMPD 53 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | 0 |
| COCKLEBUR | 3G | 0 | 0 | 0 |
| VELVETLEAF | 3C,8G | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | — | 7H | 0 | 0 |
| COTTON | 0 | 0 | 0 | 0 |
| PREEMERGENCE | | | | |
| MORNINGGLORY | 0 | 0 | 0 | 0 |
| COCKLEBUR | — | 0 | 0 | 0 |
| VELVETLEAF | 0 | 0 | 0 | 0 |
| NUTSEDGE | 0 | 0 | 0 | 0 |
| CRABGRASS | 0 | 0 | — | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 0 | 0 | 0 | 0 |
| COTTON | 0 | 0 | 0 | 0 |

| | CMPD 54 | | CMPD 55 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | 0 |
| COCKLEBUR | 0 | 0 | 0 | 0 |
| VELVETLEAF | 0 | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 4G | 0 | 0 | 0 |
| COTTON | 0 | 0 | 0 | 0 |
| PREEMERGENCE | | | | |
| MORNINGGLORY | 0 | 0 | 0 | 0 |
| COCKLEBUR | 0 | 0 | 0 | 0 |
| VELVETLEAF | 0 | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 4G | 0 | 0 | 0 |
| COTTON | 0 | 0 | 0 | 0 |

| | CMPD 56 | | CMPD 57 | |
|---|---|---|---|---|
| RATE = KG/HA | 0.05 | 0.01 | 0.05 | 0.01 |
| POSTEMERGENCE | | | | |
| MORNINGGLORY | 0 | 0 | 4C,9G | 2G |
| COCKLEBUR | 0 | 0 | 10C | 0 |
| VELVETLEAF | 0 | 0 | 10C | 9C |
| NUTSEDGE | 0 | 0 | 3C,9G | 5G |
| CRABGRASS | 0 | 0 | 0 | 0 |
| GIANT FOXTAIL | 0 | 0 | 2G | 0 |
| BARNYARDGRASS | 0 | 0 | 3H | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 2C,9G | 4H |
| RICE | 0 | 0 | 4G | 0 |
| SORGHUM | 0 | 0 | 0 | 0 |
| SUGAR BEETS | 0 | 0 | 10C | 4C,9G |
| COTTON | 0 | 0 | 4C,9G | — |
| PREEMERGENCE | | | | |
| MORNINGGLORY | 0 | 0 | 0 | 0 |
| COCKLEBUR | 0 | 0 | 9G | 0 |
| VELVETLEAF | 0 | 0 | 5H | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 4H | 0 |
| CHEATGRASS | 0 | 0 | 2G | 0 |
| WILD OATS | 0 | 0 | 0 | 0 |
| WHEAT | 0 | 0 | 0 | 0 |
| CORN | 0 | 0 | 2G | 0 |
| BARLEY | 0 | 0 | 0 | 0 |
| SOYBEAN | 0 | 0 | 2H | 0 |
| RICE | 0 | 0 | 0 | 0 |
| SORGHUM | 0 | 0 | 0 | 0 |
| SUGAR BEETS | 0 | 0 | 7G | 2G |
| COTTON | 0 | 0 | 2G | 0 |

| | CMPD 58 | | CMPD 59 | |
|---|---|---|---|---|
| RATE = KG/HA | 0.05 | 0.01 | 0.05 | 0.01 |
| POSTEMERGENCE | | | | |
| MORNINGGLORY | 2G | 1H | 10C | 3C,8G |
| COCKLEBUR | 10C | 3C,9G | 10C | 10C |
| VELVETLEAF | 9C | 3C,7H | 9C | 9C |
| NUTSEDGE | 2C,8G | 7G | 4C,9G | 4C,9G |
| CRABGRASS | 5C | 3G | 5G | 0 |
| GIANT FOXTAIL | 0 | 0 | 7G | 3G |

TABLE A-continued

| | | | | |
|---|---|---|---|---|
| BARNYARDGRASS | 3C,9H | 3C,6H | 9C | 9C |
| CHEATGRASS | 3C,9G | 3C,8G | 4C,9G | 2C,8G |
| WILD OATS | 3C,8G | 3C,7G | 4C,8G | 2G |
| WHEAT | 3C,9G | 3C,7G | 4C,9G | 9G |
| CORN | 3C,9G | 4C,9H | 10C | 9C |
| BARLEY | 3C,6G | 0 | 2C,6G | 3G |
| SOYBEAN | 4C,9G | 5G | 5C,9G | 9C |
| RICE | 6C,9G | 6C,9G | 5C,9G | 9C |
| SORGHUM | 3C,9G | 2C,7G | 10C | 9C |
| SUGAR BEETS | 9C | 4C,8G | 10C | 10C |
| COTTON | 4C,9H | 2G | 9C | 4C,9G |
| PREEMERGENCE | | | | |
| MORNINGGLORY | 0 | 0 | 2G | 0 |
| COCKLEBUR | 2H | — | 2C | 0 |
| VELVETLEAF | 0 | 0 | 5H | 0 |
| NUTSEDGE | 0 | 0 | 5G | 0 |
| CRABGRASS | 0 | 0 | 2G | 0 |
| GIANT FOXTAIL | 0 | 0 | 0 | 0 |
| BARNYARDGRASS | 0 | 0 | 4H | 0 |
| CHEATGRASS | 0 | 0 | 8G | 0 |
| WILD OATS | 0 | 0 | 2G | 0 |
| WHEAT | 0 | 0 | 2G | 0 |
| CORN | 0 | 0 | 2C,7H | 2G |
| BARLEY | 0 | 0 | 2G | 0 |
| SOYBEAN | 0 | 0 | 7H | 2C,5G |
| RICE | 0 | 0 | 9G | 3G |
| SORGHUM | 0 | 0 | 3C,9H | 2C,6G |
| SUGAR BEETS | 2H | 0 | 7H | 3G |
| COTTON | 8G | 0 | 4G | 0 |

| | CMPD 60 | | CMPD 61 | |
|---|---|---|---|---|
| RATE = KG/HA | 0.05 | 0.01 | 0.05 | 0.01 |
| POSTEMERGENCE | | | | |
| MORNINGGLORY | 4C,8G | 1H | 2G | 0 |
| COCKLEBUR | 10C | 10C | 7G | 0 |
| VELVETLEAF | 9C | 10C | 1H | 0 |
| NUTSEDGE | 10C | 9C | 4G | 0 |
| CRABGRASS | 6G | 3G | 0 | 0 |
| GIANT FOXTAIL | 3C,8G | 2C,5G | 0 | 0 |
| BARNYARDGRASS | 9C | 9C | 2H | 0 |
| CHEATGRASS | 9C | 2C,8G | 4G | 0 |
| WILD OATS | 4C,9G | 0 | 0 | 0 |
| WHEAT | 9C | 8G | 2G | 0 |
| CORN | 10C | 10C | 3C,9G | 0 |
| BARLEY | 9G | 3G | 0 | 0 |
| SOYBEAN | 9C | 10C | 2C,3H | 0 |
| RICE | 9C | 9C | 5C,9G | 0 |
| SORGHUM | 9C | 9C | 4C,8H | 0 |
| SUGAR BEETS | 10C | 10C | 3C,3G | 0 |
| COTTON | 10C | 9C | 0 | 0 |
| PREEMERGENCE | | | | |
| MORNINGGLORY | 3G | 1H | 0 | 0 |
| COCKLEBUR | 9H | 2C,5H | 0 | 0 |
| VELVETLEAF | 2C,9G | 5G | 0 | 0 |
| NUTSEDGE | 9G | 4G | 0 | 0 |
| CRABGRASS | 2G | 0 | 0 | 0 |
| GIANT FOXTAIL | 2G | 0 | 0 | 0 |
| BARNYARDGRASS | 9H | 3G | 0 | 0 |
| CHEATGRASS | 9H | 3G | 0 | 0 |
| WILD OATS | 5G | 0 | 0 | 0 |
| WHEAT | 8G | 6G | 0 | 0 |
| CORN | 3C,9G | 5H | 0 | 0 |
| BARLEY | 2C,7G | 0 | 0 | 0 |
| SOYBEAN | 9H | 3C,8H | 0 | 0 |
| RICE | 9H | 10E | 0 | 0 |
| SORGHUM | 9H | 10H | 0 | 0 |
| SUGAR BEETS | 9C | 6H | 0 | 0 |
| COTTON | 9G | 8G | 0 | 0 |

| | CMPD 62 | | CMPD 63 | |
|---|---|---|---|---|
| RATE = KG/HA | 0.05 | 0.01 | 0.05 | 0.01 |
| POSTEMERGENCE | | | | |
| MORNINGGLORY | 0 | 0 | 4C,9G | 2H |
| COCKLEBUR | 0 | 0 | 10C | 4C,9H |
| VELVETLEAF | 2G | 0 | 4C,8H | 2C,6H |
| NUTSEDGE | 0 | 0 | 4C,9G | 8G |
| CRABGRASS | 0 | 0 | 6G | 2G |
| GIANT FOXTAIL | 0 | 0 | 3C,6G | 2G |
| BARNYARDGRASS | 0 | 0 | 9C | 9C |
| CHEATGRASS | 5G | 0 | 9C | 9G |
| WILD OATS | 0 | 0 | 9C | 3C,8G |
| WHEAT | 0 | 0 | 6C,9G | 9G |
| CORN | 6H | 0 | 10C | 5U,9C |
| BARLEY | 0 | 0 | 4C,9G | 6G |
| SOYBEAN | 0 | 0 | 5C,9G | 3C,8H |
| RICE | 8G | 0 | 10C | 9C |
| SORGHUM | 2C,5G | 0 | 10C | 4C,9G |
| SUGAR BEETS | 1H | 0 | 9C | 5C,9G |
| COTTON | 0 | 0 | 5C,9G | 2C,5G |
| PREEMERGENCE | | | | |
| MORNINGGLORY | 0 | 0 | 6G | 2G |
| COCKLEBUR | 2H | 0 | 2C,2H | 0 |
| VELVETLEAF | 0 | 0 | 1C,2H | 0 |
| NUTSEDGE | 0 | 0 | 0 | 0 |
| CRABGRASS | 0 | 0 | 2G | 0 |
| GIANT FOXTAIL | 0 | 0 | 1H | 0 |
| BARNYARDGRASS | 0 | 0 | 7H | 0 |
| CHEATGRASS | 0 | 0 | 7G | 0 |
| WILD OATS | 0 | 0 | 2C,8H | 0 |
| WHEAT | 0 | 0 | 9H | 6G |
| CORN | 0 | 0 | 3C,8H | 1H |
| BARLEY | 0 | 0 | 2G | 0 |
| SOYBEAN | 0 | 0 | 2C,4G | 6G |
| RICE | 0 | 0 | 10E | 8G |
| SORGHUM | 0 | 0 | 5C,9H | 3C,4H |
| SUGAR BEETS | 0 | 0 | 0 | 0 |
| COTTON | 0 | 0 | 8G | 0 |

| | CMPD 64 | | CMPD 65 | |
|---|---|---|---|---|
| RATE = KG/HA | 0.05 | 0.01 | 0.05 | 0.01 |
| POSTEMERGENCE | | | | |
| MORING GLORY | 3C,8G | 2C,4G | 0 | 0 |
| COCKLEBUR | 5C,9H | 3C,9G | 3C,9H | 2G |
| VELVETLEAF | 3C,9H | 3C,8H | 3C,7H | 0 |
| NUTSEDGE | 3C,9G | 3C,6G | 0 | 0 |
| CRABGRASS | 7G | 2G | 0 | 0 |
| GIANT FOXTAIL | 9C | 5G | 2C,5G | 3G |
| BARNYARDGRASS | 9C | 5C,9H | 0 | 0 |
| CHEATGRASS | 9C | 4C,9G | 2G | 3G |
| WILD OATS | 4C,9G | 8G | 2G | 0 |
| WHEAT | 3C,9G | 3C,9G | 2G | 2G |
| CORN | 9C | 4C,9G | 3C,7H | 3C,9H |
| BARLEY | 4C,9G | 9G | 3G | 0 |
| SOYBEAN | 5C,9G | 2C,5G | 3C,7H | 0 |
| RICE | 9C | 9C | 4C,9G | 8G |
| SORGHUM | 9C | 4C,9G | 4G | 2C,7G |
| SUGAR BEETS | 5C,9G | 3C,8G | 0 | 0 |
| COTTON | 4C,9G | 3C,7H | 2G | 0 |
| PREEMERGENCE | | | | |
| MORNINGGLORY | 2G | 0 | 0 | 0 |
| COCKLEBUR | 0 | 0 | — | 1H |
| VELVETLEAF | 2H | 0 | 0 | 0 |
| NUTSEDGE | 0 | 0 | 0 | 0 |
| CRABGRASS | 0 | 0 | 0 | 0 |
| GIANT FOXTAIL | 3G | 0 | 0 | 0 |
| BARNYARDGRASS | 7G | 0 | 0 | 0 |
| CHEATGRASS | 7G | 0 | 0 | 0 |
| WILD OATS | 2C,2G | 0 | 0 | 0 |
| WHEAT | 7G | 0 | 0 | 0 |
| CORN | 3C,8H | 1H | 0 | 0 |
| BARLEY | 0 | 0 | 0 | 0 |
| SOYBEAN | 2C,5G | 1H | 0 | 0 |
| RICE | 5C,9G | 4C,9G | 0 | 0 |
| SORGHUM | 4C,9H | 3C,8H | 0 | 0 |
| SUGAR BEETS | 0 | 1H | 2H | 0 |
| COTTON | 3G | 3G | 0 | 0 |

| | CMPD 66 | | CMPD 67 | |
|---|---|---|---|---|
| RATE = KG/HA | 0.05 | 0.01 | 0.05 | 0.01 |
| POSTEMERGENCE | | | | |
| MORNINGGLORY | 3C,8H | 3C,6G | 10C | 10C |
| COCKLEBUR | 9C | 2C,7G | 9C | 10C |
| VELVETLEAF | 9C | 3C,8G | 10C | 10C |
| NUTSEDGE | 2C,9G | 0 | 9C | 4C,9G |
| CRABGRASS | 3G | 0 | 5C,9G | 3C,8G |
| GIANT FOXTAIL | 5G | 0 | 9C | 3C,8H |
| BARNYARDGRASS | 3C,9H | 3C,7H | 10C | 9C |
| CHEATGRASS | 5C,9G | 3C,7G | 9C | 9C |
| WILD OATS | 4C,8G | 2C,5G | 9C | 5C,9G |
| WHEAT | 4C,9G | 2C,8G | 9C | 3C,9G |
| CORN | 5C,9G | 2C,9G | 10C | 9C |
| BARLEY | 3C,6G | 2G | 5C,9G | 3C,9G |

TABLE A-continued

| | | | | |
|---|---|---|---|---|
| SOYBEAN | 4C,9G | 3C,6G | 5C,9G | 4C,9G |
| RICE | 9C | 5C,9G | 9C | 6C,9G |
| SORGHUM | 3C,9G | 9G | 10C | 10C |
| SUGAR BEETS | 10C | 5C,9G | 10C | 10C |
| COTTON | — | — | — | — |
| PREEMERGENCE | | | | |
| MORNINGGLORY | 0 | 0 | 0 | 0 |
| COCKLEBUR | 0 | — | 5H | 0 |
| VELVETLEAF | 0 | 0 | 5H | 0 |
| NUTSEDGE | 0 | 0 | 3C,7G | 0 |
| CRABGRASS | 0 | 0 | 7G | 0 |
| GIANT FOXTAIL | 0 | 0 | 3G | 0 |
| BARNYARDGRASS | 0 | 0 | 8H | 0 |
| CHEATGRASS | 0 | 0 | 8G | 0 |
| WILD OATS | 0 | 0 | 8H | 0 |
| WHEAT | 0 | 0 | 9H | 0 |
| CORN | 0 | 0 | 3C,9H | 0 |
| BARLEY | 0 | 0 | 5G | 0 |
| SOYBEAN | 0 | 0 | 2C,4G | 0 |
| RICE | 0 | 0 | 8G | 0 |
| SORGHUM | 0 | 0 | 5C,9G | 0 |
| SUGAR BEETS | 0 | 0 | 0 | 0 |
| COTTON | 0 | 0 | 0 | 0 |

| | CMPD 68 | | CMPD 69 | |
|---|---|---|---|---|
| RATE = KG/HA | 0.05 | 0.01 | 0.05 | 0.01 |
| POSTEMERGENCE | | | | |
| MORNINGGLORY | 10C | 10C | 10C | 10C |
| COCKLEBUR | 10C | 10C | 10C | 10C |
| VELVETLEAF | 10C | 10C | 10C | 4C,9G |
| NUTSEDGE | 9C | 10C | 9C | 3C,8G |
| CRABGRASS | 5C,9G | 7G | 5G | 2G |
| GIANT FOXTAIL | 10C | 10C | 3C,5G | 3G |
| BARNYARDGRASS | 10C | 10C | 4C,9H | 3C,9H |
| CHEATGRASS | 10C | 9C | 5C,9G | 3C,5G |
| WILD OATS | 9C | 5C,9G | 3G | 0 |
| WHEAT | 10C | 6C,9G | 8G | 3G |
| CORN | 10C | 10C | 9C | 3C,9G |
| BARLEY | 9C | 3C,9G | 2C,5G | 0 |
| SOYBEAN | 9C | 9C | 3C,8G | 1H |
| RICE | 9C | 9C | 9C | 4C,9G |
| SORGHUM | 10C | 9C | 9C | 3C,9G |
| SUGAR BEETS | 10C | 10C | 10C | 10C |
| COTTON | — | — | — | — |
| PREEMERGENCE | | | | |
| MORNINGGLORY | 9H | 4G | 5G | 0 |
| COCKLEBUR | 8H | 0 | 2C | 0 |
| VELVETLEAF | 4C,9G | 4G | 7G | 0 |
| NUTSEDGE | 9G | 0 | 0 | 0 |
| CRABGRASS | 9G | 7G | 0 | 0 |
| GIANT FOXTAIL | 9G | 3G | 0 | 0 |
| BARNYARDGRASS | 9H | 5H | 0 | 0 |
| CHEATGRASS | 9G | 6G | 7G | 0 |
| WILD OATS | 3C,8G | 2C,5G | 2G | 0 |
| WHEAT | 8H | 8G | 5G | 0 |
| CORN | 9H | 3C,6G | 7G | 0 |
| BARLEY | 9G | 2C,7G | 0 | 0 |
| SOYBEAN | 3C,8G | 2C,2G | 2G | 0 |
| RICE | 3C,9G | 9H | 8G | 5G |
| SORGHUM | 9H | 3C,8H | 9G | 3C,6G |
| SUGAR BEETS | 7G | 0 | 0 | 0 |
| COTTON | 9G | 2G | 0 | 0 |

| | CMPD 70 | | CMPD 71 | |
|---|---|---|---|---|
| RATE = KG/HA | 0.05 | 0.01 | 0.05 | 0.01 |
| POSTEMERGENCE | | | | |
| MORNINGGLORY | 10C | 10C | 2H | 3G |
| COCKLEBUR | 10C | 9C | 10C | 9C |
| VELVETLEAF | 10C | 9C | 9C | 4C,9G |
| NUTSEDGE | 9C | 9C | 5C,9G | 5C,8G |
| CRABGRASS | 3C,8G | 6G | 5G | 0 |
| GIANT FOXTAIL | 9C | 3G | 2G | 3G |
| BARNYARDGRASS | 9C | 9C | 5C,9H | 3C,8G |
| CHEATGRASS | 10C | 9C | 9G | 3C,7G |
| WILD OATS | 5C,9G | 9C | 3C,7G | 2C |
| WHEAT | 10C | 9C | 9G | 3G |
| CORN | 10C | 10C | 9C | 9G |
| BARLEY | 6C,9G | 4C,9G | 2C,3G | 0 |
| SOYBEAN | 6C,9G | 5C,9G | 4C,9G | 4C,9G |
| RICE | 9C | 9C | 5C,9G | 3C,7G |
| SORGHUM | 9C | 9C | 5C,9G | 3C,8H |

| | | | | |
|---|---|---|---|---|
| SUGAR BEETS | 10C | 10C | 10C | 10C |
| COTTON | — | — | 4C,9G | 6G |
| PREEMERGENCE | | | | |
| MORNINGGLORY | 9G | 6G | 0 | 0 |
| COCKLEBUR | 3C,7H | 0 | 2G | 0 |
| VELVETLEAF | 3C,8H | 3H | 1H | 0 |
| NUTSEDGE | 10E | 0 | 0 | 0 |
| CRABGRASS | 5G | 3G | 3G | 0 |
| GIANT FOXTAIL | 2G | 0 | 2G | 0 |
| BARNYARDGRASS | 9H | 8H | 2H | 0 |
| CHEATGRASS | 9G | 6G | 3G | 0 |
| WILD OATS | 7G | 2C,4G | 0 | 0 |
| WHEAT | 9H | 7G | 0 | 0 |
| CORN | 3C,9H | 3C,8H | 3C,3G | 0 |
| BARLEY | 9G | 3C,4G | 0 | 0 |
| SOYBEAN | 3C,9H | 3C,4G | 2C | 0 |
| RICE | 10E | 3C,8H | 3G | 0 |
| SORGHUM | 6C,9H | 9H | 3C,7G | 0 |
| SUGAR BEETS | 3C,7H | 3H | 8G | 0 |
| COTTON | 8G | 3G | 0 | 0 |

| | CMPD 72 | | CMPD 73 | |
|---|---|---|---|---|
| RATE = KG/HA | 0.05 | 0.01 | 0.05 | 0.01 |
| POSTEMERGENCE | | | | |
| MORNINGGLORY | 10C | 4C,9G | 4C,9G | 2C,7G |
| COCKLEBUR | 10C | 10C | 10C | 10C |
| VELVETLEAF | 10C | 10C | 10C | 9C |
| NUTSEDGE | 3C,8G | 3C,9G | 9C | 3C,8G |
| CRABGRASS | 3C,8G | 7G | 3C,7G | 4G |
| GIANT FOXTAIL | 3C,6G | 3C,5G | 5C,9G | 9C |
| BARNYARDGRASS | 9C | 9C | 9C | 9C |
| CHEATGRASS | 5C,9G | 7G | 5C,9G | 4C,9G |
| WILD OATS | 4C,8G | 3C,6G | 3C,7G | 3C,7G |
| WHEAT | 9G | 4G | 4C,9G | 5G |
| CORN | 9C | 9C | 9C | 5C,9G |
| BARLEY | 3C,5G | 1C | 3G | 3C,5G |
| SOYBEAN | 9C | 4C,8G | 9C | 9C |
| RICE | 5C,9G | 8G | 5C,9G | 9C |
| SORGHUM | 5C,9G | 4C,9G | 4C,9G | 4C,9G |
| SUGAR BEETS | 9C | 10C | 9C | 9C |
| COTTON | 9C | 9C | 10C | 10C |
| PREEMERGENCE | | | | |
| MORNINGGLORY | 2H | 0 | 2G | 0 |
| COCKLEBUR | 0 | 0 | 5H | 0 |
| VELVETLEAF | 6G | 1H | 5H | 0 |
| NUTSEDGE | 9G | 0 | 7G | 0 |
| CRABGRASS | 6G | 0 | 3G | 0 |
| GIANT FOXTAIL | 3G | 0 | 4G | 0 |
| BARNYARDGRASS | 7H | 0 | 3C,9H | 0 |
| CHEATGRASS | 6G | 4G | 7G | 0 |
| WILD OATS | 2G | 0 | 2G | 0 |
| WHEAT | 4G | 0 | 3G | 0 |
| CORN | 3C,9G | 2C,2G | 3C,7G | 2C,2G |
| BARLEY | 2G | 0 | 0 | 0 |
| SOYBEAN | 3C,6H | 0 | 3C,4H | 1H |
| RICE | 8G | 5G | 9H | 3G |
| SORGHUM | 3C,9H | 3C,4G | 9H | 3C,6G |
| SUGAR BEETS | 4G | 2H | 8G | 2H |
| COTTON | 5G | 0 | 2G | 2G |

| | CMPD 74 | | CMPD 75 | |
|---|---|---|---|---|
| RATE = KG/HA | 0.05 | 0.01 | 0.05 | 0.01 |
| POSTEMERGENCE | | | | |
| MORNINGGLORY | 3C,7G | 3C,6G | 4C,9G | 3C,7G |
| COCKLEBUR | 10C | 10C | 10C | 9H |
| VELVETLEAF | 8G | 7H | 4C,9G | 3H |
| NUTSEDGE | 3C,5G | 3C,5G | 3C,6G | 2C,5G |
| CRABGRASS | 0 | 0 | 4G | 0 |
| GIANT FOXTAIL | 2C | 2C | 3G | 3C,3G |
| BARNYARDGRASS | 4C,9H | 3C,8H | 4C,9H | 4C,9H |
| CHEATGRASS | 5G | 2G | 2C,6G | 3C,5G |
| WILD OATS | 0 | 2C | 3C,8G | 2C,4G |
| WHEAT | 0 | 2C | 9G | 8G |
| CORN | 9C | 5C,9G | 9C | 5C,9G |
| BARLEY | 0 | 2G | 2G | 0 |
| SOYBEAN | 4H | 4H | 4C,9G | 5C,9G |
| RICE | 9G | 8G | 9C | 9C |
| SORGHUM | 3C,9H | 4C,8H | 9C | 3C,9H |
| SUGAR BEETS | 10C | 9C | 9C | 9C |
| COTTON | 5C,9G | 4G | 3C,7G | 2G |

TABLE A-continued

| PREEMERGENCE | | | | |
|---|---|---|---|---|
| MORNINGGLORY | 0 | 0 | 0 | 0 |
| COCKLEBUR | 0 | — | 2C,2H | 0 |
| VELVETLEAF | 0 | 0 | 2C,2H | 0 |
| NUTSEDGE | 0 | 0 | 2C | 0 |
| CRABGRASS | 0 | 0 | 3C,4G | 0 |
| GIANT FOXTAIL | 0 | 0 | 3G | 3G |
| BARNYARDGRASS | 0 | 0 | 3C,5G | 2G |
| CHEATGRASS | 0 | 0 | 7G | 2G |
| WILD OATS | 0 | 0 | 3C,5G | 0 |
| WHEAT | 0 | 0 | 7G | 3G |
| CORN | 3C,4G | 3G | 3C,8G | 3C,4G |
| BARLEY | 1C | 0 | 2G | 1C |
| SOYBEAN | 2H | 0 | 3C,3H | 0 |
| RICE | 5G | 2G | 5C,9H | 8H |
| SORGHUM | 4C,8G | 3C,3G | 4C,9H | 3C,8H |
| SUGAR BEETS | 2H | 0 | 5C,9G | 3H |
| COTTON | 0 | 0 | 2G | 0 |

| | CMPD 76 | | CMPD 77 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | — |
| COCKLEBUR | 2C,5G | 2G | 1H | — |
| VELVETLEAF | 5G | 0 | 3C,8H | — |
| NUTSEDGE | 0 | 0 | 3C,8G | — |
| CRABGRASS | 0 | 0 | 0 | — |
| GIANT FOXTAIL | 2G | 2G | 0 | — |
| BARNYARDGRASS | 0 | 0 | 0 | — |
| CHEATGRASS | 3G | 0 | 0 | — |
| WILD OATS | 2C,5G | 4G | 0 | — |
| WHEAT | 5G | 3C,8H | 0 | — |
| CORN | 4C,9H | 3C,8H | 0 | — |
| BARLEY | 4G | 0 | 0 | — |
| SOYBEAN | 4C,8G | 3C,8G | 3C,7H | — |
| RICE | 3C,9G | 9G | 3G | — |
| SORGHUM | 2C,5G | 3C,8G | 0 | — |
| SUGAR BEETS | 0 | 0 | 9C | — |
| COTTON | 3G | 0 | 3C,9G | — |
| PREEMERGENCE | | | | |
| MORNINGGLORY | 0 | 0 | 0 | — |
| COCKLEBUR | 2H | 0 | 0 | — |
| VELVETLEAF | 0 | 0 | 0 | — |
| NUTSEDGE | 0 | 0 | 0 | — |
| CRABGRASS | 0 | 0 | 0 | — |
| GIANT FOXTAIL | 0 | 0 | 0 | — |
| BARNYARDGRASS | 0 | 0 | 0 | — |
| CHEATGRASS | 0 | 0 | 0 | — |
| WILD OATS | 0 | 0 | 0 | — |
| WHEAT | 0 | 0 | 0 | — |
| CORN | 0 | 0 | 0 | — |
| BARLEY | 0 | 0 | 0 | — |
| SOYBEAN | 2H | 0 | 0 | — |
| RICE | 0 | 0 | 0 | — |
| SORGHUM | 5G | 0 | 0 | — |
| SUGAR BEETS | 0 | 0 | 0 | — |
| COTTON | 0 | 0 | 0 | — |

| | CMPD 78 | | CMPD 79 | |
|---|---|---|---|---|
| RATE = KG/HA | 0.05 | 0.01 | 0.05 | 0.01 |
| POSTEMERGENCE | | | | |
| MORNINGGLORY | 2C,5G | — | 9C | — |
| COCKLEBUR | 9C | — | 9C | — |
| VELVETLEAF | 10C | — | 9C | — |
| NUTSEDGE | 3C,8G | — | — | — |
| CRABGRASS | 0 | — | 2G | — |
| GIANT FOXTAIL | 2G | — | 5G | — |
| BARNYARDGRASS | 7H | — | 3C,8H | — |
| CHEATGRASS | 2G | — | 0 | — |
| WILD OATS | 2G | — | 0 | — |
| WHEAT | 2G | — | 0 | — |
| CORN | 2C,4H | — | 2C,7H | — |
| BARLEY | 2C | — | 0 | — |
| SOYBEAN | 5C,9G | — | 5C,9G | — |
| RICE | 4G | — | 3G | — |
| SORGHUM | 2C,4G | — | 9H | — |
| SUGAR BEETS | 9C | — | 9C | — |
| COTTON | 5C,9G | — | 9C | — |
| PREEMERGENCE | | | | |
| MORNINGGLORY | 0 | — | 0 | — |
| COCKLEBUR | 0 | — | — | — |
| VELVETLEAF | 3C,6H | — | 8G | — |
| NUTSEDGE | 3C,7G | — | 9G | — |
| CRABGRASS | 0 | — | 0 | — |
| GIANT FOXTAIL | 0 | — | 3G | — |
| BARNYARDGRASS | 3C,7H | — | 8H | — |
| CHEATGRASS | 0 | — | 2G | — |
| WILD OATS | 0 | — | 0 | — |
| WHEAT | 0 | — | 0 | — |
| CORN | 2C | — | 2C,3G | — |
| BARLEY | 0 | — | 0 | — |
| SOYBEAN | 3C,4H | — | 2C,2H | — |
| RICE | 7G | — | 5G | — |
| SORGHUM | 0 | — | 8H | — |
| SUGAR BEETS | 3C,8G | — | 6G | — |
| COTTON | 3G | — | 3G | — |

| | CMPD 80 | | CMPD 81 | |
|---|---|---|---|---|
| RATE = KG/HA | 0.05 | 0.01 | 0.05 | 0.01 |
| POSTEMERGENCE | | | | |
| MORNINGGLORY | 3C,8H | — | 2C,1H | — |
| COCKLEBUR | 9C | — | 6H | — |
| VELVETLEAF | 3C,8H | — | 2C,4G | — |
| NUTSEDGE | 0 | — | 0 | — |
| CRABGRASS | 0 | — | 0 | — |
| GIANT FOXTAIL | 0 | — | 5G | — |
| BARNYARDGRASS | 0 | — | 4H | — |
| CHEATGRASS | 0 | — | 2G | — |
| WILD OATS | 0 | — | 0 | — |
| WHEAT | 0 | — | 0 | — |
| CORN | 0 | — | 3C,9H | — |
| BARLEY | 0 | — | 0 | — |
| SOYBEAN | 5H | — | 3C,3H | — |
| RICE | 0 | — | 2C,5G | — |
| SORGHUM | 0 | — | 7G | — |
| SUGAR BEETS | 3C,8G | — | 3C,8H | — |
| COTTON | 7G | — | 6G | — |
| PREEMERGENCE | | | | |
| MORNINGGLORY | 0 | — | 0 | — |
| COCKLEBUR | 0 | — | — | — |
| VELVETLEAF | 0 | — | 1H | — |
| NUTSEDGE | 0 | — | 0 | — |
| CRABGRASS | 0 | — | 0 | — |
| GIANT FOXTAIL | 0 | — | 0 | — |
| BARNYARDGRASS | 0 | — | 0 | — |
| CHEATGRASS | 0 | — | 0 | — |
| WILD OATS | 0 | — | 0 | — |
| WHEAT | 0 | — | 0 | — |
| CORN | 0 | — | 1C | — |
| BARLEY | 0 | — | 0 | — |
| SOYBEAN | 0 | — | 0 | — |
| RICE | 2G | — | 3C,7G | — |
| SORGHUM | 2C | — | 3C,6G | — |
| SUGAR BEETS | 3H | — | 1H | — |
| COTTON | 0 | — | 0 | — |

| | CMPD 82 | | CMPD 83 | |
|---|---|---|---|---|
| RATE = KG/HA | 0.05 | 0.01 | 0.05 | 0.01 |
| POSTEMERGENCE | | | | |
| MORNINGGLORY | 0 | — | 0 | 0 |
| COCKLEBUR | 7G | — | 5G | 4G |
| VELVETLEAF | 7H | — | 3C,7H | 2C,7H |
| NUTSEDGE | 0 | — | 2C,8G | 0 |
| CRABGRASS | 0 | — | 0 | 0 |
| GIANT FOXTAIL | 3G | — | 3G | 0 |
| BARNYARDGRASS | 0 | — | 2C,7H | 4G |
| CHEATGRASS | 4G | — | 7G | 4G |
| WILD OATS | 0 | — | 3C,9G | 2C,3G |
| WHEAT | 0 | — | 2C,8G | 2C,3G |
| CORN | 2H | — | 9G | 2C,6H |
| BARLEY | 0 | — | 2C,7G | 4G |
| SOYBEAN | 2C,5H | — | 2C,8G | 2C,6H |
| RICE | 3C,8G | — | 9G | 2C,8G |
| SORGHUM | 2C,7G | — | 2C,9H | 2C,7G |
| SUGAR BEETS | 2C,5G | — | 2C,6G | 0 |
| COTTON | 6G | — | 2C,7H | 2C,5H |
| PREEMERGENCE | | | | |
| MORNINGGLORY | 0 | — | 0 | 0 |
| COCKLEBUR | 0 | — | 0 | 7H |
| VELVETLEAF | 0 | — | 0 | 0 |
| NUTSEDGE | 0 | — | 0 | 0 |

TABLE A-continued

|  | | | |
|---|---|---|---|
| CRABGRASS | 0 | — | — | 0 |
| GIANT FOXTAIL | 0 | — | 0 | 0 |
| BARNYARDGRASS | 0 | — | 0 | 0 |
| CHEATGRASS | 0 | — | 0 | 0 |
| WILD OATS | 0 | — | 0 | 0 |
| WHEAT | 0 | — | 0 | 0 |
| CORN | 0 | — | 0 | 0 |
| BARLEY | 0 | — | 0 | 0 |
| SOYBEAN | 0 | — | 0 | 0 |
| RICE | 5G | — | 0 | 0 |
| SORGHUM | 2C | — | 0 | 0 |
| SUGAR BEETS | 0 | — | 3H | 2H |
| COTTON | 0 | — | 0 | 0 |

|  | CMPD 84 | | CMPD 85 | |
|---|---|---|---|---|
| RATE = KG/HA | 0.05 | 0.01 | 0.05 | 0.01 |
| POSTEMERGENCE | | | | |
| MORNINGGLORY | 4C,9G | 2C,6G | 10C | 10C |
| COCKLEBUR | 10C | 2C,9H | 10C | 10C |
| VELVETLEAF | 10C | 10C | 10C | 10C |
| NUTSEDGE | 5C,9G | 3C,9G | 10C | 10C |
| CRABGRASS | 2C,9G | 5G | 2C,8G | 2C,7G |
| GIANT FOXTAIL | 3C,8G | 7G | 3C,7G | 2C,7G |
| BARNYARDGRASS | 9C | 9C | 9C | 9C |
| CHEATGRASS | 2C,7G | 2C,8G | 9C | 2C,8G |
| WILD OATS | 9C | 2C,9G | 2C,9G | 2C,9G |
| WHEAT | 9C | 10C | 2C,9G | 2C,8G |
| CORN | 2C,9G | 2C,9G | 2C,9G | 3C,9G |
| BARLEY | 4C,9G | 2C,7G | 9G | 6G |
| SOYBEAN | 3C,8G | 3C,7G | 3C,9G | 3C,9G |
| RICE | 3C,8G | 2C,9G | 5C,9G | 3C,9G |
| SORGHUM | 9C | 2C,9G | 9C | 4C,9G |
| SUGAR BEETS | 9C | 3C,7G | 10C | 10C |
| COTTON | 5C,9G | 2C,8G | 9C | 3C,9G |
| PREEMERGENCE | | | | |
| MORNINGGLORY | 5G | 3G | 1H,7G | 4G |
| COCKLEBUR | 2C,4H | 0 | 5G | 0 |
| VELVETLEAF | 2C,7H | 2C,4H | 2C,7H | 5H |
| NUTSEDGE | 2C,9G | 0 | 9G | 7G |
| CRABGRASS | 2C,7G | 0 | 2C,8G | 2G |
| GIANT FOXTAIL | 2C,7H | 0 | 2C,6H | 0 |
| BARNYARDGRASS | 2C,9H | 2C,7H | 3C,9H | 2C,9H |
| CHEATGRASS | 3C,9H | 2C,8H | 2C,9H | 5G |
| WILD OATS | 3C,8G | 3G | 2C,7G | 5G |
| WHEAT | 2C,9G | 0 | 6G | 2G |
| CORN | 3C,8H | 0 | 3C,9H | 0 |
| BARLEY | 6G | 5G | 7G | 4G |
| SOYBEAN | 3C,7H | 2C,5G | 2C,7H | 4G |
| RICE | 3C,9H | 2C,6G | 3C,9H | 2C,6H |
| SORGHUM | 10H | 3C,8H | 10H | 3C,9H |
| SUGAR BEETS | 3C,8G | 2C,3G | 9C | 2C,3G |
| COTTON | 2C,7G | 2C,3G | 7G | 6G |

|  | CMPD 86 | | CMPD 87 | |
|---|---|---|---|---|
| RATE = KG/HA | 0.05 | 0.01 | 0.05 | 0.01 |
| POSTEMERGENCE | | | | |
| MORNINGGLORY | 10C | 2C,5G | 0 | 0 |
| COCKLEBUR | 7H | 0 | 0 | 0 |
| VELVETLEAF | 3C,8H | 7G | 2C,5G | 0 |
| NUTSEDGE | 5C,9G | 2C,6G | 0 | 0 |
| CRABGRASS | 0 | 0 | 0 | 0 |
| GIANT FOXTAIL | 0 | 0 | 0 | 0 |
| BARNYARDGRASS | 3G | 0 | 3H | 0 |
| CHEATGRASS | 6G | 0 | 5G | 0 |
| WILD OATS | 3C,8G | 6G | 0 | 0 |
| WHEAT | 3G | 3G | 0 | 0 |
| CORN | 3C,7H | 3C,4H | 2C,5H | 0 |
| BARLEY | 0 | 0 | 0 | 0 |
| SOYBEAN | 2C,7H | 4H | 3C,7H | 0 |
| RICE | 2C,9G | 7G | 3C,9G | 7G |
| SORGHUM | 2C,9G | 3C,9G | 3C,8G | 3C,6H |
| SUGAR BEETS | 3C,7G | 3C,7G | 1C,3G | 0 |
| COTTON | 3C,8H | 2C,7H | 2C,7H | 0 |
| PREEMERGENCE | | | | |
| MORNINGGLORY | 5G | 0 | 0 | 0 |
| COCKLEBUR | 2G | 0 | 0 | — |
| VELVETLEAF | 4H | 0 | 0 | 2H |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 0 | 0 | 0 | 0 |
| RICE | 2C,7H | 0 | 2C | 0 |
| SORGHUM | 3C,9H | 0 | 3C | 0 |
| SUGAR BEETS | 2C,7G | 0 | 2H | 0 |
| COTTON | 2G | 0 | 0 | 0 |

|  | CMPD 88 | | CMPD 89 | |
|---|---|---|---|---|
| RATE = KG/HA | 0.05 | 0.01 | 0.05 | 0.01 |
| POSTEMERGENCE | | | | |
| MORNINGGLORY | 10C | 7G | 10C | 10C |
| COCKLEBUR | 10C | 3C,9G | 10C | 2C,8G |
| VELVETLEAF | 9C | 4C,9H | 6C,9H | 2C,8H |
| NUTSEDGE | 10C | 10C | 10C | 5C,9G |
| CRABGRASS | 4G | 0 | 4G | 0 |
| GIANT FOXTAIL | 3C,8G | 6G | 5G | 0 |
| BARNYARDGRASS | 5C,9G | 3C,7H | 3C,8H | 2C,6H |
| CHEATGRASS | 2C,9G | 2C,6G | 3C,7G | 5G |
| WILD OATS | 5C,9G | 3C,9G | 5C,9G | 3C,9G |
| WHEAT | 4C,9G | 2C,8G | 2C,7G | 2C,7G |
| CORN | 4C,9G | 3C,9G | 3C,8G | 2C,9H |
| BARLEY | 2C,8G | 5G | 7G | 0 |
| SOYBEAN | 3C,9G | 4C,8G | 5C,8H | 3C,8H |
| RICE | 6C,9G | 4C,9G | 5C,9G | 5C,9G |
| SORGHUM | 4C,9G | 4C,9G | 3C,9G | 3C,9G |
| SUGAR BEETS | 10C | 9C | 10C | 10C |
| COTTON | 4C,9G | 2C,7H | 9C | 3C,7H |
| PREEMERGENCE | | | | |
| MORNINGGLORY | 9H | 6G | 9H | 7H |
| COCKLEBUR | 8H | 0 | 3C,6G | 6G |
| VELVETLEAF | 2C,7H | 3C,4H | 2C,7H | 3C,6H |
| NUTSEDGE | 10E | 2C,9G | 2C,9G | 7G |
| CRABGRASS | 2C | 0 | 5G | 2G |
| GIANT FOXTAIL | 2C,6G | 0 | 2G | 0 |
| BARNYARDGRASS | 2C,7H | 4H | 0 | 0 |
| CHEATGRASS | 2C,8H | 2C,3G | 2C,3G | 3G |
| WILD OATS | 3C,8G | 2C,6G | 2C,6G | 0 |
| WHEAT | 3C,8G | 2G | 4G | 0 |
| CORN | 2C,9H | 2C,7G | 2C,8H | 0 |
| BARLEY | 8G | 5G | 4G | 0 |
| SOYBEAN | 4C,7G | 2C,5G | 4C,7H | 2C,6G |
| RICE | 4C,9H | 4C,8H | 4C,9H | 2C,7H |
| SORGHUM | 10H | 3C,9H | 3C,9H | 3C,6G |
| SUGAR BEETS | 9C | 4C,6G | 5C,7G | 2C,5G |
| COTTON | 3C,7G | 2C,4H | 2C,7H | 2C,4H |

|  | CMPD 90 | | CMPD 91 | |
|---|---|---|---|---|
| RATE = KG/HA | 0.05 | 0.01 | 0.05 | 0.01 |
| POSTEMERGENCE | | | | |
| MORNINGGLORY | 2C,7G | 2C,5G | 0 | 0 |
| COCKLEBUR | 3G | 3G | 3H | 0 |
| VELVETLEAF | 3G | 0 | 3G | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 2G | 2G | 2G | 0 |
| CHEATGRASS | 4G | 4G | 2G | 0 |
| WILD OATS | 0 | 0 | 0 | 0 |
| WHEAT | 0 | 0 | 0 | 0 |
| CORN | 2C,4H | 2C,3H | 0 | 0 |
| BARLEY | 0 | 0 | 0 | 0 |
| SOYBEAN | 2C,7H | 3H | 0 | 0 |
| RICE | 8G | 2C,7G | 2G | 0 |
| SORGHUM | 3C,8H | 3C,7H | 3G | 0 |
| SUGAR BEETS | 2C,6G | 0 | 5G | 0 |
| COTTON | 3C,6H | 2C | 3C,3G | 0 |
| PREEMERGENCE | | | | |
| MORNINGGLORY | 0 | 0 | 0 | 0 |
| COCKLEBUR | 0 | 0 | 0 | 0 |
| VELVETLEAF | 2H | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |

TABLE A-continued

| | CMPD 91 (cont.) | | | |
|---|---|---|---|---|
| CORN | 0 | 0 | 0 | 0 |
| BARLEY | 0 | 0 | 0 | 0 |
| SOYBEAN | 0 | 0 | 0 | 0 |
| RICE | 0 | 0 | 0 | 0 |
| SORGHUM | 0 | 0 | 0 | 0 |
| SUGAR BEETS | 4H | 0 | 0 | 0 |
| COTTON | 0 | — | 0 | 0 |

| | CMPD 92 | | CMPD 93 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | 0 |
| COCKLEBUR | 10C | 2C,9G | 9C | 8H |
| VELVETLEAF | 9C | 3C,8H | 5C,9G | 3C,7H |
| NUTSEDGE | 8G | 3C,5G | 3C,8G | 8G |
| CRABGRASS | 3G | 0 | 0 | 0 |
| GIANT FOXTAIL | 4G | 0 | 3G | 0 |
| BARNYARDGRASS | 3C,8H | 5H | 3C,7H | 3C,5H |
| CHEATGRASS | 3C,9G | 4G | 3C,9G | 3G |
| WILD OATS | 2C,2G | 0 | 4G | 0 |
| WHEAT | 4G | 0 | 2G | 0 |
| CORN | 4C,9G | 3C,9H | 9H | 3C,8G |
| BARLEY | 0 | 0 | 5G | 0 |
| SOYBEAN | 5C,9G | 3C,7H | 4C,9G | 4C,8G |
| RICE | 5C,9G | 5G | 4C,9G | 3G |
| SORGHUM | 3C,9G | 3C,5G | 4C,9H | 4C,8G |
| SUGAR BEETS | 9C | 3C,8H | 10C | 5C,9G |
| COTTON | 9H | 4C,7G | 3C,9G | 4C,9H |
| PREEMERGENCE | | | | |
| MORNINGGLORY | 0 | 0 | 0 | 0 |
| COCKLEBUR | 0 | 0 | 0 | 0 |
| VELVETLEAF | 3C,3H | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 2C,2G | 0 | 2C | 0 |
| BARLEY | 0 | 0 | 0 | 0 |
| SOYBEAN | 2C | 0 | 2C | 0 |
| RICE | 0 | 0 | 2C,3G | 0 |
| SORGHUM | 2C,7G | 3C,4G | 3C,5G | 0 |
| SUGAR BEETS | 5H | 3H | 2H | 0 |
| COTTON | 0 | 0 | 0 | 0 |

| | CMPD 94 | | CMPD 95 | |
|---|---|---|---|---|
| RATE = KG/HA | 0.05 | 0.01 | 0.05 | 0.01 |
| POSTEMERGENCE | | | | |
| MORNINGGLORY | 1H | 0 | 0 | 0 |
| COCKLEBUR | 9H | 3G | 8H | 2H |
| VELVETLEAF | 5G | 2H | 0 | 0 |
| NUTSEDGE | 0 | 0 | 0 | 0 |
| CRABGRASS | 0 | 0 | 0 | 0 |
| GIANT FOXTAIL | 0 | 0 | 7G | 0 |
| BARNYARDGRASS | 0 | 0 | 7H | 2H |
| CHEATGRASS | 0 | 0 | 0 | 0 |
| WILD OATS | 0 | 0 | 0 | 0 |
| WHEAT | 0 | 0 | 0 | 0 |
| CORN | 2G | 0 | 3C,9G | 2C,5H |
| BARLEY | 0 | 0 | 0 | 0 |
| SOYBEAN | 0 | 0 | 3H | 0 |
| RICE | 2G | 2G | 5C,9G | 3C,6G |
| SORGHUM | 3C,5G | 2G | 3C,9G | 2C,5G |
| SUGAR BEETS | 5G | 2G | 3C,6G | 0 |
| COTTON | 3C,7G | 3C,5G | 3C,7G | 2G |
| PREEMERGENCE | | | | |
| MORNINGGLORY | 0 | 0 | 0 | 0 |
| COCKLEBUR | 0 | — | 0 | 0 |
| VELVETLEAF | 0 | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 2G | 0 | 0 | 0 |
| RICE | 0 | 0 | 2C,5G | 0 |
| SORGHUM | 2C,5G | 0 | 3C,5G | 0 |
| SUGAR BEETS | 2G | 0 | 0 | 0 |
| COTTON | 0 | 0 | 0 | 0 |

| | CMPD 96 | | CMPD 97 | |
|---|---|---|---|---|
| RATE = KG/HA | 0.05 | 0.01 | 0.05 | 0.01 |
| POSTEMERGENCE | | | | |
| MORNINGGLORY | 0 | 0 | 0 | 0 |
| COCKLEBUR | 3C,8H | 0 | 0 | 0 |
| VELVETLEAF | 1C | 0 | 0 | 0 |
| NUTSEDGE | 0 | 0 | 0 | 0 |
| CRABGRASS | 0 | 0 | 0 | 0 |
| GIANT FOXTAIL | 2G | 0 | 0 | 0 |
| BARNYARDGRASS | 4G | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 3C,7H | 0 | 0 | 0 |
| BARLEY | 0 | 0 | 0 | 0 |
| SOYBEAN | 2C,2H | 0 | 0 | 0 |
| RICE | 4C,9G | 0 | 0 | 0 |
| SORGHUM | 3C,5G | 0 | 0 | 0 |
| SUGAR BEETS | 2C | 0 | 0 | 0 |
| COTTON | 3C,6H | 0 | 0 | 0 |
| PREEMERGENCE | | | | |
| MORNINGGLORY | 0 | 0 | 0 | 0 |
| COCKLEBUR | 0 | 2H | 0 | 0 |
| VELVETLEAF | 0 | 0 | 0 | 0 |
| NUTSEDGE | 0 | 0 | 10E | 10E |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 0 | 0 |
| SOYBEAN | 7G | 0 | 0 | 0 |
| RICE | 2G | 0 | 0 | 0 |
| SORGHUM | 3C,4G | 0 | 0 | 0 |
| SUGAR BEETS | 5G | 3G | 0 | 0 |
| COTTON | 0 | 0 | 0 | 0 |

| | CMPD 98 | | CMPD 99 | |
|---|---|---|---|---|
| RATE = KG/HA | 0.05 | 0.01 | 0.05 | 0.01 |
| POSTEMERGENCE | | | | |
| MORNINGGLORY | 0 | 0 | 2C | 0 |
| COCKLEBUR | 5H | 0 | 5C,9G | 7H |
| VELVETLEAF | 2C | 0 | 5C,9G | 3G |
| NUTSEDGE | — | 0 | 0 | 0 |
| CRABGRASS | 0 | 0 | 0 | 0 |
| GIANT FOXTAIL | 0 | 0 | 1C | 0 |
| BARNYARDGRASS | 0 | 0 | 3C,6H | 0 |
| CHEATGRASS | 0 | 0 | 4C,8G | 6G |
| WILD OATS | 0 | 0 | 4G | 0 |
| WHEAT | 0 | 0 | 4G | 0 |
| CORN | 2C,3G | 0 | 9H | 3C,8H |
| BARLEY | 0 | 0 | 2G | 0 |
| SOYBEAN | 0 | 0 | 4C,9G | 4C,9G |
| RICE | 3C,6G | 0 | 3C,9G | 4G |
| SORGHUM | 3C,7G | 0 | 3C,9G | 5G |
| SUGAR BEETS | 0 | 0 | 9C | 4G |
| COTTON | 0 | 0 | 3C,9H | 3G |
| PREEMERGENCE | | | | |
| MORNINGGLORY | 0 | 0 | 0 | 0 |
| COCKLEBUR | 0 | 0 | 0 | 0 |
| VELVETLEAF | 0 | 0 | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 2C | 0 |
| BARLEY | 0 | 0 | 0 | 0 |
| SOYBEAN | 0 | 0 | 2C | 0 |
| RICE | 0 | 0 | 7G | 0 |
| SORGHUM | 0 | 0 | 3C,7H | 0 |
| SUGAR BEETS | 0 | 0 | 0 | 0 |

TABLE A-continued

| | | | | |
|---|---|---|---|---|
| COTTON | 0 | 0 | 0 | 0 |

| | CMPD 100 | | CMPD 101 | |
|---|---|---|---|---|
| RATE = KG/HA | 0.05 | 0.01 | 0.05 | 0.01 |
| POSTEMERGENCE | | | | |
| MORNINGGLORY | 10C | 10C | 10C | 10C |
| COCKLEBUR | 10C | 9C | 10C | 10C |
| VELVETLEAF | 10C | 9C | 10C | 5C,9G |
| NUTSEDGE | 5C,9G | 4C,9G | 10C | 9C |
| CRABGRASS | 3C,9H | 7G | 4C,9G | 2C,8G |
| GIANT FOXTAIL | 4C,9H | 3C,7G | 4C,9G | 3C,7G |
| BARNYARDGRASS | 6C,9G | 9C | 9C | 9C |
| CHEATGRASS | 9C | 9C | 9C | 9C |
| WILD OATS | 9C | 3C,8H | 3C,9G | 4C,9G |
| WHEAT | 9C | 3C,9G | 3C,9G | 9C |
| CORN | 9C | 5C,9G | 9C | 3C,9G |
| BARLEY | 3C,9G | 7G | 3C,9G | 6G |
| SOYBEAN | 9C | 9C | 9C | 9C |
| RICE | 9C | 6C,9G | 9C | 9C |
| SORGHUM | 5C,9G | 4C,9H | 9C | 9C |
| SUGAR BEETS | 10C | 9C | 10C | 10C |
| COTTON | 10C | 4C,9G | 10C | 10C |
| PREEMERGENCE | | | | |
| MORNINGGLORY | 5G | 3G | 9H | 3G |
| COCKLEBUR | 8H | 2H | 9H | 8H |
| VELVETLEAF | 9H | 2H | 9G | 7G |
| NUTSEDGE | 8G | 0 | 10E | 9G |
| CRABGRASS | 5G | 3G | 9H | 2G |
| GIANT FOXTAIL | 3C,9H | 2G | 9H | 4G |
| BARNYARDGRASS | 9H | 4G | 9H | 8H |
| CHEATGRASS | 9G | 8G | 9G | 8G |
| WILD OATS | 3C,7G | 2C,5G | 9G | 3G |
| WHEAT | 9H | 2C,8G | 9H | 3C,7G |
| CORN | 3C,9H | 9H | 9H | 9H |
| BARLEY | 9G | 3C,7G | 9G | 2G |
| SOYBEAN | 9H | 3C,7H | 9H | 3C,7H |
| RICE | 9H | 4C,9H | 9H | 3C,9H |
| SORGHUM | 9H | 4C,9H | 10H | 9G |
| SUGAR BEETS | 3C,9G | 7H | 9G | 8G |
| COTTON | 3C,8H | 0 | 9G | 7H |

| | CMPD 102 | | CMPD 103 | |
|---|---|---|---|---|
| RATE = KG/HA | 0.05 | 0.01 | 0.05 | 0.01 |
| POSTEMERGENCE | | | | |
| MORNINGGLORY | 9C | 2C,6G | 0 | 0 |
| COCKLEBUR | 10C | 4C,9G | 0 | 0 |
| VELVETLEAF | 9C | 4C,8H | 0 | 0 |
| NUTSEDGE | 5C,9G | 2G | 0 | 0 |
| CRABGRASS | 3G | 0 | 0 | 0 |
| GIANT FOXTAIL | 2G | 0 | 0 | 0 |
| BARNYARDGRASS | 8H | 7H | 0 | 0 |
| CHEATGRASS | 8G | 4G | 5G | 0 |
| WILD OATS | 3G | 0 | 0 | 0 |
| WHEAT | 5G | 0 | 0 | 0 |
| CORN | 9H | 3C,9H | 2H | 0 |
| BARLEY | 0 | 0 | 0 | 0 |
| SOYBEAN | 3C,9G | 5H | 2H | 0 |
| RICE | 5C,9G | 8G | 3C,8G | 0 |
| SORGHUM | 4C,9H | 3C,9H | 5G | 0 |
| SUGAR BEETS | 9C | 9C | 0 | 0 |
| COTTON | 9C | 7G | 0 | 0 |
| PREEMERGENCE | | | | |
| MORNINGGLORY | 4H | 0 | 0 | 0 |
| COCKLEBUR | 1H | 1H | 0 | 0 |
| VELVETLEAF | 4H | 1H | 0 | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 8H | 0 | 0 | 0 |
| CHEATGRASS | 6G | 5G | 0 | 0 |
| WILD OATS | 3G | 0 | 0 | 0 |
| WHEAT | 5G | 0 | 0 | 0 |
| CORN | 3C,9G | 0 | 0 | 0 |
| BARLEY | 3G | 0 | 0 | 0 |
| SOYBEAN | 3C,6G | 2G | 0 | 0 |
| RICE | 9H | 9H | 0 | 0 |
| SORGHUM | 9H | 3C,8H | 0 | 0 |
| SUGAR BEETS | 8H | 3H | 0 | 0 |
| COTTON | 4G | 0 | 0 | 0 |

| | CMPD 104 | | CMPD 105 | |
|---|---|---|---|---|
| RATE = KG/HA | 0.05 | 0.01 | 0.05 | 0.01 |
| POSTEMERGENCE | | | | |
| MORNINGGLORY | 5C,9G | 3C,8H | 9C | 3C,8H |
| COCKLEBUR | 9C | 3C,9H | 5C,9G | 3C,7H |
| VELVETLEAF | 5C,9H | 3C,7H | 5C,9H | 2C,4G |
| NUTSEDGE | 3C,7G | 4G | 4C,8G | 0 |
| CRABGRASS | 5C,9G | 3C,7G | 5C,9G | 3G |
| GIANT FOXTAIL | 9C | 3C,7H | 5C,9G | 3G |
| BARNYARDGRASS | 10C | 9C | 9C | 4C,9H |
| CHEATGRASS | 9C | 9C | 9C | 6C,9G |
| WILD OATS | 6C,9G | 5C,9G | 9C | 6C,9G |
| WHEAT | 9C | 5C,9G | 10C | 6C,9G |
| CORN | 9C | 5C,9G | 5C,9G | 4C,9G |
| BARLEY | 4C,9G | 5C,9G | 5C,9G | 2C,8G |
| SOYBEAN | 5C,9G | 4C,9G | 5C,9G | 4C,8G |
| RICE | 9C | 9C | 9C | 5C,9G |
| SORGHUM | 10C | 9C | 9C | 5C,9G |
| SUGAR BEETS | 10C | 9C | 9C | 9C |
| COTTON | 7G | 4C,9H | 4C,9H | 4C,8H |
| PREEMERGENCE | | | | |
| MORNINGGLORY | 7G | 1H | 0 | 0 |
| COCKLEBUR | — | 2C | 1C | 0 |
| VELVETLEAF | 6G | 0 | 0 | 0 |
| NUTSEDGE | 4G | 0 | 5G | 0 |
| CRABGRASS | 3C,5G | 0 | 0 | 0 |
| GIANT FOXTAIL | 3C,5G | 0 | 0 | 0 |
| BARNYARDGRASS | 9H | 3G | 7H | 0 |
| CHEATGRASS | 3C,9H | 9G | 9G | 7G |
| WILD OATS | 3C,8H | 3C,6G | 3C,7G | 2G |
| WHEAT | 9H | 9H | 8H | 4G |
| CORN | 3C,9H | 2C,9G | 2C,9G | 3C,7H |
| BARLEY | 9H | 3C,8G | 2C,9G | 3C,8G |
| SOYBEAN | 3C,8H | 3C,4G | 3C,6G | 2C,4G |
| RICE | 10E | 5C,9H | 9H | 9H |
| SORGHUM | 4C,9H | 5C,9H | 9H | 3C,9H |
| SUGAR BEETS | 9G | 7G | 9G | 2H |
| COTTON | 5G | 1C | 0 | 0 |

| | CMPD 106 | | CMPD 107 | |
|---|---|---|---|---|
| RATE = KG/HA | 0.05 | 0.01 | 0.05 | 0.01 |
| POSTEMERGENCE | | | | |
| MORNINGGLORY | 2C,4H | 0 | 9C | 3C,6H |
| COCKLEBUR | 0 | 0 | 10C | 5C,9H |
| VELVETLEAF | 5H | 0 | 6C,9G | 3C,8H |
| NUTSEDGE | 0 | 0 | 2C,8G | 3C,6G |
| CRABGRASS | 0 | 0 | 6G | 0 |
| GIANT FOXTAIL | 2G | 0 | 3C,8G | 4G |
| BARNYARDGRASS | 5H | 0 | 4C,9H | 3C,8H |
| CHEATGRASS | 4C,9G | 5G | 2C,8G | 3C,6G |
| WILD OATS | 5G | 0 | 3G | 0 |
| WHEAT | 2G | 0 | 7G | 0 |
| CORN | 9G | 4H | 3C,9G | 3C,9G |
| BARLEY | 0 | 0 | 1C | 0 |
| SOYBEAN | 4C,8G | 3C,4G | 4C,9G | 3C,8H |
| RICE | 4C,8G | 2G | 3C,9G | 3C,7G |
| SORGHUM | 3C,9H | 3C,8H | 4C,9G | 3C,9H |
| SUGAR BEETS | 2H | 0 | 4C,9G | 3C,5G |
| COTTON | 1C | 0 | 9C | 5C,9G |
| PREEMERGENCE | | | | |
| MORNINGGLORY | 0 | 0 | 3C,5G | 0 |
| COCKLEBUR | 0 | 0 | — | — |
| VELVETLEAF | 0 | 0 | 2H | 0 |
| NUTSEDGE | 0 | 0 | 0 | 0 |
| CRABGRASS | 0 | 0 | 0 | 0 |
| GIANT FOXTAIL | 0 | 0 | 0 | 0 |
| BARNYARDGRASS | 0 | 0 | 0 | 0 |
| CHEATGRASS | 0 | 0 | 0 | 0 |
| WILD OATS | 0 | 0 | 0 | 0 |
| WHEAT | 0 | 0 | 0 | 0 |
| CORN | 0 | 0 | 0 | 0 |
| BARLEY | 0 | 0 | 1C | 0 |
| SOYBEAN | 0 | 0 | 2C | 0 |
| RICE | 0 | 0 | 0 | 0 |
| SORGHUM | 3C,5G | 0 | 0 | 0 |
| SUGAR BEETS | 0 | 0 | 3G | 0 |
| COTTON | 0 | 0 | 0 | 0 |

| | CMPD 108 | | CMPD 109 | |
|---|---|---|---|---|
| RATE = KG/HA | 0.05 | 0.01 | 0.05 | 0.01 |
| POSTEMERGENCE | | | | |

TABLE A-continued

| | | | | |
|---|---|---|---|---|
| MORNINGGLORY | 4C,9G | 3C,8H | 9C | 4C,9H |
| COCKLEBUR | 10C | 9C | 10C | 10C |
| VELVETLEAF | 5C,9G | 3C,8H | 10C | 3C,7H |
| NUTSEDGE | 3C,9G | 8G | 9C | 3C,8G |
| CRABGRASS | 3G | 2G | 3C,8G | 3C,3G |
| GIANT FOXTAIL | 3C,7H | 2C,4G | 4C,9G | 4C,8G |
| BARNYARDGRASS | 4C,9H | 3C,8H | 9C | 5C,9H |
| CHEATGRASS | 7G | 6G | 6C,9G | 2C,8G |
| WILD OATS | 2G | 0 | 3C,5G | 3G |
| WHEAT | 2G | 0 | 2C,9G | 4G |
| CORN | 5C,9G | 9G | 9C | 3C,9G |
| BARLEY | 1C | 0 | 0 | 0 |
| SOYBEAN | 4C,9G | 3C,9G | 4C,9G | 4C,9G |
| RICE | 4C,9G | 7G | 9C | 2C,9G |
| SORGHUM | 4C,9G | 2C,9G | 9C | 5C,9G |
| SUGAR BEETS | 5C,9G | 2G | 9C | 4C,8H |
| COTTON | 2C,9G | 9G | 9G | 4C,9H |
| PREEMERGENCE | | | | |
| MORNINGGLORY | 0 | 0 | 3C,5G | 0 |
| COCKLEBUR | 2C,3H | 0 | 2C,3H | 0 |
| VELVETLEAF | 1H | 0 | 2C,2H | 0 |
| NUTSEDGE | 0 | 0 | 10E | 0 |
| CRABGRASS | 0 | 0 | 3G | 0 |
| GIANT FOXTAIL | 0 | 0 | 3C,7G | 0 |
| BARNYARDGRASS | 0 | 0 | 3C,8G | 2H |
| CHEATGRASS | 0 | 0 | 9G | 0 |
| WILD OATS | 0 | 0 | 2G | 0 |
| WHEAT | 0 | 0 | 8G | 0 |
| CORN | 0 | 0 | 3C,4G | 0 |
| BARLEY | 0 | 0 | 4G | 0 |
| SOYBEAN | 4G | 0 | 3C,6H | 2C,2H |
| RICE | 0 | 0 | 3C,7G | 0 |
| SORGHUM | 0 | 0 | 3C,8H | 2G |
| SUGAR BEETS | 7G | 0 | 5C,9G | 2H |
| COTTON | 0 | 0 | 2C,3G | 4G |

| | CMPD 110 | | CMPD 111 | |
|---|---|---|---|---|
| RATE = KG/HA | 0.01 | 0.05 | 0.01 | 0.05 |
| POSTEMERGENCE | | | | |
| BARLEY | 5C,8G | 10C | 3C,7G | 6C,9G |
| BARNYARDGRASS | 0 | 3C,6H | 0 | 3C,6H |
| CHEATGRASS | 5C,8G | 9C | 4C,8G | 5C,9G |
| COCKLEBUR | 9C | 10C | 6H | 10C |
| CORN | 6C,9G | 10C | 5C,9G | 9C |
| COTTON | 2C,4G | 9C | 2C,4G | 9C |
| CRABGRASS | 0 | 8G | 2G | 7G |
| GIANT FOXTAIL | 2C,5G | 9C | 3C,5G | 5C,9G |
| MORNINGGLORY | 3H | 2C,7H | 3C,4H | 6C,9H |
| NUTSEDGE | 2G | 9C | 4C | 4C,8G |
| RICE | 5C,9G | 5C,9G | 5C,9G | 10C |
| SORGHUM | 3C,7H | 3C,9G | 3C,7H | 4C,9H |
| SOYBEAN | 6C,9G | 5C,9G | 4C,8G | 6C,9G |
| SUGAR BEETS | 3G | 7G | 2G | 3G |
| VEVETLEAF | 2C,6H | 3C,8H | 2C,6H | 4C,9H |
| WHEAT | 9G | 5C,9G | 4C,6G | 5C,9G |
| WILD OATS | 9G | 5C,9G | 4C,5G | 9C |
| PREEMERGENCE | | | | |
| BARLEY | 0 | 4G | 0 | 2G |
| BARNYARDGRASS | 3G | 5G | 4G | 2C,4G |
| CHEATGRASS | 2G | 8G | 4G | 3G |
| COCKLEBUR | 2G | 3H | 3G | 7G |
| CORN | 0 | 3C | 0 | 0 |
| COTTON | 0 | 3G | 6G | 3G |
| CRABGRASS | 2G | 5G | 2G | 3C,4G |
| GIANT FOXTAIL | 2G | 7H | 2G | 3C,6H |
| MORNINGGLORY | 2G | 5H | 3C,4G | 3G |
| NUTSEDGE | 0 | 2G | 2G | 2C |
| RICE | 2C | 10H | 2G | 3G |
| SORGHUM | 0 | 3C,6H | 0 | 3G |
| SOYBEAN | 2C,3G | 3C,5G | 3G | 2C,3G |
| SUGAR BEETS | 0 | 5G | 4H | 4G |
| VELVETLEAF | 2C,3G | 2G | 4C | 3C |
| WHEAT | 2G | 2C,6G | 3G | 4G |
| WILD OATS | 0 | 4G | 6H | 2C,4G |

| | CMPD 112 | | CMPD 113 | |
|---|---|---|---|---|
| RATE = KG/HA | 0.05 | 0.01 | 0.05 | 0.01 |
| POSTEMERGENCE | | | | |
| BARLEY | 2C,4G | 4C,8G | 0 | 0 |
| BARNYARDGRASS | 2C | 3C,8H | 0 | 0 |
| CHEATGRASS | 3C,7G | 8G | 0 | 0 |
| COCKLEBUR | 4G | 9C | 0 | 0 |
| CORN | 3C,4G | 4C,8G | 0 | 0 |
| COTTON | 2G | 2C,3G | 0 | 0 |
| CRABGRASS | 0 | 2G | 0 | 0 |
| GIANT FOXTAIL | 0 | 3G | 0 | 0 |
| MORNINGGLORY | 2C,3H | 2C,5H | 0 | 0 |
| NUTSEDGE | 0 | 6C | 0 | 0 |
| RICE | 3C,7G | 5C,9G | 0 | 0 |
| SORGHUM | 4C,7H | 4C,9H | 0 | 0 |
| SOYBEAN | 5C,8G | 5C,8G | 0 | 0 |
| SUGAR BEETS | 5G | 8H | 0 | 0 |
| VELVETLEAF | 0 | 3C,7H | 0 | 0 |
| WHEAT | 5G | 3C,9G | 0 | 0 |
| WILD OATS | 3C,6G | 3C,9G | 0 | 0 |
| PREEMERGENCE | | | | |
| BARLEY | 0 | 4G | 0 | 0 |
| BARNYARDGRASS | 0 | 4G | 0 | 0 |
| CHEATGRASS | 0 | 7H | 0 | 0 |
| COCKLEBUR | — | 3G | 0 | — |
| CORN | 0 | 4G | 0 | 0 |
| COTTON | 3C | 6G | 0 | 0 |
| CRABGRASS | 0 | 7H | 0 | 0 |
| GIANT FOXTAIL | 2G | 6G | 0 | — |
| MORNINGGLORY | 2G | 6H | 0 | 0 |
| NUTSEDGE | 0 | 6G | 0 | 0 |
| RICE | 3C | 3C,5G | 0 | 0 |
| SORGHUM | 2G | 3C,5H | 0 | 0 |
| SOYBEAN | 2G | 2C,4G | 0 | 0 |
| SUGAR BEETS | 0 | 6G | 0 | 0 |
| VELVETLEAF | 2C | 2C | 0 | 0 |
| WHEAT | 0 | 5H | 0 | 0 |
| WILD OATS | 0 | 6H | 0 | 0 |

| | CMPD 114 | | CMPD 115 | |
|---|---|---|---|---|
| RATE = KG/HA | 0.01 | 0.05 | 0.01 | 0.05 |
| POSTEMERGENCE | | | | |
| BARLEY | 3C,9G | 9C | 0 | 0 |
| BARNYARDGRASS | 3C,5H | 9H | 0 | 0 |
| CHEATGRASS | 9G | 9G | 0 | 0 |
| COCKLEBUR | 2G | 3C,9G | 0 | 0 |
| CORN | 3C,9H | 5U,9G | 0 | 0 |
| COTTON | 2G | 3C,6G | 0 | 0 |
| CRABGRASS | 6G | 7G | 0 | 0 |
| GIANT FOXTAIL | 4G | 3C,8G | 0 | 0 |
| MORNINGGLORY | 3C,6G | 4C,8G | 0 | 0 |
| NUTSEDGE | 0 | 8G | 0 | 0 |
| RICE | 7G | 6C,9G | 0 | 0 |
| SORGHUM | 3G | 4C,8H | 0 | 0 |
| SOYBEAN | 4C,8G | 5C,9G | 0 | 0 |
| SUGAR BEETS | 3H | 3C,7H | 0 | 0 |
| VELVETLEAF | 3C,6G | 3C,7G | 0 | 0 |
| WHEAT | 5G | 3C,8G | 0 | 0 |
| WILD OATS | 4G | 5C,9G | 0 | 0 |
| PREEMERGENCE | | | | |
| BARLEY | 2G | 0 | 0 | 0 |
| BARNYARDGRASS | 5G | 2G | 0 | 0 |
| CHEATGRASS | 6G | 2G | 0 | 0 |
| COCKLEBUR | 0 | 0 | 0 | 0 |
| CORN | 0 | 0 | 0 | 0 |
| COTTON | 0 | 0 | 0 | 0 |
| CRABGRASS | 0 | 3G | 0 | 0 |
| GIANT FOXTAIL | 0 | 5G | 0 | 0 |
| MORNINGGLORY | 0 | 0 | 0 | 0 |
| NUTSEDGE | 10E | 0 | 0 | 0 |
| RICE | 3G | 0 | 0 | 0 |
| SORGHUM | 2G | 0 | 0 | 0 |
| SOYBEAN | 0 | 0 | 0 | 0 |
| SUGAR BEETS | 0 | 0 | 0 | 0 |
| VELVETLEAF | 0 | 0 | 0 | 0 |
| WHEAT | 0 | 0 | 0 | 0 |
| WILD OATS | 0 | 0 | 0 | 0 |

| | CMPD 116 | | CMPD 117 | |
|---|---|---|---|---|
| RATE = KG/HA | 0.01 | 0.05 | 0.01 | 0.05 |
| POSTEMERGENCE | | | | |
| BARLEY | 0 | 0 | — | 0 |
| BARNYARDGRASS | 0 | 0 | 0 | 0 |
| CHEATGRASS | 0 | 0 | 7G | 3C,7G |
| COCKLEBUR | 0 | 0 | 4G | 2G |
| CORN | 0 | 0 | 3C,9G | 3C,9G |
| COTTON | 0 | 0 | 1C | 3C,6G |

TABLE A-continued

| | | | | |
|---|---|---|---|---|
| CRABGRASS | 0 | 0 | 5G | 4G |
| GIANT FOXTAIL | 0 | 0 | 4G | 5G |
| MORNINGGLORY | 0 | 0 | 5G | 4G |
| NUTSEDGE | 0 | 0 | 2G | 0 |
| RICE | 0 | 0 | 4C,9G | 3C,8G |
| SORGHUM | 0 | 0 | 4C,8H | 4C,9G |
| SOYBEAN | 0 | 0 | 4C,8G | 5C,9G |
| SUGAR BEETS | 0 | 0 | 3C,7G | 0 |
| VELVETLEAF | 0 | 0 | 0 | 3C,6G |
| WHEAT | 0 | 0 | 8G | 9G |
| WILD OATS | 0 | 0 | 4C,8G | 2C,6G |
| PREEMERGENCE | | | | |
| BARLEY | 0 | 0 | 0 | 0 |
| BARNYARDGRASS | 0 | 0 | 0 | 0 |
| CHEATGRASS | 0 | 0 | 0 | 0 |
| COCKLEBUR | — | 0 | 0 | — |
| CORN | 0 | 0 | 0 | 0 |
| COTTON | 0 | 0 | 0 | 2G |
| CRABGRASS | — | 0 | — | 5G |
| GIANT FOXTAIL | 0 | 0 | — | 6G |
| MORNINGGLORY | 0 | 0 | 0 | 2G |
| NUTSEDGE | 0 | 0 | 0 | 0 |
| RICE | 0 | 0 | 0 | 0 |
| SORGHUM | 0 | 0 | 0 | 0 |
| SOYBEAN | 0 | 0 | 0 | 0 |
| SUGAR BEETS | 0 | 0 | 3G | 7G |
| VELVETLEAF | 0 | 0 | 0 | 2G |
| WHEAT | 0 | 0 | 0 | 0 |
| WILD OATS | 0 | 0 | 0 | 0 |

| | CMPD 118 | | CMPD 119 | |
|---|---|---|---|---|
| RATE = KG/HA | 0.01 | 0.05 | 0.01 | 0.05 |
| POSTEMERGENCE | | | | |
| BARLEY | 0 | 4G | 0 | 0 |
| BARNYARDGRASS | 0 | 3C,8H | 0 | 0 |
| CHEATGRASS | 2C,9G | 4C,9G | 0 | 3G |
| COCKLEBUR | 0 | 4C,9H | 0 | 0 |
| CORN | 3C,5H | 4U,9G | 0 | 3C,9H |
| COTTON | 3C,3G | 4C,9G | 0 | 0 |
| CRABGRASS | 3G | 7G | 0 | 0 |
| GIANT FOXTAIL | 4G | 3C,8G | 0 | 0 |
| MORNINGGLORY | 0 | 4C,9G | 0 | 0 |
| NUTSEDGE | 0 | 3C,9G | 0 | 0 |
| RICE | 5C,9G | 5C,9G | 0 | 5G |
| SORGHUM | 2G | 3C,6G | 0 | 0 |
| SOYBEAN | 3C,7G | 3C,9G | 0 | 0 |
| SUGAR BEETS | 3C,6H | 6C,9G | 0 | 0 |
| VELVETLEAF | 3C,3H | 4C,9H | 0 | 0 |
| WHEAT | 0 | 7G | 0 | 0 |
| WILD OATS | 0 | 7G | 0 | 0 |
| PREEMERGENCE | | | | |
| BARLEY | 0 | 0 | 0 | 0 |
| BARNYARDGRASS | 0 | 0 | 0 | 0 |
| CHEATGRASS | 0 | 0 | 0 | 0 |
| COCKLEBUR | 0 | — | 0 | 0 |
| CORN | 0 | 0 | 0 | 2G |
| COTTON | 0 | 0 | 0 | 0 |
| CRABGRASS | 0 | — | 0 | 0 |
| GIANT FOXTAIL | 0 | 3G | 0 | — |
| MORNINGGLORY | 0 | 0 | 0 | 0 |
| NUTSEDGE | 0 | 0 | 0 | 0 |
| RICE | 0 | 2G | 0 | 0 |
| SORGHUM | 0 | 0 | 0 | 0 |
| SOYBEAN | 0 | 2G | 0 | 0 |
| SUGAR BEETS | 0 | 2G | 0 | 0 |
| VELVETLEAF | 0 | 0 | 0 | 4G |
| WHEAT | 0 | 0 | 0 | 0 |
| WILD OATS | 0 | 0 | 0 | 0 |

| | CMPD 120 | |
|---|---|---|
| RATE = KG/HA | 0.01 | 0.05 |
| POSTEMERGENCE | | |
| BARLEY | 3C,6G | 4C,9G |
| BARNYARDGRASS | 3C,7H | 4C,9G |
| CHEATGRASS | 0 | 9G |
| COCKLEBUR | 0 | 4C,9G |
| CORN | 2C,9G | 4U,9G |
| COTTON | 2G | 4C,8G |
| CRABGRASS | 3G | 3C,8G |
| GIANT FOXTAIL | 3G | 4C,9G |
| MORNINGGLORY | 0 | 4C,8G |
| NUTSEDGE | 0 | 6G |
| RICE | 3C,7G | 6C,9G |
| SORGHUM | 3C,6G | 4C,9G |
| SOYBEAN | 3C,5G | 4C,9G |
| SUGAR BEETS | 0 | 2G |
| VELVETLEAF | 0 | 3C,5G |
| WHEAT | 7G | 9G |
| WILD OATS | 3G | 5C,9G |
| PREEMERGENCE | | |
| BARLEY | 0 | 0 |
| BARNYARDGRASS | 0 | 2G |
| CHEATGRASS | 0 | 3G |
| COCKLEBUR | 0 | 0 |
| CORN | 0 | 2C |
| COTTON | 0 | 0 |
| CRABGRASS | — | 7G |
| GIANT FOXTAIL | 0 | 4G |
| MORNINGGLORY | 0 | 0 |
| NUTSEDGE | 0 | 0 |
| RICE | 0 | 0 |
| SORGHUM | 0 | 0 |
| SOYBEAN | 0 | 0 |
| SUGAR BEETS | 0 | 3G |
| VELVETLEAF | 0 | 0 |
| WHEAT | 0 | 0 |
| WILD OATS | 0 | 3G |

| | CMPD 121 | | CMPD 122 | |
|---|---|---|---|---|
| RATE = KG/HA | 0.01 | 0.05 | 0.01 | 0.05 |
| POSTEMERGENCE | | | | |
| BARLEY | 0 | 0 | 0 | 0 |
| BARNYARDGRASS | 0 | 3G | 0 | 4G |
| CHEATGRASS | 0 | 2C,9G | 0 | 8G |
| COCKLEBUR | 0 | 2G | 0 | 2C,5G |
| CORN | 0 | 4G | 0 | 1C,2G |
| COTTON | 0 | 0 | 0 | 1C,7G |
| CRABGRASS | 0 | 0 | 0 | 0 |
| GIANT FOXTAIL | 0 | 2C,9G | 0 | 6G |
| MORNINGGLORY | 0 | 0 | 0 | 1C,2G |
| NUTSEDGE | 0 | 0 | 0 | 0 |
| RICE | 0 | 0 | 0 | 1C,2G |
| SORGHUM | 0 | 0 | 0 | 0 |
| SOYBEAN | 0 | 1C,3G | 1C,2G | 2C,4G |
| SUGAR BEETS | 0 | 2C,8H | 0 | 3C,7G |
| VELVETLEAF | 0 | 0 | 0 | 2C,8G |
| WHEAT | 0 | 0 | 0 | 8G |
| WILD OATS | 0 | 0 | 0 | 2C,5G |
| PREEMERGENCE | | | | |
| BARLEY | 0 | 0 | 0 | 0 |
| BARNYARDGRASS | 0 | 0 | 0 | 0 |
| CHEATGRASS | 0 | 0 | 0 | 0 |
| COCKLEBUR | 0 | 0 | 0 | 0 |
| CORN | 0 | 0 | 0 | 0 |
| COTTON | 0 | 0 | 0 | 0 |
| CRABGRASS | 0 | 0 | 0 | 0 |
| GIANT FOXTAIL | 0 | 0 | 0 | 0 |
| MORNINGGLORY | 0 | 0 | 0 | 0 |
| NUTSEDGE | 0 | 4G | 0 | 0 |
| RICE | 0 | 0 | 0 | 0 |
| SORGHUM | 0 | 0 | 0 | 0 |
| SOYBEAN | 0 | 0 | 0 | 0 |
| SUGAR BEETS | 0 | 5G | 0 | 0 |
| VELVETLEAF | 0 | 4G | 0 | 0 |
| WHEAT | 0 | 0 | 0 | 0 |
| WILD OATS | 0 | 0 | 0 | 0 |

| | CMPD 123 | | CMPD 124 | |
|---|---|---|---|---|
| RATE = KG/HA | 0.01 | 0.05 | 0.01 | 0.05 |
| POSTEMERGENCE | | | | |
| BARLEY | 8G | 2C,9G | 0 | 5G |
| BARNYARDGRASS | 3C,9H | 4C,9G | 0 | 6G |
| CHEATGRASS | 3C,9G | 3C,9G | 0 | 5G |
| COCKLEBUR | 3C,8G | 5C,9G | 0 | 5G |
| CORN | 9G | 9C | 0 | 2C,6G |
| COTTON | 2C,6G | 3C,8G | 0 | 2G |
| CRABGRASS | 2C,6G | 3C,9G | 0 | 0 |
| GIANT FOXTAIL | 9G | 10C | 0 | 6G |
| MORNINGGLORY | 5C,9H | 6C,9G | 0 | 0 |
| NUTSEDGE | 5G | 8G | 0 | 0 |
| RICE | 2C,8G | 4C,9G | 0 | 2C,5G |
| SORGHUM | 2C,7G | 2C,9G | 0 | 4G |

TABLE A-continued

| | | | | |
|---|---|---|---|---|
| SOYBEAN | 3C,8G | 3C,8G | 0 | 2C,2G |
| SUGAR BEETS | 3C,8G | 3C,8G | 0 | 2C,6G |
| VELVETLEAF | 4C,8G | 6C,9G | 0 | 4G |
| WHEAT | 9G | 3C,9G | 0 | 2G |
| WILD OATS | 9G | 3C,9G | 0 | 2G |
| PREEMERGENCE | | | | |
| BARLEY | 0 | 2G | 0 | 0 |
| BARNYARDGRASS | 2G | 4G | 0 | 0 |
| CHEATGRASS | 0 | 6G | 0 | 0 |
| COCKLEBUR | 4G | 5G | 0 | 7G |
| CORN | 0 | 2C,7G | 0 | 0 |
| COTTON | 0 | 0 | 0 | 0 |
| CRABGRASS | 0 | 2C,8G | 0 | 4G |
| GIANT FOXTAIL | 4G | 2C,7G | 0 | 5G |
| MORNINGGLORY | 3G | 6G | 0 | 6G |
| NUTSEDGE | 0 | 10E | 0 | 3G |
| RICE | 5G | 2C,8H | 0 | 0 |
| SORGHUM | 0 | 0 | 0 | 3G |
| SOYBEAN | 2G | 1C | 0 | 0 |
| SUGAR BEETS | 7G | 4C,9G | 0 | 0 |
| VELVETLEAF | 3G | 3G | 0 | 1C,2G |
| WHEAT | 0 | 2G | 0 | 0 |
| WILD OATS | 0 | 0 | 0 | 0 |

| | CMPD 125 | | CMPD 126 | |
|---|---|---|---|---|
| RATE = KG/HA | 0.01 | 0.05 | 0.01 | 0.05 |
| POSTEMERGENCE | | | | |
| BARLEY | 0 | 0 | 0 | 0 |
| BARNYARDGRASS | 0 | 0 | 0 | 0 |
| CHEATGRASS | 0 | 0 | 0 | 0 |
| COCKLEBUR | 0 | 0 | 0 | 0 |
| CORN | 0 | 0 | 0 | 0 |
| COTTON | 0 | 0 | 0 | 0 |
| CRABGRASS | 0 | 0 | 0 | 0 |
| GIANT FOXTAIL | 0 | 0 | 0 | 0 |
| MORNINGGLORY | 0 | 0 | 0 | 0 |
| NUTSEDGE | 0 | 0 | 0 | 0 |
| RICE | 0 | 0 | 0 | 0 |
| SORGHUM | 0 | 0 | 0 | 0 |
| SOYBEAN | 0 | 0 | 0 | 0 |
| SUGAR BEETS | 0 | 0 | 0 | 0 |
| VELVETLEAF | 0 | 0 | 0 | 0 |
| WHEAT | 0 | 0 | 0 | 0 |
| WILD OATS | 0 | 0 | 0 | 0 |
| PREEMERGENCE | | | | |
| BARLEY | 0 | 0 | 0 | 0 |
| BARNYARDGRASS | 0 | 0 | 0 | 0 |
| CHEATGRASS | 0 | 0 | 0 | 0 |
| COCKLEBUR | 0 | 0 | 0 | 0 |
| CORN | 0 | 0 | 0 | 0 |
| COTTON | 0 | 0 | 0 | 3G |
| CRABGRASS | 0 | 0 | 0 | 0 |
| GIANT FOXTAIL | 0 | 0 | 0 | 0 |
| MORNINGGLORY | 0 | 0 | 0 | 2G |
| NUTSEDGE | 0 | 4G | 0 | 0 |
| RICE | 0 | 0 | 0 | 0 |
| SORGHUM | 0 | 0 | 0 | 0 |
| SOYBEAN | 0 | 2G | 0 | 0 |
| SUGAR BEETS | 0 | 0 | 0 | 0 |
| VELVETLEAF | 0 | 0 | 0 | 2G |
| WHEAT | 0 | 0 | 0 | 0 |
| WILD OATS | 0 | 0 | 0 | 0 |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xantium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus* L.), cheatgrass (*Bromus secalinus* L.), sugarbeet (*Beta vulgaris*), wild oats (*Avena fatua*), viola (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (—) response means no test.

Response ratings are contained in Table B.

TABLE B

| | POST-EMERGENCE | | | | PRE-EMERGENCE | | | |
|---|---|---|---|---|---|---|---|---|
| Rate g/ha | 62 | 16 | 4 | 1 | 250 | 62 | 16 | 4 |
| CMPD 1 | | | | | | | | |
| Corn | 100 | 70 | 50 | 20 | 60 | 30 | 20 | 0 |
| Wheat | 70 | 40 | 30 | 0 | 50 | 20 | 0 | 0 |
| Barley | 40 | 0 | 0 | 0 | 50 | 20 | 0 | 0 |
| Rice | 90 | 60 | 30 | 0 | 100 | 100 | 50 | 0 |
| Soybean | 90 | 40 | 0 | 0 | 60 | 0 | 0 | 0 |
| Cotton | 40 | 0 | 0 | 0 | 60 | 30 | 0 | 0 |
| Sugar Beet | 90 | 70 | 50 | 30 | 90 | 70 | 50 | 30 |
| Rape | 60 | 30 | 0 | 0 | 100 | 90 | 60 | 30 |
| Crabgrass | 70 | 50 | 30 | 0 | 90 | 70 | 50 | 30 |
| Johnsongrass | 70 | 50 | 30 | 0 | 90 | 70 | 50 | 30 |
| Blackgrass | 70 | 50 | 30 | 0 | 90 | 60 | 30 | 0 |
| Barnyardgrass | 70 | 30 | 0 | 0 | 50 | 30 | 0 | 0 |
| Nutsedge | 50 | 30 | 0 | 0 | 90 | 70 | 50 | 30 |
| Giant Foxtail | 0 | 0 | 0 | 0 | 60 | 40 | 0 | 0 |
| Green Foxtail | 0 | 0 | 0 | 0 | 70 | 50 | 30 | 0 |
| Cheatgrass | 90 | 60 | 30 | 0 | 90 | 70 | 30 | 0 |
| Wild Oats | 70 | 40 | 0 | 0 | 40 | 0 | 0 | 0 |
| Wild Buckwheat | 60 | 30 | 0 | 0 | 100 | 60 | 30 | 0 |
| Viola | 50 | 30 | 0 | 0 | 90 | 80 | 60 | 30 |
| Lambsquarter | 60 | 30 | 0 | 0 | 100 | 60 | 30 | 0 |
| Cocklebur | 60 | 30 | 0 | 0 | 90 | 90 | 60 | 30 |
| Morningglory | 40 | 0 | 0 | 0 | 70 | 40 | 0 | 0 |
| Teaweed | 70 | 50 | 30 | 0 | 70 | 50 | 30 | 0 |
| Sicklepod | — | 50 | 30 | 0 | 90 | 70 | 50 | 30 |
| Jimsonweed | 30 | 0 | 0 | 0 | 70 | 50 | 30 | 0 |
| Velvetleaf | 90 | 30 | 20 | 0 | 70 | 50 | 30 | 0 |
| CMPD 2 | | | | | | | | |
| Corn | 100 | 100 | 90 | 60 | 90 | 70 | 40 | 0 |
| Wheat | 90 | 70 | 50 | 30 | 90 | 60 | 30 | 0 |
| Barley | 60 | 50 | 30 | 0 | 90 | 50 | 30 | 0 |
| Rice | 100 | 60 | 40 | 0 | 100 | 100 | 90 | 70 |
| Soybean | 100 | 90 | 60 | 30 | 90 | 70 | 30 | 0 |
| Cotton | 90 | 90 | 90 | 30 | 90 | 60 | 30 | 0 |
| Sugar beet | 100 | 60 | 30 | 0 | 90 | 90 | 70 | 50 |
| Rape | 100 | 40 | 0 | 0 | 100 | 90 | 70 | 50 |
| Crabgrass | 90 | 70 | 50 | 30 | 100 | 100 | 100 | 70 |
| Johnsongrass | 90 | 70 | 50 | 30 | 100 | 90 | 60 | 30 |
| Blackgrass | 100 | 70 | 50 | 0 | 100 | 100 | 90 | 60 |
| Barnyardgrass | 100 | 60 | 30 | 0 | 100 | 100 | 60 | 30 |

TABLE B-continued

| | | | | | | | | |
|---|---|---|---|---|---|---|---|---|
| Nutsedge | 70 | 50 | 30 | 0 | 100 | 70 | 50 | 30 |
| Giant Foxtail | 100 | 50 | 30 | 0 | 90 | 70 | 50 | 30 |
| Green Foxtail | 30 | 30 | 30 | 0 | 90 | 80 | 70 | 50 |
| Cheatgrass | 80 | 50 | 30 | 0 | 100 | 70 | 30 | 0 |
| Wild Oats | 80 | 60 | 40 | 0 | 70 | 50 | 0 | 0 |
| Wild Buckwheat | 50 | 30 | 0 | 0 | 90 | 70 | 50 | 30 |
| Viola | 70 | 50 | 30 | 0 | 100 | 100 | 70 | 50 |
| Lambsquarter | 100 | 70 | 50 | 30 | 100 | 100 | 90 | 70 |
| Cocklebur | 100 | 70 | 50 | 30 | 90 | 80 | 70 | 50 |
| Morningglory | 90 | 90 | 60 | 40 | 90 | 80 | 60 | 30 |
| Teaweed | 90 | 70 | 50 | 30 | 90 | 70 | 50 | 30 |
| Sicklepod | 100 | 90 | 70 | 50 | 90 | 70 | 50 | 30 |
| Jimsonweed | 90 | 70 | 50 | 30 | 100 | 90 | 60 | 30 |
| Velvetleaf | 100 | 100 | 40 | 0 | 90 | 70 | 50 | 30 |
| CMPD 3 | | | | | | | | |
| Corn | 100 | 100 | 70 | 100 | 100 | 40 | 20 | |
| Wheat | 90 | 60 | 30 | 70 | 50 | 30 | 0 | |
| Barley | 90 | 60 | 30 | 70 | 30 | 0 | 0 | |
| Rice | 100 | 100 | 0 | 100 | 100 | 90 | 70 | |
| Soybean | 100 | 100 | 50 | 90 | 70 | 30 | 0 | |
| Cotton | 90 | 90 | 40 | 90 | 70 | 50 | 30 | |
| Sugar beet | 100 | 70 | 30 | 90 | 80 | 70 | 50 | |
| Rape | 100 | 90 | 0 | 100 | 90 | 70 | 50 | |
| Crabgrass | 100 | 70 | 30 | 100 | 90 | 60 | 30 | |
| Johnsongrass | 90 | 50 | 0 | 100 | 90 | 60 | 30 | |
| Blackgrass | 100 | 70 | 30 | 90 | 80 | 70 | 50 | |
| Barnyardgrass | 100 | 70 | 30 | 90 | 70 | 50 | 30 | |
| Nutsedge | 100 | 40 | 0 | 100 | 90 | 70 | 50 | |
| Giant Foxtail | 80 | 60 | 0 | 90 | 60 | 30 | 0 | |
| Green Foxtail | 90 | 70 | 30 | 90 | 70 | 50 | 30 | |
| Cheatgrass | 90 | 60 | 0 | 90 | 80 | 60 | 30 | |
| Wild Oats | 100 | 70 | 30 | 70 | 50 | 30 | 0 | |
| Wild Buckwheat | 70 | 30 | 0 | 90 | 70 | 50 | 30 | |
| Viola | 100 | 100 | 30 | 100 | 100 | 100 | 70 | |
| Lambsquarter | 100 | 100 | 50 | 100 | 100 | 70 | 50 | |
| Cocklebur | 100 | 100 | 50 | 90 | 80 | 60 | 30 | |
| Morningglory | 100 | 70 | 30 | 90 | 80 | 50 | 30 | |
| Teaweed | 90 | 70 | 30 | 90 | 80 | 60 | 30 | |
| Sicklepod | 100 | 100 | 70 | 90 | 70 | 50 | 30 | |
| Jimsonweed | 100 | 90 | 30 | 90 | 70 | 50 | 30 | |
| Velvetleaf | 100 | 100 | 30 | 90 | 70 | 50 | 30 | |
| CMPD 4 | | | | | | | | |
| Corn | 100 | 90 | 80 | 60 | 70 | 40 | 0 | 0 |
| Wheat | 70 | 50 | 30 | 0 | 50 | 30 | 0 | 0 |
| Barley | 0 | 0 | 0 | 0 | 30 | 0 | 0 | 0 |
| Rice | 100 | 100 | 0 | 0 | 100 | 90 | 70 | 30 |
| Soybean | 60 | 30 | 0 | 0 | 80 | 40 | 0 | 0 |
| Cotton | 100 | 60 | 30 | 0 | 80 | 30 | 0 | 0 |
| Sugar Beet | 70 | 50 | 30 | 0 | 90 | 70 | 50 | 30 |
| Rape | 70 | 50 | 0 | 0 | 100 | 90 | 60 | 30 |
| Crabgrass | 80 | 50 | 30 | 0 | 90 | 70 | 50 | 30 |
| Johnsongrass | 70 | 30 | 0 | 0 | 100 | 90 | 70 | 30 |
| Blackgrass | 50 | 30 | 0 | 0 | 90 | 70 | 50 | 30 |
| Barnyardgrass | 70 | 30 | 0 | 0 | 90 | 70 | 30 | 0 |
| Nutsedge | 40 | 0 | 0 | 0 | 100 | 90 | 70 | 50 |
| Giant Foxtail | 40 | 0 | 0 | 0 | 50 | 30 | 0 | 0 |
| Green Foxtail | 50 | 30 | 0 | 0 | 50 | 30 | 0 | 0 |
| Cheatgrass | 50 | 0 | 0 | 0 | 90 | 60 | 30 | 0 |
| Wild Oats | 0 | 0 | 0 | 0 | 30 | 0 | 0 | 0 |
| Wild Buckwheat | 70 | 50 | 30 | 0 | 90 | 70 | 50 | 30 |
| Viola | 70 | 50 | 30 | 0 | 100 | 90 | 60 | 30 |
| Lambsquarter | 100 | 70 | 50 | 30 | 90 | 70 | 50 | 30 |
| Cocklebur | 90 | 60 | 30 | 0 | 90 | 80 | 70 | 50 |
| Morningglory | 100 | 60 | 30 | 0 | 90 | 70 | 50 | 30 |
| Teaweed | 90 | 60 | 30 | 0 | 90 | 70 | 50 | 30 |
| Sicklepod | 100 | 60 | 30 | 0 | 100 | 70 | 50 | 30 |
| Jimsonweed | 100 | 60 | 30 | 0 | 90 | 80 | 50 | 30 |
| Velvetleaf | 100 | 60 | 30 | 0 | 90 | 70 | 50 | 30 |
| CMPD 6 | | | | | | | | |
| Corn | 100 | 100 | 70 | 40 | 90 | 70 | 30 | 0 |
| Wheat | 100 | 90 | 70 | 40 | 90 | 60 | 30 | 0 |
| Barley | 90 | 60 | 30 | 0 | 70 | 30 | 0 | 0 |
| Rice | 100 | 70 | 30 | 0 | 100 | 90 | 70 | 50 |
| Soybean | 90 | 70 | 30 | 0 | 90 | 70 | 30 | 0 |
| Cotton | 30 | 0 | 0 | 0 | 80 | 50 | 30 | 0 |
| Sugar beet | 90 | 60 | 30 | 0 | 100 | 70 | 30 | 0 |
| Rape | 60 | 30 | 0 | 0 | 90 | 80 | 60 | 30 |
| Crabgrass | 90 | 70 | 50 | 30 | 90 | 70 | 50 | 30 |
| Johnsongrass | 90 | 70 | 50 | 30 | 90 | 80 | 70 | 50 |
| Blackgrass | 100 | 90 | 70 | 40 | 100 | 90 | 70 | 50 |
| Barnyardgrass | 90 | 70 | 30 | 0 | 100 | 90 | 60 | 30 |

TABLE B-continued

| | | | | | | | | |
|---|---|---|---|---|---|---|---|---|
| Nutsedge | 50 | 30 | 0 | 0 | 90 | 60 | 30 | 0 |
| Giant Foxtail | 40 | 0 | 0 | 0 | 90 | 50 | 30 | 0 |
| Green Foxtail | 30 | 0 | 0 | 0 | 100 | 60 | 30 | 0 |
| Cheatgrass | 90 | 60 | 30 | 0 | 100 | 70 | 50 | 30 |
| Wild Oats | 100 | 70 | 50 | 30 | 80 | 30 | 0 | 0 |
| Wild Buckwheat | 30 | 0 | 0 | 0 | 90 | 60 | 30 | 0 |
| Viola | 90 | 70 | 50 | 30 | 90 | 80 | 70 | 40 |
| Lambsquarter | 80 | 70 | 50 | 30 | 100 | 100 | 100 | 100 |
| Cocklebur | 90 | 70 | 50 | 30 | 90 | 70 | 50 | 30 |
| Morningglory | 90 | 60 | 30 | 0 | 90 | 80 | 70 | 50 |
| Teaweed | 70 | 50 | 30 | 0 | 80 | 60 | 30 | 0 |
| Sicklepod | 100 | 70 | 50 | 30 | 90 | 70 | 50 | 30 |
| Jimsonweed | 90 | 70 | 30 | 0 | 90 | 80 | 60 | 30 |
| Velvetleaf | 70 | 30 | 0 | 0 | 90 | 70 | 50 | 30 |
| CMPD 7 | | | | | | | | |
| Corn | 100 | 100 | 70 | 50 | 80 | 50 | 0 | 0 |
| Wheat | 100 | 70 | 50 | 40 | 90 | 50 | 0 | 0 |
| Barley | 90 | 60 | 30 | 0 | 70 | 50 | 30 | 0 |
| Rice | 100 | 60 | 0 | 0 | 100 | 100 | 90 | 70 |
| Soybean | 90 | 60 | 0 | 0 | 80 | 30 | 0 | 0 |
| Cotton | 30 | 0 | 0 | 0 | 70 | 30 | 0 | 0 |
| Sugar beet | 70 | 50 | 30 | 0 | 90 | 80 | 70 | 50 |
| Rape | 100 | 60 | 20 | 0 | 90 | 60 | 30 | 0 |
| Crabgrass | 90 | 40 | 0 | 0 | 90 | 70 | 50 | 30 |
| Johnsongrass | 90 | 70 | 50 | 30 | 90 | 80 | 70 | 50 |
| Blackgrass | 100 | 90 | 70 | 50 | 100 | 90 | 70 | 50 |
| Barnyardgrass | 80 | 40 | 30 | 0 | 90 | 70 | 20 | 0 |
| Nutsedge | 40 | 0 | 0 | 0 | 100 | 80 | 30 | 30 |
| Giant Foxtail | 0 | 0 | 0 | 0 | 50 | 30 | 0 | 0 |
| Green Foxtail | 0 | 0 | 0 | 0 | 70 | 50 | 30 | 0 |
| Cheatgrass | 90 | 60 | 30 | 0 | 90 | 60 | 30 | 0 |
| Wild Oats | 90 | 60 | 30 | 0 | 70 | 50 | 30 | 0 |
| Wild Buckwheat | 0 | 0 | 0 | 0 | 50 | 30 | 0 | 0 |
| Viola | 70 | 30 | 0 | 0 | 90 | 70 | 50 | 30 |
| Lambsquarter | 70 | 50 | 30 | 0 | 100 | 100 | 100 | 90 |
| Cocklebur | 100 | 90 | 60 | 30 | 90 | 60 | 30 | 0 |
| Morningglory | 70 | 50 | 30 | 0 | 90 | 60 | 30 | 0 |
| Teaweed | 70 | 50 | 30 | 0 | 80 | 60 | 30 | 0 |
| Sicklepod | 90 | 70 | 50 | 30 | 90 | 70 | 50 | 30 |
| Jimsonweed | 100 | 70 | 30 | 0 | 90 | 70 | 50 | 30 |
| Velvetleaf | 50 | 40 | 20 | 0 | 70 | 40 | 0 | 0 |

| RATE = G/HA | 0250 | 0062 | 0016 | 0004 | 0001 |
|---|---|---|---|---|---|
| CMPD 59 | | | | | |
| POSTEMERGENCE | | | | | |
| GIANT FOXTAIL | — | 30 | 20 | 0 | 0 |
| VELVETLEAF | — | 100 | 100 | 70 | 30 |
| SUGAR BEETS | — | 100 | 60 | 30 | 0 |
| CRABGRASS | — | 60 | 30 | 0 | 0 |
| TEAWEED | — | 80 | 50 | 30 | 0 |
| JIMSONWEED | — | 100 | 60 | 30 | 0 |
| RICE | — | 100 | 100 | 90 | 60 |
| COCKLEBUR | — | 100 | 100 | 60 | 30 |
| COTTON | — | 70 | 20 | 0 | 0 |
| SOYBEAN | — | 100 | 100 | 70 | 50 |
| BARNYARD GRASS | — | 100 | 100 | 70 | 50 |
| WILD OATS | — | 70 | 30 | 0 | 0 |
| MORNINGGLORY | — | 60 | 30 | 0 | 0 |
| WHEAT | — | 100 | 90 | 60 | 30 |
| CASSIA | — | 100 | 90 | 80 | 70 |
| JOHNSONGRASS | — | 100 | 80 | 50 | 30 |
| NUTSEDGE | — | 90 | 60 | 30 | 0 |
| CORN | — | 100 | 100 | 90 | 70 |
| WILD BUCKWHEAT | — | 70 | 50 | 30 | 0 |
| BLACK GRASS | — | 70 | 30 | 0 | 0 |
| RAPESEED | — | 100 | 90 | 70 | 50 |
| BARLEY | — | 70 | 50 | 30 | 0 |
| GREEN FOXTAIL | — | 30 | 20 | 0 | 0 |
| CHEAT GRASS | — | 60 | 30 | 0 | 0 |
| BUCKWHEAT | — | — | — | — | — |
| VIOLA | — | 90 | 50 | 30 | 0 |
| LAMBSQUARTER | — | 100 | 90 | 70 | 50 |
| CHICK WEED | — | — | — | — | — |
| PREEMERGENCE | | | | | |
| GIANT FOXTAIL | 50 | 30 | — | — | — |
| VELVETLEAF | 90 | 60 | — | — | — |
| SUGAR BEETS | 70 | 50 | — | — | — |
| CRABGRASS | 70 | 30 | — | — | — |
| TEAWEED | 70 | 50 | — | — | — |
| JIMSONWEED | 90 | 60 | — | — | — |
| RICE | 90 | 60 | — | — | — |

TABLE B-continued

| Weed | | | | | |
|---|---|---|---|---|---|
| COCKLEBUR | 80 | 60 | — | — | — |
| COTTON | 0 | 0 | — | — | — |
| SOYBEAN | 80 | 40 | — | — | — |
| BARNYARD GRASS | 90 | 50 | — | — | — |
| WILD OATS | 40 | 0 | — | — | — |
| MORNINGGLORY | 50 | 30 | — | — | — |
| WHEAT | 70 | 30 | — | — | — |
| CASSIA | 70 | 50 | — | — | — |
| JOHNSONGRASS | 90 | 70 | — | — | — |
| NUTSEDGE | 0 | 0 | — | — | — |
| CORN | 80 | 0 | — | — | — |
| WILD BUCKWHEAT | 50 | 30 | — | — | — |
| BLACK GRASS | 70 | 50 | — | — | — |
| RAPESEED | 90 | 60 | — | — | — |
| BARLEY | 0 | 0 | — | — | — |
| GREEN FOXTAIL | 50 | 30 | — | — | — |
| CHEAT GRASS | 30 | 0 | — | — | — |
| BUCKWHEAT | — | — | — | — | — |
| VIOLA | — | — | — | — | — |
| LAMBSQUARTER | 90 | 70 | — | — | — |
| CHICK WEED | — | — | — | — | — |

CMPD 60
POSTEMERGENCE

| Weed | | | | | |
|---|---|---|---|---|---|
| GIANT FOXTAIL | — | 70 | 50 | 30 | 0 |
| VELVETLEAF | — | 100 | 90 | 70 | 60 |
| SUGAR BEETS | — | 100 | 100 | 90 | 60 |
| CRABGRASS | — | 60 | 30 | 0 | 0 |
| TEAWEED | — | 100 | 70 | 50 | 30 |
| JIMSONWEED | — | 100 | 100 | 90 | 70 |
| RICE | — | 100 | 100 | 90 | 70 |
| COCKLEBUR | — | 90 | 80 | 70 | 60 |
| COTTON | — | 100 | 70 | 30 | 0 |
| SOYBEAN | — | 100 | 100 | 100 | 100 |
| BARNYARD GRASS | — | 100 | 100 | 100 | 60 |
| WILD OATS | — | 60 | 30 | 0 | 0 |
| MORNINGGLORY | — | 60 | 50 | 40 | 30 |
| WHEAT | — | 100 | 70 | 50 | 30 |
| CASSIA | — | 100 | 100 | 100 | 70 |
| JOHNSONGRASS | — | 100 | 100 | 100 | 60 |
| NUTSEDGE | — | 100 | 100 | 100 | 50 |
| CORN | — | 100 | 100 | 100 | 100 |
| WILD BUCKWHEAT | — | 100 | 90 | 60 | 30 |
| BLACK GRASS | — | 90 | 70 | 50 | 30 |
| RAPESEED | — | 100 | 100 | 100 | 90 |
| BARLEY | — | 0 | 0 | 0 | 0 |
| GREEN FOXTAIL | — | 70 | 50 | 30 | 0 |
| CHEAT GRASS | — | 60 | 30 | 0 | 0 |
| BUCKWHEAT | — | — | — | — | — |
| VIOLA | — | 100 | 100 | 60 | 30 |
| LAMBSQUARTER | — | 100 | 100 | 90 | 70 |
| CHICK WEED | — | — | — | — | — |

PREEMERGENCE

| Weed | | | | | |
|---|---|---|---|---|---|
| GIANT FOXTAIL | 70 | 50 | 30 | 20 | — |
| VELVETLEAF | 90 | 80 | 60 | 30 | — |
| SUGAR BEETS | 90 | 70 | 50 | 30 | — |
| CRABGRASS | 90 | 70 | 50 | 30 | — |
| TEAWEED | 100 | 80 | 60 | 40 | — |
| JIMSONWEED | 100 | 70 | 50 | 30 | — |
| RICE | 100 | 100 | 90 | 80 | — |
| COCKLEBUR | 90 | 80 | 50 | 30 | — |
| COTTON | 50 | 30 | 0 | 0 | — |
| SOYBEAN | 90 | 70 | 50 | 30 | — |
| BARNYARD GRASS | 100 | 90 | 70 | 30 | — |
| WILD OATS | 50 | 30 | 0 | 0 | — |
| MORNINGGLORY | 0 | 0 | 0 | 0 | — |
| WHEAT | 80 | 50 | 30 | 0 | — |
| CASSIA | 90 | 70 | 50 | 30 | — |
| JOHNSONGRASS | 100 | 100 | 90 | 60 | — |
| NUTSEDGE | 100 | 60 | 30 | 0 | — |
| CORN | 100 | 90 | 60 | 0 | — |
| WILD BUCKWHEAT | 80 | 70 | 50 | 30 | — |
| BLACK GRASS | 90 | 60 | 30 | 0 | — |
| RAPESEED | 100 | 90 | 80 | 70 | — |
| BARLEY | 0 | 0 | 0 | 0 | — |
| GREEN FOXTAIL | 70 | 50 | 30 | 20 | — |
| CHEAT GRASS | 70 | 50 | 30 | 0 | — |
| BUCKWHEAT | — | — | — | — | — |
| VIOLA | — | — | — | — | — |
| LAMBSQUARTER | 100 | 100 | 90 | 70 | — |
| CHICK WEED | — | — | — | — | — |

CMPD 63
POSTEMERGENCE

| Weed | | | | | |
|---|---|---|---|---|---|
| GIANT FOXTAIL | — | 40 | 0 | 0 | 0 |
| VELVETLEAF | — | 90 | 70 | 50 | 30 |
| SUGAR BEETS | — | 70 | 30 | 0 | 0 |
| CRABGRASS | — | 50 | 30 | 0 | 0 |
| TEAWEED | — | 60 | 30 | 0 | 0 |
| JIMSONWEED | — | 90 | 70 | 50 | 30 |
| RICE | — | 100 | 90 | 60 | 30 |
| COCKLEBUR | — | 100 | 70 | 50 | 30 |
| COTTON | — | 50 | 30 | 0 | 0 |
| SOYBEAN | — | 60 | 50 | 30 | 20 |
| BARNYARD GRASS | — | 100 | 70 | 50 | 30 |
| WILD OATS | — | 50 | 30 | 0 | 0 |
| MORNINGGLORY | — | 80 | 50 | 30 | 0 |
| WHEAT | — | 90 | 70 | 50 | 30 |
| CASSIA | — | 90 | 60 | 30 | 0 |
| JOHNSONGRASS | — | 100 | 70 | 50 | 30 |
| NUTSEDGE | — | 0 | 0 | 0 | 0 |
| CORN | — | 100 | 100 | 90 | 70 |
| WILD BUCKWHEAT | — | 80 | 50 | 30 | 0 |
| BLACK GRASS | — | 90 | 40 | 0 | 0 |
| RAPESEED | — | 90 | 70 | 50 | 30 |
| BARLEY | — | 70 | 30 | 0 | 0 |
| GREEN FOXTAIL | — | 40 | 0 | 0 | 0 |
| CHEAT GRASS | — | 40 | 0 | 0 | 0 |
| BUCKWHEAT | — | — | — | — | — |
| VIOLA | — | 100 | 50 | 0 | 0 |
| LAMBSQUARTER | — | 100 | 100 | 70 | 50 |
| CHICK WEED | — | — | — | — | — |

PREEMERGENCE

| Weed | | |
|---|---|---|
| GIANT FOXTAIL | 60 | 30 |
| VELVETLEAF | 80 | 70 |
| SUGAR BEETS | 90 | 70 |
| CRABGRASS | 60 | 30 |
| TEAWEED | 100 | 90 |
| JIMSONWEED | 100 | 90 |
| RICE | 100 | 90 |
| COCKLEBUR | 70 | 60 |
| COTTON | 50 | 30 |
| SOYBEAN | 60 | 0 |
| BARNYARD GRASS | 90 | 60 |
| WILD OATS | 80 | 50 |
| MORNINGGLORY | 90 | 80 |
| WHEAT | 80 | 60 |
| CASSIA | 90 | 70 |
| JOHNSONGRASS | 100 | 90 |
| NUTSEDGE | 0 | 0 |
| CORN | 100 | 100 |
| WILD BUCKWHEAT | 50 | 30 |
| BLACK GRASS | 100 | 70 |
| RAPESEED | 80 | 0 |
| BARLEY | 60 | 0 |
| GREEN FOXTAIL | 60 | 30 |
| CHEAT GRASS | 50 | 30 |
| BUCKWHEAT | — | — |
| VIOLA | — | — |
| LAMBSQUARTER | 90 | 70 |
| CHICK WEED | — | — |

CMPD 64
POSTEMERGENCE

| Weed | | | | | |
|---|---|---|---|---|---|
| GIANT FOXTAIL | — | 70 | 50 | 30 | 0 |
| VELVETLEAF | — | 100 | 50 | 0 | 0 |
| SUGAR BEETS | — | 30 | 0 | 0 | 0 |
| CRABGRASS | — | 60 | 30 | 0 | 0 |
| TEAWEED | — | 60 | 30 | 20 | 0 |
| JIMSONWEED | — | 100 | 80 | 50 | 30 |
| RICE | — | 100 | 90 | 80 | 70 |
| COCKLEBUR | — | 100 | 70 | 30 | 0 |
| COTTON | — | 50 | 0 | 0 | 0 |
| SOYBEAN | — | 90 | 60 | 30 | 0 |
| BARNYARD GRASS | — | 100 | 90 | 70 | 50 |
| WILD OATS | — | 40 | 0 | 0 | 0 |
| MORNINGGLORY | — | 70 | 50 | 30 | 0 |
| WHEAT | — | 100 | 90 | 70 | 50 |
| CASSIA | — | 90 | 60 | 30 | 0 |
| JOHNSONGRASS | — | 100 | 100 | 70 | 50 |
| NUTSEDGE | — | 50 | 0 | 0 | 0 |
| CORN | — | 100 | 90 | 70 | 50 |
| WILD BUCKWHEAT | — | 80 | 50 | 30 | 0 |
| BLACK GRASS | — | 60 | 30 | 0 | 0 |
| RAPESEED | — | 100 | 100 | 90 | 60 |

TABLE B-continued

| | | | | |
|---|---|---|---|---|
| BARLEY | — | 90 | 70 | 50 | 30 |
| GREEN FOXTAIL | — | 70 | 50 | 30 | 0 |
| CHEAT GRASS | — | 40 | 0 | 0 | 0 |
| BUCKWHEAT | — | — | — | — | — |
| VIOLA | — | 70 | 50 | 30 | 0 |
| LAMBSQUARTER | — | 70 | 50 | 30 | 0 |
| CHICK WEED | — | — | — | — | — |
| PREEMERGENCE | | | | | |
| GIANT FOXTAIL | 70 | 30 | — | — | — |
| VELVETLEAF | 90 | 30 | — | — | — |
| SUGAR BEETS | 100 | 90 | — | — | — |
| CRABGRASS | 80 | 50 | — | — | — |
| TEAWEED | 100 | 70 | — | — | — |
| JIMSONWEED | 90 | 80 | — | — | — |
| RICE | 100 | 90 | — | — | — |
| COCKLEBUR | 60 | 40 | — | — | — |
| COTTON | 60 | 0 | — | — | — |
| SOYBEAN | 60 | 0 | — | — | — |
| BARNYARD GRASS | 90 | 40 | — | — | — |
| WILD OATS | 90 | 70 | — | — | — |
| MORNINGGLORY | 80 | 30 | — | — | — |
| WHEAT | 90 | 60 | — | — | — |
| CASSIA | 100 | 80 | — | — | — |
| JOHNSONGRASS | 90 | 70 | — | — | — |
| NUTSEDGE | 80 | 0 | — | — | — |
| CORN | 100 | 70 | — | — | — |
| WILD BUCKWHEAT | 60 | 30 | — | — | — |
| BLACK GRASS | 100 | 70 | — | — | — |
| RAPESEED | 90 | 40 | — | — | — |
| BARLEY | 70 | 0 | — | — | — |
| GREEN FOXTAIL | 90 | 40 | — | — | — |
| CHEAT GRASS | 80 | 50 | — | — | — |
| BUCKWHEAT | — | — | — | — | — |
| VIOLA | — | — | — | — | — |
| LAMBSQUARTER | 80 | 60 | — | — | — |
| CHICK WEED | — | — | — | — | — |
| CMPD 67 | | | | | |
| POSTEMERGENCE | | | | | |
| GIANT FOXTAIL | — | — | 70 | 30 | 0 |
| VELVETLEAF | — | — | 100 | 70 | 50 |
| SUGAR BEETS | — | — | 90 | 70 | 50 |
| CRABGRASS | — | — | 80 | 60 | 40 |
| TEAWEED | — | — | 60 | 30 | 0 |
| JIMSONWEED | — | — | 90 | 70 | 50 |
| RICE | — | — | 90 | 60 | 30 |
| COCKLEBUR | — | — | 100 | 100 | 30 |
| COTTON | — | — | 100 | 60 | 30 |
| SOYBEAN | — | — | 100 | 80 | 50 |
| BARNYARD GRASS | — | — | 100 | 100 | 70 |
| WILD OATS | — | — | 50 | 30 | 0 |
| MORNINGGLORY | — | — | 100 | 70 | 50 |
| WHEAT | — | — | 70 | 50 | 30 |
| CASSIA | — | — | 90 | 60 | 30 |
| JOHNSONGRASS | — | — | 100 | 100 | 80 |
| NUTSEDGE | — | — | 100 | 70 | 30 |
| CORN | — | — | 100 | 90 | 70 |
| WILD BUCKWHEAT | — | — | 40 | 0 | 0 |
| BLACK GRASS | — | — | 50 | 30 | 0 |
| RAPESEED | — | — | 100 | 100 | 70 |
| BARLEY | — | — | 40 | 0 | 0 |
| GREEN FOXTAIL | — | — | 80 | 60 | 30 |
| CHEAT GRASS | — | — | 70 | 50 | 30 |
| BUCKWHEAT | — | — | — | — | — |
| VIOLA | — | — | — | — | — |
| LAMBSQUARTER | — | — | 100 | 100 | 70 |
| CHICK WEED | — | — | — | — | — |
| PREEMERGENCE | | | | | |
| GIANT FOXTAIL | — | 70 | 50 | 30 | 0 |
| VELVETLEAF | — | 60 | 30 | 20 | 0 |
| SUGAR BEETS | — | 50 | 30 | 0 | 0 |
| CRABGRASS | — | 80 | 50 | 30 | 0 |
| TEAWEED | — | 70 | 30 | 0 | 0 |
| JIMSONWEED | — | 70 | 50 | 30 | 0 |
| RICE | — | 80 | 50 | 30 | 0 |
| COCKLEBUR | — | 50 | 30 | 0 | 0 |
| COTTON | — | 20 | 0 | 0 | 0 |
| SOYBEAN | — | 60 | 30 | 0 | 0 |
| BARNYARD GRASS | — | 50 | 30 | 0 | 0 |
| WILD OATS | — | 30 | 20 | 0 | 0 |
| MORNINGGLORY | — | 0 | 0 | 0 | 0 |
| WHEAT | — | 30 | 0 | 0 | 0 |
| CASSIA | — | 40 | 0 | 0 | 0 |
| JOHNSONGRASS | — | 90 | 60 | 30 | 0 |
| NUTSEDGE | — | 30 | 20 | 0 | 0 |
| CORN | — | 60 | 20 | 0 | 0 |
| WILD BUCKWHEAT | — | 60 | 30 | 0 | 0 |
| BLACK GRASS | — | 70 | 30 | 0 | 0 |
| RAPESEED | — | 60 | 30 | 0 | 0 |
| BARLEY | — | 30 | 0 | 0 | 0 |
| GREEN FOXTAIL | — | 70 | 30 | 0 | 0 |
| CHEAT GRASS | — | 70 | 30 | 0 | 0 |
| BUCKWHEAT | — | — | — | — | — |
| VIOLA | — | — | — | — | — |
| LAMBSQUARTER | — | 100 | 90 | 70 | 50 |
| CHICK WEED | — | — | — | — | — |
| CMPD 68 | | | | | |
| POSTEMERGENCE | | | | | |
| GIANT FOXTAIL | — | — | 100 | 100 | 60 |
| VELVETLEAF | — | — | 100 | 100 | 90 |
| SUGAR BEETS | — | — | 100 | 100 | 70 |
| CRABGRASS | — | — | 80 | 60 | 40 |
| TEAWEED | — | — | 90 | 70 | 50 |
| JIMSONWEED | — | — | 80 | 70 | 50 |
| RICE | — | — | 80 | 70 | 50 |
| COCKLEBUR | — | — | 100 | 100 | 60 |
| COTTON | — | — | 100 | 70 | 30 |
| SOYBEAN | — | — | 100 | 100 | 80 |
| BARNYARD GRASS | — | — | 100 | 100 | 70 |
| WILD OATS | — | — | 60 | 30 | 0 |
| MORNINGGLORY | — | — | 100 | 100 | 100 |
| WHEAT | — | — | 90 | 70 | 50 |
| CASSIA | — | — | 100 | 80 | 60 |
| JOHNSONGRASS | — | — | 100 | 100 | 90 |
| NUTSEDGE | — | — | 100 | 100 | 80 |
| CORN | — | — | 100 | 100 | 100 |
| WILD BUCKWHEAT | — | — | 70 | 50 | 30 |
| BLACK GRASS | — | — | 80 | 50 | 30 |
| RAPESEED | — | — | 100 | 100 | 90 |
| BARLEY | — | — | 70 | 50 | 30 |
| GREEN FOXTAIL | — | — | 100 | 90 | 70 |
| CHEAT GRASS | — | — | 80 | 50 | 30 |
| BUCKWHEAT | — | — | — | — | — |
| VIOLA | — | — | — | — | — |
| LAMBSQUARTER | — | — | 100 | 100 | 70 |
| CHICK WEED | — | — | — | — | — |
| PREEMERGENCE | | | | | |
| GIANT FOXTAIL | — | 90 | 70 | 50 | 30 |
| VELVETLEAF | — | 90 | 60 | 30 | 0 |
| SUGAR BEETS | — | 90 | 60 | 30 | 0 |
| CRABGRASS | — | 90 | 70 | 50 | 30 |
| TEAWEED | — | 90 | 70 | 50 | 30 |
| JIMSONWEED | — | 70 | 50 | 30 | 0 |
| RICE | — | 90 | 70 | 50 | 30 |
| COCKLEBUR | — | 90 | 70 | 50 | 30 |
| COTTON | — | 60 | 30 | 20 | 0 |
| SOYBEAN | — | 50 | 30 | 0 | 0 |
| BARNYARD GRASS | — | 90 | 70 | 50 | 30 |
| WILD OATS | — | 50 | 30 | 0 | 0 |
| MORNINGGLORY | — | 50 | 30 | 0 | 0 |
| WHEAT | — | 70 | 50 | 30 | 0 |
| CASSIA | — | 70 | 60 | 50 | 30 |
| JOHNSONGRASS | — | 90 | 60 | 30 | 0 |
| NUTSEDGE | — | 90 | 70 | 50 | 30 |
| CORN | — | 80 | 30 | 0 | 0 |
| WILD BUCKWHEAT | — | 70 | 50 | 30 | 0 |
| BLACK GRASS | — | 80 | 50 | 30 | 0 |
| RAPESEED | — | 80 | 50 | 30 | 0 |
| BARLEY | — | 60 | 30 | 0 | 0 |
| GREEN FOXTAIL | — | 100 | 80 | 50 | 0 |
| CHEAT GRASS | — | 90 | 60 | 30 | 0 |
| BUCKWHEAT | — | — | — | — | — |
| VIOLA | — | — | — | — | — |
| LAMBSQUARTER | — | 90 | 80 | 60 | 30 |
| CHICK WEED | — | — | — | — | — |
| CMPD 69 | | | | | |
| POSTEMERGENCE | | | | | |
| GIANT FOXTAIL | — | — | 50 | 30 | 0 |
| VELVETLEAF | — | — | 90 | 70 | 50 |
| SUGAR BEETS | — | — | 80 | 70 | 50 |
| CRABGRASS | — | — | 60 | 30 | 0 |
| TEAWEED | — | — | 60 | 30 | 0 |
| JIMSONWEED | — | — | 50 | 40 | 30 |

TABLE B-continued

| | | | | | |
|---|---|---|---|---|---|
| RICE | — | — | 80 | 50 | 30 |
| COCKLEBUR | — | — | 60 | 30 | 0 |
| COTTON | — | — | 50 | 30 | 0 |
| SOYBEAN | — | — | 50 | 30 | 0 |
| BARNYARD GRASS | — | — | 70 | 50 | 30 |
| WILD OATS | — | — | 0 | 0 | 0 |
| MORNINGGLORY | — | — | 90 | 60 | 20 |
| WHEAT | — | — | 0 | 0 | 0 |
| CASSIA | — | — | 70 | 50 | 30 |
| JOHNSONGRASS | — | — | 100 | 70 | 50 |
| NUTSEDGE | — | — | 90 | 30 | 0 |
| CORN | — | — | 80 | 70 | 50 |
| WILD BUCKWHEAT | — | — | — | 0 | 0 |
| BLACK GRASS | — | — | 0 | 0 | 0 |
| RAPESEED | — | — | 90 | 70 | 50 |
| BARLEY | — | — | 0 | 0 | 0 |
| GREEN FOXTAIL | — | — | 50 | 30 | 0 |
| CHEAT GRASS | — | — | 0 | 0 | 0 |
| BUCKWHEAT | — | — | — | — | — |
| VIOLA | — | — | — | — | — |
| LAMBSQUARTER | — | — | 70 | 50 | 30 |
| CHICK WEED | — | — | — | — | — |
| PREEMERGENCE | | | | | |
| GIANT FOXTAIL | — | 30 | 0 | 0 | 0 |
| VELVETLEAF | — | 0 | 0 | 0 | 0 |
| SUGAR BEETS | — | 80 | 30 | 0 | 0 |
| CRABGRASS | — | 30 | 0 | 0 | 0 |
| TEAWEED | — | 60 | 30 | 0 | 0 |
| JIMSONWEED | — | 70 | 50 | 30 | 0 |
| RICE | — | 90 | 60 | 30 | 0 |
| COCKLEBUR | — | 50 | 30 | 0 | 0 |
| COTTON | — | 0 | 0 | 0 | 0 |
| SOYBEAN | — | 20 | 0 | 0 | 0 |
| BARNYARD GRASS | — | 70 | 30 | 0 | 0 |
| WILD OATS | — | 0 | 0 | 0 | 0 |
| MORNINGGLORY | — | 0 | 0 | 0 | 0 |
| WHEAT | — | 0 | 0 | 0 | 0 |
| CASSIA | — | 30 | 0 | 0 | 0 |
| JOHNSONGRASS | — | 80 | 50 | 30 | 0 |
| NUTSEDGE | — | 50 | 30 | 0 | 0 |
| CORN | — | 30 | 20 | 0 | 0 |
| WILD BUCKWHEAT | — | 50 | 30 | 0 | 0 |
| BLACK GRASS | — | 30 | 0 | 0 | 0 |
| RAPESEED | — | 70 | 40 | 0 | 0 |
| BARLEY | — | 0 | 0 | 0 | 0 |
| GREEN FOXTAIL | — | 30 | 0 | 0 | 0 |
| CHEAT GRASS | — | 0 | 0 | 0 | 0 |
| BUCKWHEAT | — | — | — | — | — |
| VIOLA | — | — | — | — | — |
| LAMBSQUARTER | — | 90 | 60 | 30 | 0 |
| CHICK WEED | — | — | — | — | — |
| CMPD 70 | | | | | |
| POSTEMERGENCE | | | | | |
| GIANT FOXTAIL | — | — | 30 | 0 | 0 |
| VELVETLEAF | — | — | 100 | 90 | 60 |
| SUGAR BEETS | — | — | 100 | 100 | 90 |
| CRABGRASS | — | — | 80 | 50 | 30 |
| TEAWEED | — | — | 60 | 30 | 0 |
| JIMSONWEED | — | — | 100 | 100 | 90 |
| RICE | — | — | 100 | 100 | 100 |
| COCKLEBUR | — | — | 100 | 70 | 50 |
| COTTON | — | — | 70 | 40 | 20 |
| SOYBEAN | — | — | 100 | 100 | 90 |
| BARNYARD GRASS | — | — | 100 | 100 | 60 |
| WILD OATS | — | — | 50 | 30 | 0 |
| MORNINGGLORY | — | — | 90 | 80 | 50 |
| WHEAT | — | — | 100 | 100 | 90 |
| CASSIA | — | — | 90 | 80 | 70 |
| JOHNSONGRASS | — | — | 100 | 100 | 100 |
| NUTSEDGE | — | — | 100 | 60 | 30 |
| CORN | — | — | 100 | 100 | 90 |
| WILD BUCKWHEAT | — | — | 60 | 30 | — |
| BLACK GRASS | — | — | 70 | 50 | 30 |
| RAPESEED | — | — | 100 | 100 | 80 |
| BARLEY | — | — | 70 | 50 | 30 |
| GREEN FOXTAIL | — | — | 30 | 0 | 0 |
| CHEAT GRASS | — | — | 90 | 60 | 30 |
| BUCKWHEAT | — | — | — | — | — |
| VIOLA | — | — | — | — | — |
| LAMBSQUARTER | — | — | 100 | 90 | 70 |
| CHICK WEED | — | — | — | — | — |

TABLE B-continued

| | | | | | |
|---|---|---|---|---|---|
| PREEMERGENCE | | | | | |
| GIANT FOXTAIL | — | 30 | 20 | 0 | 0 |
| VELVETLEAF | — | 80 | 50 | 30 | 0 |
| SUGAR BEETS | — | 70 | 50 | 30 | 0 |
| CRABGRASS | — | 80 | 40 | 0 | 0 |
| TEAWEED | — | 80 | 60 | 40 | 20 |
| JIMSONWEED | — | 90 | 70 | 50 | 30 |
| RICE | — | 100 | 90 | 60 | 30 |
| COCKLEBUR | — | 50 | 30 | 0 | 0 |
| COTTON | — | 50 | 30 | 0 | 0 |
| SOYBEAN | — | 50 | 30 | 0 | 0 |
| BARNYARD GRASS | — | 90 | 60 | 30 | 0 |
| WILD OATS | — | 50 | 30 | 0 | 0 |
| MORNINGGLORY | — | 0 | 0 | 0 | 0 |
| WHEAT | — | 60 | 30 | 0 | 0 |
| CASSIA | — | 40 | 0 | 0 | 0 |
| JOHNSONGRASS | — | 100 | 70 | 50 | 30 |
| NUTSEDGE | — | 80 | 30 | 0 | 0 |
| CORN | — | 60 | 30 | 0 | 0 |
| WILD BUCKWHEAT | — | 60 | 30 | 0 | 0 |
| BLACK GRASS | — | 80 | 50 | 30 | 0 |
| RAPESEED | — | 60 | 30 | 0 | 0 |
| BARLEY | — | 60 | 30 | 0 | 0 |
| GREEN FOXTAIL | — | 60 | 30 | 0 | 0 |
| CHEAT GRASS | — | 70 | 50 | 30 | 0 |
| BUCKWHEAT | — | — | — | — | — |
| VIOLA | — | — | — | — | — |
| LAMBSQUARTER | — | 100 | 90 | 60 | 30 |
| CHICK WEED | — | — | — | — | — |
| CMPD 71 | | | | | |
| POSTEMERGENCE | | | | | |
| GIANT FOXTAIL | — | — | 0 | 0 | 0 |
| VELVETLEAF | — | — | 100 | 0 | 0 |
| SUGAR BEETS | — | — | 90 | 80 | 20 |
| CRABGRASS | — | — | 30 | 0 | 0 |
| TEAWEED | — | — | 30 | 0 | 0 |
| JIMSONWEED | — | — | 40 | — | 0 |
| RICE | — | — | 50 | 50 | 40 |
| COCKLEBUR | — | — | 30 | 0 | 0 |
| COTTON | — | — | 0 | 0 | 0 |
| SOYBEAN | — | — | 80 | 30 | 0 |
| BARNYARD GRASS | — | — | 60 | 30 | 0 |
| WILD OATS | — | — | 30 | 0 | 0 |
| MORNINGGLORY | — | — | 0 | 0 | 0 |
| WHEAT | — | — | 20 | 0 | 0 |
| CASSIA | — | — | 50 | 0 | — |
| JOHNSONGRASS | — | — | 50 | 40 | 20 |
| NUTSEDGE | — | — | 30 | 20 | 0 |
| CORN | — | — | 60 | 60 | 20 |
| WILD BUCKWHEAT | — | — | 60 | 20 | 20 |
| BLACK GRASS | — | — | 0 | 0 | 0 |
| RAPESEED | — | — | 80 | 50 | 30 |
| BARLEY | — | — | 20 | 0 | 0 |
| GREEN FOXTAIL | — | — | 0 | 0 | 0 |
| CHEAT GRASS | — | — | 30 | 0 | 0 |
| BUCKWHEAT | — | — | — | — | — |
| VIOLA | — | — | 0 | 0 | 0 |
| LAMBSQUARTER | — | — | 0 | 0 | 0 |
| CHICK WEED | — | — | — | — | — |
| PREEMERGENCE | | | | | |
| GIANT FOXTAIL | 30 | 0 | 40 | 0 | — |
| VELVETLEAF | 70 | 30 | 30 | 0 | — |
| SUGAR BEETS | 90 | 90 | 40 | 50 | — |
| CRABGRASS | 60 | 60 | 0 | 0 | — |
| TEAWEED | 80 | 80 | 20 | 0 | — |
| JIMSONWEED | 30 | 20 | 20 | 0 | — |
| RICE | 90 | 70 | 40 | 0 | — |
| COCKLEBUR | 50 | 50 | 0 | 0 | — |
| COTTON | 60 | 60 | — | 20 | — |
| SOYBEAN | 30 | 30 | 0 | 0 | — |
| BARNYARD GRASS | 50 | 20 | 0 | 0 | — |
| WILD OATS | 50 | 30 | 20 | — | — |
| MORNINGGLORY | 50 | 50 | 20 | 20 | — |
| WHEAT | 0 | 0 | 0 | 0 | — |
| CASSIA | — | — | 0 | 0 | — |
| JOHNSONGRASS | 70 | 40 | 30 | 20 | — |
| NUTSEDGE | 30 | 20 | 0 | 0 | — |
| CORN | 30 | 20 | 20 | 0 | — |
| WILD BUCKWHEAT | 80 | 80 | 40 | 30 | — |
| BLACK GRASS | 70 | 30 | 30 | 0 | — |
| RAPESEED | 70 | 50 | 50 | 50 | — |

TABLE B-continued

| | | | | | |
|---|---|---|---|---|---|
| BARLEY | 40 | 30 | 30 | 30 | — |
| GREEN FOXTAIL | 30 | 30 | 40 | 30 | — |
| CHEAT GRASS | 70 | 40 | 30 | 20 | — |
| BUCKWHEAT | — | — | — | — | — |
| VIOLA | 80 | 20 | 20 | 0 | — |
| LAMBSQUARTER | 80 | 80 | 0 | 0 | — |
| CHICK WEED | — | — | — | — | — |
| CMPD 72 | | | | | |
| PREEMERGENCE | | | | | |
| GIANT FOXTAIL | 30 | 30 | 20 | — | — |
| VELVETLEAF | 90 | 80 | 20 | 0 | — |
| SUGAR BEETS | 90 | 90 | 30 | 0 | — |
| CRABGRASS | 80 | 50 | 30 | 0 | — |
| TEAWEED | 90 | 50 | 50 | 0 | — |
| JIMSONWEED | 90 | 50 | 0 | 0 | — |
| RICE | 90 | 80 | 30 | 0 | — |
| COCKLEBUR | 80 | 50 | 30 | 30 | — |
| COTTON | 80 | 70 | 70 | 30 | — |
| SOYBEAN | 50 | 40 | 30 | 30 | — |
| BARNYARD GRASS | 80 | 30 | 20 | 20 | — |
| WILD OATS | 50 | 30 | 20 | 0 | — |
| MORNINGGLORY | 80 | 70 | 50 | 50 | — |
| WHEAT | 40 | 0 | 0 | 0 | — |
| CASSIA | — | — | — | — | — |
| JOHNSONGRASS | 90 | 50 | 40 | 20 | — |
| NUTSEDGE | 70 | 20 | 20 | 20 | — |
| CORN | 70 | 30 | 30 | 20 | — |
| WILD BUCKWHEAT | 90 | — | 80 | 70 | — |
| BLACK GRASS | 90 | 40 | 30 | 30 | — |
| RAPESEED | 90 | 60 | 50 | 40 | — |
| BARLEY | 30 | 30 | 30 | 20 | — |
| GREEN FOXTAIL | 50 | 40 | 20 | — | — |
| CHEAT GRASS | 70 | 80 | 40 | 30 | — |
| BUCKWHEAT | — | — | — | — | — |
| VIOLA | 90 | 80 | 0 | 0 | — |
| LAMBSQUARTER | 100 | 90 | 30 | 0 | — |
| CHICK WEED | — | — | — | — | — |

TEST C

Two plastic windowsill trays were filled with planting medium. One was planted with seeds of speedwell (*Veronica persica*), chickweed (*Stellaria media*), redroot pigweed (*Amaranthus retroflexus*), wild mustard (*Brassica kaber*), wild raddish (*Raphanus raphanistrum*), wild buckwheat (*Polygonum convolvulus*), common lambsquarters (*Chenopodium album*), stinkweed (*Thlaspi arvense*), and rape (*Brassica napus* and *B. campestries*). The other tray was planted with seeds of Italian ryegrass (*Lolium multiflorum*), green foxtail (*Setaria viridis*), wild oats (*Avena fatua*), blackgrass (*Alopecurus myosuroides*), wheat (*Triticum aestivum*—vars. 'Nacozari', 'Centurk' and 'Park') and barley (*Hordeum vulgare*—vars. 'Klages' and 'Morex').

The trays were treated when crops and weeds had grown to 2 to 3-leaf stage (postemergence) with compounds formulated in a non-phytotoxic solvent. The degree of crop injury and weed control was visually rated 2 to 4 weeks after compound application. The plant response ratings were either based on the scale of 0 to 100 where 0=no effect, 10=minimal injury and 100=complete control or on a scale of 0 to 10 where 0=no effect and 10=complete control. The type of response is represented by letters where G=growth retardation. The results are given in Table C.

TABLE C

| | CMPD 14 | | |
|---|---|---|---|
| RATE GM/HA | 0016 | 0032 | 0064 |
| POSTEMERGENCE | | | |
| BLACK GRASS | 0 | 40 | 80 |
| CANADA RAPE | 0 | 0 | 0 |
| CENTURK WHEAT | 0 | 0 | 50 |

TABLE C-continued

| | CMPD 14 | | |
|---|---|---|---|
| RATE GM/HA | 0016 | 0032 | 0064 |
| CHICKWEED | 0 | 0 | 0 |
| GREEN FOXTAIL | 0 | 40 | 40 |
| KLAGES BARLEY | 20 | 20 | 50 |
| MOREX BARLEY | 40 | 60 | 70 |
| NACOZARI WHEAT | 20 | 30 | 70 |
| PARK WHEAT | 60 | 70 | 80 |
| PIGWEED | 0 | 40 | 80 |
| RYE GRASS | 50 | 70 | 70 |
| STINKWEED | 30 | 60 | 80 |
| VERONICA PERSCA | 0 | 0 | 0 |
| WILD BUCKWHEAT | 0 | 0 | 0 |
| WILD MUSTARD | 0 | 70 | 80 |
| WILD OATS | 0 | 0 | 30 |
| WILD RADISH | 0 | 0 | 0 |

TEST D

Seeds of the following crops and weeds are sown into 15 cm diameter pots containing Sassafras sandy loam soil: wheat (*Triticum aestivum*), barley (*Hordeum vulgare*), sugarbeet (*Beta vulgaris*), black nightshade (*Solanum nigrum*), chickweed (*Stellaria media*), common lambsquarters (*Chenopodium album*), Galium (*Galium aparine*), knotweed (*Polygonum aviculare*), Kochia (*Kochia scoparia*), Matricaria (*Martricaria inodora*), redroot pigweed (*Amaranthus retroflexus*), smartweek (*Polygonum persicaria*), speedwell (*Veronica persica*), wild buckwheat (*Polygonum convolvulus*), wild mustard (*Brassica kaber*) wild radish (*Raphanus raphanistrum*), annual bluegrass (*Poa annua*), annual ryegrass (*Lolium multiflorum*), blackgrass (*Alopecurus myosuroides*), green foxtail (*Setaria viridis*), and wild oats (*Avena fatua*). Compounds are formulated in a non-phytotoxic solvent and applied to the plants as a foliar spray. Plants are treated at three stages: (1) preemergence, (2) postemergence when sugarbeets are at the 1st true leaf stage, and (3) postemergence when sugarbeets have three leaves. Plants are grown in a temperature controlled greenhouse for the duration of the experiment.

Wee control and crop injury are evaluated visually (3 to 4 weeks following compound application), using a scale of 0 to 100%, where 0=no injury or control and 100=complete death of the plants. The results are in Table D.

TABLE D

| | CMPD 36 | | | |
|---|---|---|---|---|
| RATE GM/HA | 0030 | 0063 | 0125 | 0250 |
| POSTEMERGENCE | | | | |
| BARLEY | 75 | 100 | 70 | 50 |
| SUGARBEET CROPS | — | — | — | — |
| BLCK NIGHTSHADE | 70 | 100 | 100 | 100 |
| BLUE GRASS | 80 | 100 | 100 | 100 |
| BUCKWHEAT | 0 | 0 | 0 | 0 |
| CHICK WEED | 0 | 0 | 0 | 0 |
| GALIUM | 0 | 0 | 0 | 100 |
| GREEN FOXTAIL | 80 | 95 | 100 | 100 |
| KOCHIA | 0 | 0 | 30 | 30 |
| LAMBSQUARTER | 0 | 0 | 0 | |
| MATRA INDORA | 20 | 40 | 100 | 100 |
| MUSTARD | 100 | 100 | 100 | 100 |
| PIG WEED | 100 | 100 | 100 | 100 |
| RYE GRASS | 90 | 95 | 90 | 100 |
| SMART WEED | 0 | 0 | 0 | 0 |
| SPEEDWELL | 0 | 0 | 0 | 0 |
| SUGARBEET C/TOL | 0 | 0 | 0 | 0 |
| WHEAT | 80 | 100 | 100 | 100 |
| WILD OATS | 100 | 100 | 100 | 100 |
| WILD RADISH | 0 | 0 | 0 | 0 |
| PREEMERGENCE | | | | |

TABLE D-continued

| | CMPD 36 | | | |
|---|---|---|---|---|
| RATE GM/HA | 0030 | 0063 | 0125 | 0250 |
| BARLEY | 0 | 0 | 20 | 75 |
| SUGARBEET CROPS | — | — | — | — |
| BLCK NIGHTSHADE | 0 | 20 | 25 | 30 |
| BLUE GRASS | 0 | 75 | 100 | 100 |
| BUCKWHEAT | 0 | 0 | 0 | 0 |
| CHICK WEED | 0 | 0 | 0 | 0 |
| GALIUM | 0 | 0 | 0 | 0 |
| GREEN FOXTAIL | 40 | 100 | 100 | 100 |
| KOCHIA | 0 | 0 | 0 | 0 |
| LAMBSQUARTER | 0 | 0 | 0 | 0 |
| MATRA INDORA | 60 | 95 | 100 | 100 |
| MUSTARD | 0 | 0 | 50 | 75 |
| PIG WEED | 100 | 100 | 100 | 100 |
| RYE GRASS | 20 | 100 | 100 | 100 |
| SMART WEED | 0 | 0 | 50 | 100 |
| SPEEDWELL | 0 | 20 | 20 | 20 |
| SUGARBEET C/TOL | 0 | 10 | 20 | 40 |
| WHEAT | 0 | 10 | 15 | 20 |
| WILD OATS | 0 | 65 | 80 | 95 |
| WILD RADISH | 0 | 0 | 0 | 25 |

What is claimed is:

1. A compound of the Formula I:

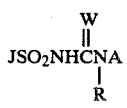

I wherein

J is

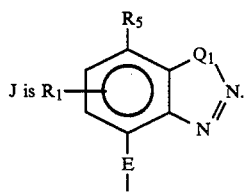

J-1

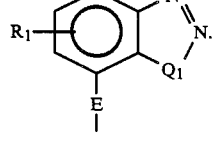

J-2

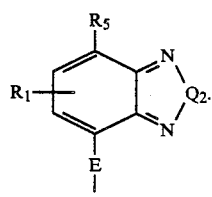

J-3

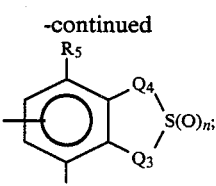

J-4

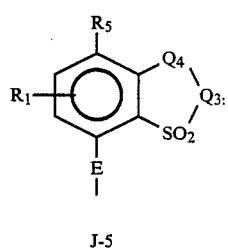

J-5

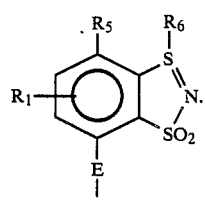

J-6 or

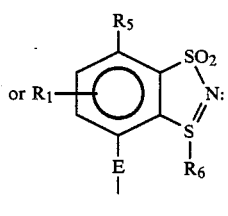

J-7

W is O or S;
R is H or $CH_3$;
E is a single bond, $CH_2$ or O;
$R_1$ is H, $C_1$–$C_3$ alkyl, $C_1$–$C_3$ haloalkyl, halogen, nitro, $C_1$–$C_3$ alkoxy, $SO_2NR_aR_b$, $C_1$–$C_3$ alkylthio, $C_1$–$C_3$ alkylsulfinyl, $C_1$–$C_3$ alkylsulfonyl, $CH_2CN$, CN, $CO_2R_c$, $C_1$–$C_3$ haloalkoxy, $C_1$–$C_3$ haloalkylthio, $C_2$–$C_4$ alkoxyalkyl, $C_2$–$C_4$ alkylthioalkyl, $CH_2N_3$ or $NR_dR_e$;
$R_a$ is H, $C_1$–$C_4$ alkyl, $C_2$–$C_3$ cyanoalkyl, methoxy or ethoxy;
$R_b$ is H, $C_1$–$C_4$ alkyl or $C_3$–$C_4$ alkenyl; or
$R_a$ and $R_b$ may be taken together as —$(CH_2)_3$—, —$(CH_2)_4$—, —$(CH_2)_5$— or —$CH_2CH_2OCH_2CH_2$—;
$R_c$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;
$R_d$ and $R_e$ are independently H or $C_1$–$C_2$ alkyl;
$Q_1$ is S, $SO_2$ or $NR_2$;
$Q_2$ is O, S or $NR_2$;
$Q_3$ is O, S or $NR_3$;
$Q_4$ is O, S or $NR_4$;
n is 0, 1 or 2;

$R_2$ is H, $C_1$-$C_3$ alkyl, phenyl, benzyl, $CH_2CH=CH_2$, $CH_2C\equiv CH$, CN, $C_1$-$C_3$ haloalkyl, OH, $OCH_3$ or $OC_2H_5$;

$R_3$ is H or $C_1$-$C_3$ alkyl;

$R_4$ is H or $CH_3$;

$R_5$ is H, halogen, $CH_3$, $CH_2CH_3$, $OCH_3$, $OCH_2CH_3$, $OCF_2H$ or halomethyl;

$R_6$ is $C_1$-$C_4$ alkyl;

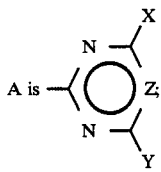

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino or $C_3$-$C_5$ cycloalkyl;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_2$-$C_4$ alkynyl, azido, cyano, $C_2$-$C_5$ alkylsulfinylalkyl, $C_2$-$C_5$ alkylsulfonylalkyl,

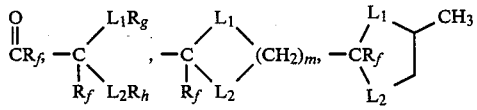

$NR_d$($C_2$-$C_3$ cyanoalkyl) or $N(OCH_3)CH_3$;

m is 2 or 3;

$L_1$ and $L_2$ are independently O or S;

$R_f$ is H or $C_1$-$C_3$ alkyl;

$R_g$ and $R_h$ are independently $C_1$-$C_3$ alkyl; and

Z is CH;

and their agriculturally suitable salts; provided that
(a) when X is Cl, F, Br or I, then Y is $OCH_3$, $OC_2H_5$, $N(OCH_3)CH_3$, $NHCH_3$, $N(CH_3)_2$ or $OCF_2H$;
(b) when W is S, then E is a single bond, R is H and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;
(c) when the total number of carbons of X and Y is greater than four, then the number of carbons of $R_1$ must be less than or equal to two;
(d) $Q_3$ and $Q_4$ are not simultaneously S;
(e) when J is J-5, then $Q_3$ is $NR_3$ and $Q_4$ is $NR_4$;
(f) when n is 0, then $Q_3$ is $NR_3$ and $Q_4$ is $NR_4$; and
(g) when $R_5$ is other than H, then R is H, $R_1$ is H, W is O, and E is a single bond.

2. The compounds of claim 1 where E is a single bond.

3. The compounds of claim 1 where E is $CH_2$ and $R_5$ is H.

4. The compounds of claim 1 wherein E is O and $R_5$ is H.

5. The compounds of claim 2 where
W is O;
$R_1$ is H, F, Cl, Br, $C_1$-$C_2$ alkyl, $C_1$-$C_3$ alkoxy, $C_1$-$C_3$ alkylthio, $C_1$-$C_2$ alkyl, $C_1$-$C_3$ alkoxy substituted with 1-3 atoms of F, Cl, or Br or $C_1$-$C_3$ alkylthio substituted with 1-3 atoms of F, Cl or Br;
$R_2$ is H or $C_1$-$C_3$ alkyl;
$R_5$ is H;
X is $C_1$-$C_2$ alkyl, $C_1$-$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
Y is H, $C_1$-$C_2$ alkyl, $C_1$-$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

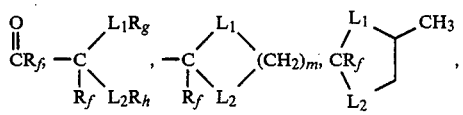

$OCF_2H$, $OCF_2Br$, $SCF_2H$, cyclopropyl, $C\equiv CH$ or $C\equiv CCH_3$.

6. The compounds of claim 5 where J is J-1.
7. The compounds of claim 5 where J is J-2.
8. The compounds of claim 5 where J is J-3.
9. The compounds of claim 5 where J is J-4.
10. The compounds of claim 5 where J is J-5.
11. The compounds of claim 5 where J is J-6.
12. The compounds of claim 5 where J is J-7.
13. The compounds of claim 5 where J is J-7.
14. The compounds of claim 3 where
R is H;
J is J-1;
$R_1$ is H;
$R_2$ is H or $CH_3$;
X is $CH_3$, $OCH_3$, Cl or $OCF_2H$; and
Y is $CH_3$, $OCH_3$, $C_2H_5$, $CH_2OCH_3$, $NHCH_3$, $CH(OCH_3)_2$ or cyclopropyl.

15. The compounds of claim 4 where
R is H;
J is J-1;
$R_1$ is H;
$R_2$ is H or $CH_3$;
X is $CH_3$, $OCH_3$, $OCH_2CH_3$, Cl or $OCF_2H$; and
Y is $CH_3$, $OCH_3$, $C_2H_5$, $CH_2OCH_3$, $NHCH_3$, $CH(OCH_3)_2$ or cyclopropyl.

16. The compound of claim 1 which is N-[(4,6-dimethoxypyrimidin-2-yl)aminocarbonyl]-5-methoxy-1,2,3-benzothiadiazole-4-sulfonamide.

17. An agriculturally suitable composition for controlling the growth of undesired vegetation comprising an effective amount of a compound of claim 1 and at least one of the following: surfactant, solid or liquid diluent.

18. An agriculturally suitable composition for controlling the growth of undesired vegetation comprising an effective amount of a compound of claim 2 and at least one of the following: surfactant, solid or liquid diluent.

19. An agriculturally suitable composition for controlling the growth of undesired vegetation comprising an effective amount of a compound of claim 3 and at least one of the following: surfactant, solid or liquid diluent.

20. An agriculturally suitable composition for controlling the growth of undesired vegetation comprising an effective amount of a compound of claim 4 and at least one of the following: surfactant, solid or liquid diluent.

21. An agriculturally suitable composition for controlling the growth of undesired vegetation comprising an effective amount of a compound of claim 5 and at least one of the following: surfactant, solid or liquid diluent.

22. An agriculturally suitable composition for controlling the growth of undesired vegetation comprising an effective amount of a compound of claim 6 and at least one of the following: surfactant, solid or liquid diluent.

23. An agriculturally suitable composition for controlling the growth of undesired vegetation comprising an effective amount of a compound of claim 7 and at least one of the following: surfactant, solid or liquid diluent.

24. An agriculturally suitable composition for controlling the growth of undesired vegetation comprising an effective amount of a compound of claim 8 and at least one of the following: surfactant, solid or liquid diluent.

25. An agriculturally suitable composition for controlling the growth of undesired vegetation comprising an effective amount of a compound of claim 9 and at least one of the following: surfactant, solid or liquid diluent.

26. An agriculturally suitable composition for controlling the growth of undesired vegetation comprising an effective amount of a compound of claim 10 and at least one of the following: surfactant, solid or liquid diluent.

27. An agriculturally suitable composition for controlling the growth of undesired vegetation comprising an effective amount of a compound of claim 11 and at least one of the following: surfactant, solid or liquid diluent.

28. An agriculturally suitable composition for controlling the growth of undesired vegetation comprising an effective amount of a compound of claim 12 and at least one of the following: surfactant, solid or liquid diluent.

29. An agriculturally suitable composition for controlling the growth of undesired vegetation comprising an effective amount of a compound of claim 13 and at least one of the following: surfactant, solid or liquid diluent.

30. An agriculturally suitable composition for controlling the growth of undesired vegetation comprising an effective amount of a compound of claim 14 and at least one of the following: surfactant, solid or liquid diluent.

31. An agriculturally suitable composition for controlling the growth of undesired vegetation comprising an effective amount of a compound of claim 15 and at least one of the following: surfactant, solid or liquid diluent.

32. An agriculturally suitable composition for controlling the growth of undesired vegetation comprising an effective amount of a compound of claim 16 and at least one of the following: surfactant, solid or liquid diluent.

33. A method for controlling the growth of undesired vegetation which comprises applying to the locus to be protected an effective amount of a compound of claim 1.

34. A method for controlling the growth of undesired vegetation which comprises applying to the locus to be protected an effective amount of a compound of claim 2.

35. A method for controlling the growth of undesired vegetation which comprises applying to the locus to be protected an effective amount of a compound of claim 3.

36. A method for controlling the growth of undesired vegetation which comprises applying to the locus to be protected an effective amount of a compound of claim 4.

37. A method for controlling the growth of undesired vegetation which comprises applying to the locus to be protected an effective amount of a compound of claim 5.

38. A method for controlling the growth of undesired vegetation which comprises applying to the locus to be protected an effective amount of a compound of claim 6.

39. A method for controlling the growth of undesired vegetation which comprises applying to the locus to be protected an effective amount of a compound of claim 7.

40. A method for controlling the growth of undesired vegetation which comprises applying to the locus to be protected an effective amount of a compound of claim 8.

41. A method for controlling the growth of undesired vegetation which comprises applying to the locus to be protected an effective amount of a compound of claim 9.

42. A method for controlling the growth of undesired vegetation which comprises applying to the locus to be protected an effective amount of a compound of claim 10.

43. A method for controlling the growth of undesired vegetation which comprises applying to the locus to be protected an effective amount of a compound of claim 11.

44. A method for controlling the growth of undesired vegetation which comprises applying to the locus to be protected an effective amount of a compound of claim 12.

45. A method for controlling the growth of undesired vegetation which comprises applying to the locus to be protected an effective amount of a compound of claim 13.

46. A method for controlling the growth of undesired vegetation which comprises applying to the locus to be protected an effective amount of a compound of claim 14.

47. A method for controlling the growth of undesired vegetation which comprises applying to the locus to be protected an effective amount of a compound of claim 15.

48. A method for controlling the growth of undesired vegetation which comprises applying to the locus to be protected an effective amount of a compound of claim 16.

* * * * *